United States Patent
Takeda et al.

(10) Patent No.: US 11,917,908 B2
(45) Date of Patent: Feb. 27, 2024

(54) ORGANIC COMPOUND, OPTICAL DEVICE, LIGHT-EMITTING DEVICE, LIGHT-EMITTING APPARATUS, ELECTRONIC DEVICE, AND LIGHTING DEVICE

(71) Applicant: SEMICONDUCTOR ENERGY LABORATORY CO., LTD., Atsugi (JP)

(72) Inventors: Kyoko Takeda, Kanagawa (JP); Harue Osaka, Kanagawa (JP); Hiroshi Kadoma, Kanagawa (JP); Satoshi Seo, Kanagawa (JP); Tsunenori Suzuki, Kanagawa (JP); Naoaki Hashimoto, Kanagawa (JP)

(73) Assignee: Semiconductor Energy Laboratory Co., Ltd., Atsugi (JP)

( * ) Notice: Subject to any disclaimer, the term of this patent is extended or adjusted under 35 U.S.C. 154(b) by 424 days.

(21) Appl. No.: 17/116,222

(22) Filed: Dec. 9, 2020

(65) Prior Publication Data
US 2021/0193930 A1 Jun. 24, 2021

(30) Foreign Application Priority Data
Dec. 12, 2019 (JP) .................. 2019-224651

(51) Int. Cl.
H01L 51/00 (2006.01)
C07D 493/04 (2006.01)
(Continued)

(52) U.S. Cl.
CPC ......... H10K 85/636 (2023.02); C07D 209/88 (2013.01); C07D 405/12 (2013.01);
(Continued)

(58) Field of Classification Search
None
See application file for complete search history.

(56) References Cited

FOREIGN PATENT DOCUMENTS

JP 2017109929 A * 6/2017
JP 2019-085387 A 6/2019

OTHER PUBLICATIONS

Machine English translation of Miyazaki et al. (JP-2017109929-A). Apr. 10, 23.*

* cited by examiner

Primary Examiner — Jay Yang
(74) Attorney, Agent, or Firm — Fish & Richardson P.C.

(57) ABSTRACT

A novel organic compound represented by General Formula (G1) is provided. In General Formula (G1), $X^1$ and $X^2$ each independently represent a secondary or tertiary alkyl group having 3 to 6 carbon atoms and having a branched carbon atom which is bonded to a phenyl group. In addition, $Ar^1$ represents a substituted or unsubstituted condensed aromatic ring skeleton having 10 to 60 carbon atoms and composed of two or more rings or a substituted or unsubstituted condensed heteroaromatic ring skeleton having 8 to 60 carbon atoms and composed of two or more rings. Furthermore, $Ar^2$ represents a substituted or unsubstituted aryl group having 6 to 25 carbon atoms. Moreover, n represents any of 1 to 3, and in the case where n is 2 or more, two or more groups bonded to $Ar^1$ may be identical or different.

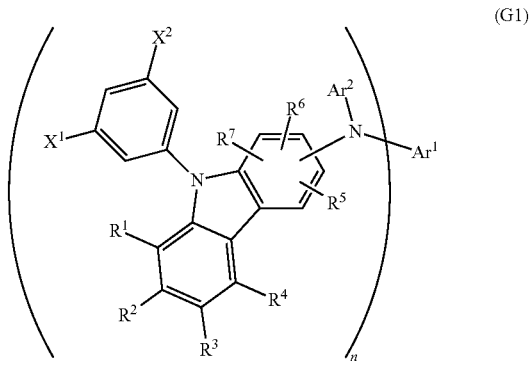

12 Claims, 56 Drawing Sheets

(51) Int. Cl.
 *C09K 11/06* (2006.01)
 *C07D 209/88* (2006.01)
 *C07D 405/12* (2006.01)
 *H10K 85/60* (2023.01)
 *H10K 50/11* (2023.01)

(52) U.S. Cl.
 CPC ............ *C07D 493/04* (2013.01); *C09K 11/06* (2013.01); *H10K 85/633* (2023.02); *C09K 2211/1022* (2013.01); *H10K 50/11* (2023.02); *H10K 85/615* (2023.02); *H10K 85/622* (2023.02); *H10K 85/6572* (2023.02); *H10K 85/6574* (2023.02)

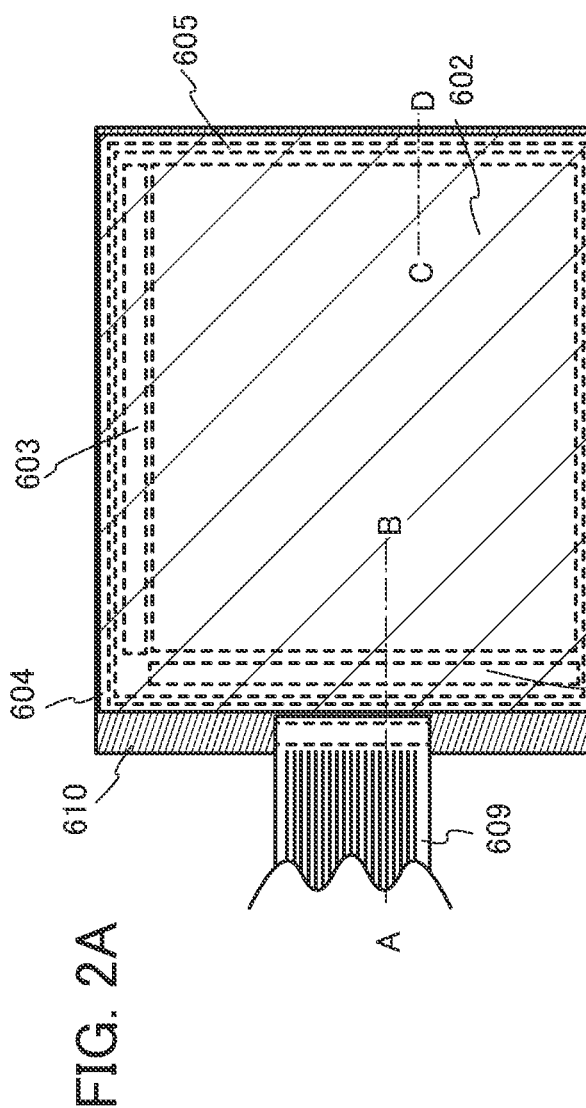
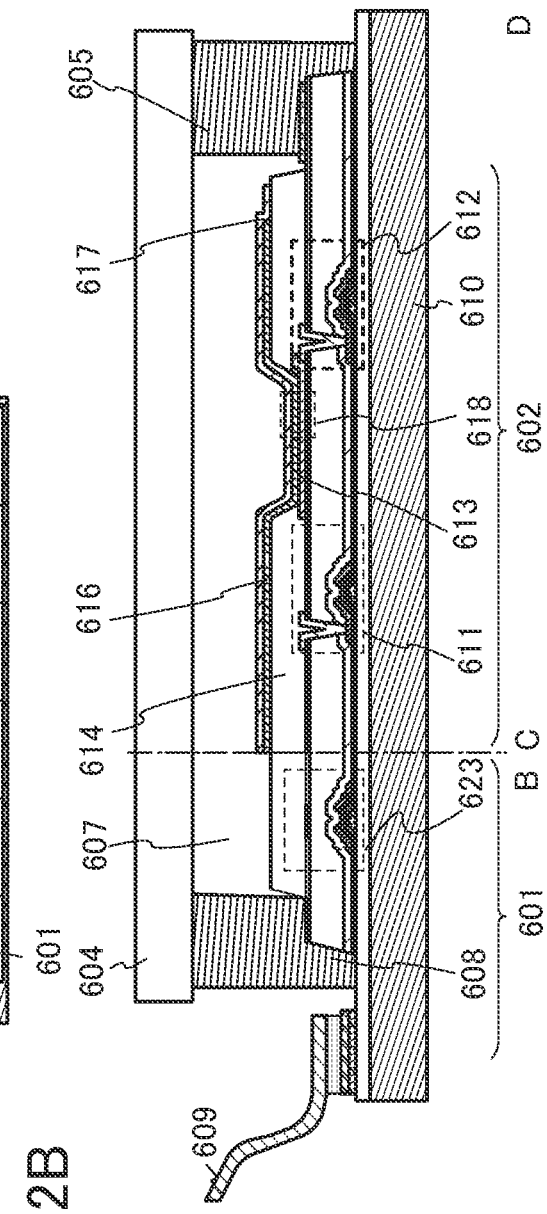
FIG. 2A
FIG. 2B

னorganic compound, optical device, light-emitting device, light-emitting apparatus, electronic device, and lighting device

ORGANIC COMPOUND, OPTICAL DEVICE, LIGHT-EMITTING DEVICE, LIGHT-EMITTING APPARATUS, ELECTRONIC DEVICE, AND LIGHTING DEVICE

BACKGROUND OF THE INVENTION

1. Field of the Invention

One embodiment of the present invention relates to an organic compound, a light-emitting element, a light-emitting device, a display module, a lighting module, a display device, a light-emitting apparatus, an electronic device, and a lighting device. Note that one embodiment of the present invention is not limited to the above technical field. The technical field of one embodiment of the invention disclosed in this specification and the like relates to an object, a method, or a manufacturing method. One embodiment of the present invention relates to a process, a machine, manufacture, or a composition of matter. Specifically, examples of the technical field of one embodiment of the present invention disclosed in this specification include a semiconductor device, a display device, a liquid crystal display device, a light-emitting apparatus, a lighting device, a power storage device, a memory device, an imaging device, a driving method thereof, and a manufacturing method thereof.

2. Description of the Related Art

Light-emitting devices (organic EL devices) utilizing electroluminescence (EL) of organic compounds have been put to more practical use. In the basic structure of such light-emitting devices, an organic compound layer containing a light-emitting material (an EL layer) is interposed between a pair of electrodes. Carriers are injected by application of voltage to the device, and recombination energy of the carriers is used, whereby light emission can be obtained from the light-emitting material.

Such light-emitting devices are of self-luminous type and thus have advantages over liquid crystal displays, such as high visibility and no need for backlight when used as pixels of a display, and are suitable as flat panel display devices. Displays including such light-emitting devices are also highly advantageous in that they can be thin and lightweight. Moreover, such light-emitting devices also have a feature of extremely fast response speed.

Since light-emitting layers of such light-emitting devices can be successively formed two-dimensionally, planar light emission can be achieved. This feature is difficult to realize with point light sources typified by incandescent lamps and LEDs or linear light sources typified by fluorescent lamps; thus, the light-emitting devices also have great potential as planar light sources, which can be applied to lighting devices and the like.

Displays or lighting devices including light-emitting devices are suitable for a variety of electronic devices as described above, and research and development of light-emitting devices have progressed for more favorable characteristics (see Patent Document 1).

REFERENCE

Patent Document

[Patent Document 1] Japanese Published Patent Application No. 2019-085387

SUMMARY OF THE INVENTION

An object of one embodiment of the present invention is to provide a novel organic compound. Another object of one embodiment of the present invention is to provide an organic compound with favorable thermophysical properties. Another object of one embodiment of the present invention is to provide an organic compound with high solubility. Another object of one embodiment of the present invention is to provide an organic compound with favorable color purity and low evaporation temperature.

Another object of one embodiment of the present invention is to provide a novel blue light-emitting material. Another object of one embodiment of the present invention is to provide a blue light-emitting material with favorable thermophysical properties. Another object of one embodiment of the present invention is to provide a blue light-emitting material with high color purity and a low evaporation temperature.

Another object of one embodiment of the present invention is to provide an organic compound that has a low evaporation temperature and enables a light-emitting device with favorable characteristics. Another object of one embodiment of the present invention is to provide an organic compound that has a low evaporation temperature and enables a long-life light-emitting device.

Another object of one embodiment of the present invention is to provide a blue light-emitting material that has a low evaporation temperature and enables a light-emitting device with favorable characteristics. Another object of one embodiment of the present invention is to provide a blue light-emitting material that has a low evaporation temperature and enables a long-life light-emitting device. Another object of one embodiment of the present invention is to provide a blue light-emitting material that has favorable initial characteristics, a long lifetime, and a low evaporation temperature. Another object of one embodiment of the present invention is to provide a light-emitting device having a long driving lifetime at high temperature.

Another object of one embodiment of the present invention is to provide a light-emitting device, a light-emitting apparatus, an electronic device, and a display device, each of which has a long lifetime and can be fabricated easily.

Note that the descriptions of these objects do not preclude the existence of other objects. One embodiment of the present invention does not necessarily achieve all these objects. Other objects will be apparent from and can be derived from the descriptions of the specification, the drawings, the claims, and the like.

It is only necessary that at least one of the above-described objects be achieved in the present invention.

One embodiment of the present invention is an organic compound represented by General Formula (G1) below.

[Chemical Formula 1]

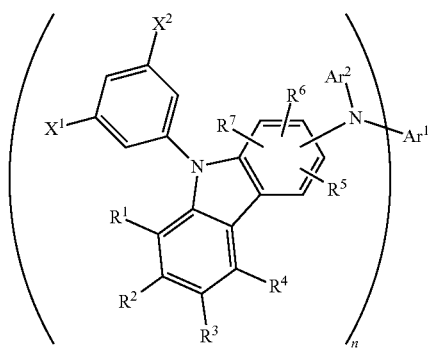

(G1)

In General Formula (G1), $X^1$ and $X^2$ each independently represent a secondary or tertiary alkyl group having 3 to 6 carbon atoms and having a branched carbon atom which is bonded to a phenyl group. In addition, $Ar^1$ represents a substituted or unsubstituted condensed aromatic ring skeleton having 10 to 60 carbon atoms and composed of two or more rings or a substituted or unsubstituted condensed heteroaromatic ring skeleton having 8 to 60 carbon atoms and composed of two or more rings. Furthermore, $Ar^2$ represents a substituted or unsubstituted aryl group having 6 to 25 carbon atoms. Moreover, $R^1$ to $R^7$ each independently represent any of hydrogen, an alkyl group having 1 to 6 carbon atoms, a cycloalkyl group having 3 to 12 carbon atoms, and an aryl group having 6 to 13 carbon atoms which is unsubstituted or to which an alkyl group is bonded as a substituent. Furthermore, n represents any of 1 to 3, and in the case where n is 2 or more, two or more groups bonded to $Ar^1$ may be identical or different.

Another embodiment of the present invention is the organic compound in the above-described structure, in which $Ar^1$ is a substituted or unsubstituted condensed aromatic ring skeleton having 10 to 60 carbon atoms and composed of three to nine rings or a substituted or unsubstituted condensed heteroaromatic ring skeleton having 8 to 60 carbon atoms and composed of three to nine rings.

Another embodiment of the present invention is the organic compound in the above-described structure, in which $Ar^1$ is a substituted or unsubstituted condensed heteroaromatic ring skeleton having 8 to 60 carbon atoms and composed of three to seven rings.

Another embodiment of the present invention is the organic compound in the above-described structure, in which $X^1$ or $X^2$ each independently represent a secondary or tertiary alkyl group having 3 or 4 carbon atoms and having a branched carbon atom which is bonded to the phenyl group.

Another embodiment of the present invention is the organic compound in the above-described structure, in which n is 2.

Another embodiment of the present invention is the organic compound in the above-described structure, in which $Ar^1$ represents any of heteroaromatic ring skeletons represented by General Formulae (B1) to (B4).

[Chemical Formula 2]

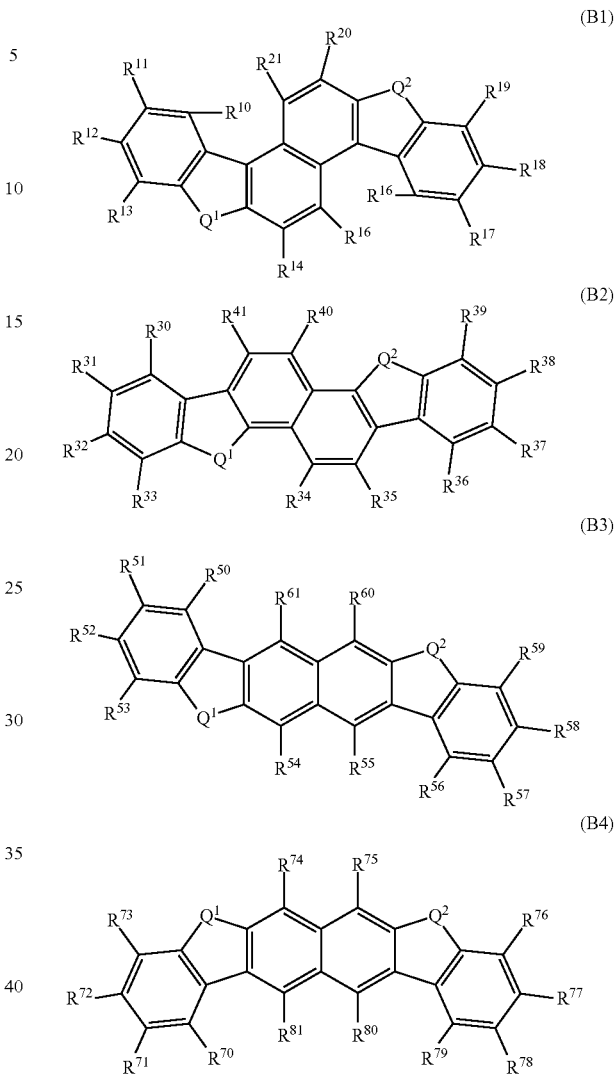

In the formula, $Q^1$ and $Q^2$ each independently represent an oxygen atom or a sulfur atom. In General Formula (B1), any one or two of $R^{10}$ to $R^{21}$ represents a single bond, and the others each independently represent any of hydrogen, an alkyl group having 1 to 6 carbon atoms, a cycloalkyl group having 3 to 12 carbon atoms, and an aryl group having 6 to 13 carbon atoms which is unsubstituted or to which an alkyl group is bonded as a substituent. In General Formula (B2), any one or two of $R^{30}$ to $R^{41}$ represents a single bond, and the others each independently represent any of hydrogen, an alkyl group having 1 to 6 carbon atoms, a cycloalkyl group having 3 to 12 carbon atoms, and an aryl group having 6 to 13 carbon atoms which is unsubstituted or to which an alkyl group is bonded as a substituent. In General Formula (B3), any one or two of $R^{50}$ to $R^{61}$ represents a single bond, and the others each independently represent any of hydrogen, an alkyl group having 1 to 6 carbon atoms, a cycloalkyl group having 3 to 12 carbon atoms, and an aryl group having 6 to 13 carbon atoms which is unsubstituted or to which an alkyl group is bonded as a substituent. In General Formula (B4), any one or two of $R^{70}$ to $R^{81}$ represents a single bond, and the others each independently represent any of hydrogen, an alkyl group having 1 to 6 carbon atoms, a cycloalkyl group having 3 to 12 carbon atoms, and an aryl group having 6 to 13 carbon atoms which is unsubstituted or to which an alkyl group is bonded as a substituent.

Another embodiment of the present invention is the organic compound in the above-described structure, in which $Ar^1$ represents a heteroaromatic ring skeleton represented by General Formula (B1-1) or (B3-1).

[Chemical Formula 3]

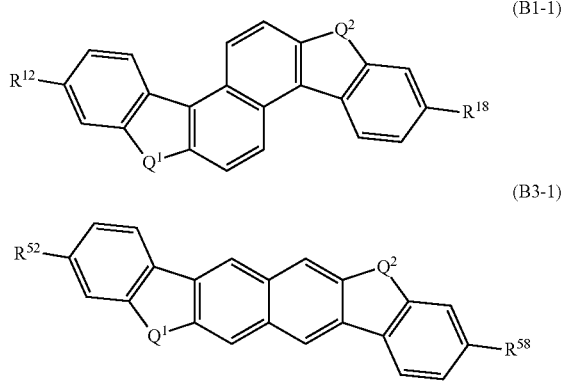

In the formula, $Q^1$ and $Q^2$ each independently represent an oxygen atom or a sulfur atom. Furthermore, $R^{12}$, $R^{18}$, $R^{52}$, and $R^{58}$ represent a single bond.

Another embodiment of the present invention is an organic compound represented by General Formula (G1-1) below.

[Chemical Formula 4]

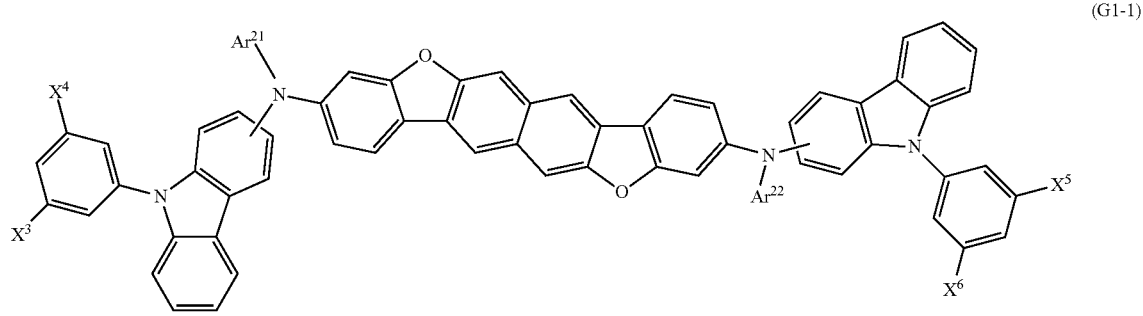

In General Formula (G1-1) above, $X^3$ to $X^6$ each independently represent a secondary or tertiary alkyl group having 3 to 6 carbon atoms and having a branched carbon atom which is bonded to a phenyl group. Furthermore, $Ar^{21}$ and $Ar^{22}$ each independently represent a substituted or unsubstituted aryl group having 6 to 25 carbon atoms.

Another embodiment of the present invention is a light-emitting device including any of the above-described organic compounds.

Another embodiment of the present invention is an electronic device including the above-described light-emitting device, a sensor, an operation button, a speaker, or a microphone.

Another embodiment of the present invention is a light-emitting apparatus including the above-described light-emitting device, a transistor, or a substrate.

Another embodiment of the present invention is a lighting device including the above-described light-emitting device and a housing.

Note that the light-emitting apparatus in this specification includes, in its category, an image display device that uses a light-emitting device. The light-emitting apparatus may include a module in which a light-emitting device is provided with a connector such as an anisotropic conductive film or a tape carrier package (TCP), a module in which a printed wiring board is provided at the end of a TCP, and a module in which an integrated circuit (IC) is directly mounted on a light-emitting device by a chip on glass (COG) method. Furthermore, a lighting apparatus or the like may include the light-emitting apparatus.

With one embodiment of the present invention, a novel organic compound can be provided. With another embodiment of the present invention, an organic compound with favorable thermophysical properties can be provided. With another embodiment of the present invention, an organic compound with favorable color purity and a low evaporation temperature can be provided.

With another embodiment of the present invention, a novel blue light-emitting material can be provided. With another embodiment of the present invention, a blue light-emitting material with favorable thermophysical properties can be provided. With another embodiment of the present invention, a blue light-emitting material with favorable color purity and a low evaporation temperature can be provided.

With another embodiment of the present invention, an organic compound that has a low evaporation temperature and enables a light-emitting device with favorable characteristics can be provided. With another embodiment of the present invention, an organic compound that has a low evaporation temperature and enables a long-life light-emitting device can be provided. With another embodiment of the present invention, an organic compound that has favorable initial characteristics, a long lifetime, and a low evaporation temperature can be provided.

With another embodiment of the present invention, a blue light-emitting material that has a low evaporation temperature and enables a light-emitting device with favorable characteristics can be provided. With another embodiment of the present invention, a blue light-emitting material that has a low evaporation temperature and enables a long-life light-emitting device can be provided. With another embodiment of the present invention, a blue light-emitting material that has favorable initial characteristics, a long lifetime, and a low evaporation temperature can be provided.

With another embodiment of the present invention, a light-emitting device, a light-emitting apparatus, an electronic device, and a display device, each of which has a long lifetime and can be fabricated easily, can be provided. With another embodiment of the present invention, a light-emitting device having a long driving lifetime at high temperature can be provided.

Note that the descriptions of these effects do not preclude the existence of other effects. One embodiment of the present invention does not necessarily have all these effects. Other effects will be apparent from and can be derived from the descriptions of the specification, the drawings, the claims, and the like.

BRIEF DESCRIPTION OF THE DRAWINGS

In the accompanying drawings:

FIG. 2A and FIG. 2B are conceptual views of an active matrix light-emitting apparatus;

FIG. 3A and FIG. 3B are conceptual views of active matrix light-emitting apparatuses;

FIG. 7A, FIG. 7B1, FIG. 7B2, and FIG. 7C illustrate electronic devices;

DETAILED DESCRIPTION OF THE INVENTION

Figure 1A:
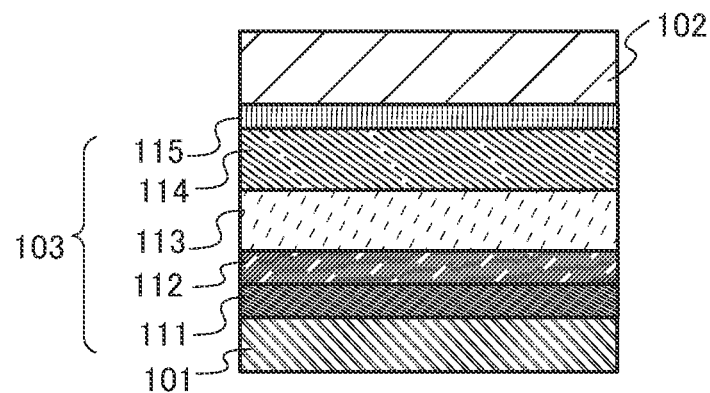
FIG. 1A, FIG. 1B, and FIG. 1C are schematic views of light-emitting devices.

Embodiments of the present invention will be described in detail below with reference to the drawings. Note that the present invention is not limited to the following description, and it will be readily appreciated by those skilled in the art that modes and details of the present invention can be modified in various ways without departing from the spirit and scope of the present invention. Therefore, the present invention should not be construed as being limited to the description in the following embodiments.

Embodiment 1

In this embodiment, an organic compound of one embodiment of the present invention will be described.

The organic compound of one embodiment of the present invention is represented by General Formula (G1) below.

[Chemical Formula 5]

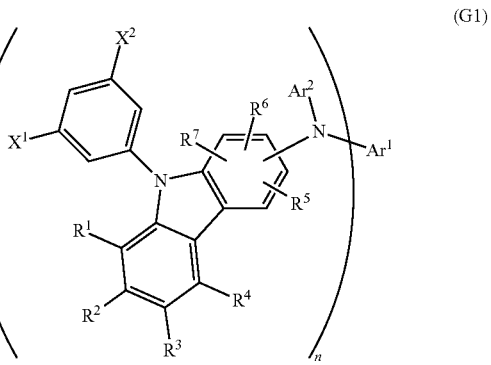

(G1)

The organic compound represented by General Formula (G1) above has $X^1$ and $X^2$, which are substituents at two meta-positions of a phenyl group bonded to the 9-position of a carbazolyl group and each independently represent an alkyl group having 3 to 6 carbon atoms; this substitution improves sublimability and solubility in a solvent. This facilitates film formation or purification and increases productivity and reliability. Furthermore, it is preferable that $X^1$ and $X^2$ be each independently an alkyl group having 3 or 4 carbon atoms in terms of low synthesis cost and high sublimability.

Bonding of the alkyl groups hardly influences the HOMO level and the LUMO level because the bonding positions of the alkyl groups are $X^1$ and $X^2$, which is a feature of the organic compound represented by General Formula (G1) above. By having the alkyl groups as $X^1$ and $X^2$, the organic compound of one embodiment of the present invention represented by General Formula (G1) above can have improved sublimability and solubility with little influence on the HOMO level, the LUMO level, the emission spectrum, and the bandgap.

Note that a secondary or tertiary alkyl group having a branched carbon atom which is bonded to a phenyl group at the 9-position of a carbazolyl group, that is, an alkyl group in which a carbon atom that is directly bonded to a phenyl group has a branch among alkyl groups bonded to phenyl groups, is preferable for improving the reliability of a light-emitting device using the organic compound.

For the above-described reasons, $X^1$ and $X^2$ of the organic compound represented by General Formula (G1) above are preferably secondary or tertiary alkyl groups having 3 to 6 carbon atoms and having a branched carbon atom which is bonded to the phenyl group in terms of low synthesis cost and high sublimability. In other words, branching of the carbon atom bonded to the phenyl group at the 9-position of the carbazolyl group can suppress intermolecular interaction. Furthermore, substitution of such alkyl groups at positions which do not easily cause molecular distortion (two meta-positons, i.e., $X^1$ and $X^2$) can suppress intermolecular interaction more than the case where substitution of such an alkyl group is conducted at only one of the two meta-positions. Furthermore, because conjugation does not easily spread from the carbazolyl group to the phenyl group at the 9-position of the carbazolyl group, the introduction of the alkyl groups to the phenyl group does not easily cause changes of the emission spectrum or the absorption spectrum. Moreover, the introduction of the alkyl groups to the phenyl group is preferable because it improves heat resistance of the organic compound.

Furthermore, $X^1$ and $X^2$ of the organic compound represented by General Formula (G1) above are further preferably secondary or tertiary alkyl groups having 3 or 4 carbon atoms and having a branched carbon atom which is bonded to the phenyl group.

As the secondary or tertiary alkyl groups having 3 to 6 carbon atoms and having a branched carbon atom which is bonded to the phenyl group, groups represented by Structural Formulae (X-1) to (X-9) below can be specifically used.

[Chemical Formula 6]

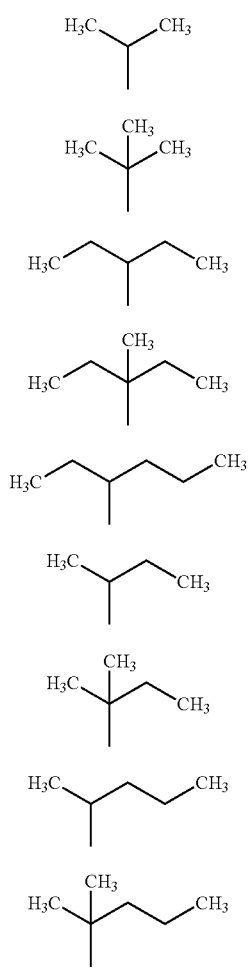

Furthermore, $R^1$ to $R^7$ each independently represent any of hydrogen, an alkyl group having 1 to 6 carbon atoms, a cycloalkyl group having 3 to 12 carbon atoms, and an aryl group having 6 to 13 carbon atoms which is unsubstituted or to which an alkyl group is bonded as a substituent.

Specific examples of the alkyl group having 1 to 6 carbon atoms include a methyl group, an ethyl group, a propyl group, an isopropyl group, a butyl group, a tert-butyl group, a pentyl group, and a hexyl group. Specific examples of the cycloalkyl group having 3 to 12 carbon atoms include a cyclopropyl group, a cyclohexyl group, a norbornyl group, and an adamantyl group, and specific examples of the aryl group having 6 to 13 carbon atoms which is unsubstituted or to which an alkyl group is bonded as a substituent include a phenyl group, a biphenyl group, a naphthyl group, and a dimethylfluorenyl group.

Furthermore, n represents any of 1 to 3. In the case where n is 2 or more, two or more groups bonded to $Ar^1$ may be identical or different. In other words, in the case where n is 2 or 3, the same substituents may be bonded to $Ar^1$; alternatively, substituents having different structures may be bonded to $Ar^1$.

Moreover, $Ar^1$ represents a substituted or unsubstituted condensed aromatic ring skeleton having 10 to 60 carbon atoms and composed of two or more rings or a substituted or unsubstituted condensed heteroaromatic ring skeleton having 8 to 60 carbon atoms and composed of two or more rings.

Specific examples of the substituted or unsubstituted condensed aromatic ring skeleton having 10 to 60 carbon atoms and composed of two or more rings or the substituted or unsubstituted condensed heteroaromatic ring skeleton having 8 to 60 carbon atoms and composed of two or more rings, which are mentioned as examples of the group represented by $Ar^1$, can be represented by Structural Formulae ($Ar^1$-1) to ($Ar^1$-56) below.

[Chemical Formula 7]

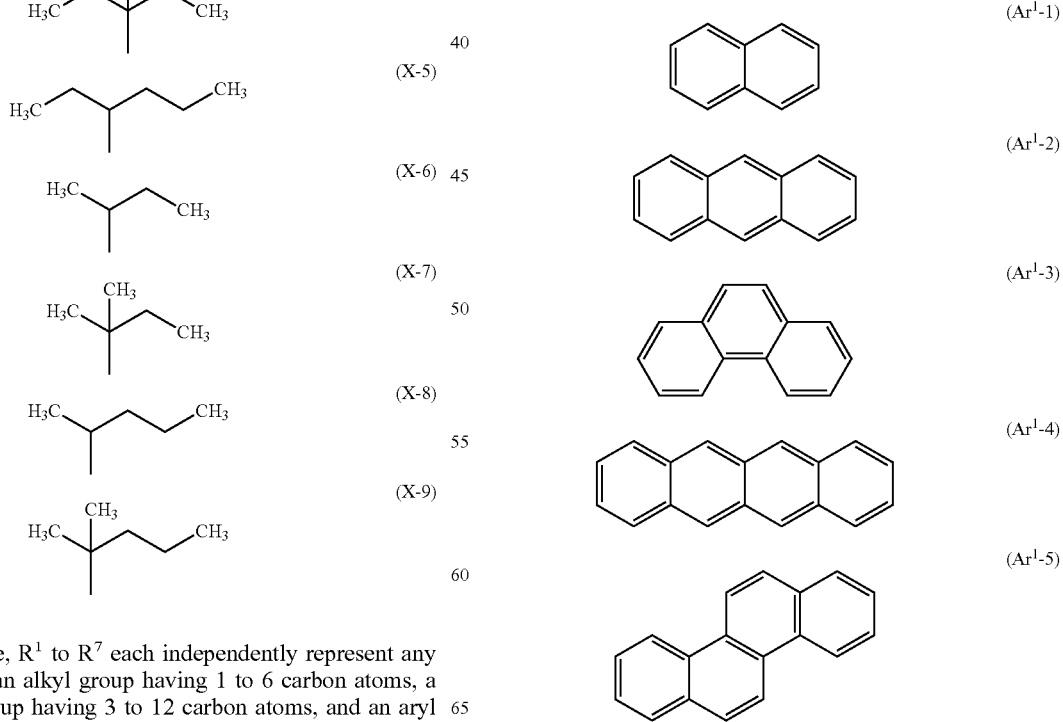

-continued
(Ar¹-6)
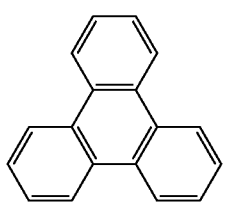
(Ar¹-7)
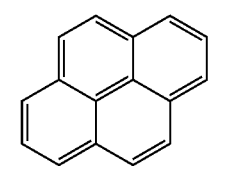
(Ar¹-8)
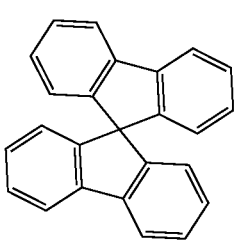
(Ar¹-9)
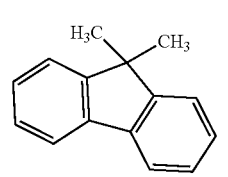
(Ar¹-10)
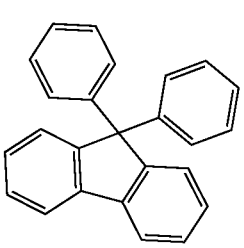
(Ar¹-11)
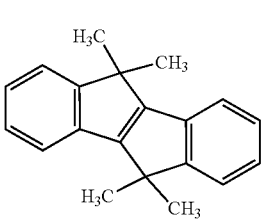
(Ar¹-12)
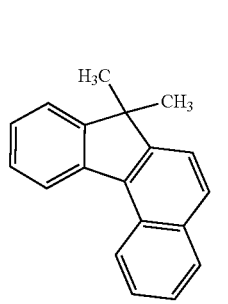
-continued
(Ar¹-13)
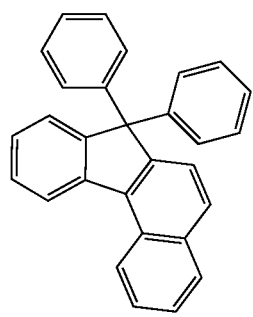
(Ar¹-14)
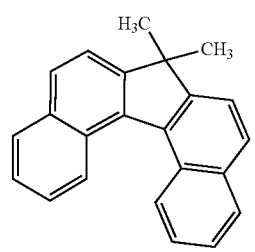
(Ar¹-15)
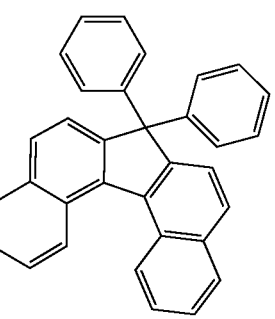
(Ar¹-16)
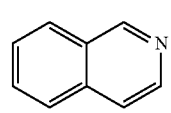
(Ar¹-17)
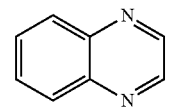
(Ar¹-18)
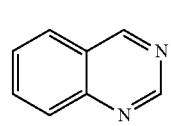
(Ar¹-19)
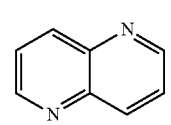
(Ar¹-20)
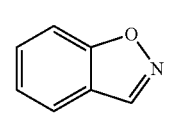
(Ar¹-21)
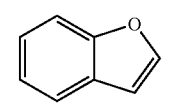

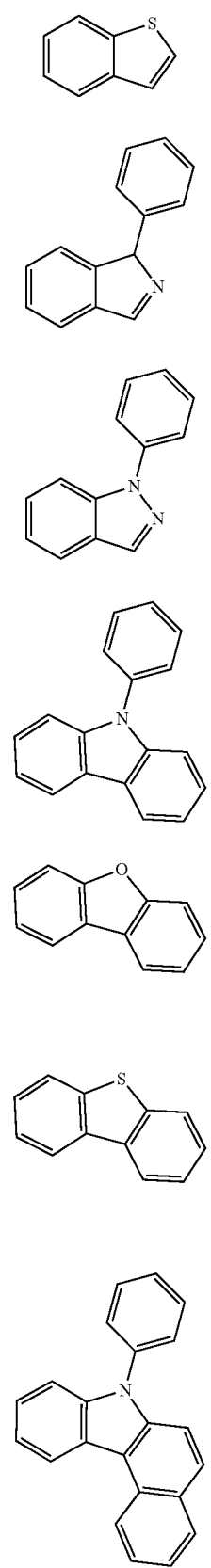
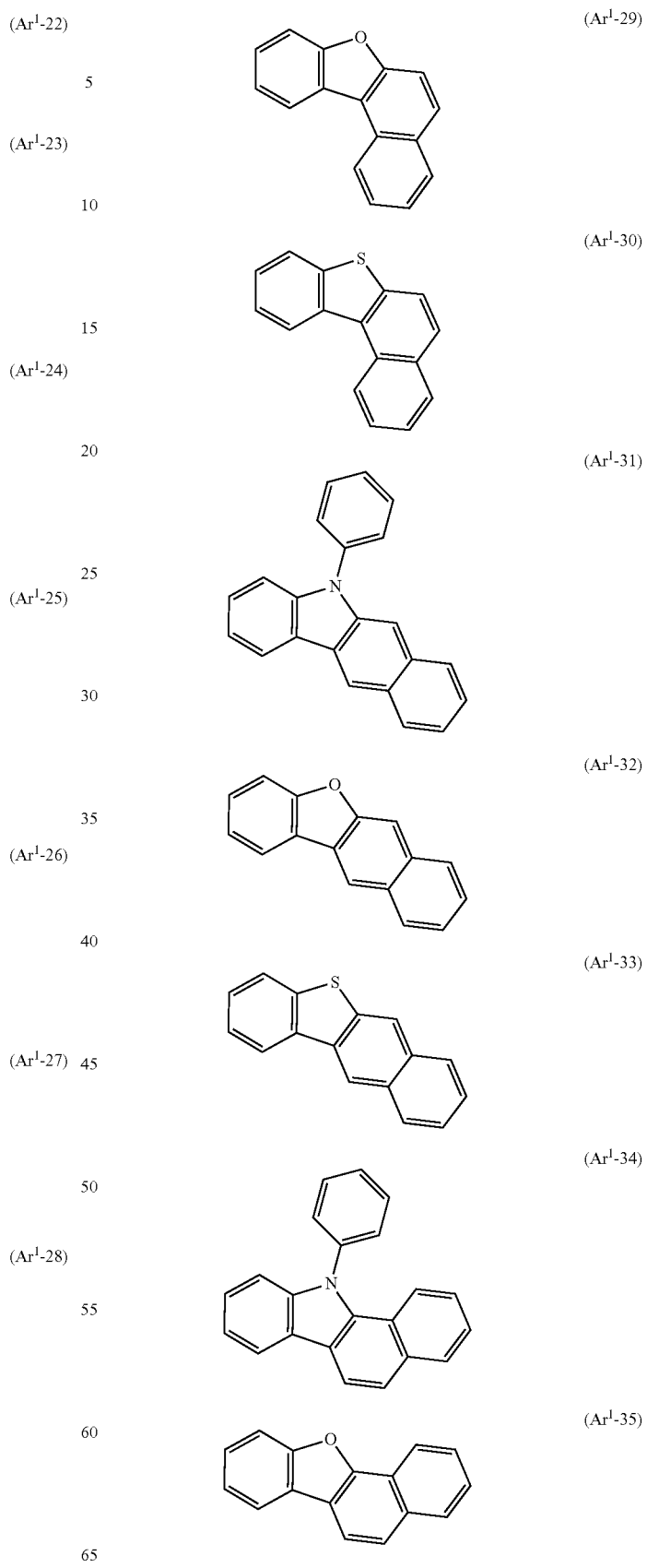

[Chemical Formula 8]
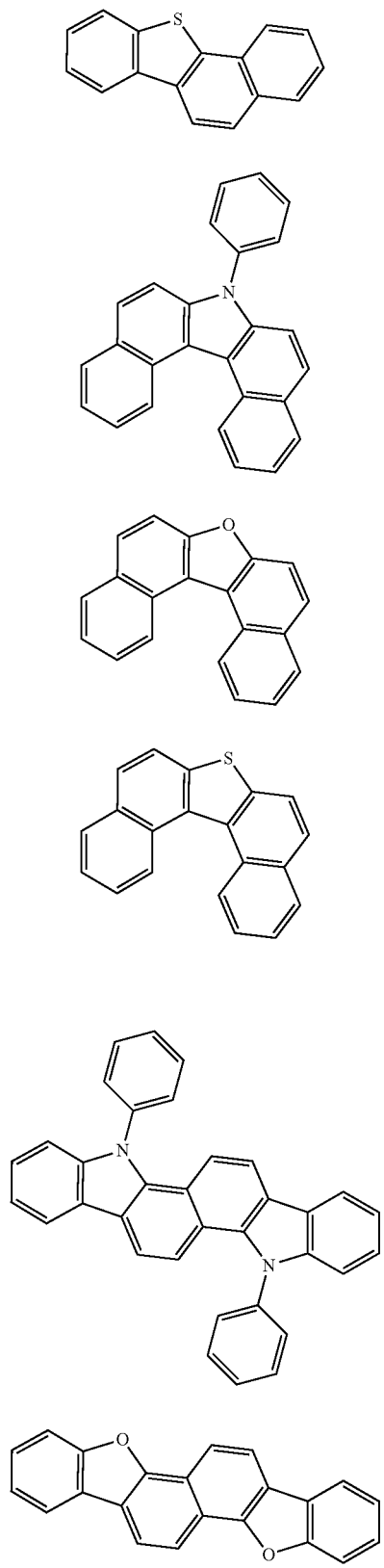
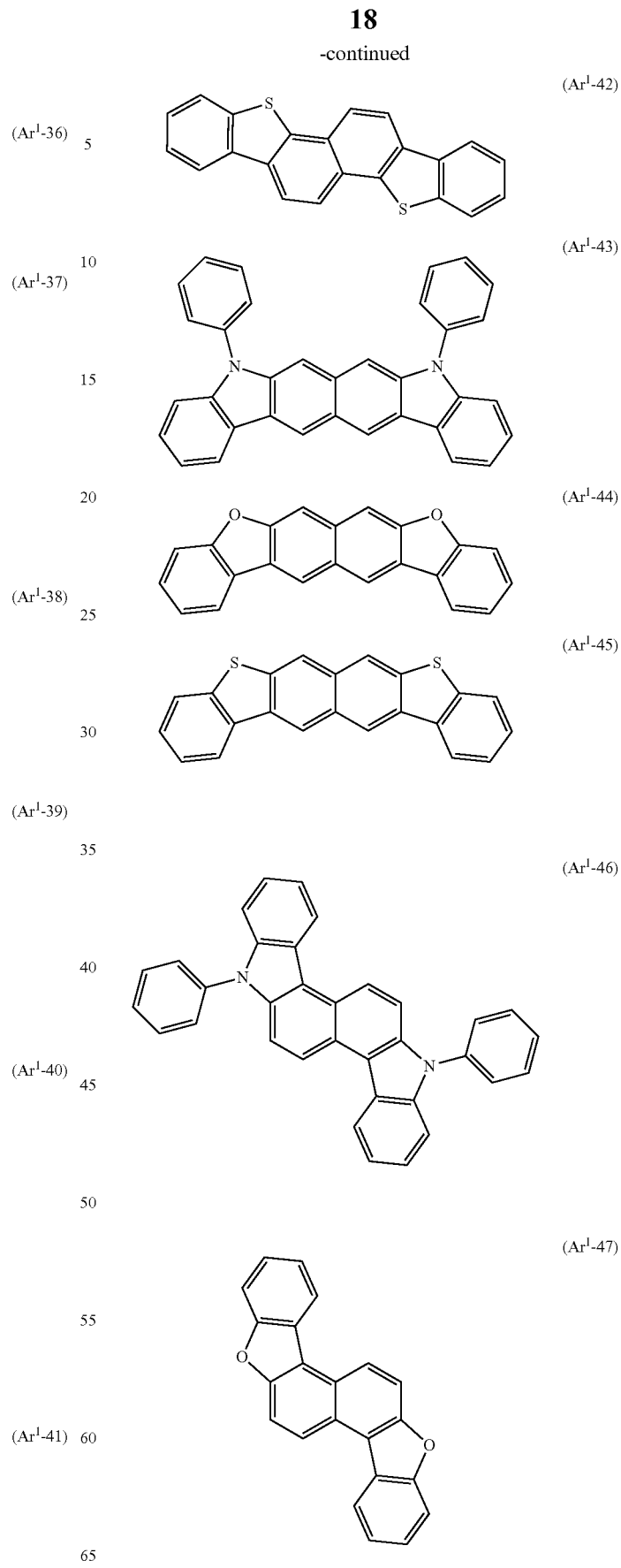

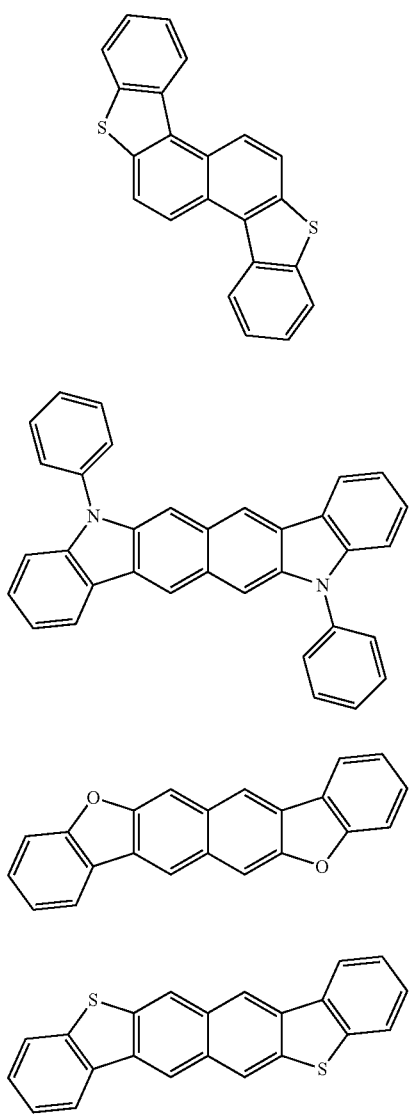
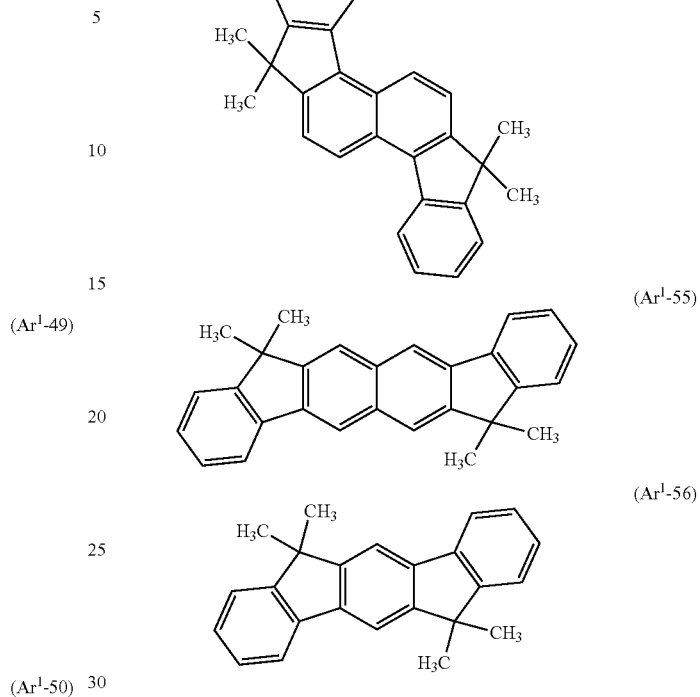

In terms of high sublimability, $Ar^1$ is preferably a substituted or unsubstituted condensed aromatic ring skeleton having 10 to 60 carbon atoms and composed of three to nine rings or a substituted or unsubstituted condensed heteroaromatic ring skeleton having 8 to 60 carbon atoms and composed of three to nine rings. In terms of high heat resistance, $Ar^1$ is preferably a substituted or unsubstituted condensed heteroaromatic ring skeleton having 8 to 60 carbon atoms and composed of three to seven rings.

Among those described above, the organic compound where $Ar^1$ is any of heteroaromatic ring skeletons represented by General Formulae (B1) to (B4) below is further preferable because it exhibits favorable blue light emission.

[Chemical Formula 9]

(B3)

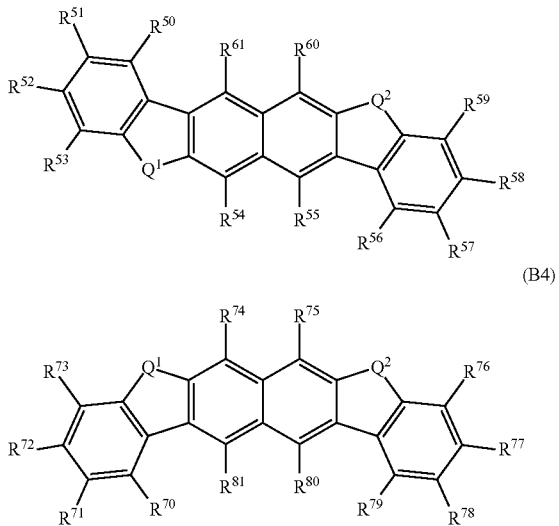

(B4)

In General Formulae (B1) to (B4) above, $Q^1$ and $Q^2$ each independently represent an oxygen atom or a sulfur atom. In General Formula (B1) above, any one or two of $R^{10}$ to $R^{21}$ represents a single bond, and the others each independently represent any of hydrogen, an alkyl group having 1 to 6 carbon atoms, a cycloalkyl group having 3 to 12 carbon atoms, and an aryl group having 6 to 13 carbon atoms which is unsubstituted or to which an alkyl group is bonded as a substituent. In General Formula (B2) above, any one or two of $R^{30}$ to $R^{41}$ represents a single bond, and the others each independently represent any of hydrogen, an alkyl group having 1 to 6 carbon atoms, a cycloalkyl group having 3 to 12 carbon atoms, and an aryl group having 6 to 13 carbon atoms which is unsubstituted or to which an alkyl group is bonded as a substituent. In General Formula (B3) above, any one or two of $R^{50}$ to $R^{61}$ represents a single bond, and the others each independently represent any of hydrogen, an alkyl group having 1 to 6 carbon atoms, a cycloalkyl group having 3 to 12 carbon atoms, and an aryl group having 6 to 13 carbon atoms which is unsubstituted or to which an alkyl group is bonded as a substituent. In General Formula (B4) above, any one or two of $R^{70}$ to $R^{81}$ represents a single bond, and the others each independently represent any of hydrogen, an alkyl group having 1 to 6 carbon atoms, a cycloalkyl group having 3 to 12 carbon atoms, and an aryl group having 6 to 13 carbon atoms which is unsubstituted or to which an alkyl group is bonded as a substituent.

Specific examples of the alkyl group having 1 to 6 carbon atoms include a methyl group, an ethyl group, a propyl group, an isopropyl group, a butyl group, a tert-butyl group, a pentyl group, and a hexyl group. Examples of the cycloalkyl group having 3 to 10 carbon atoms include a cyclopropyl group, a cyclohexyl group, anorbornyl group, a decahydronaphthyl group, and an adamantyl group. Examples of the aryl group having 6 to 13 carbon atoms include a phenyl group, a biphenyl group, a naphthyl group, and a fluorenyl group.

Among those represented by General Formulae (B1) to (B4) above, the heteroaromatic ring skeleton represented by General Formula (B1) or (B3) is further preferable for blue light emission, and the heteroaromatic ring skeleton represented by General Formula (B1-1) or (B3-1) below is still further preferable in terms of high luminescence quantum yield. In the formulae, $Q^1$ and $Q^2$ each independently represent an oxygen atom or a sulfur atom. Furthermore, $R^{12}$, $R^{18}$, $R^{52}$, and $R^{58}$ represent a single bond.

[Chemical Formula 10]

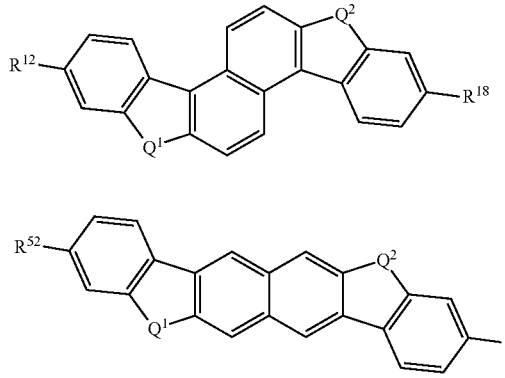

Furthermore, $Ar^2$ represents a substituted or unsubstituted aryl group having 6 to 25 carbon atoms. Examples of the substituted or unsubstituted aryl group having 6 to 25 carbon atoms include a phenyl group, a tolyl group, a dimethylphenyl group, a trimethylphenyl group, a propylphenyl group, a dipropylphenyl group, a butylphenyl group, a dibutylphenyl group, a cyclohexylphenyl group, a naphthyl group, a naphthylphenyl group, a phenylnaphthyl group, a biphenyl group, a terphenyl group, a fluorenyl group, a 9,9-dimethylfluorenyl group, a phenanthryl group, a 9,9-diphenylfluorenyl group, a spirofluorenyl group, a triphenylenyl group, a pyrenyl group, an anthryl group, and a 9-phenylanthryl group. Specifically, groups represented by Structural Formulae ($Ar^2$-1) to ($Ar^2$-49) below can be given, for example.

[Chemical Formula 11]

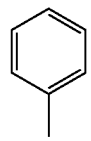

($Ar^2$-1)

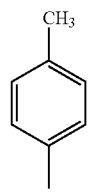

($Ar^2$-2)

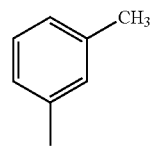

($Ar^2$-3)

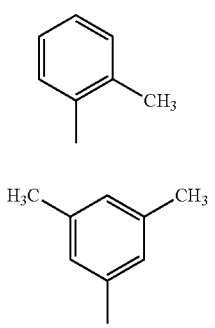
(Ar²-4)
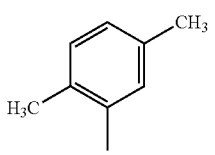
(Ar²-5)
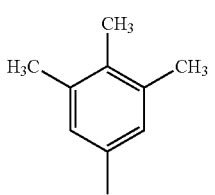
(Ar²-6)
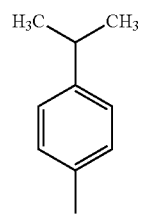
(Ar²-7)
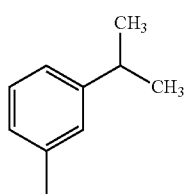
(Ar²-8)
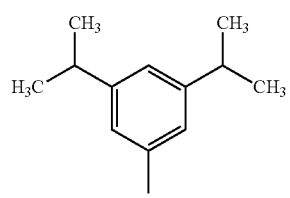
(Ar²-9)
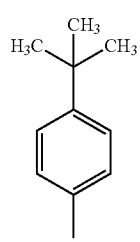
(Ar²-10)
(Ar²-11)
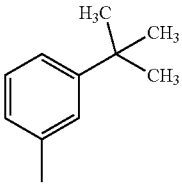
(Ar²-12)
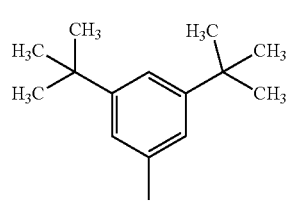
(Ar²-13)
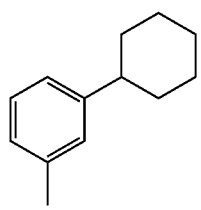
(Ar²-14)
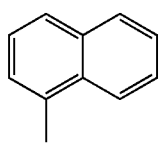
(Ar²-15)
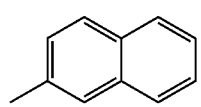
(Ar²-16)
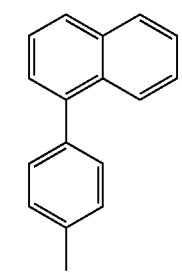
(Ar²-17)
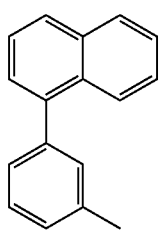
(Ar²-18)

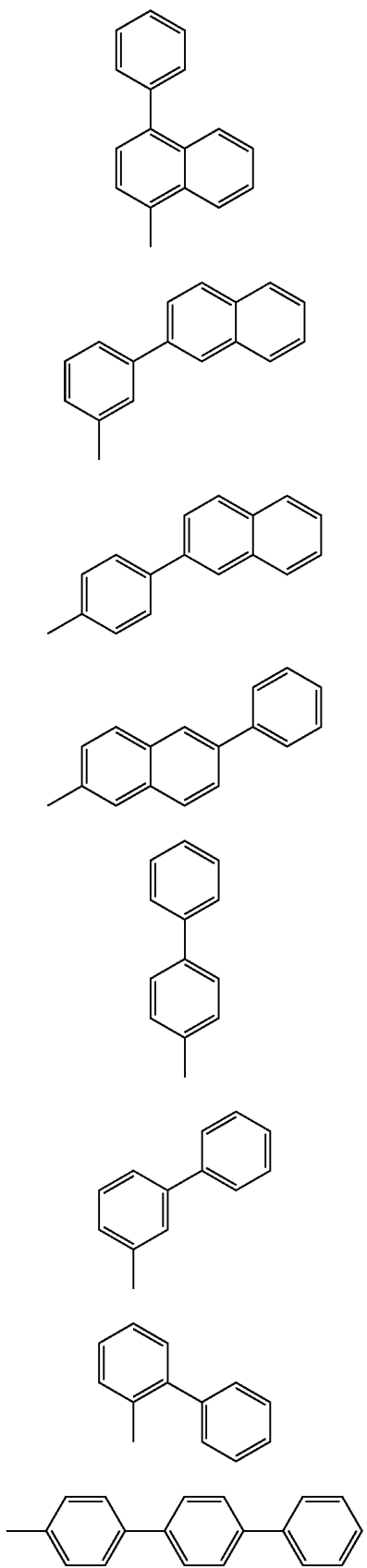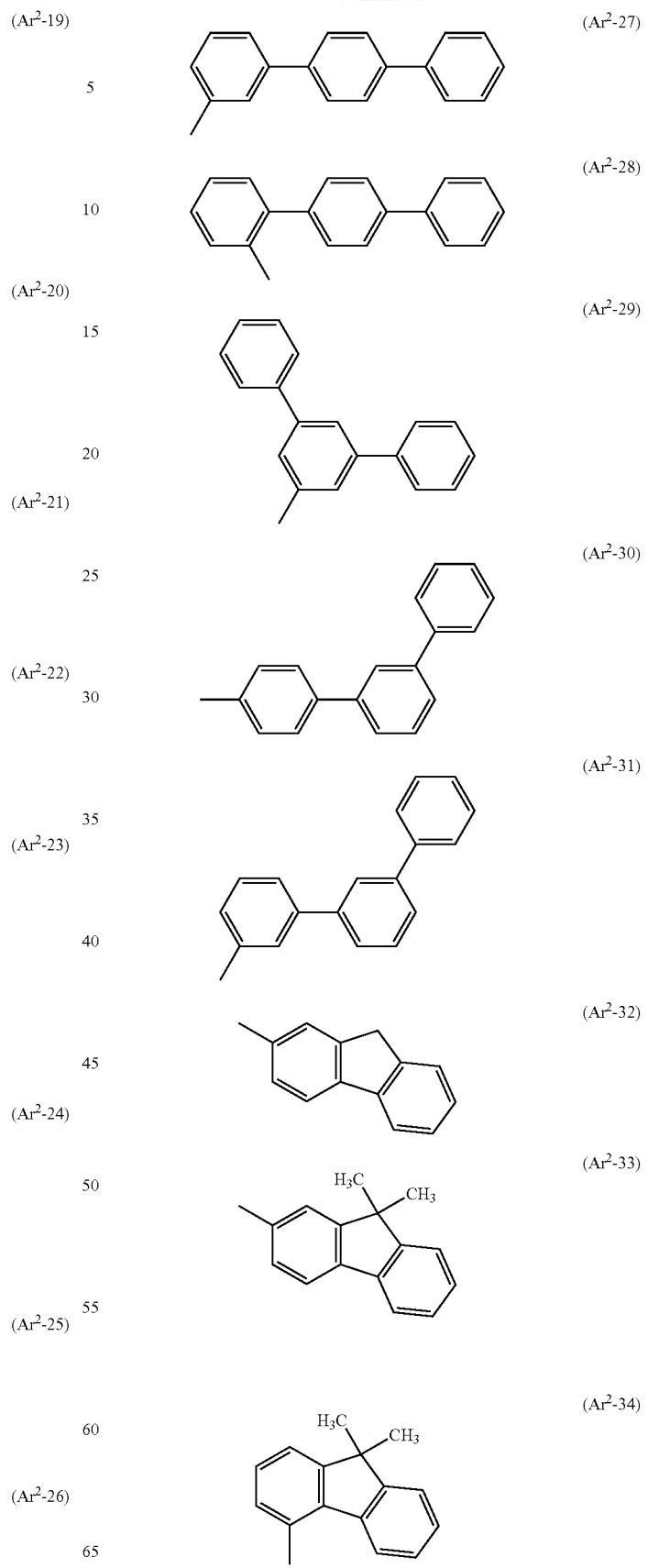

(Ar²-35)
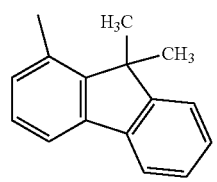
(Ar²-36)
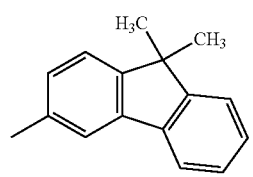
[Chemical Formula 12]
(Ar²-37)
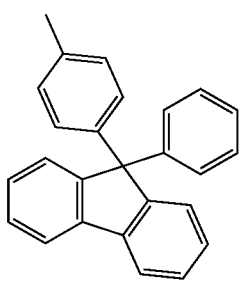
(Ar²-38)
(Ar²-39)
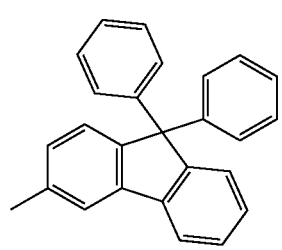
(Ar²-40)
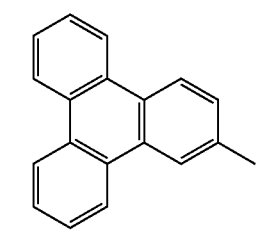
(Ar²-41)
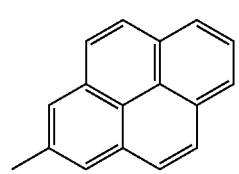
(Ar²-42)
(Ar²-43)
(Ar²-44)
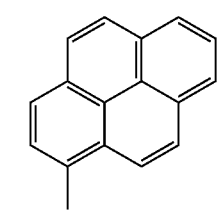
(Ar²-45)
(Ar²-46)
(Ar²-47)
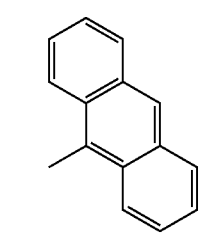

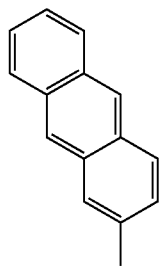
(Ar²-48)

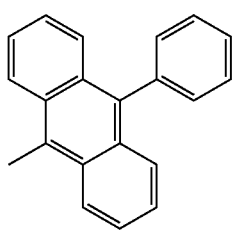
(Ar²-49)

In the organic compound represented by General Formula (G1) above, $Ar^1$ is preferably the heteroaromatic ring skeleton represented by General Formula (B3-1) above in order that the organic compound can exhibit favorable blue light emission with high color purity. Moreover, $R^1$ to $R^7$ are preferably hydrogen for easy synthesis. That is, the organic compound of one embodiment of the present invention is preferably an organic compound represented by General Formula (G1-1) below.

[Chemical Formula 13]

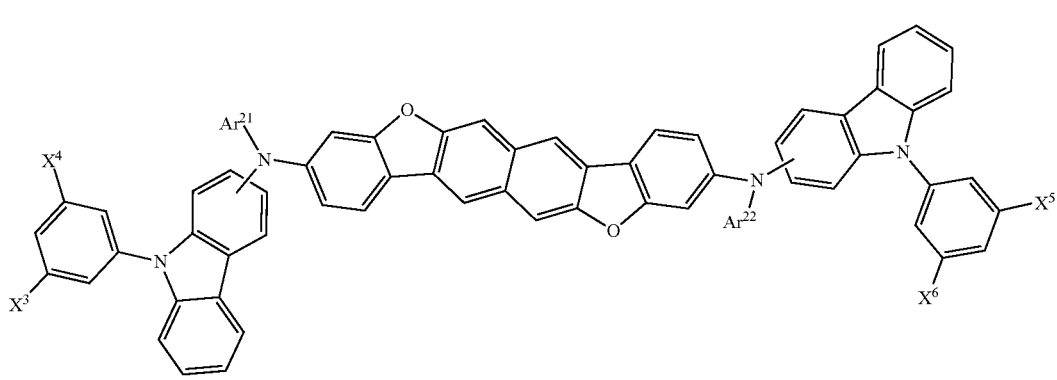
(G1-1)

In General Formula (G1-1) above, $X^3$ to $X^6$ each independently represent a secondary or tertiary alkyl group having 3 to 6 carbon atoms and having a branched carbon atom which is bonded to the phenyl group, that is, groups that can be used as $X^1$ and $X^2$ in General Formula (G1) above can be similarly selected. Furthermore, $Ar^{21}$ and $Ar^{22}$ each independently represent a substituted or unsubstituted aryl group having 6 to 25 carbon atoms, that is, groups that can be used as $Ar^2$ in General Formula (G1) above can be similarly selected.

The organic compound represented by General Formula (G1-1) above is an organic compound which exhibits favorable blue light emission. By having $X^3$ to $X^6$, the organic compound can have higher sublimability.

The organic compound represented by General Formula (G1-1) above from which $X^3$ to $X^6$ are excluded has a large molecular weight and includes a plurality of amine skeletons or furan rings in the molecule, which makes the temperature of the sublimation purification close to 400° C. At a heating temperature of approximately 400° C., the organic compound might be burnt before being sublimated, in some cases. When the organic compound of one embodiment of the present invention includes $X^3$ to $X^6$, the intermolecular interaction can be reduced, lowering the sublimation temperature. This can suppress generation of burning at the time of sublimation purification. Furthermore, the evaporation temperature is also reduced, which improves productivity.

The organic compound represented by General Formula (G1-1) above from which $X^3$ to $X^6$ are excluded is difficult to produce because of its poor solubility in a solvent. In contrast, the organic compound of one embodiment of the present invention including $X^3$ to $X^6$ has higher solubility in a solvent and can be easily purified with a solvent.

In the above description, in the case where the groups or rings described as being "substituted or unsubstituted" have a substituent, the substituent can be selected from an alkyl group having 1 to 6 carbon atoms, a cycloalkyl group having 3 to 12 carbon atoms, and an aryl group having 6 to 13 carbon atoms which is unsubstituted or to which an alkyl group is bonded as a substituent. The substituent is preferably an alkyl group having 1 to 6 carbon atoms or a cycloalkyl group having 3 to 12 carbon atoms, and further preferably an alkyl group having 1 to 6 carbon atoms. In terms of synthesis easiness or availability of materials, it is preferable that the groups or rings described as being "substituted or unsubstituted" be unsubstituted.

Preferable examples of the alkyl group having 1 to 6 carbon atoms described above include a methyl group, an ethyl group, a propyl group, an isopropyl group, a butyl group, a tert-butyl group, a pentyl group, and a hexyl group. Preferable examples of the cycloalkyl group having 3 to 12 carbon atoms include a cyclopropyl group, a cyclohexyl group, a norbornyl group, a decahydronaphthyl group, and an adamantyl group. Preferable examples of the aryl group having 6 to 13 carbon atoms include a phenyl group, a biphenyl group, a naphthyl group, and a fluorenyl group.

Specific examples of the organic compound having the above-described structures are shown below.

[Chemical Formula 14]
(100)
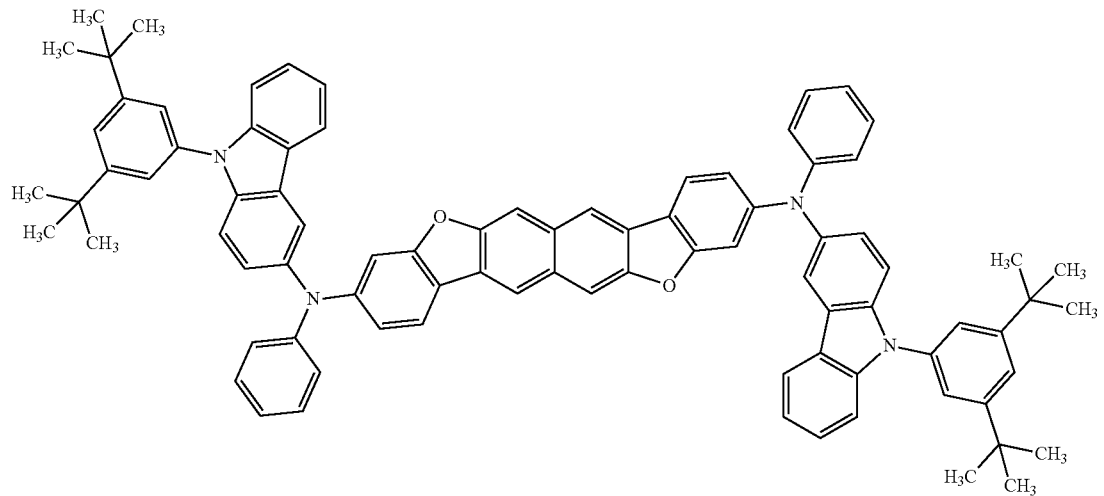
(101)
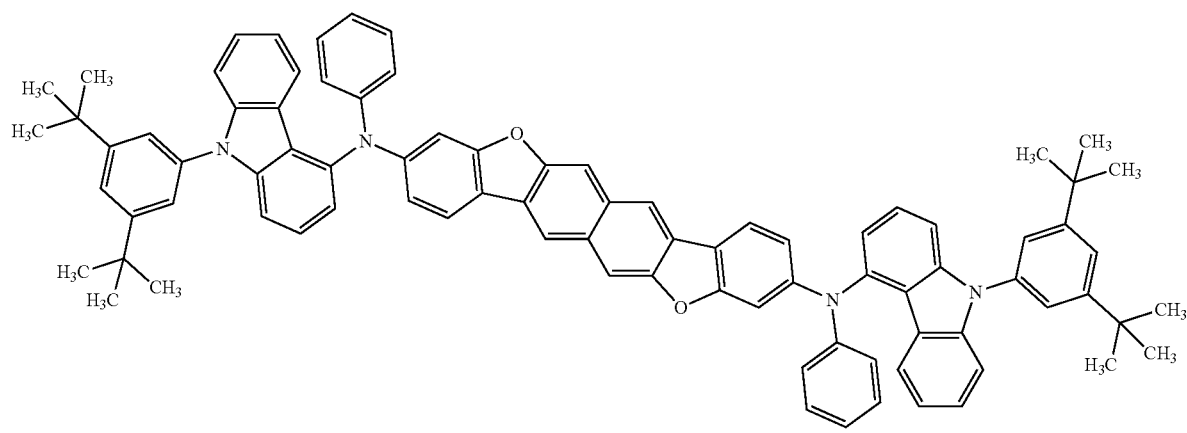
(102)
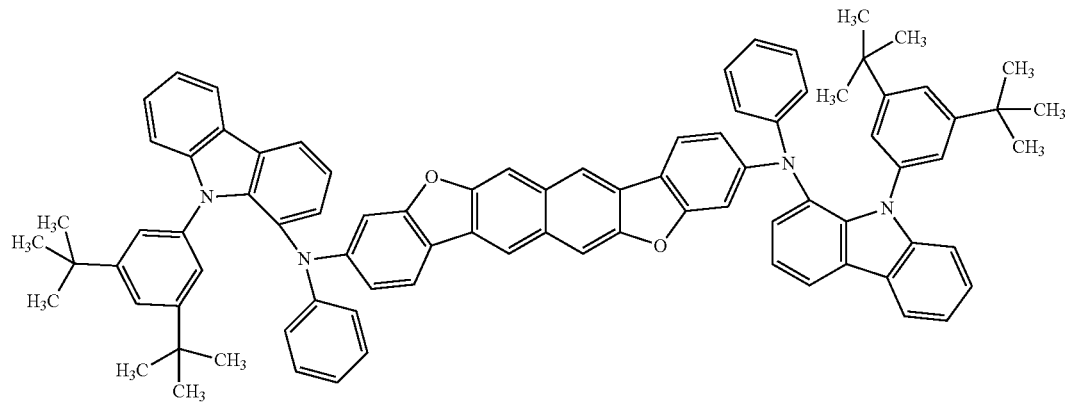

(103)
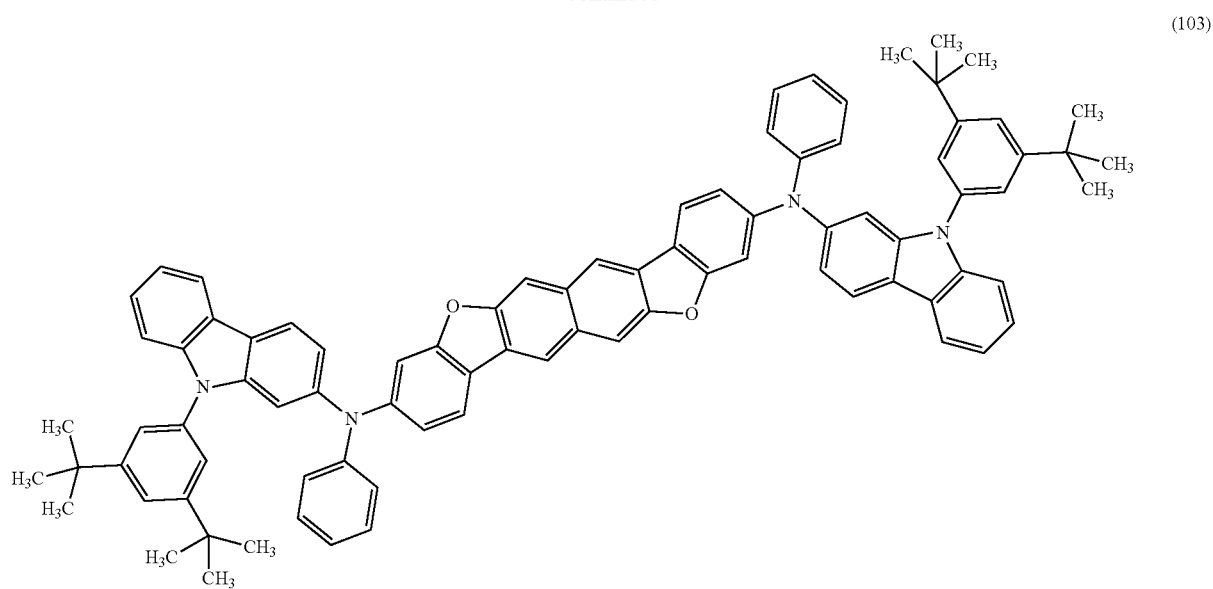
(104)
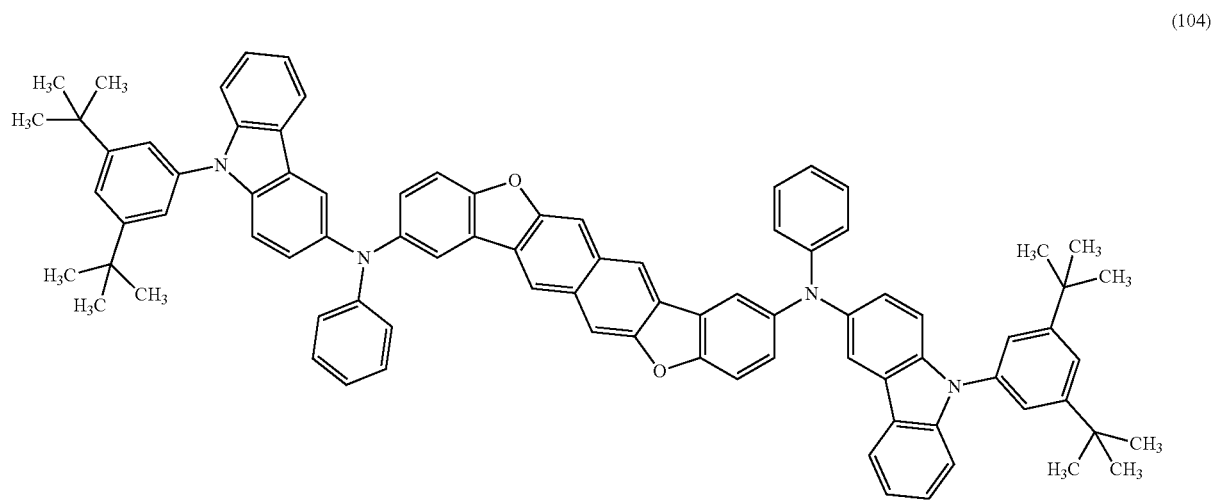
[Chemical Formula 15]
(105)
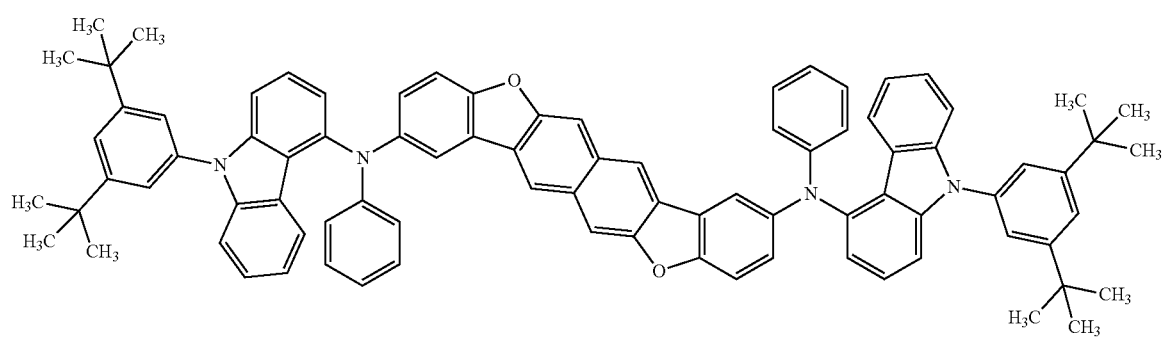

(106)
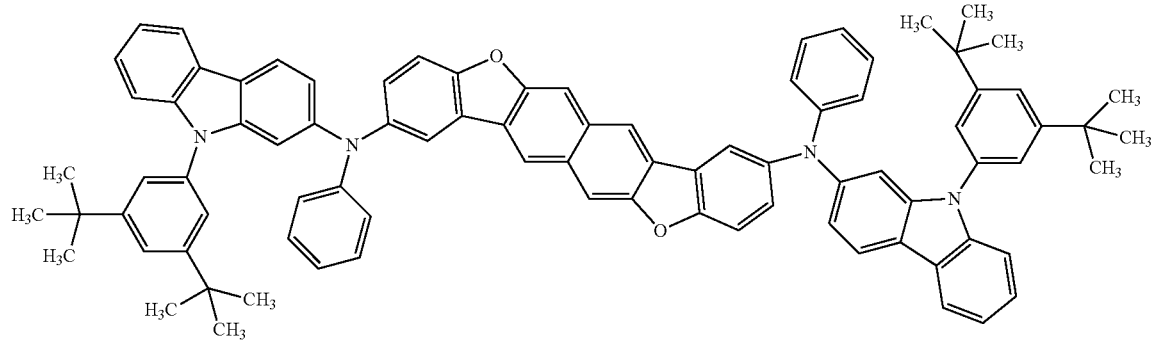
(107)
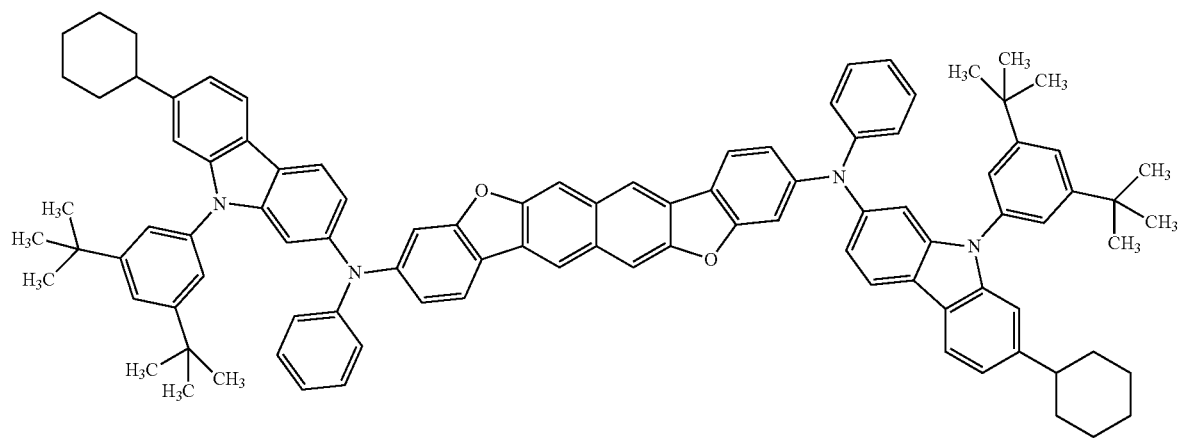
(108)
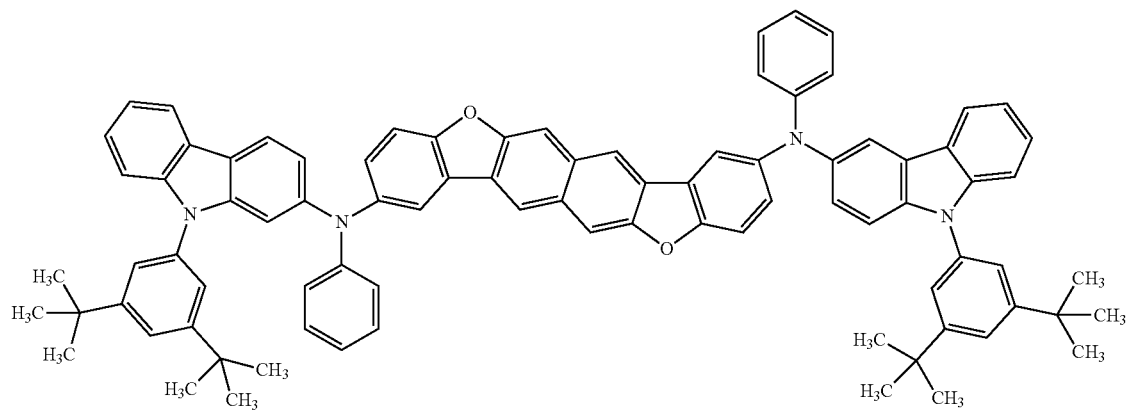

(109)
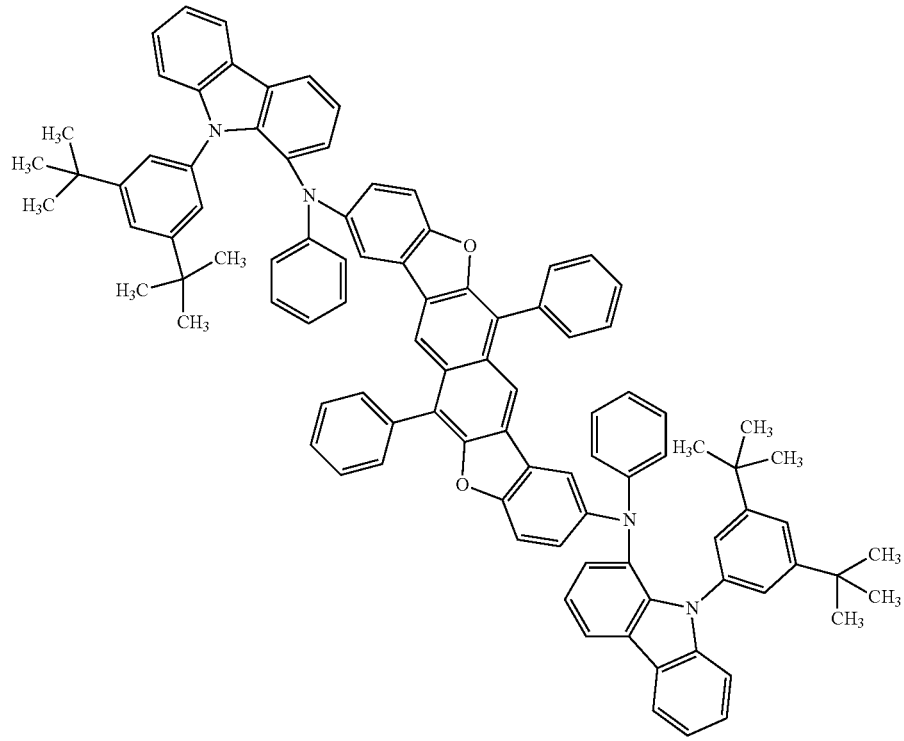
[Chemical Formula 16]
(110)
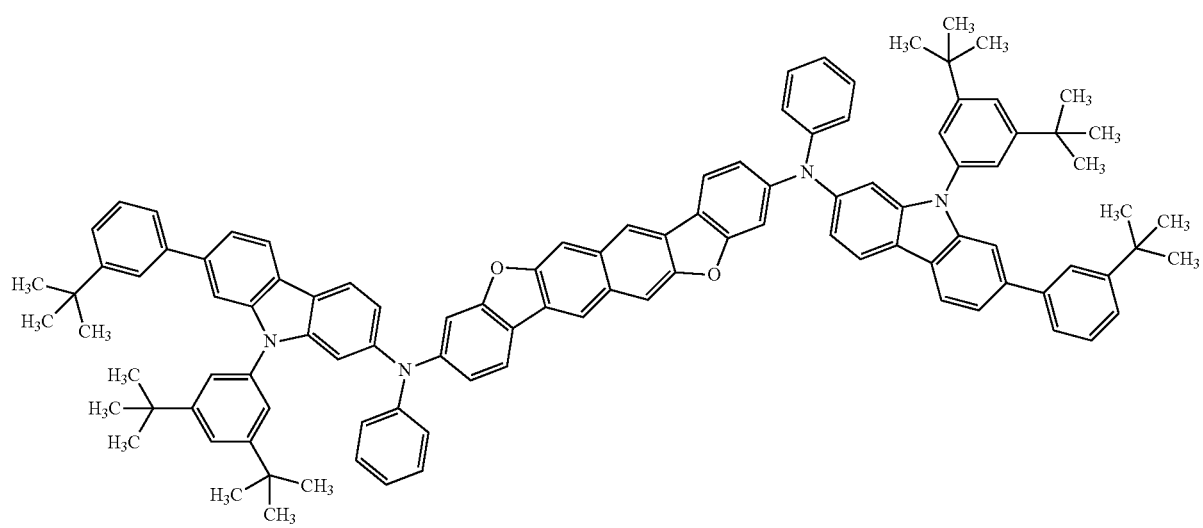

-continued
(111)
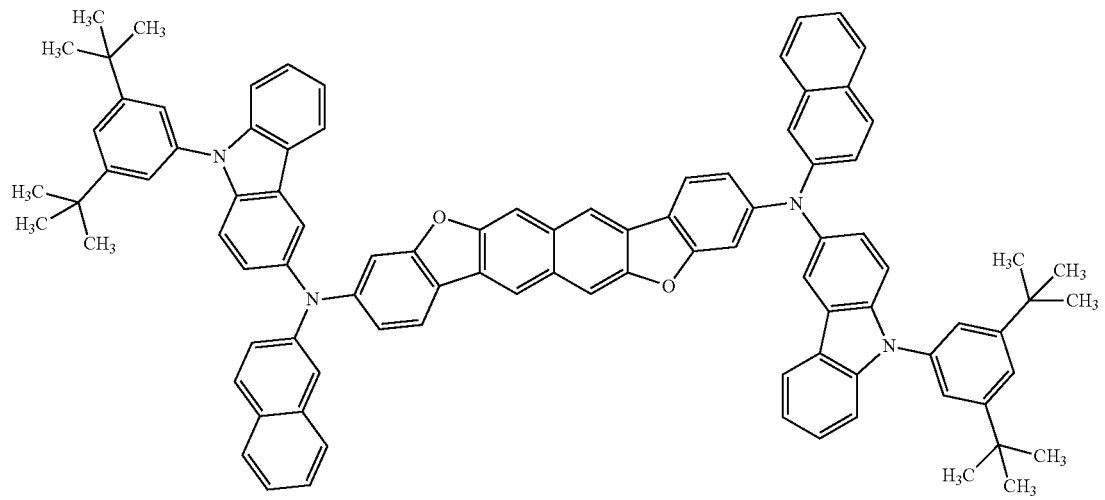
(112)
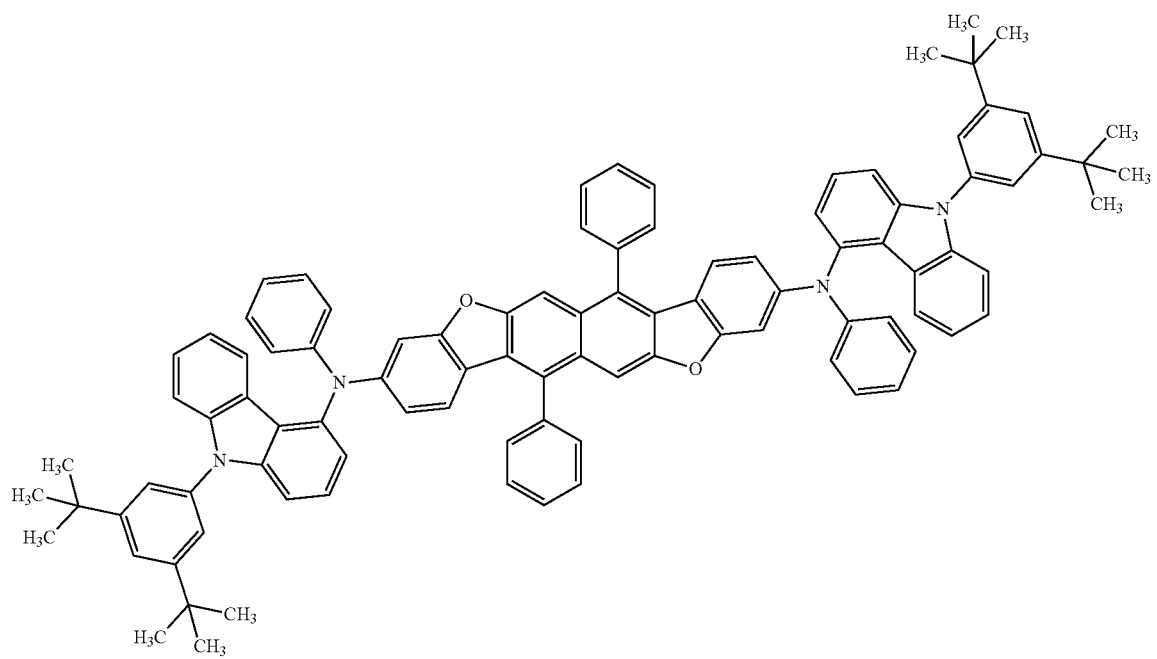

(113)
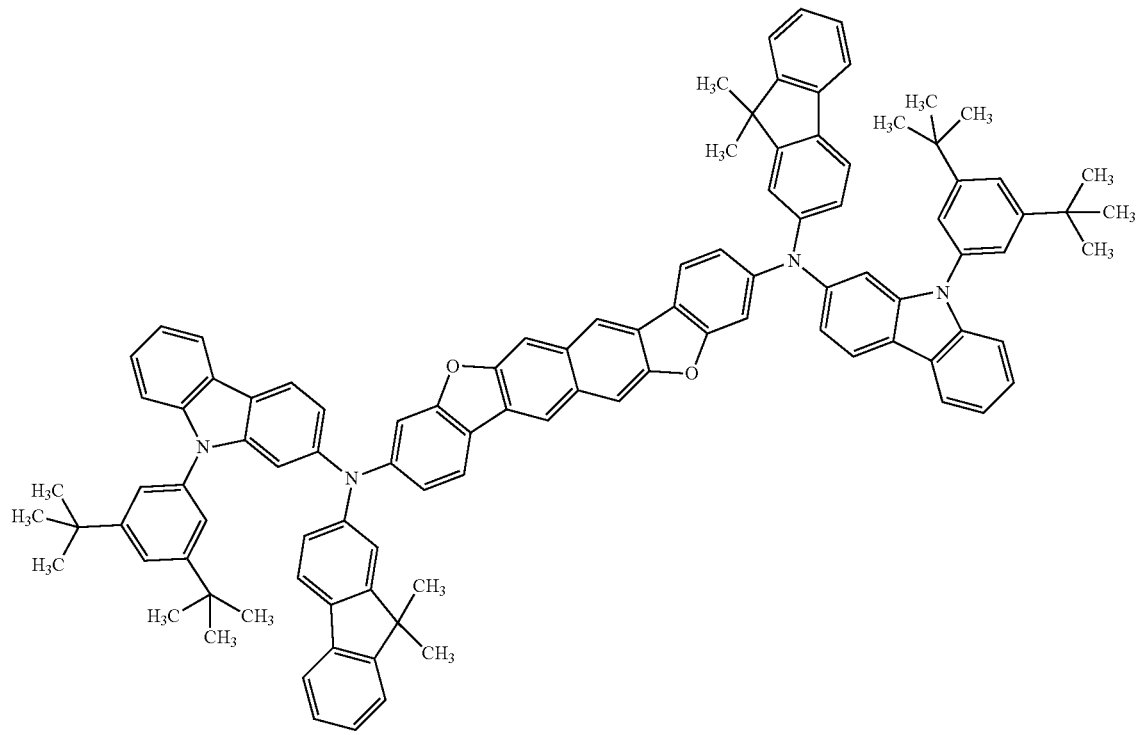
[Chemical Formula 17]
(114)
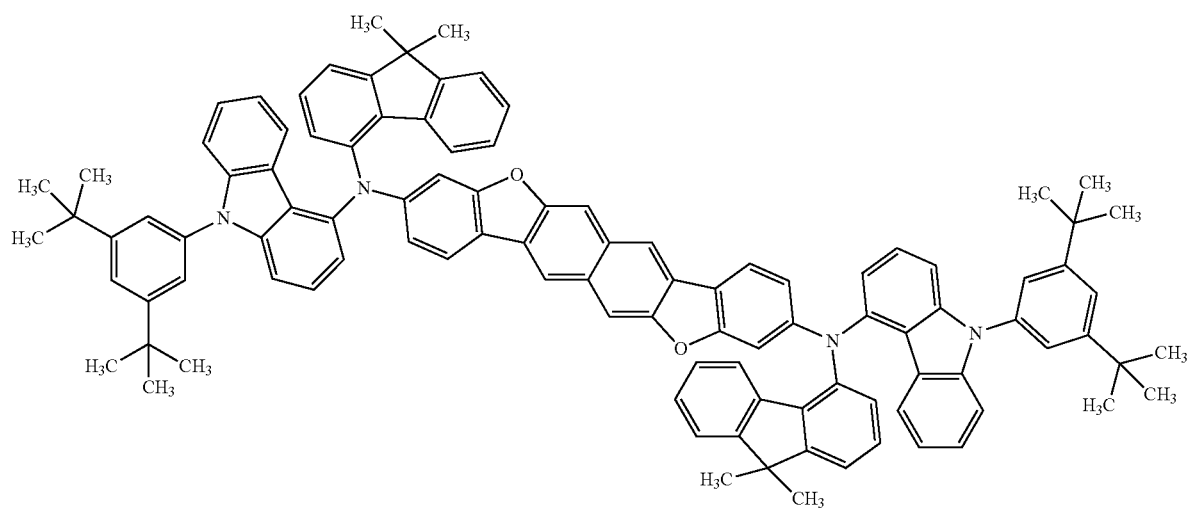

(115)
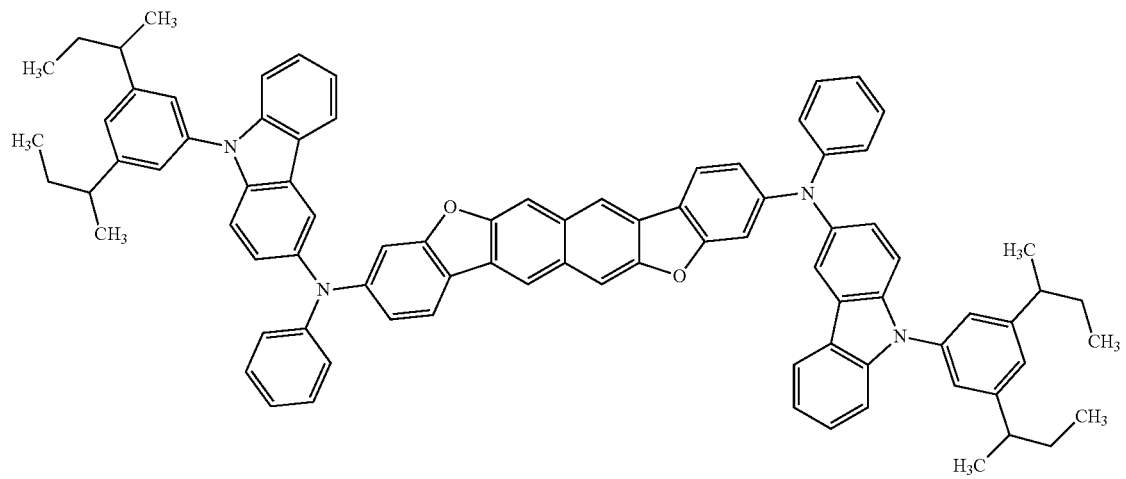
(116)
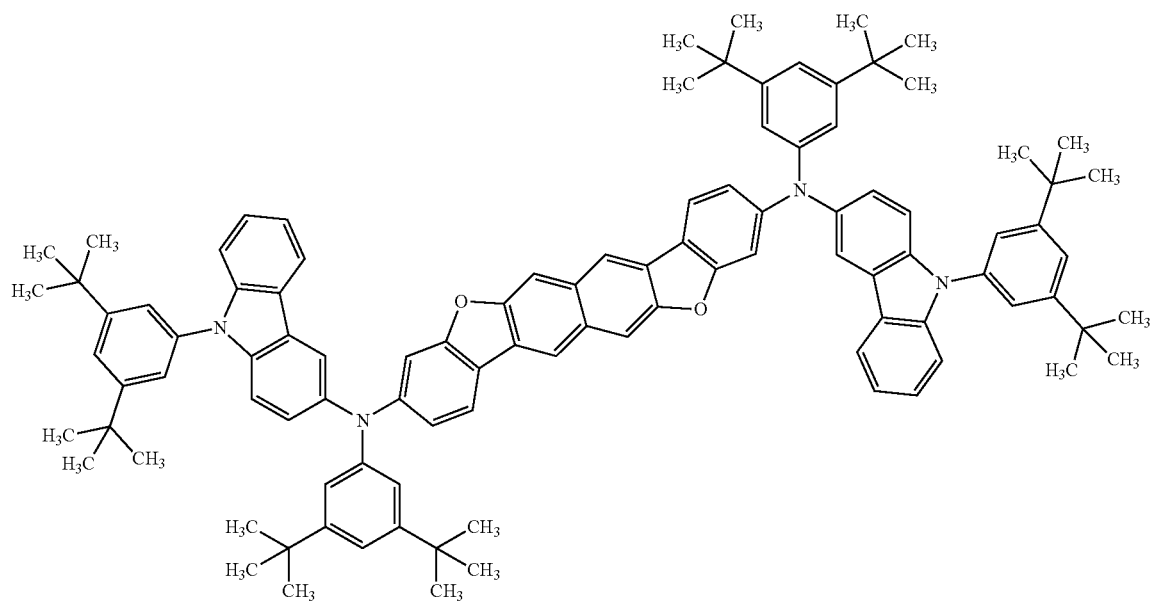
(117)
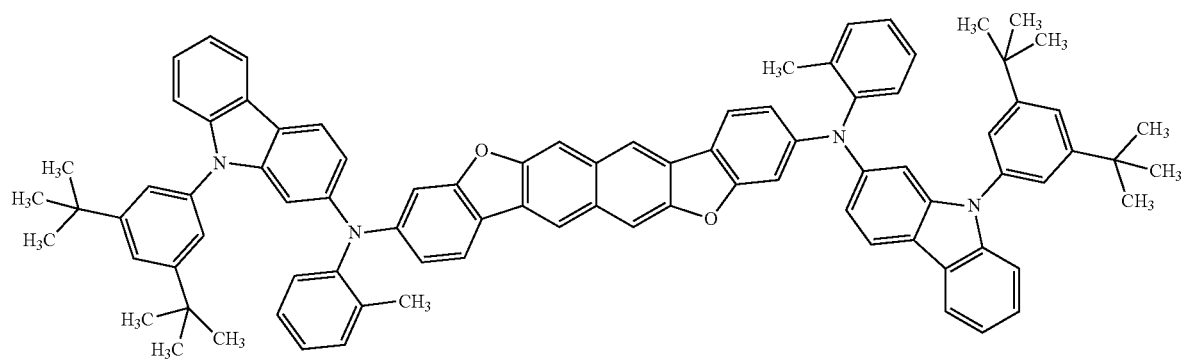

[Chemical Formula 18]
(118)
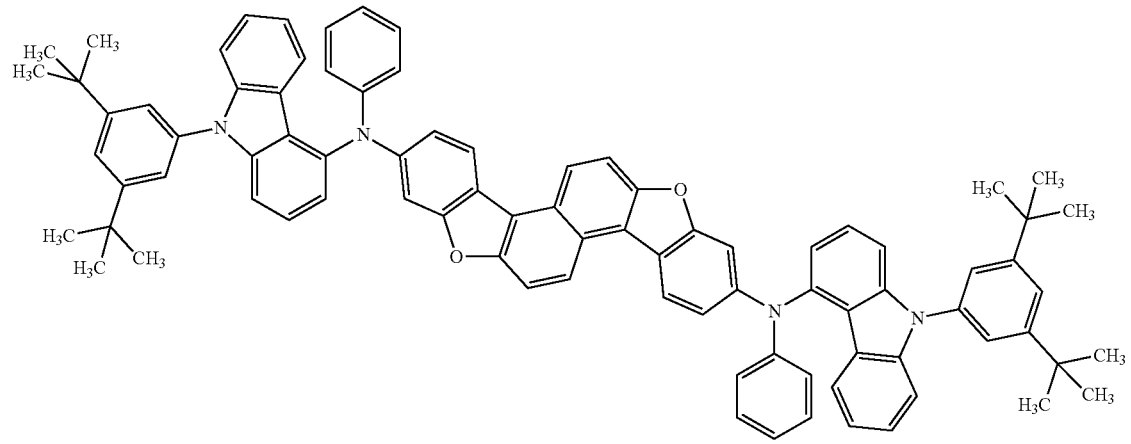
(119)
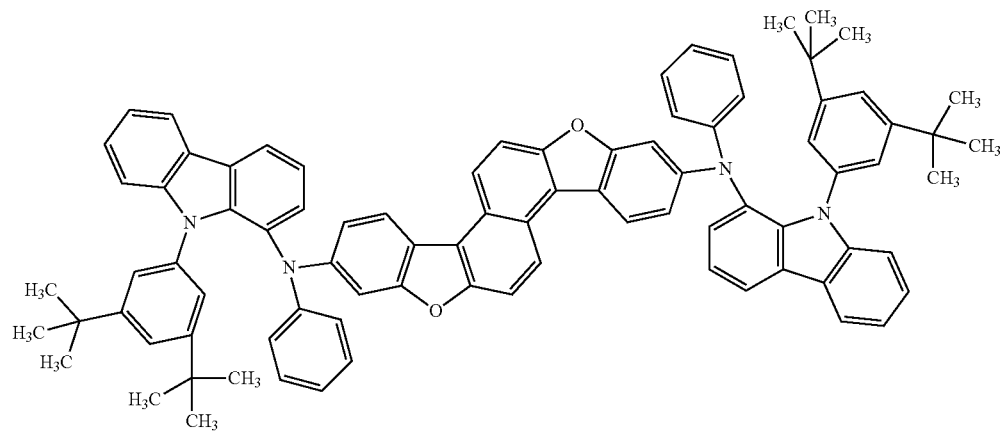
(120)
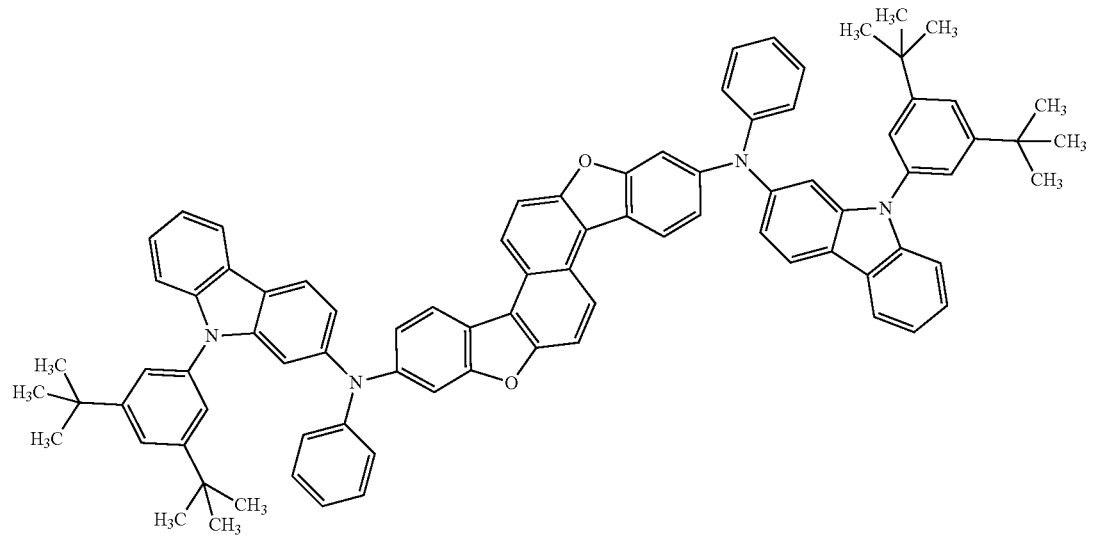

-continued
(121)
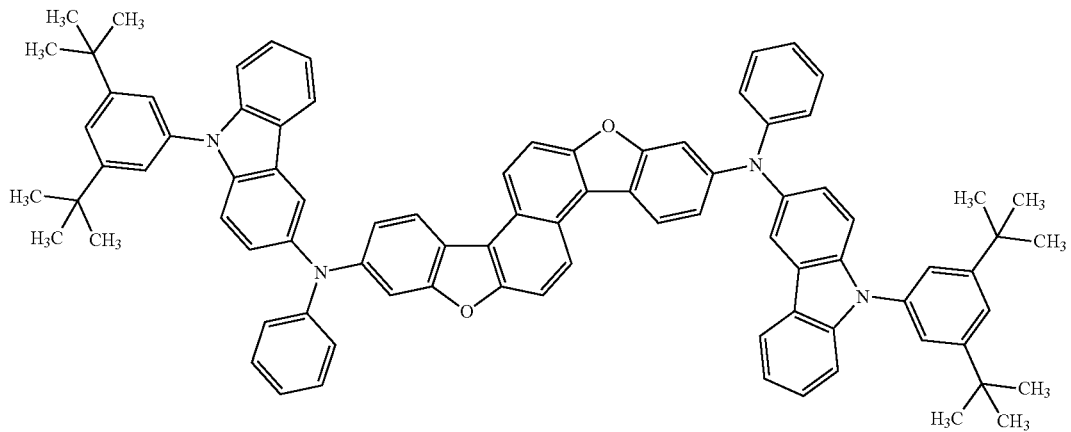
(122)
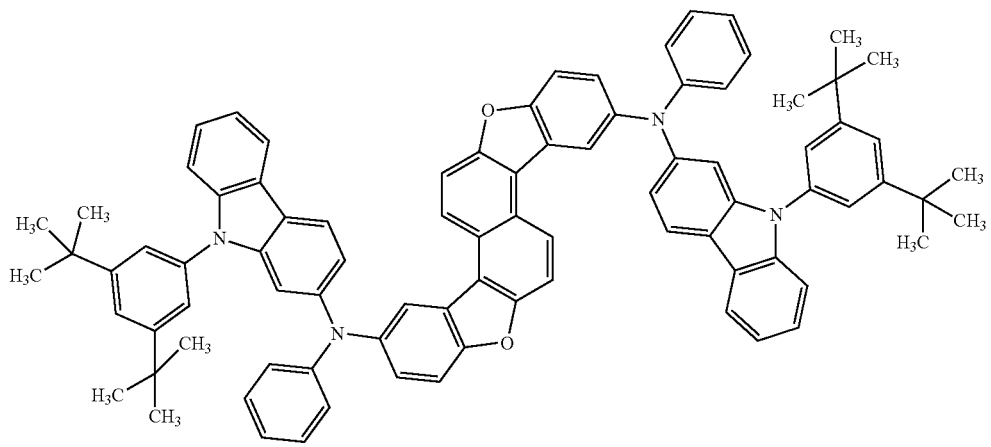
[Chemical Formula 19]
(123)
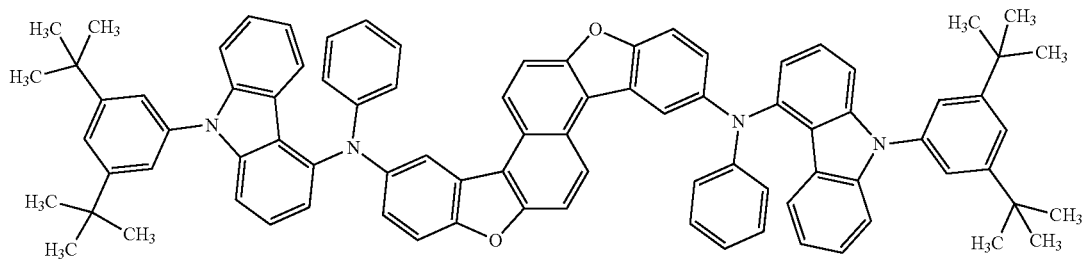
(124)
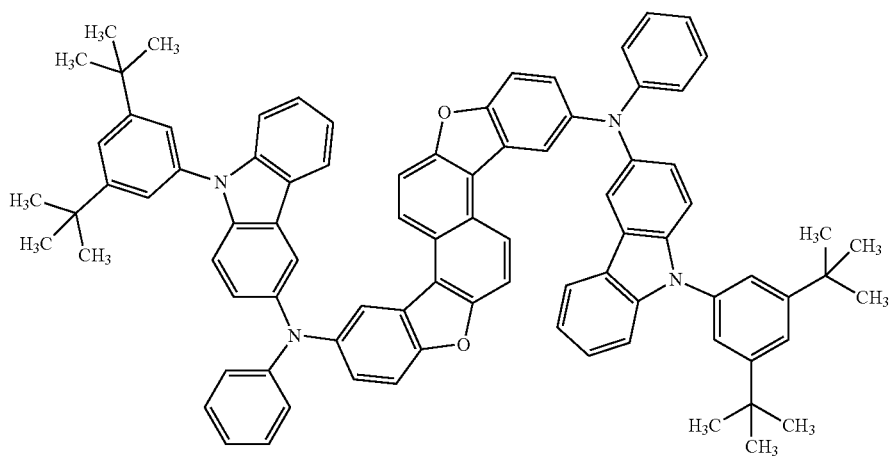

(125)
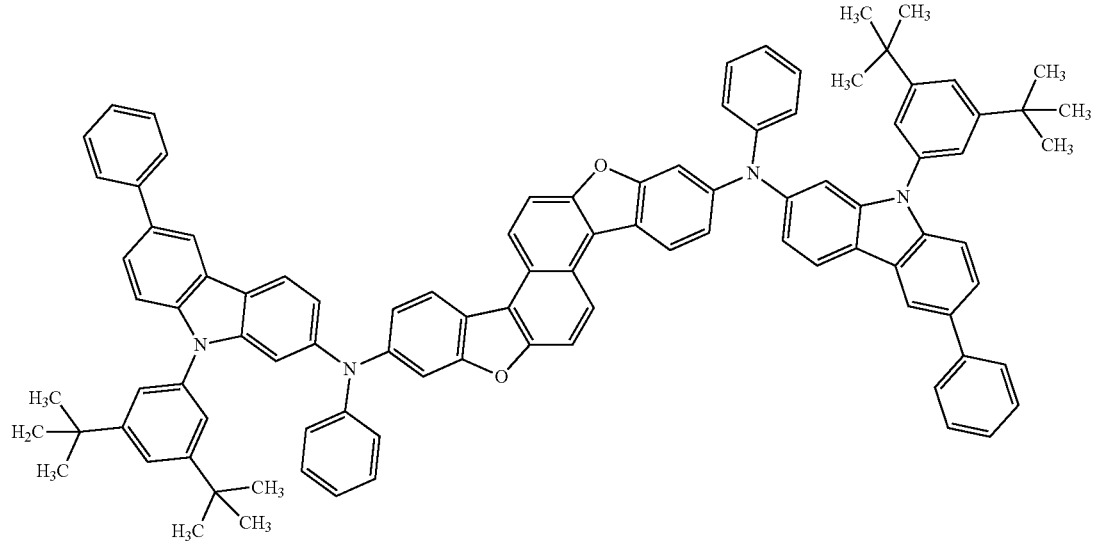
(126)
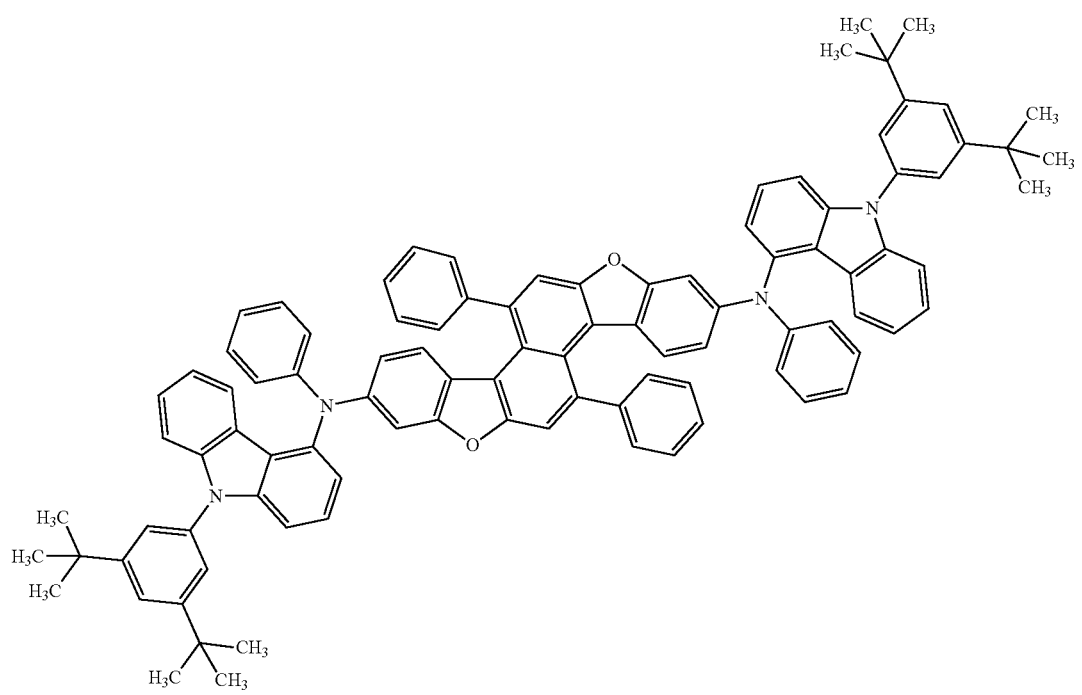

(127)
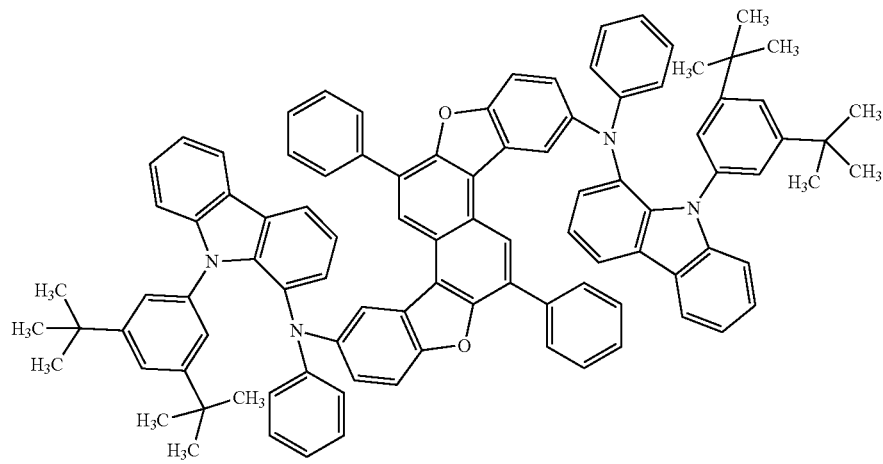
[Chemical Formula 20]
(128)
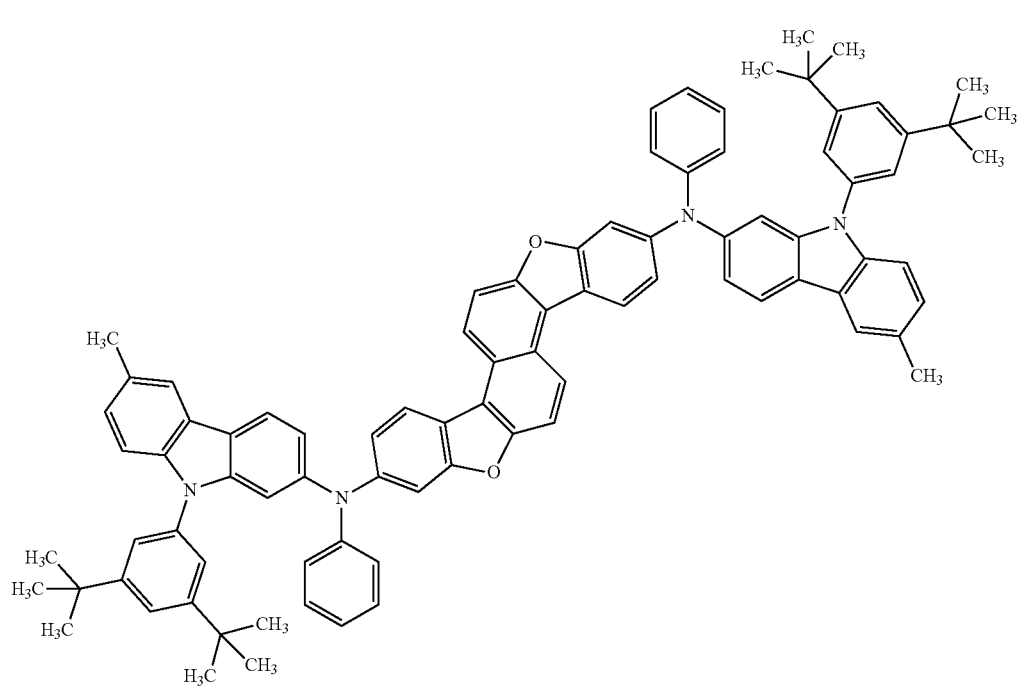
(129)
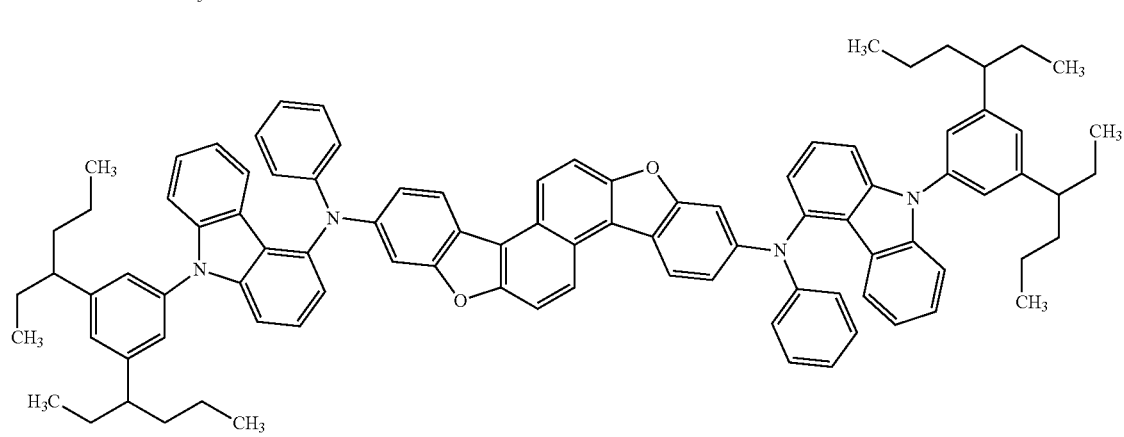

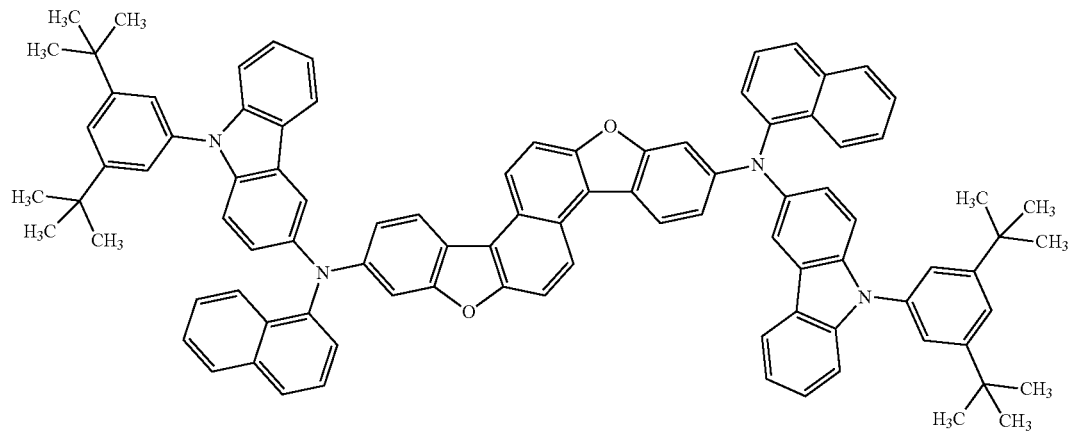
(130)
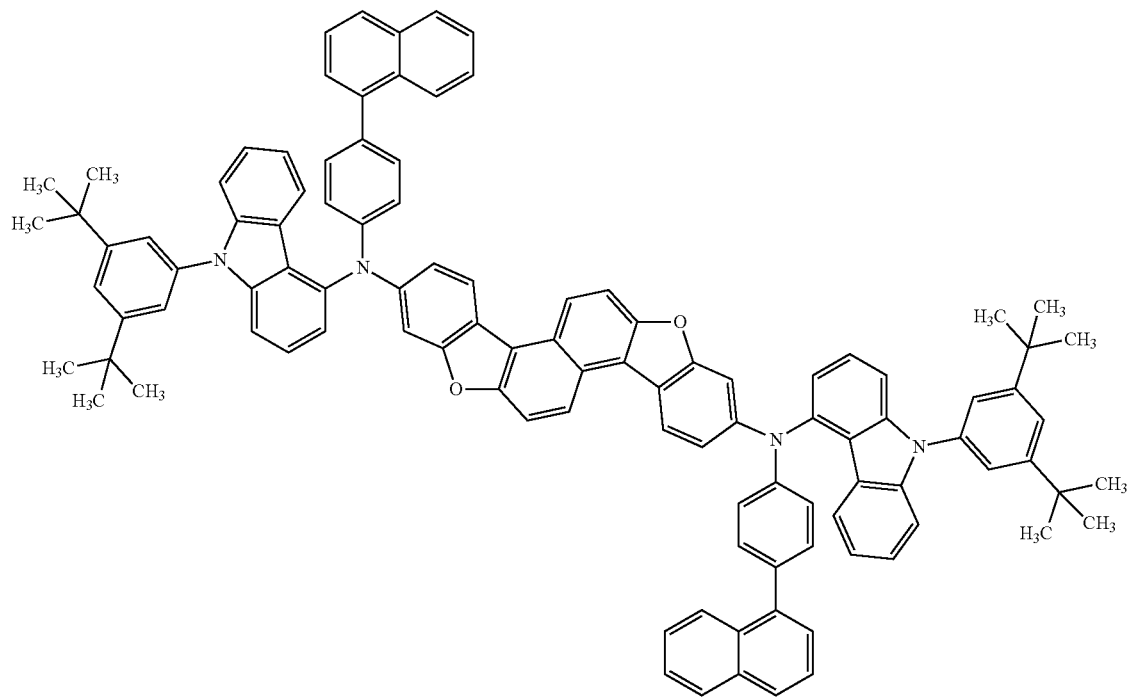
(131)

[Chemical Formula 21]
(132)
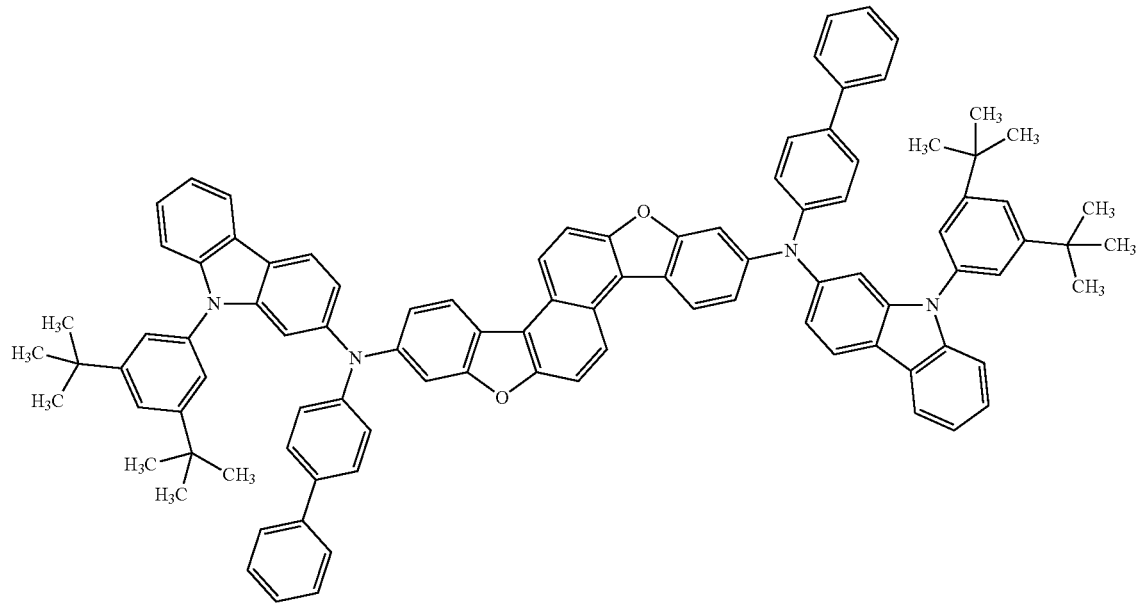
(133)
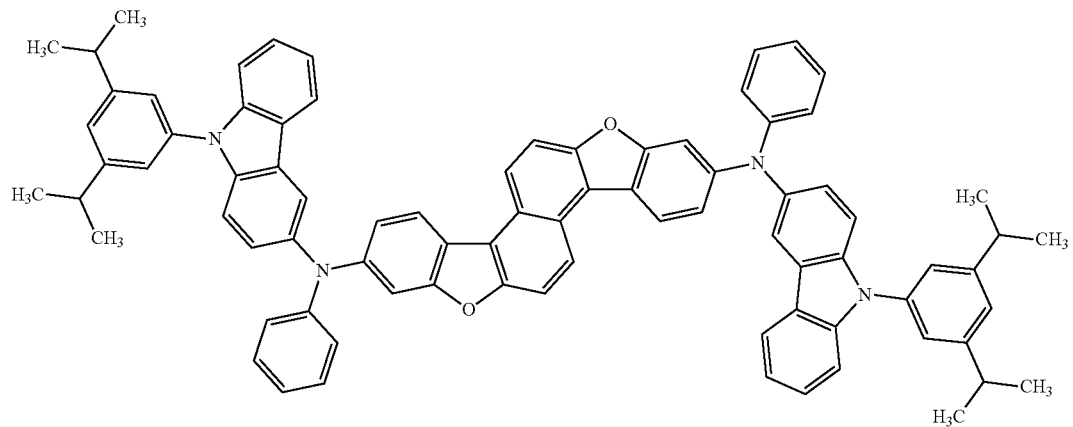
(134)
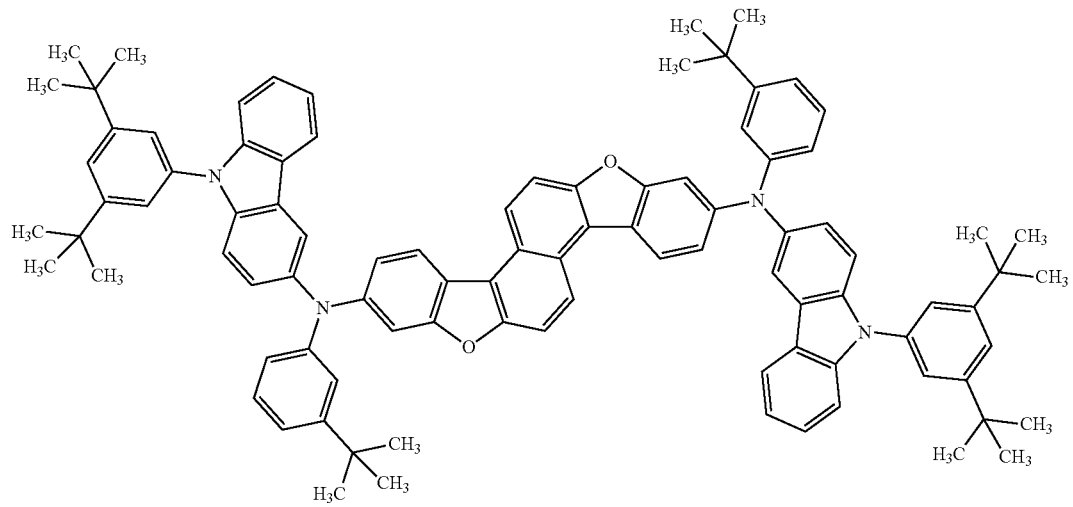

(135)
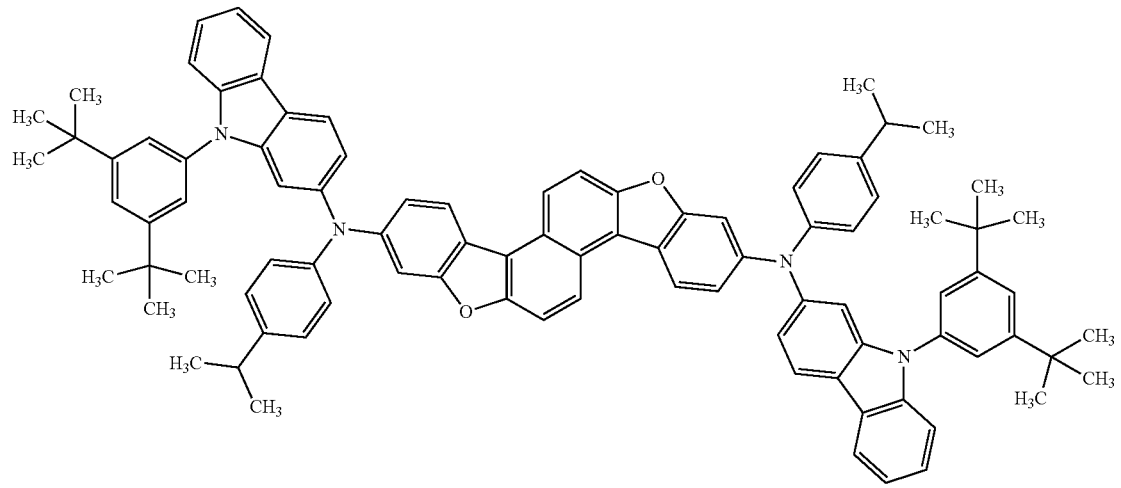
[Chemical Formula 22]
(136)
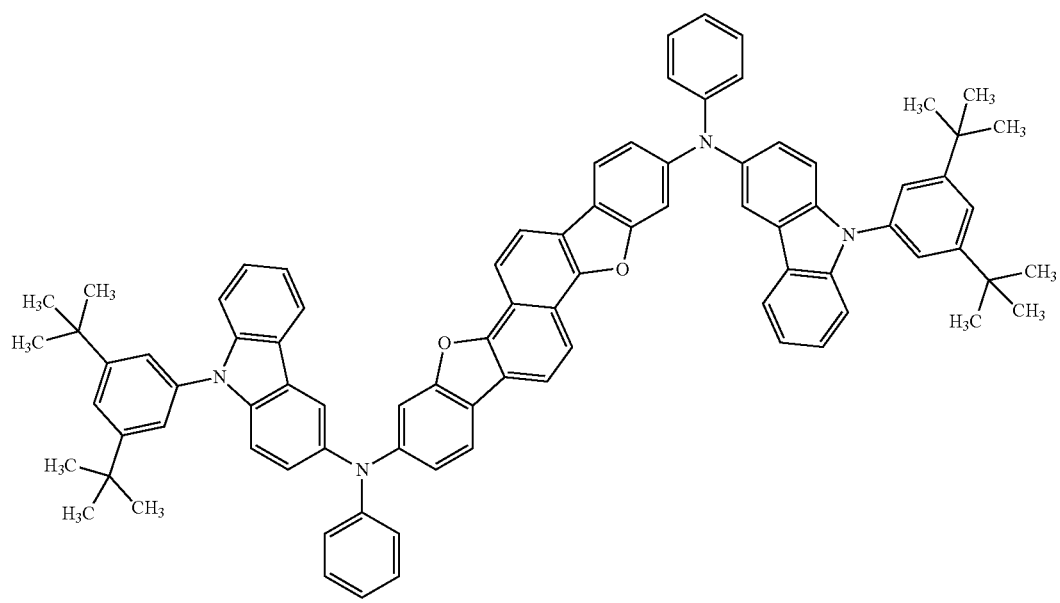
(137)
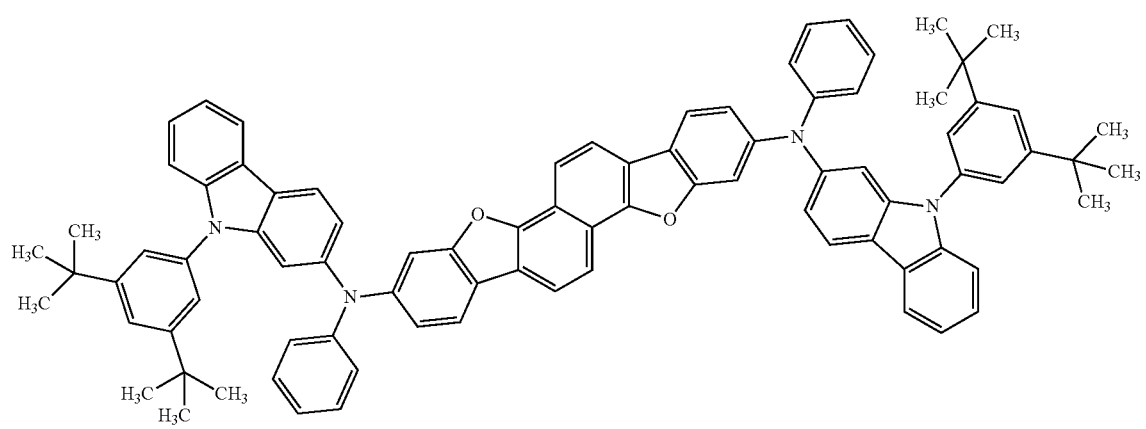

(138)
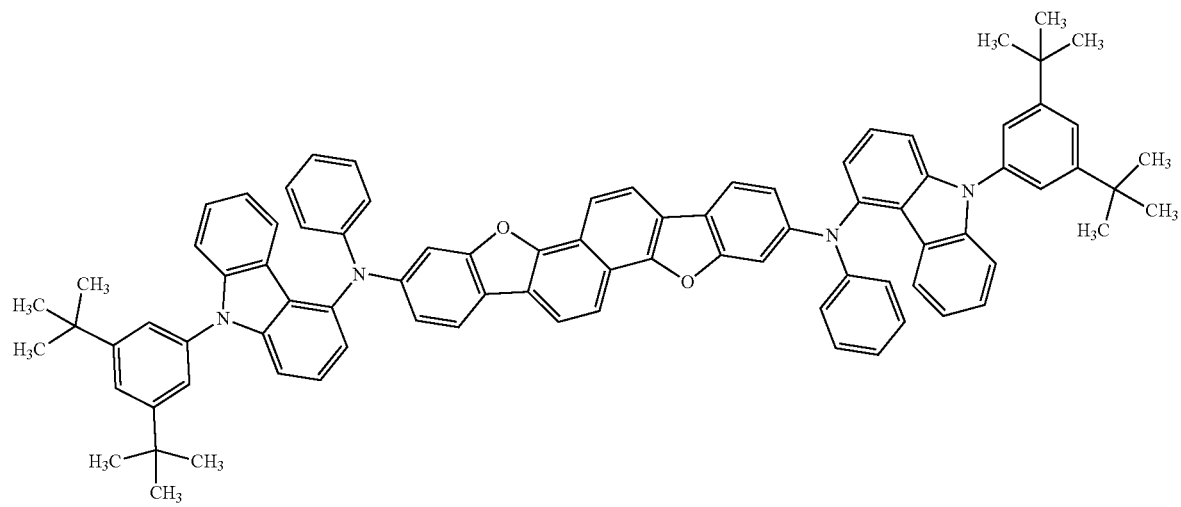
(139)
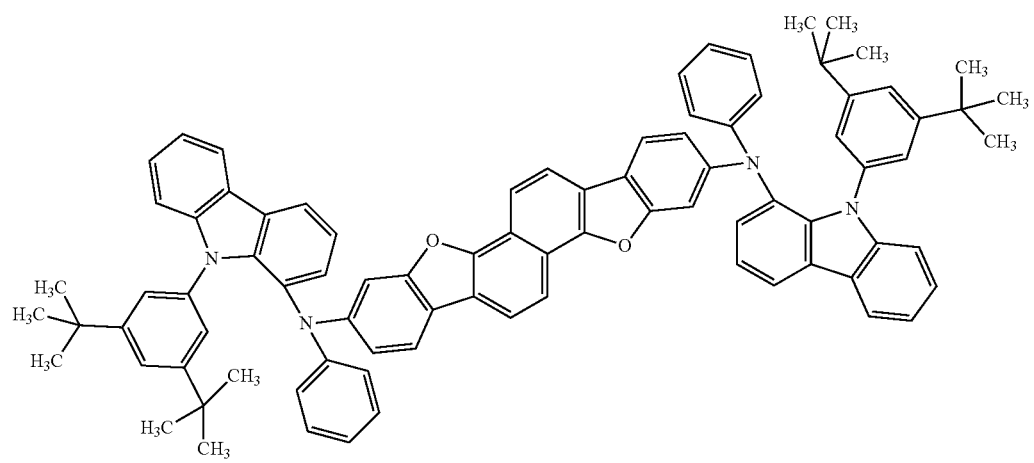
(140)
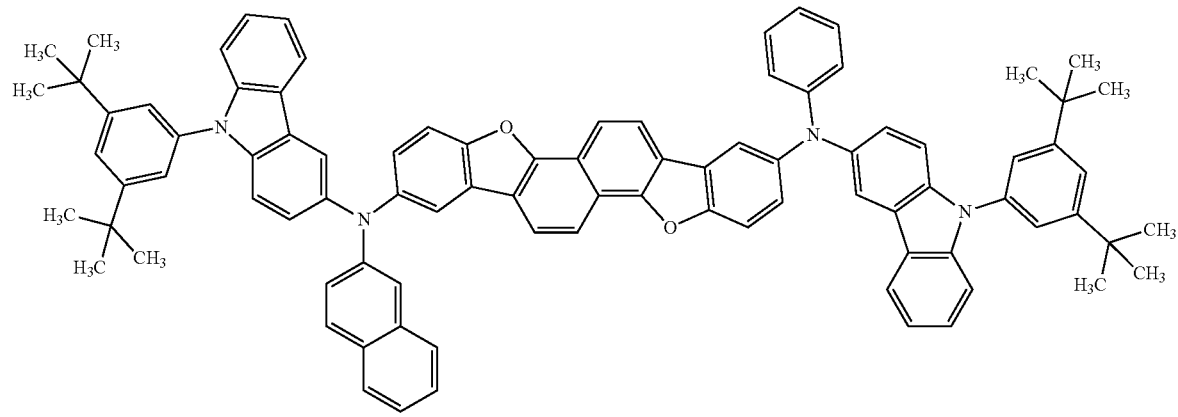

[Chemical Formula 23]
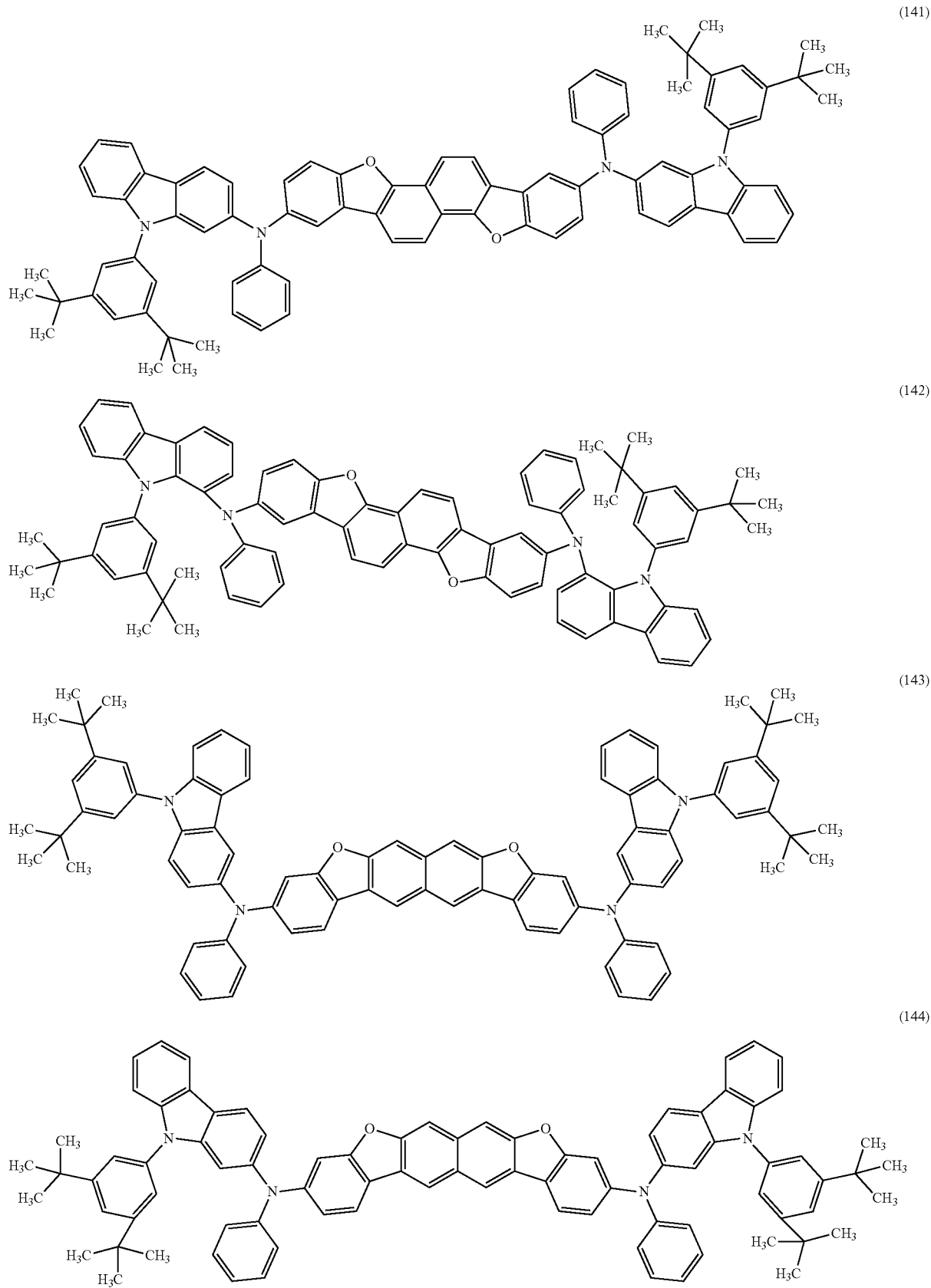
(141)
(142)
(143)
(144)

(145)
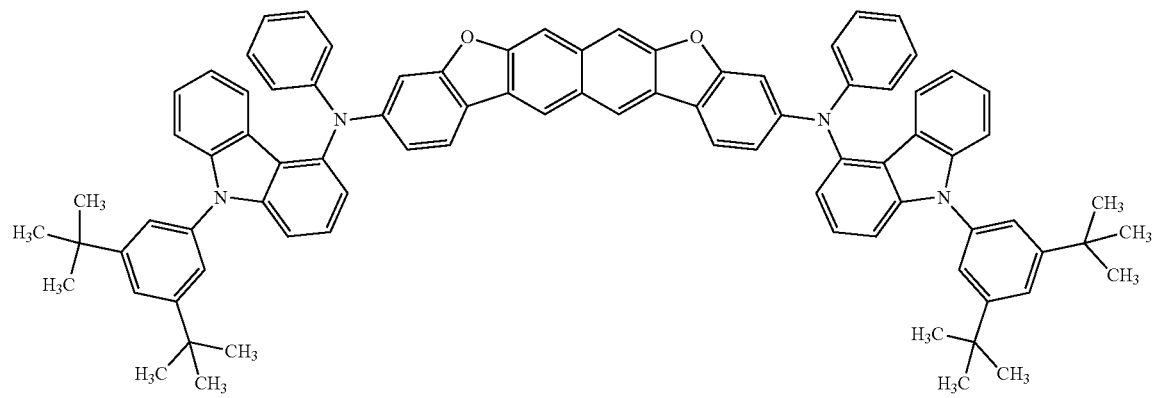
[Chemical Formula 24]
(146)
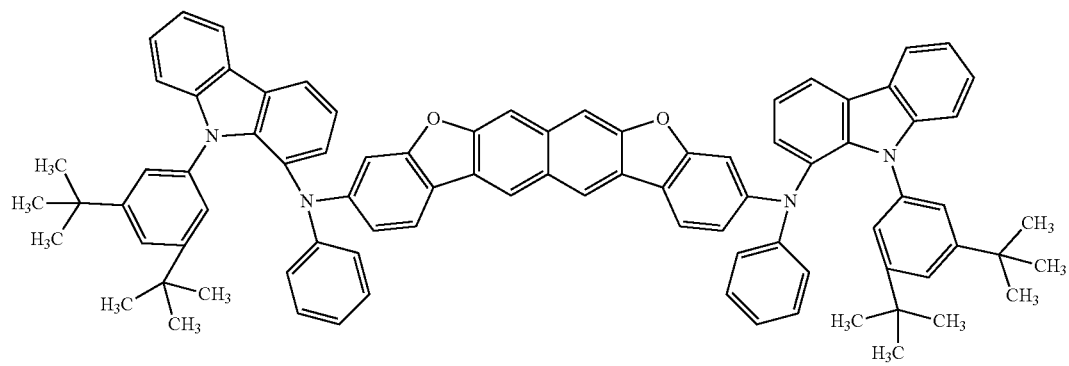
(147)
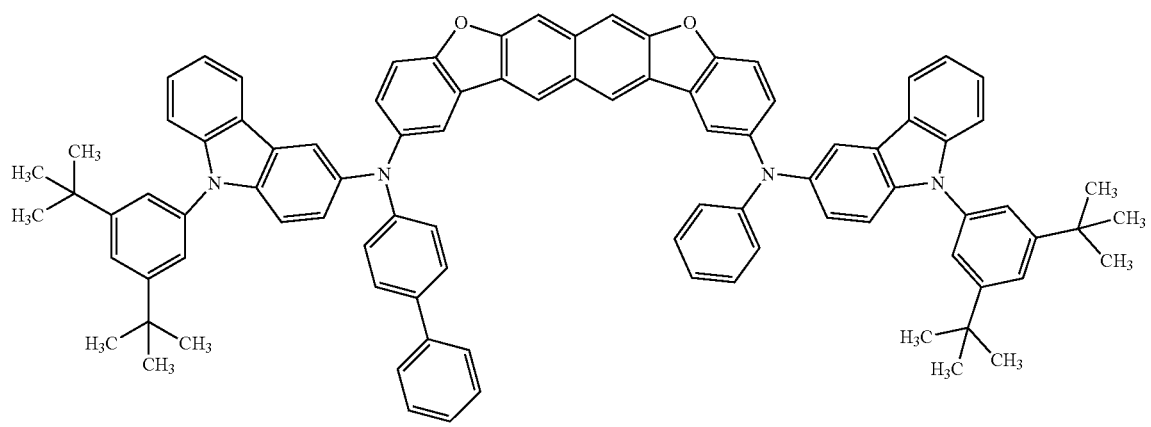

(148)
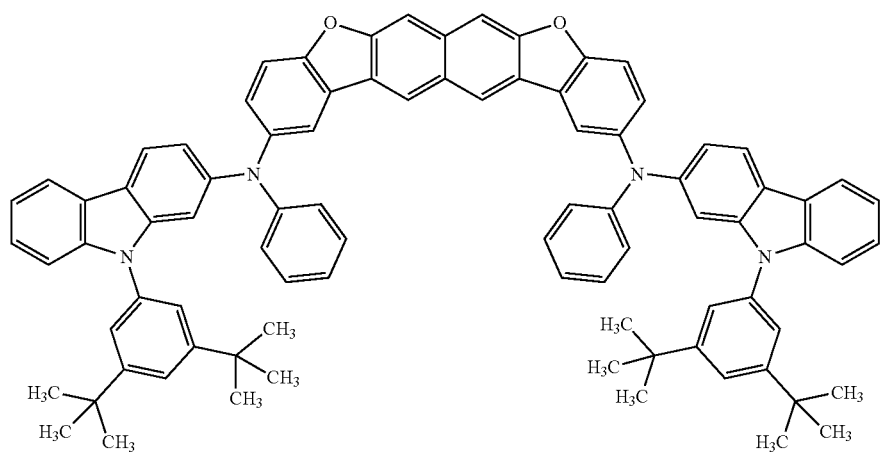
(149)
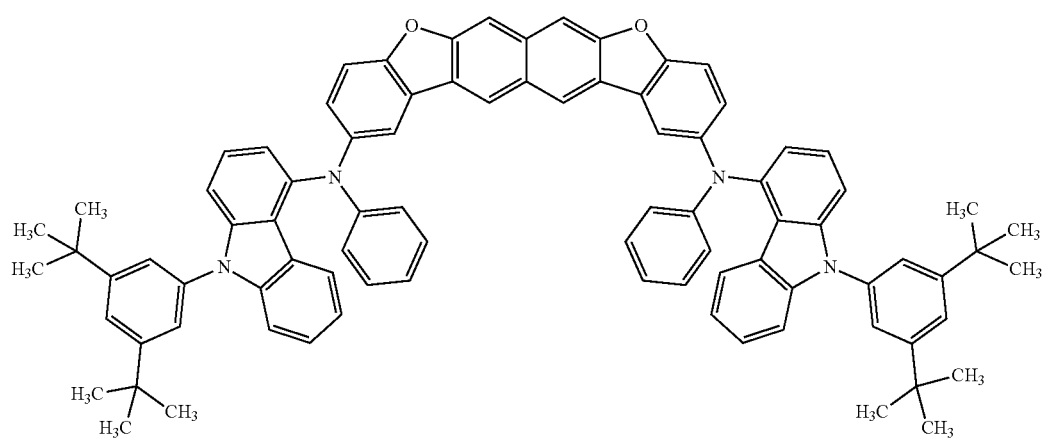
[Chemical Formula 25]
(150)
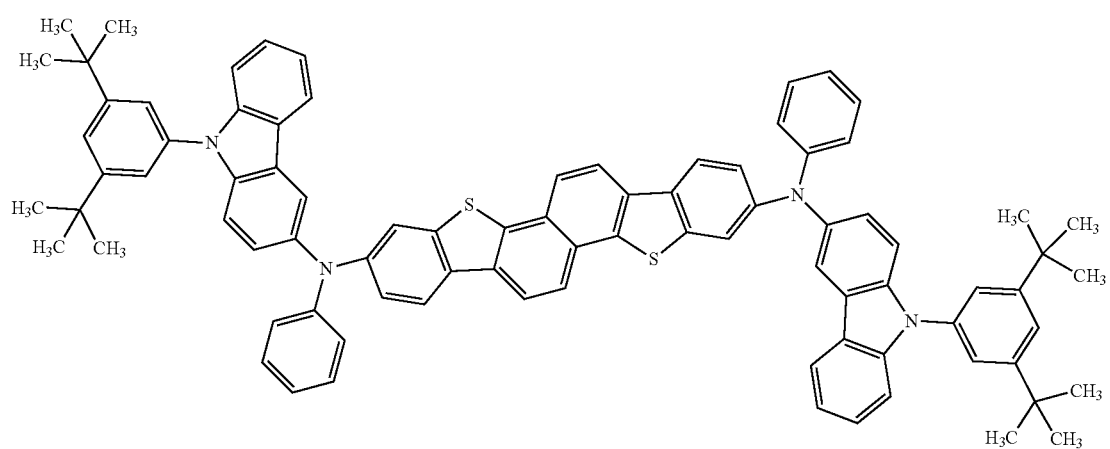

-continued
(151)
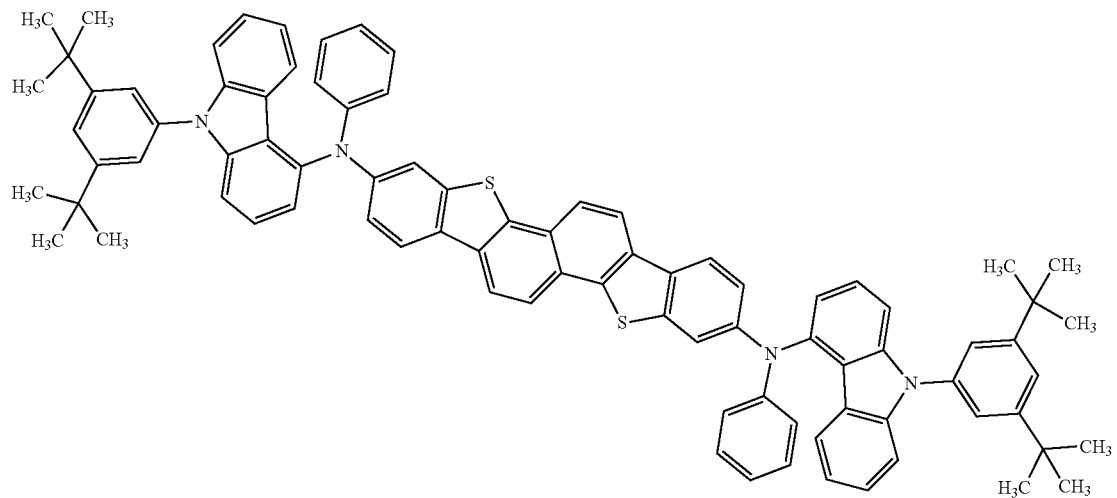
(152)
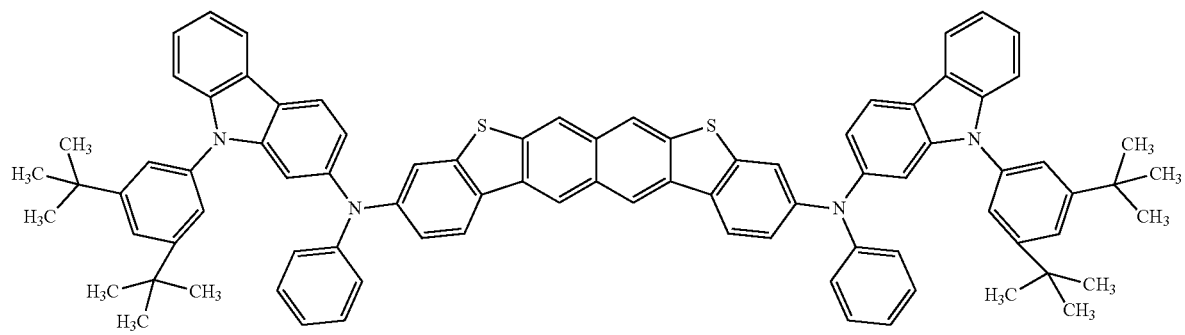
(153)
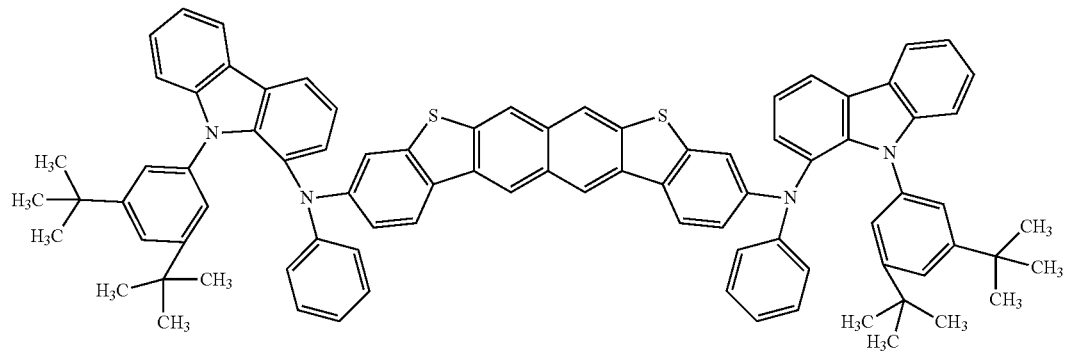
(154)
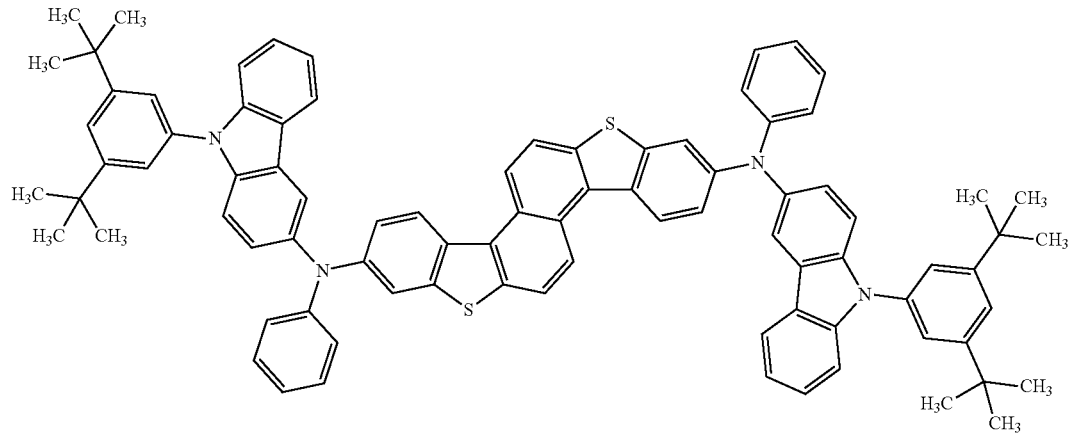

[Chemical Formula 26]
(155)
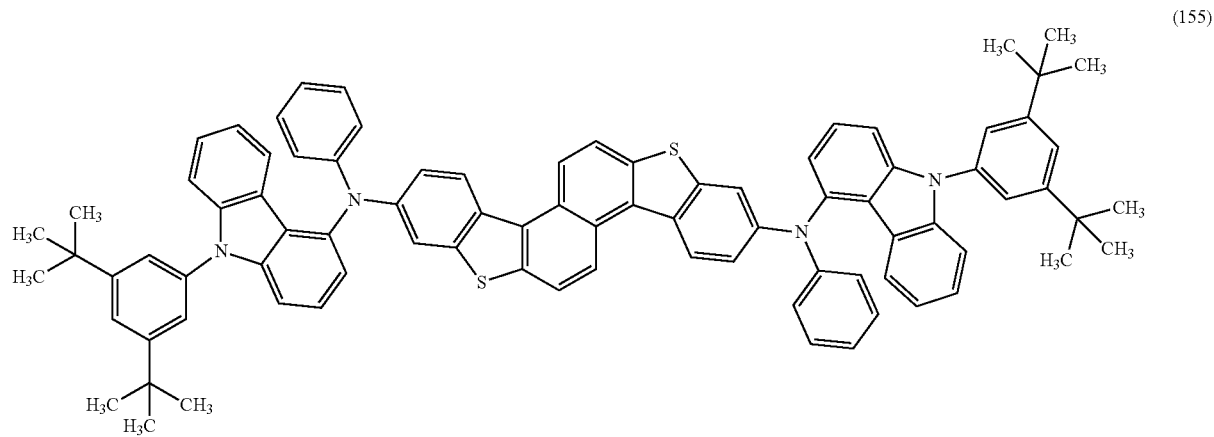
(156)
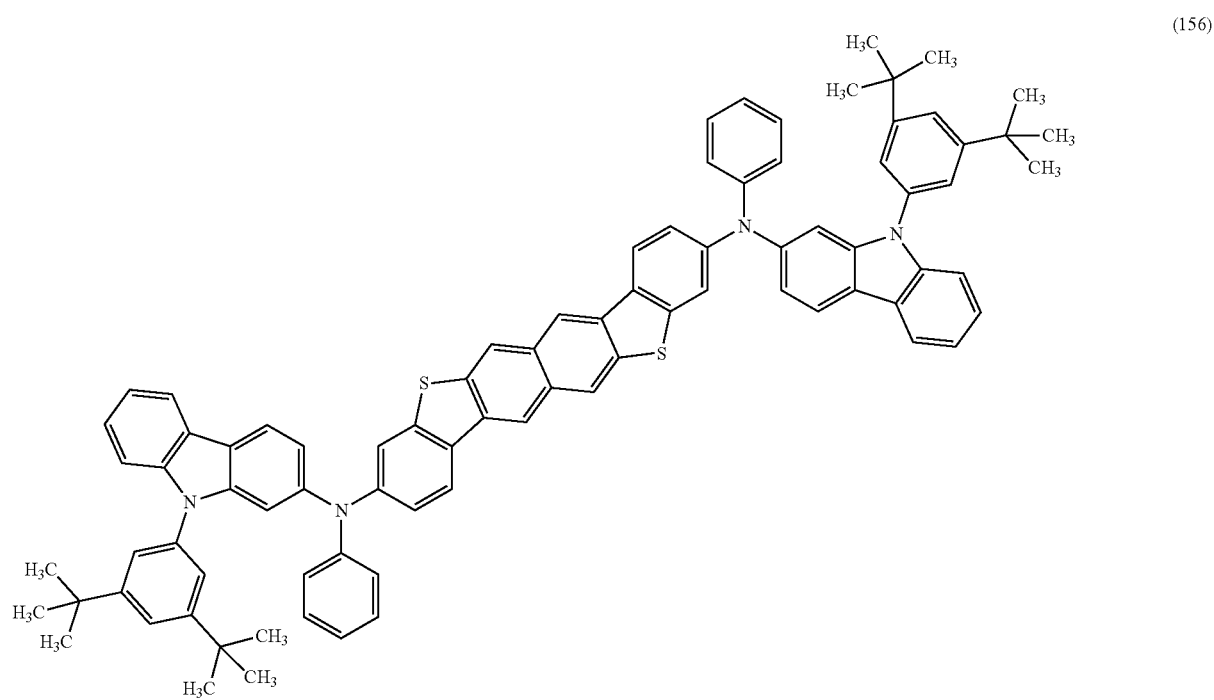

(157)
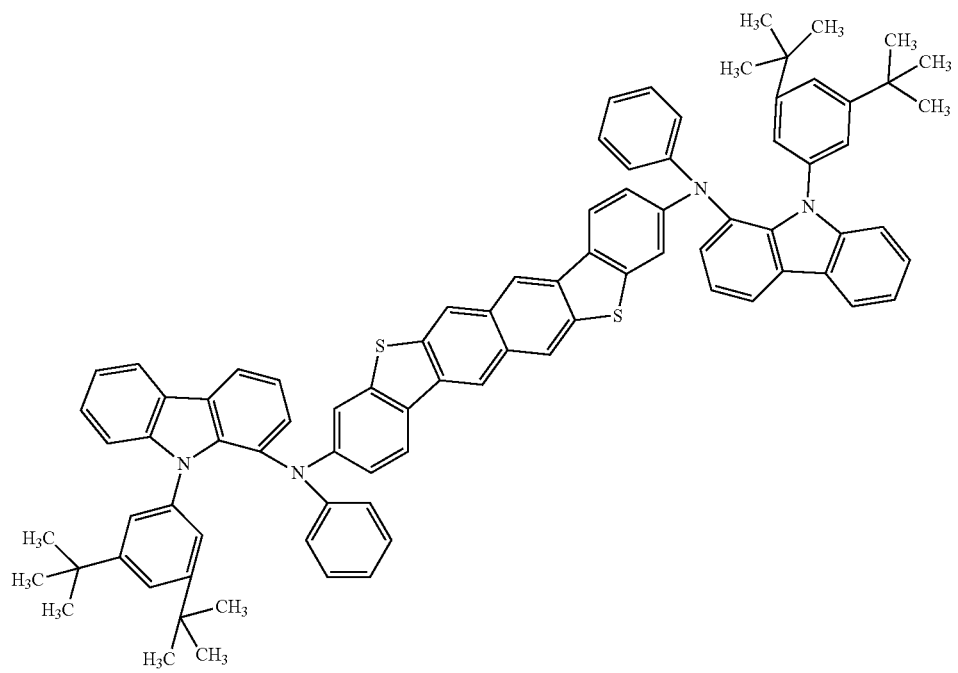
[Chemical Formula 27]
(158)
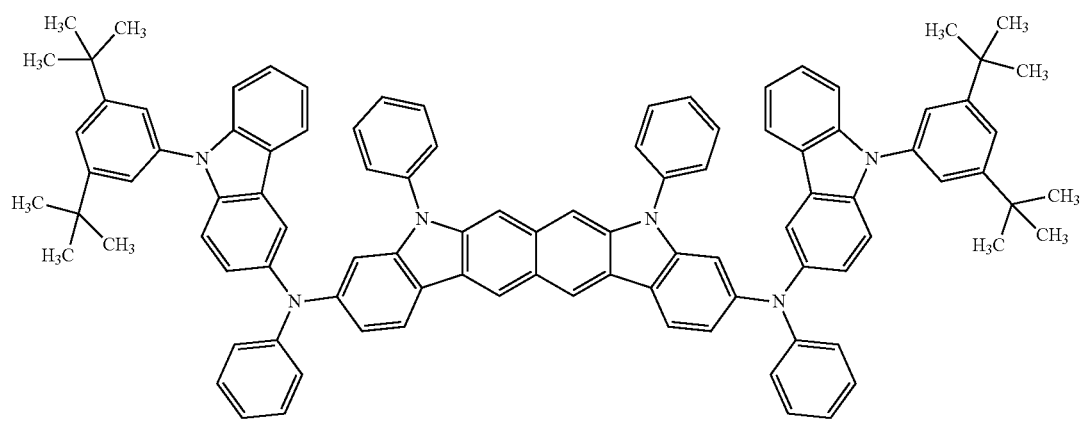

(159)
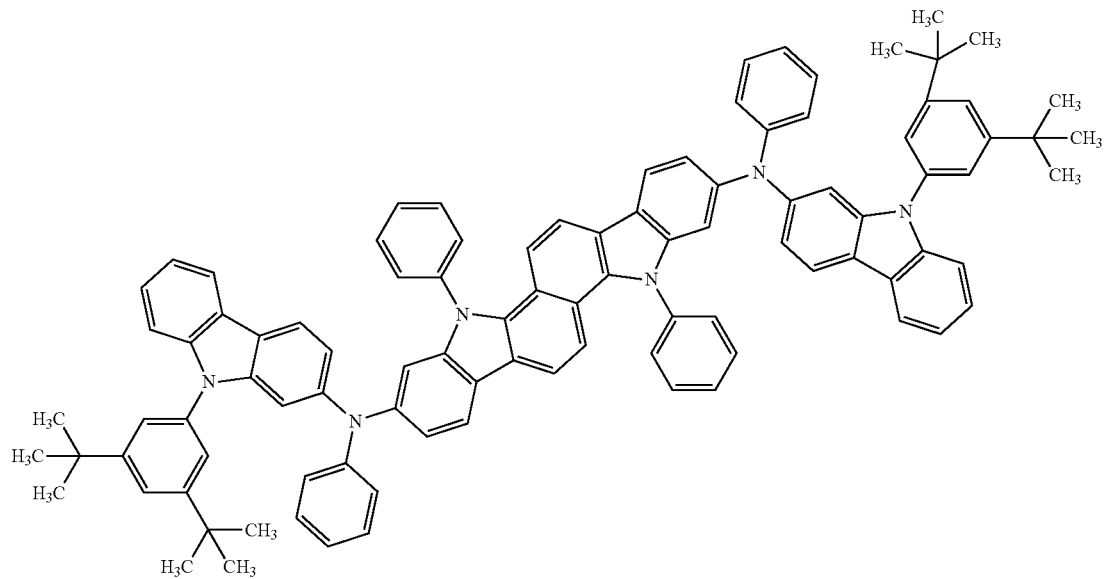
(160)
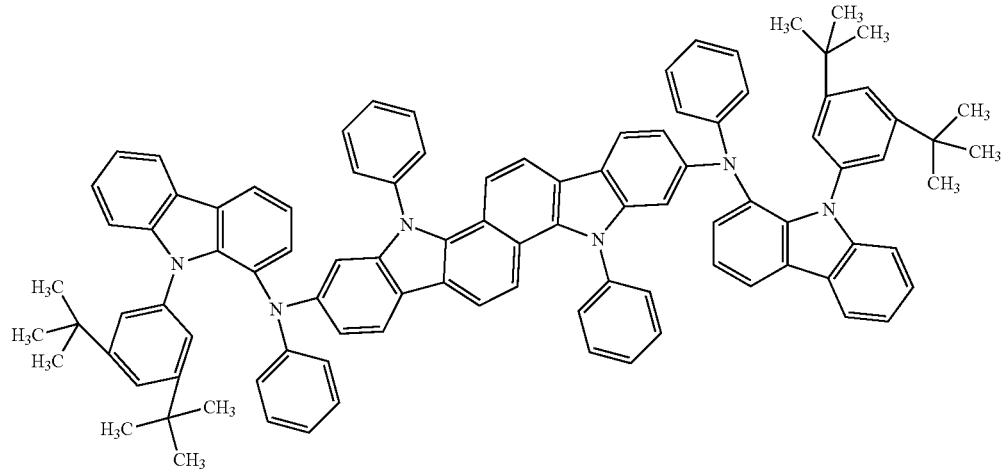
(161)
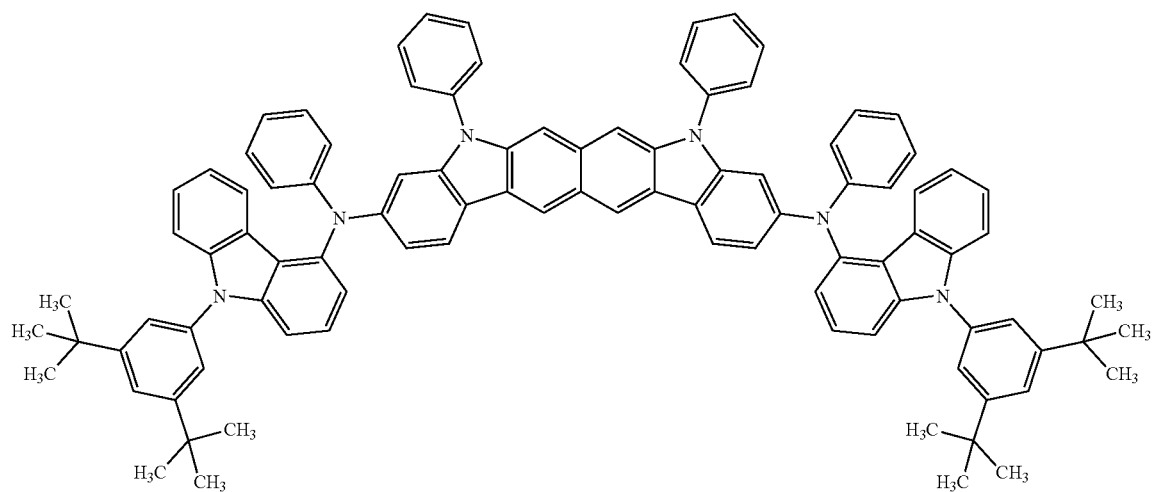

[Chemical Formula 28]
(162)
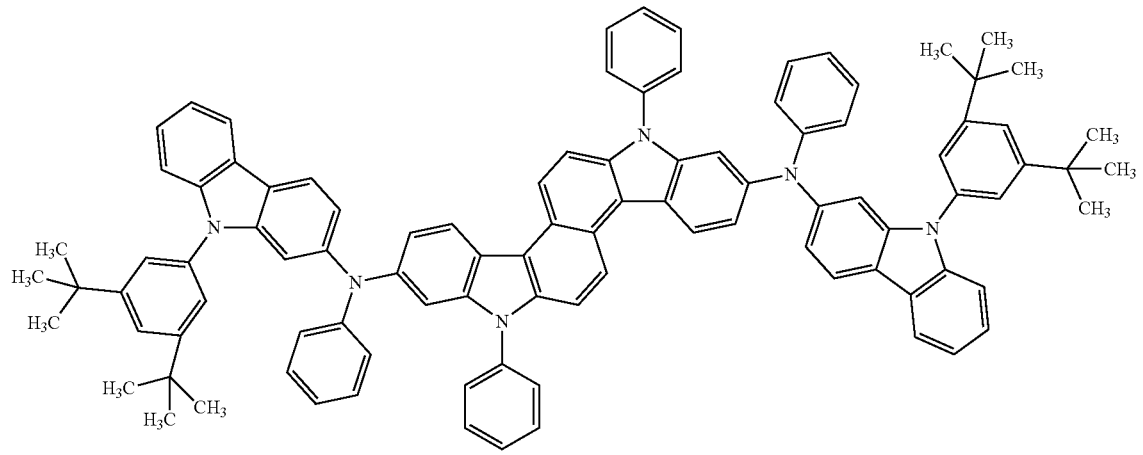
(163)
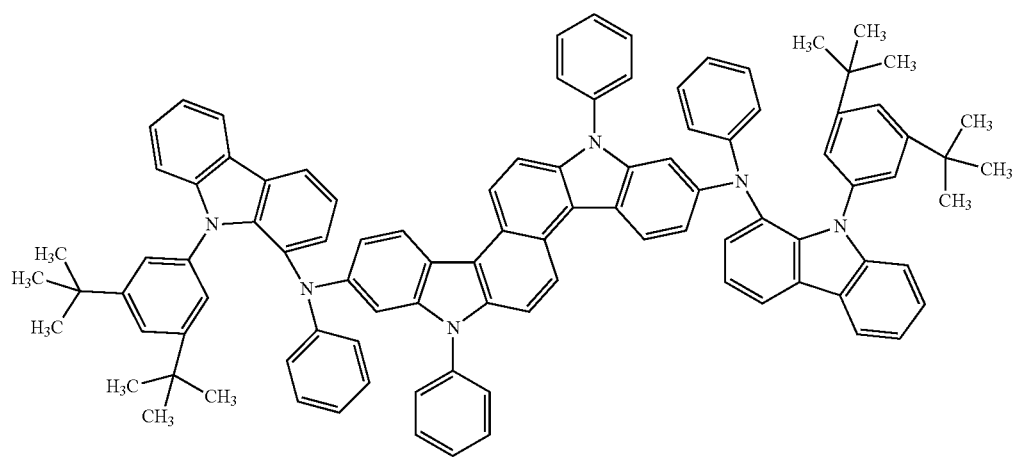
(164)
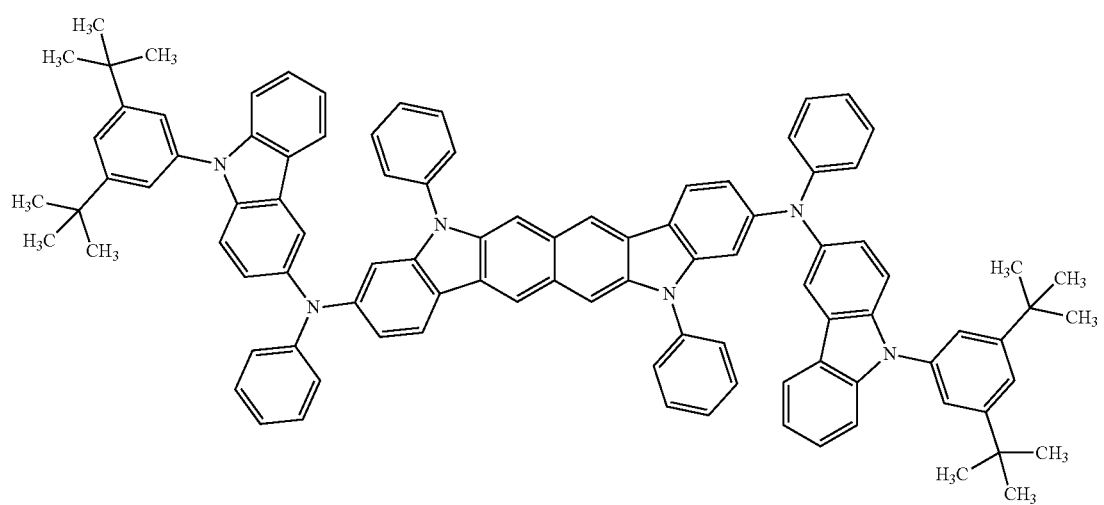

(165)
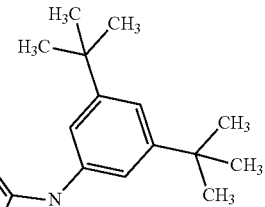
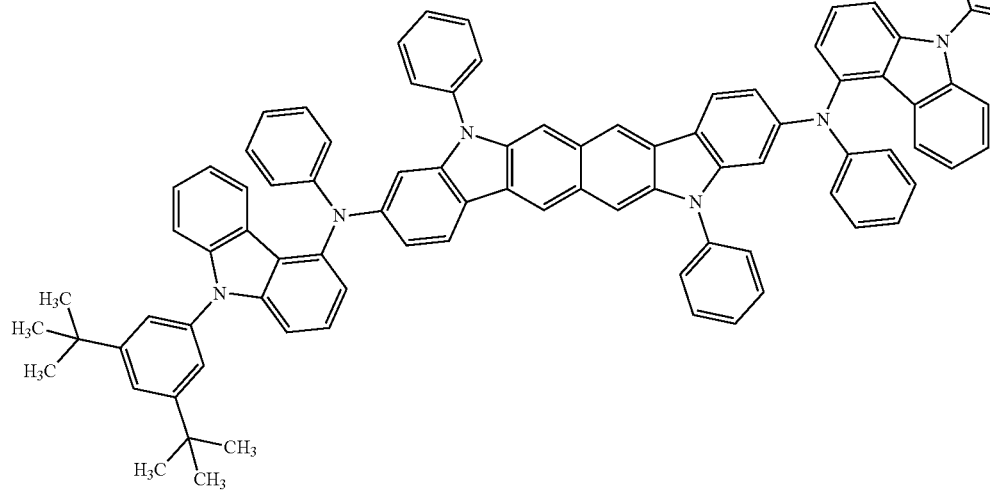
[Chemical Formula 29]
(166)
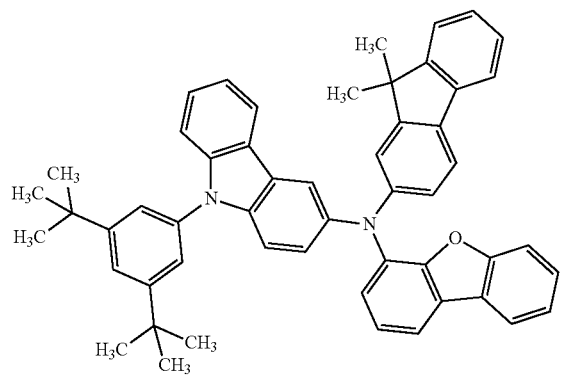
(167)
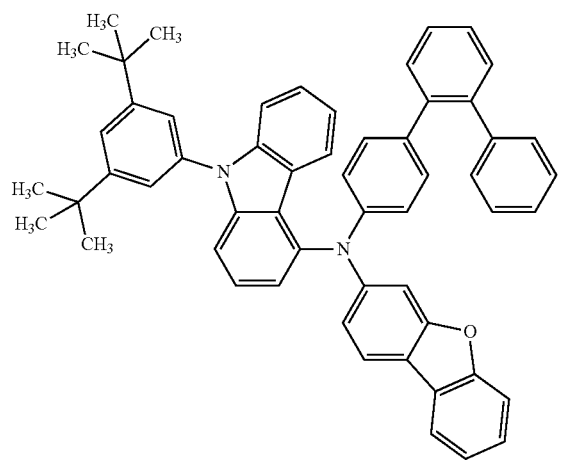

-continued
(168)
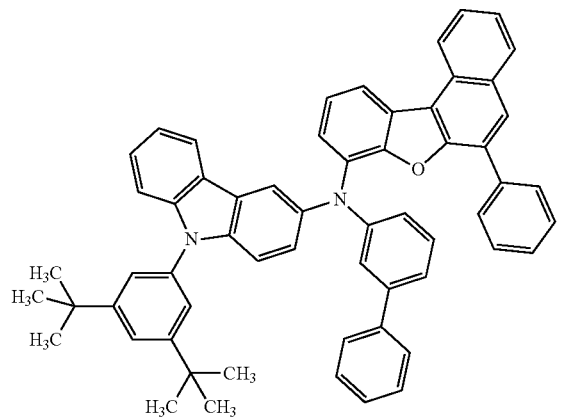
(169)
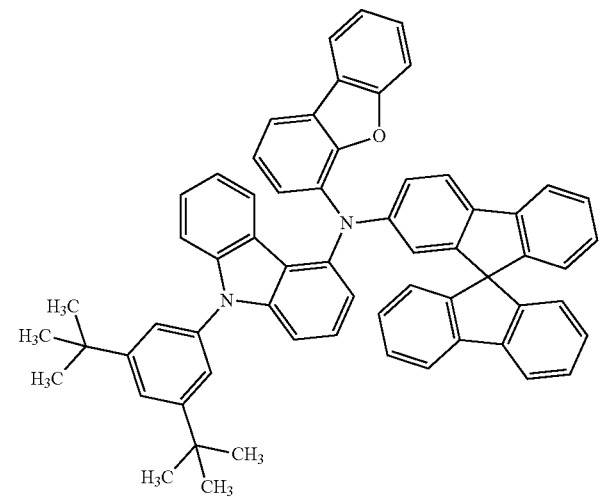
(170)
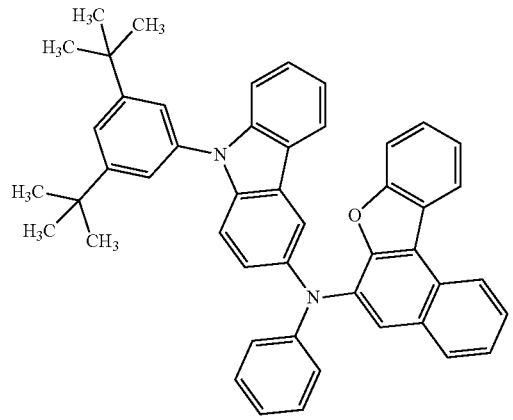
(171)
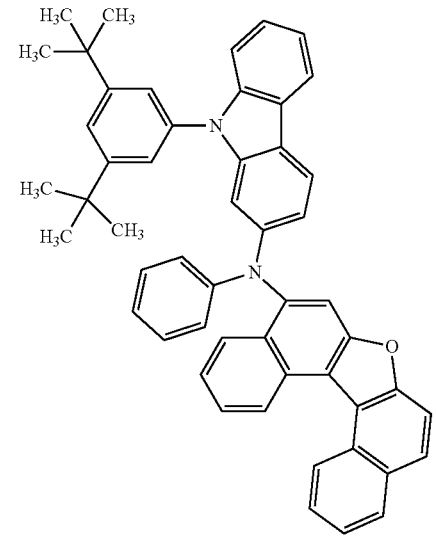
(172)
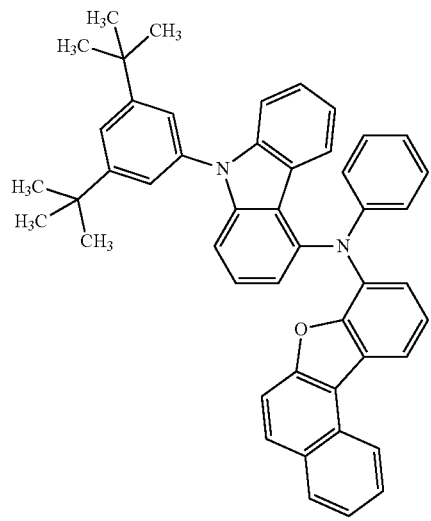
(173)
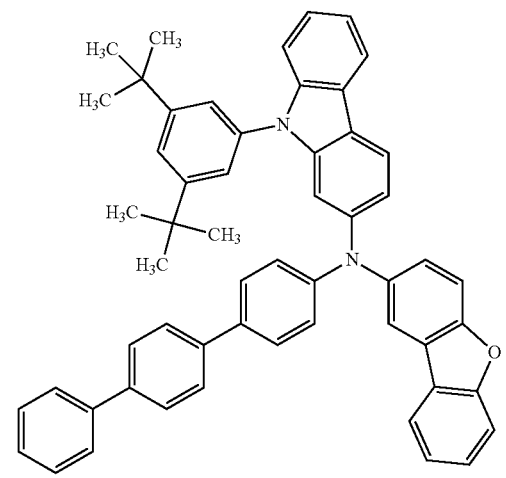

[Chemical Formula 30]
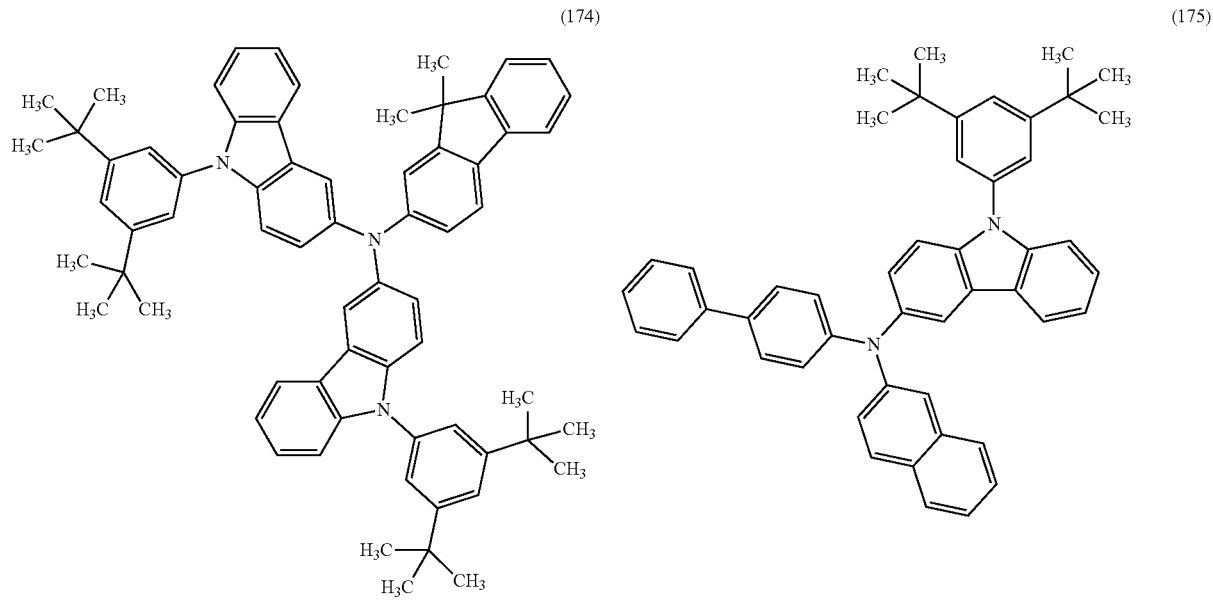
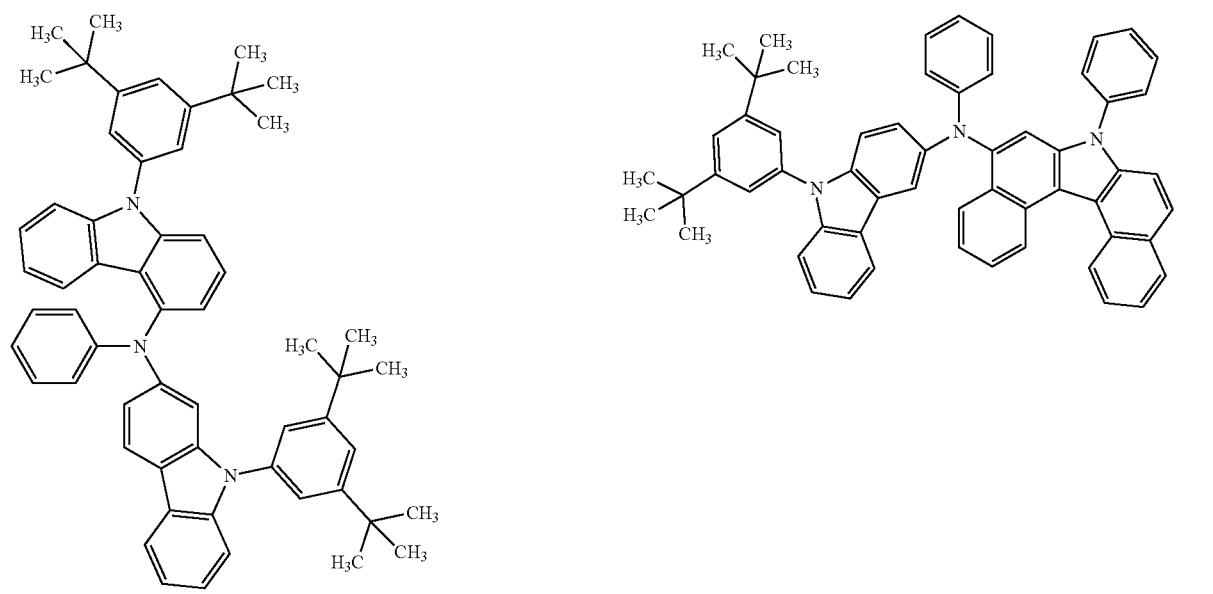

-continued
(178)
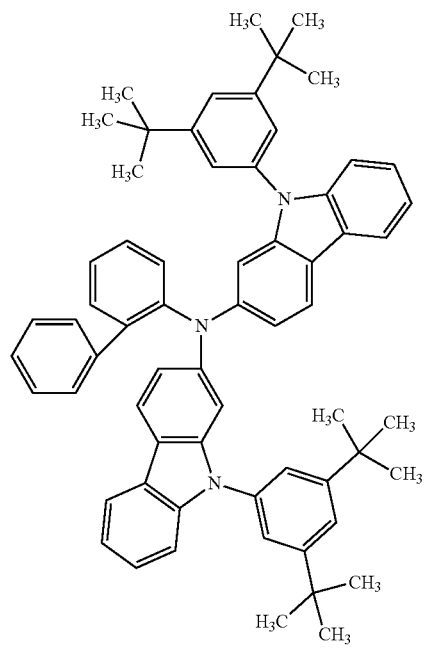
(179)
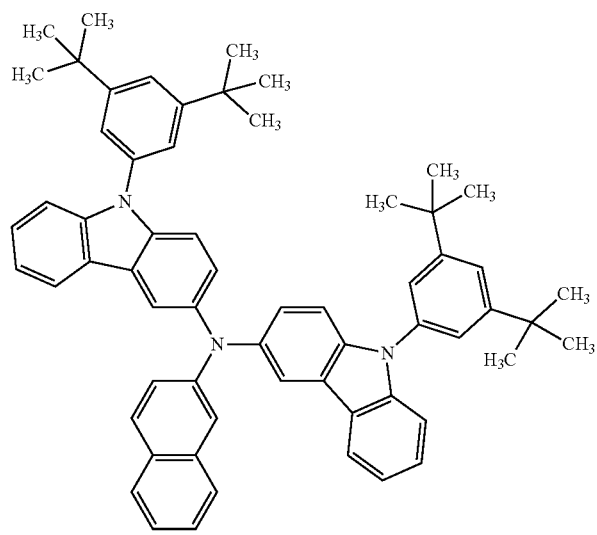
(180)
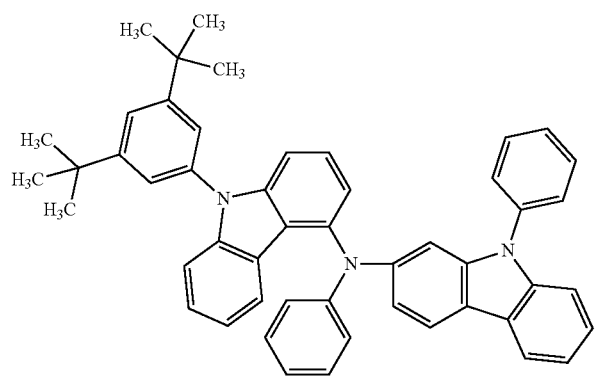
(181)
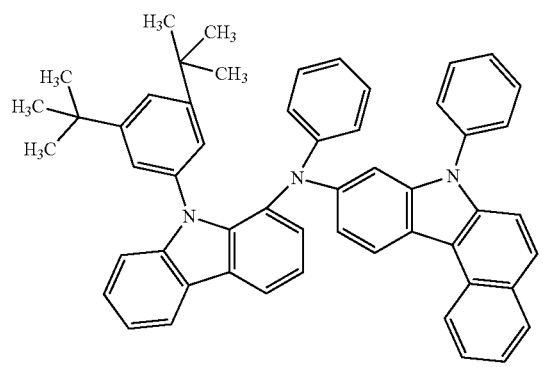
(182)
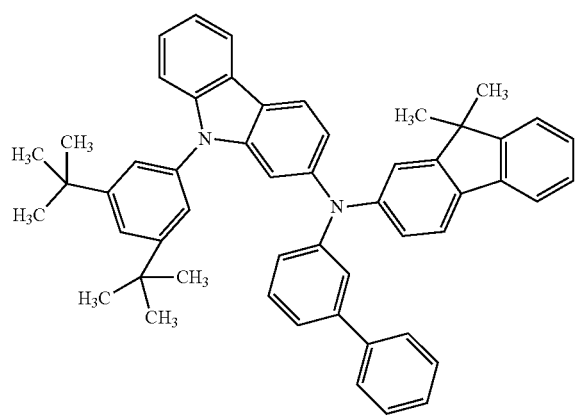

[Chemical Formula 31]
(183)
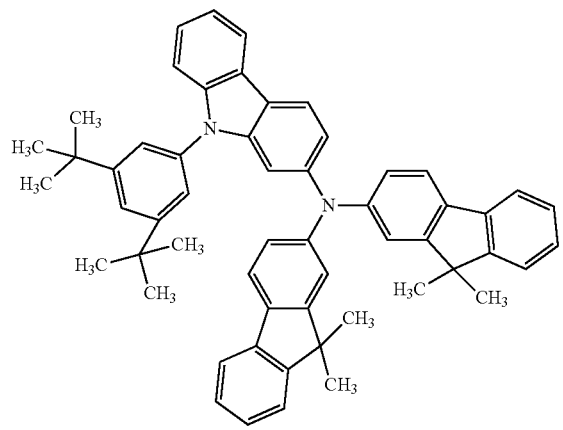
(184)
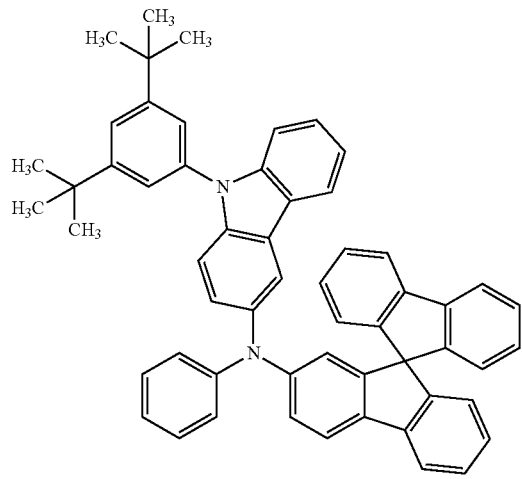
(185)
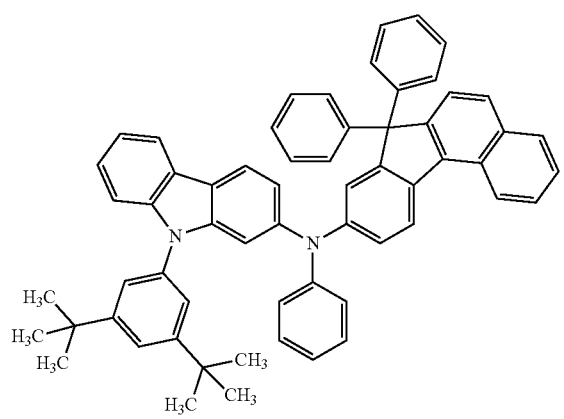
(186)
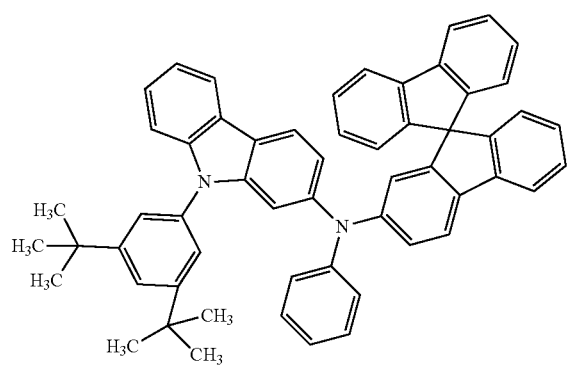
(187)
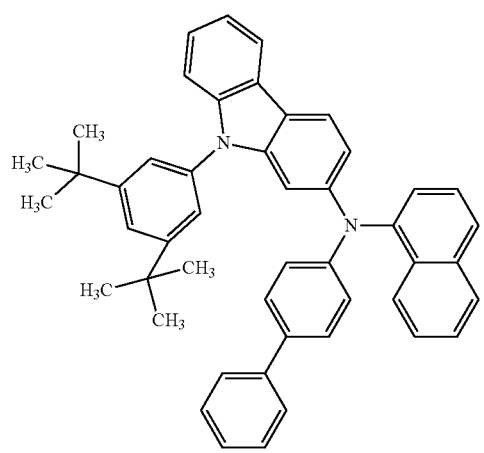
(188)
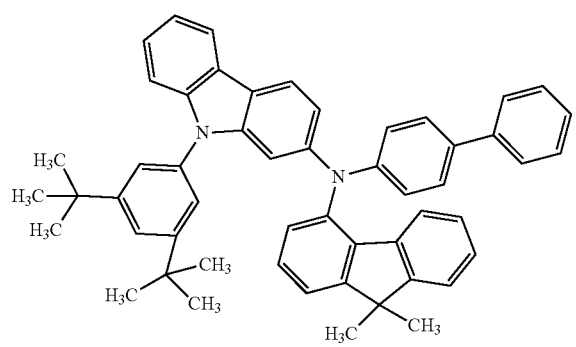

-continued
(189)
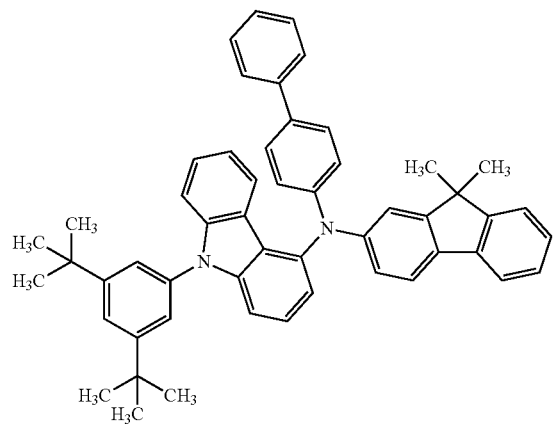
(190)
(191)
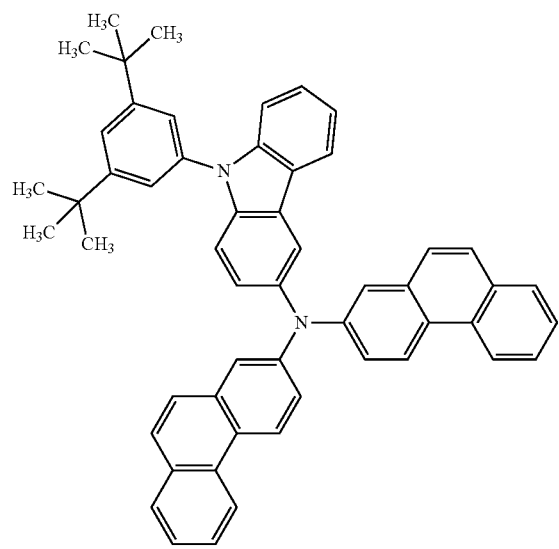
(192)
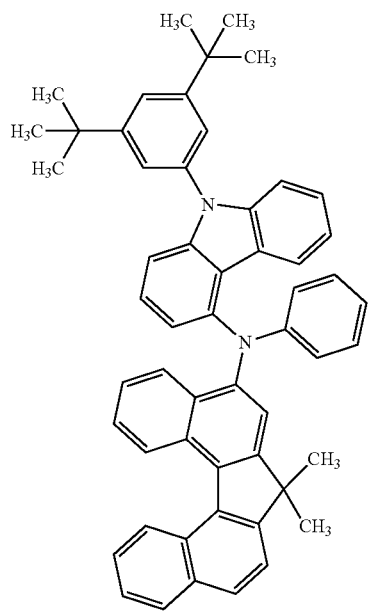
(193)
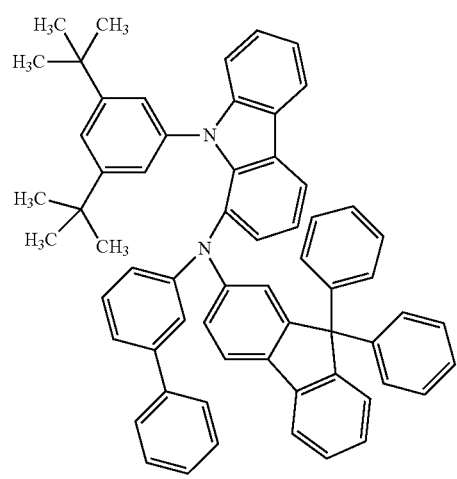

[Chemical Formula 32]
(194)
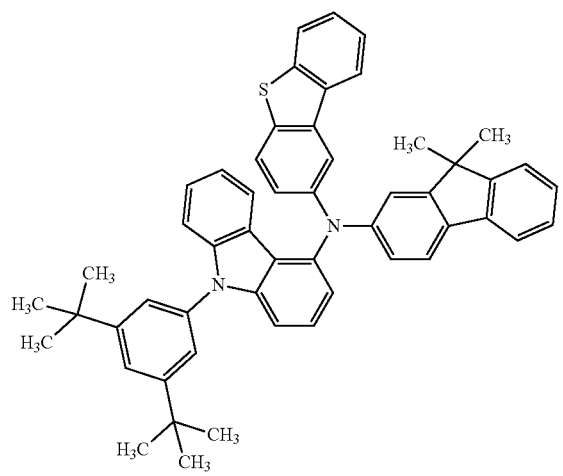
(195)
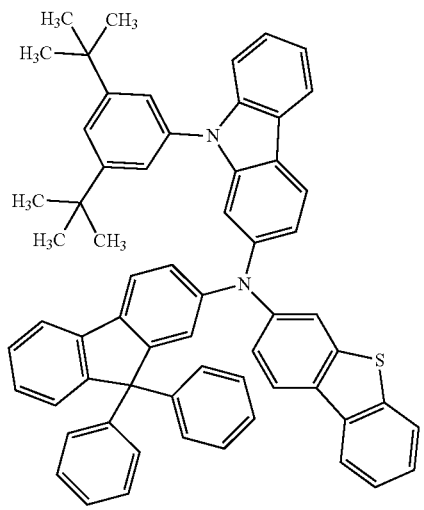
(196)
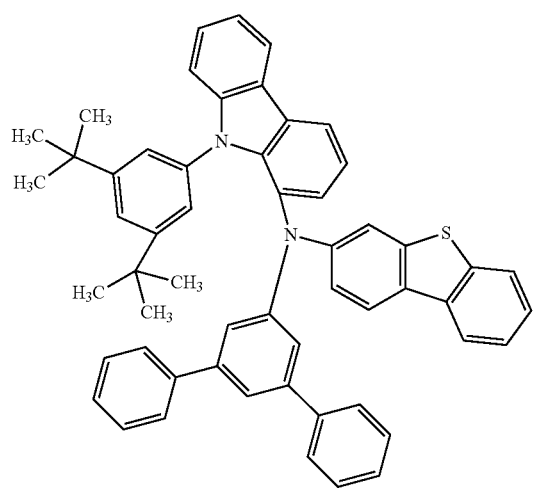
(197)
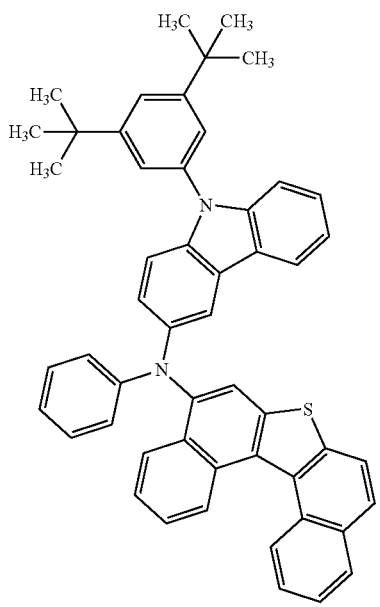
(198)
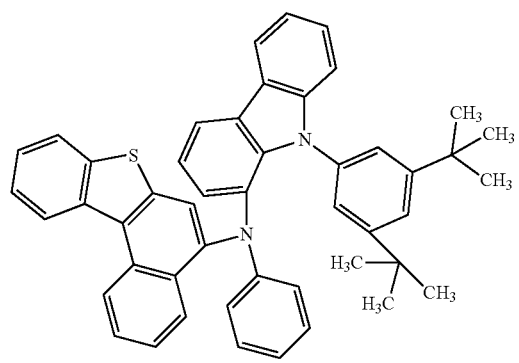

[Chemical Formula 33]

(199)

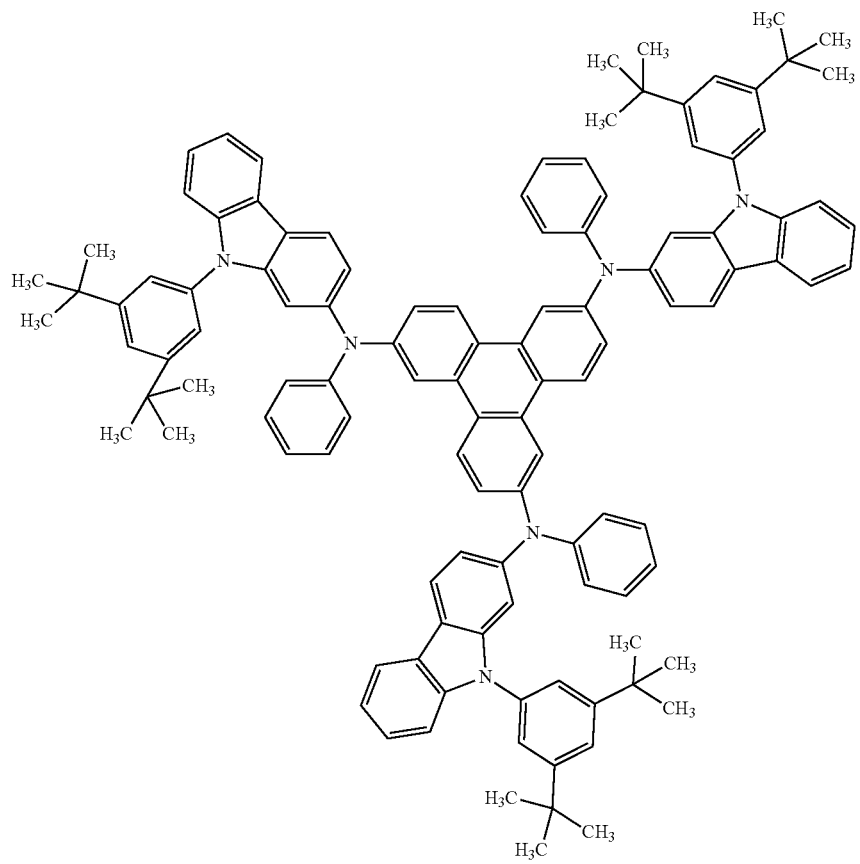

Next, an example of a method for synthesizing the above-described organic compound of the present invention will be described. The organic compound represented by General Formula (G1) is shown below.

[Chemical Formula 34]

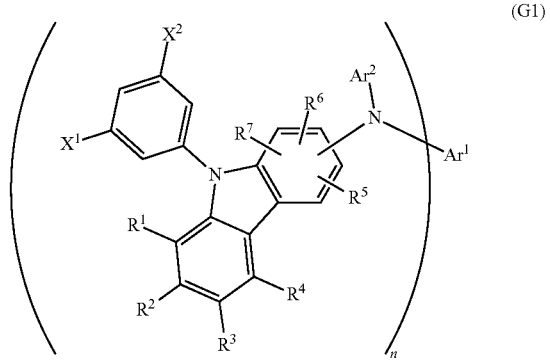

(G1)

In General Formula (G1) above, $X^1$ and $X^2$ each independently represent a secondary or tertiary alkyl group having 3 to 6 carbon atoms and having a branched carbon atom which is bonded to the phenyl group. Moreover, $Ar^1$ represents a substituted or unsubstituted condensed aromatic ring skeleton having 10 to 60 carbon atoms and composed of two or more rings or a substituted or unsubstituted condensed heteroaromatic ring skeleton having 8 to 60 carbon atoms and composed of two or more rings. Furthermore, $Ar^2$ represents a substituted or unsubstituted aryl group having 6 to 25 carbon atoms. Furthermore, $R^1$ to $R^7$ each independently represent any of hydrogen, an alkyl group having 1 to 6 carbon atoms, a cycloalkyl group having 3 to 12 carbon atoms, and an aryl group having 6 to 13 carbon atoms which is unsubstituted or to which an alkyl group is bonded as a substituent. Furthermore, n represents any of 1 to 3. In the case where n is 2 or more, two or more groups bonded to $Ar^1$ may be identical or different.

The organic compound represented by General Formula (G1) can be obtained by causing a cross coupling reaction of a compound (a1) and an arylamine compound (a2) as shown in the following synthesis scheme. Examples of $B^1$ include halogen such as chlorine, bromine, or iodine and a triflate group. Examples of $B^2$ include hydrogen and an organotin group.

[Chemical Formula 35]

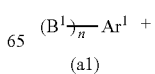

(a1)

-continued

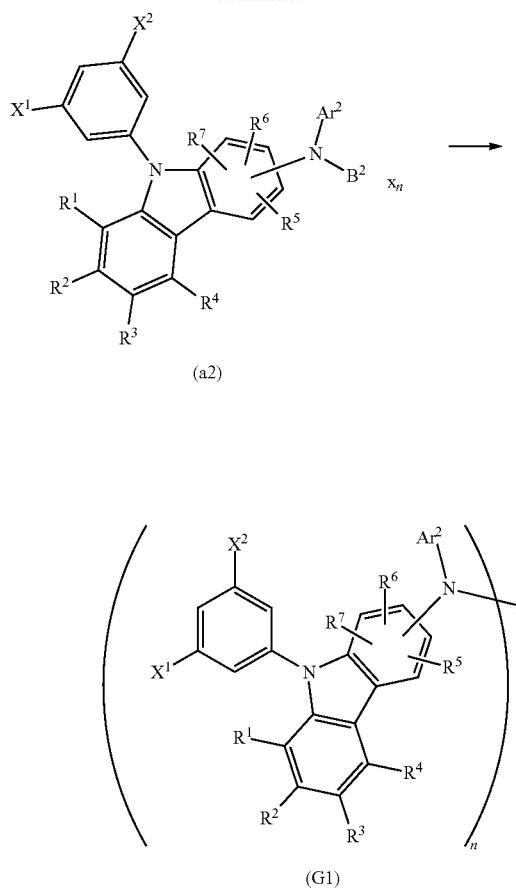

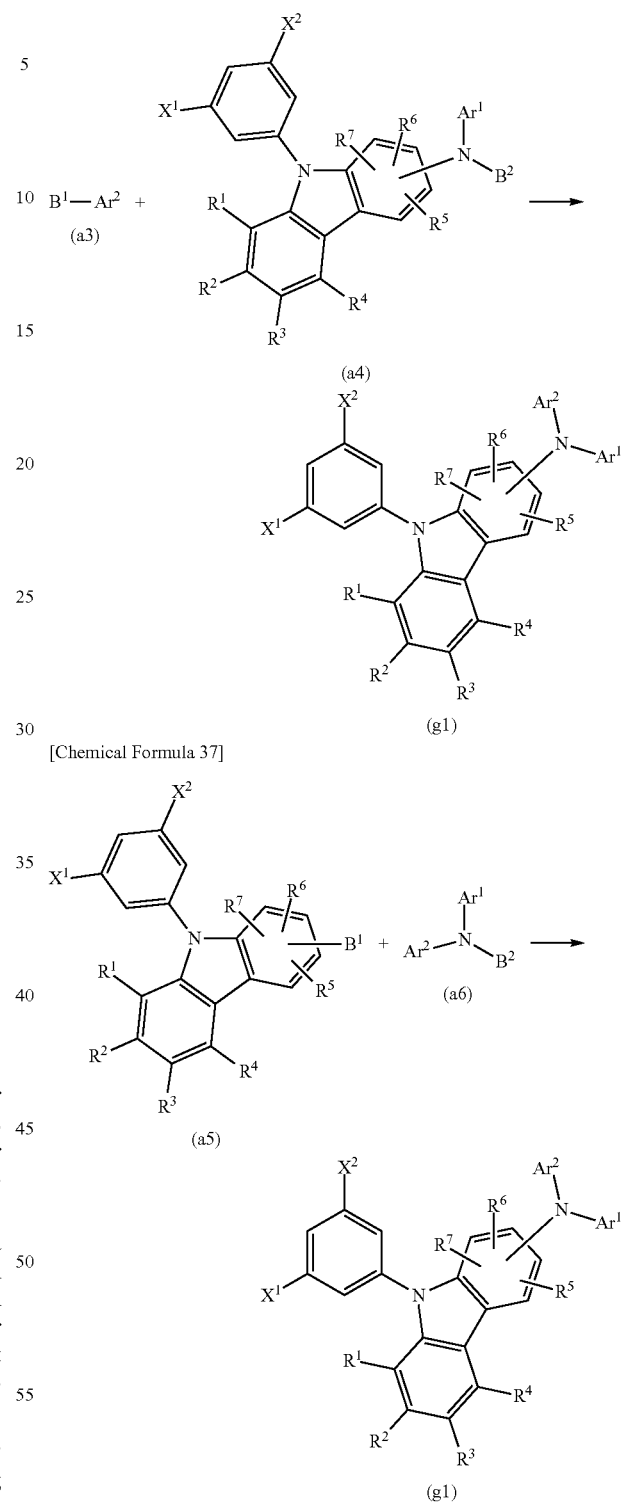

This reaction can proceed under various conditions; for example, a synthesis method in which a metal catalyst is used under the presence of a base can be employed. For example, Ullmann coupling or the Buchwald-Hartwig reaction can be used.

Note that n equivalents of the compound (a2) are reacted with the compound (a1) here; however, in the case where n is 2 or more, that is, two or more substituents shown in parentheses in the compound (G1) are bonded to each other and when the substituents are not the same, the different kinds of compounds (a2) may be reacted with the compounds (a1) separately.

In the case where n is 1, the organic compound represented by General Formula (g1) can be obtained by causing a cross coupling reaction of a compound (a3) and an arylamine compound (a4) or a cross coupling reaction of a compound (a5) and an arylamine compound (a6) as shown in the following synthesis schemes. Examples of $B^1$ include halogen such as chlorine, bromine, or iodine and a triflate group. Examples of $B^2$ include hydrogen and an organotin group.

The organic compound of one embodiment of the present invention can be synthesized in the above-described manner.

Embodiment 2

In this embodiment, a light-emitting device of one embodiment of the present invention will be described.

FIG. 1A illustrates a light-emitting device of one embodiment of the present invention. The light-emitting device of one embodiment of the present invention includes a first electrode 101, a second electrode 102, and an EL layer 103. The EL layer 103 includes the organic compound described in Embodiment 1.

The EL layer 103 includes a light-emitting layer 113, and the light-emitting layer 113 contains a light-emitting material. A hole-injection layer 111 and/or a hole-transport layer 112 are/is provided between the light-emitting layer 113 and the first electrode 101. The organic compound described in Embodiment 1 is preferably used as the light-emitting material because it exhibits blue fluorescence efficiently.

The light-emitting layer 113 may contain a host material in addition to the light-emitting material. The host material is an organic compound having a carrier-transport property. The light-emitting layer 113 may contain one or more kinds of host materials. When a plurality of kinds of host materials are contained, the plurality of organic compounds are preferably an organic compound having an electron-transport property and an organic compound having a hole-transport property, in which case the carrier balance in the light-emitting layer 113 can be adjusted. Alternatively, the plurality of organic compounds may be organic compounds having an electron-transport property, and when the electron-transport properties are different, the electron-transport property of the light-emitting layer 113 can also be adjusted. Proper adjustment of the carrier balance enables a long-life light-emitting device to be provided. In addition, the plurality of organic compounds that are host materials may form an exciplex, or the host material and the light-emitting material may form an exciplex. The exciplex having an appropriate emission wavelength allows efficient energy transfer to the light-emitting material, achieving a light-emitting device with a high efficiency and a long lifetime.

Note that in FIG. 1A, the EL layer 103 includes an electron-transport layer 114 and an electron-injection layer 115 in addition to the light-emitting layer 113, the hole-injection layer 111, and the hole-transport layer 112; however, the structure of the light-emitting device is not limited thereto. Any of these layers may be omitted or a layer having another function may be included.

Next, examples of specific structures and materials of the above-described light-emitting device will be described. As described above, the light-emitting device of one embodiment of the present invention includes, between the pair of electrodes of the first electrode 101 and the second electrode 102, the EL layer 103 including a plurality of layers; the EL layer 103 includes the organic compound disclosed in Embodiment 1 in any of the layers.

The first electrode 101 is preferably formed using any of metals, alloys, and conductive compounds with a high work function (specifically, higher than or equal to 4.0 eV), mixtures thereof, and the like. Specific examples include indium oxide-tin oxide (ITO: indium tin oxide), indium oxide-tin oxide containing silicon or silicon oxide, indium oxide-zinc oxide, and indium oxide containing tungsten oxide and zinc oxide (IWZO). Such conductive metal oxide films are usually formed by a sputtering method, but may be formed by application of a sol-gel method or the like. In an example of the formation method, indium oxide-zinc oxide is deposited by a sputtering method using a target obtained by adding 1 wt % to 20 wt % of zinc oxide to indium oxide. Furthermore, a film of indium oxide containing tungsten oxide and zinc oxide (IWZO) can be formed by a sputtering method using a target in which tungsten oxide and zinc oxide are added to indium oxide at 0.5 wt % to 5 wt % and 0.1 wt % to 1 wt %, respectively. Alternatively, gold (Au), platinum (Pt), nickel (Ni), tungsten (W), chromium (Cr), molybdenum (Mo), iron (Fe), cobalt (Co), copper (Cu), palladium (Pd), nitride of a metal material (e.g., titanium nitride), or the like can be used. Graphene can also be used. Note that when a composite material described later is used for a layer in the EL layer 103 that is in contact with the first electrode 101, an electrode material can be selected regardless of its work function.

Although the EL layer 103 preferably has a stacked-layer structure, there is no particular limitation on the stacked-layer structure, and various layers such as a hole-injection layer, a hole-transport layer, a light-emitting layer, an electron-transport layer, an electron-injection layer, a carrier-blocking layer, an exciton-blocking layer, and a charge-generation layer can be employed. Two kinds of stacked-layer structure of the EL layer 103 are described in this embodiment: the structure illustrated in FIG. 1A, which includes the electron-transport layer 114 and the electron-injection layer 115 in addition to the hole-injection layer 111, the hole-transport layer 112, and the light-emitting layer 113; and the structure illustrated in FIG. 1B, which includes the electron-transport layer 114 and a charge-generation layer 116 in addition to the hole-injection layer 111, the hole-transport layer 112, and the light-emitting layer 113. Materials for forming each layer will be specifically described below.

The hole-injection layer 111 contains a substance having an acceptor property. Either an organic compound or an inorganic compound can be used as the substance having an acceptor property.

As the substance having an acceptor property, it is possible to use a compound having an electron-withdrawing group (a halogen group or a cyano group); for example, 7,7,8,8-tetracyano-2,3,5,6-tetrafluoroquinodimethane (abbreviation: $F_4$-TCNQ), chloranil, 2,3,6,7,10,11-hexacyano-1,4,5,8,9,12-hexaazatriphenylene (abbreviation: HAT-CN), 1,3,4,5,7,8-hexafluorotetracyano-naphthoquinodimethane (abbreviation: F6-TCNNQ), or 2-(7-dicyanomethylene-1,3,4,5,6,8,9,10-octafluoro-7H-pyren-2-ylidene)malononitrile can be used. A compound in which electron-withdrawing groups are bonded to a condensed aromatic ring having a plurality of heteroatoms, such as HAT-CN, is particularly preferable because it is thermally stable. A [3]radialene derivative having an electron-withdrawing group (in particular, a cyano group or a halogen group such as a fluoro group) has a very high electron-accepting property and thus is preferable. Specific examples include α,α',α''-1,2,3-cyclopropanetriylidenetris[4-cyano-2,3,5,6-tetrafluorobenzeneacetonitrile], α,α',α''-1,2,3-cyclopropanetriylidenetris[2,6-dichloro-3,5-difluoro-4-(trifluoromethyl)benzeneacetonitrile], and α,α',α''-1,2,3-cyclopropanetriylidenetris[2,3,4,5,6-pentafluorobenzeneacetonitrile]. As the substance having an acceptor property, molybdenum oxide, vanadium oxide, ruthenium oxide, tungsten oxide, manganese oxide, or the like can be used, other than the above-described organic compounds. Alternatively, the hole-injection layer 111 can be formed using a phthalocyanine-based complex compound such as phthalocyanine (abbreviation: $H_2$Pc) and copper phthalocyanine (CuPc), an aromatic amine compound such as 4,4'-bis[N-(4-diphenylaminophenyl)-N-phenylamino]biphenyl (abbreviation: DPAB) and N,N'-bis{4-[bis(3-methylphenyl)amino]phenyl}-N,N'-diphenyl-(1,1'-biphenyl)-4,4'-diamine (abbreviation: DNTPD), or a high molecular compound such as poly(3,4-ethylenedioxythiophene)/poly(styrenesulfonic acid) (PEDOT/PSS). The substance having an acceptor property can extract electrons from an adjacent hole-transport layer (or hole-transport material) by the application of an electric field.

Alternatively, a composite material in which a material having a hole-transport property contains any of the aforementioned substances having an acceptor property can be used for the hole-injection layer 111. By using a composite material in which a material having a hole-transport property contains an acceptor substance, a material used to form an electrode can be selected regardless of its work function. In other words, besides a material having a high work function, a material having a low work function can be used for the first electrode 101.

As the material having a hole-transport property used for the composite material, any of a variety of organic compounds such as aromatic amine compounds, carbazole derivatives, aromatic hydrocarbons, and high molecular compounds (e.g., oligomers, dendrimers, or polymers) can be used. Note that the material having a hole-transport property used for the composite material preferably has a hole mobility of $1×10^{-6}$ cm$^2$Vs or higher. Organic compounds which can be used as the material having a hole-transport property in the composite material are specifically given below.

Examples of the aromatic amine compounds that can be used for the composite material include N,N-di(p-tolyl)-N,N-diphenyl-p-phenylenediamine (abbreviation: DTDPPA), 4,4'-bis[N-(4-diphenylaminophenyl)-N-phenylamino]biphenyl (abbreviation: DPAB), N,N'-bis{4-[bis(3-methylphenyl)amino]phenyl}-N,N-diphenyl-(1,1'-biphenyl)-4,4'-diamine (abbreviation: DNTPD), and 1,3,5-tris[N-(4-diphenylaminophenyl)-N-phenylamino]benzene (abbreviation: DPA3B). Specific examples of the carbazole derivative include 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), 4,4'-di(N-carbazolyl)biphenyl (abbreviation: CBP), 1,3,5-tris[4-(N-carbazolyl)phenyl]benzene (abbreviation: TCPB), 9-[4-(N-carbazolyl)]phenyl-10-phenylanthracene (abbreviation: CzPA), and 1,4-bis[4-(N-carbazolyl)phenyl]-2,3,5,6-tetraphenylbenzene. Examples of the aromatic hydrocarbon include 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, and 2,5,8,11-tetra (tert-butyl)perylene. Other examples include pentacene and coronene. The aromatic hydrocarbon may have a vinyl skeleton. Examples of the aromatic hydrocarbon having a vinyl group include 4,4'-bis(2,2-diphenylvinyl)biphenyl (abbreviation: DPVBi) and 9,10-bis[4-(2,2-diphenylvinyl)phenyl]anthracene (abbreviation: DPVPA).

Other examples include high molecular compounds such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N-phenylamino}phenyl)methacrylamide] (abbreviation: PTPDMA), and poly[N,N'-bis(4-butylphenyl)-N,N-bis(phenyl)benzidine] (abbreviation: poly-TPD).

The material having a hole-transport property that is used in the composite material further preferably has any of a carbazole skeleton, a dibenzofuran skeleton, a dibenzothiophene skeleton, and an anthracene skeleton. In particular, an aromatic amine having a substituent that includes a dibenzofuran ring or a dibenzothiophene ring, an aromatic monoamine that includes a naphthalene ring, or an aromatic monoamine in which a 9-fluorenyl group is bonded to nitrogen of amine through an arylene group may be used. Note that the second organic compound having an N,N-bis(4-biphenyl)amino group is preferable because a light-emitting device having a long lifetime can be fabricated. Specific examples of the second organic compound include N-(4-biphenyl)-6,N-diphenylbenzo[b]naphtho[1,2-d]furan-8-amine (abbreviation: BnfABP), N,N-bis(4-biphenyl)-6-phenylbenzo[b]naphtho[1,2-d]furan-8-amine (abbreviation: BBABnf), 4,4'-bis(6-phenylbenzo[b]naphtho[1,2-d]furan-8-yl)-4"-phenyltriphenylamine (abbreviation: BnfBB1BP), N,N-bis(4-biphenyl)benzo[b]naphtho[1,2-d]furan-6-amine (abbreviation: BBABnf(6)), N,N-bis(4-biphenyl)benzo[b]naphtho[1,2-d]furan-8-amine (abbreviation: BBABnf(8)), N,N-bis(4-biphenyl)benzo[b]naphtho[2,3-d]furan-4-amine (abbreviation: BBABnf(II) (4)), N,N-bis[4-(dibenzofuran-4-yl)phenyl]-4-amino-p-terphenyl (abbreviation: DBfBB1TP), N-[4-(dibenzothiophen-4-yl)phenyl]-N-phenyl-4-biphenylamine (abbreviation: ThBA1BP), 4-(2-naphthyl)-4',4"-diphenyltriphenylamine (abbreviation: BBAβNB), 4-[4-(2-naphthyl)phenyl]-4',4"-diphenyltriphenylamine (abbreviation: BBAβNBi), 4,4'-diphenyl-4"-(6;1'-binaphthyl-2-yl)triphenylamine (abbreviation: BBAαNβNB), 4,4'-diphenyl-4"-(7;1'-binaphthyl-2-yl)triphenylamine (abbreviation: BBAαNβNB-03), 4,4'-diphenyl-4"-(7-phenyl)naphthyl-2-yltriphenylamine (abbreviation: BBAPβNB-03), 4,4'-diphenyl-4"-(6;2-binaphthyl-2-yl)triphenylamine (abbreviation: BBA(βN2)B), 4,4'-diphenyl-4"-(7;2'-binaphthyl-2-yl)triphenylamine (abbreviation: BBA(βN2)B-03), 4,4'-diphenyl-4"-(4;2'-binaphthyl-1-yl)triphenylamine (abbreviation: BBAβNαNB), 4,4'-diphenyl-4"-(5;2'-binaphthyl-1-yl)triphenylamine (abbreviation: BBAβNαNB-02), 4-(4-biphenylyl)-4'-(2-naphthyl)-4"-phenyltriphenylamine (abbreviation: TPBiAPNB), 4-(3-biphenylyl)-4'-[4-(2-naphthyl)phenyl]-4"-phenyltriphenylamine (abbreviation: mTPBiAβNBi), 4-(4-biphenylyl)-4'-[4-(2-naphthyl)phenyl]-4"-phenyltriphenylamine (abbreviation: TPBiAPNBi), 4-phenyl-4'-(1-naphthyl)triphenylamine (abbreviation: αNBA1BP), 4,4'-bis(1-naphthyl)triphenylamine (abbreviation: aNBB1BP), 4,4'-diphenyl-4"-[4'-(carbazol-9-yl)biphenyl-4-yl]triphenylamine (abbreviation: YGTBi1BP), 4'-[4-(3-phenyl-9H-carbazol-9-yl)phenyl]tris (1,1'-biphenyl-4-yl)amine (abbreviation: YGTBi1BP-02), 4-[4'-(carbazol-9-yl)biphenyl-4-yl]-4'-(2-naphthyl)-4"-phenyltriphenylamine (abbreviation: YGTBiβNB), N-[4-(9-phenyl-9H-carbazol-3-yl)phenyl]-N-[4-(1-naphthyl)phenyl]-9,9'-spirobi[9H-fluoren]-2-amine (abbreviation: PCBNBSF), N,N-bis([1,1'-biphenyl]-4-yl)-9,9'-spirobi[9H-fluoren]-2-amine (abbreviation: BBASF), N,N-bis([1,1'-biphenyl]-4-yl)-9,9'-spirobi[9H-fluoren]-4-amine (abbreviation: BBASF(4)), N-(1,1'-biphenyl-2-yl)-N-(9,9-dimethyl-9H-fluoren-2-yl)-9,9'-spirobi[9H-fluoren]-4-amine (abbreviation: oFBiSF), N-(4-biphenyl)-N-(9,9-dimethyl-9H-fluoren-2-yl)dibenzofuran-4-amine (abbreviation: FrBiF), N-[4-(1-naphthyl)phenyl]-N-[3-(6-phenyldibenzofuran-4-yl)phenyl]-1-naphthylamine (abbreviation: mPDBfBNBN), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-[4-(9-phenylfluoren-9-yl)phenyl]triphenylamine (abbreviation: BPAFLBi), 4-phenyl-4'-(9-phenyl-9H-carbazol-3-yl)triphenylamine (abbreviation: PCBA1BP), 4,4'-diphenyl-4''-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4''-(9-phenyl-9H-carbazol-3-yl)triphenylamine (abbreviation: PCBNBB), N-phenyl-N-[4-(9-phenyl-9H-carbazol-3-yl)phenyl]-9,9'-spirobi[9H-fluoren]-2-amine (abbreviation: PCBASF), N-(1,1'-biphenyl-4-yl)-N-[4-(9-phenyl-9H-carbazol-3-yl)phenyl]-9,9-dimethyl-9H-fluoren-2-amine (abbreviation: PCBBiF), N,N-bis(9,9-dimethyl-9H-fluoren-2-yl)-9,9'-spirobi[9H-fluoren]-4-amine, N,N-bis(9,9-dimethyl-9H-fluoren-2-yl)-9,9'-spirobi[9H-fluoren]-3-amine, N,N-bis(9,9-dimethyl-9H-fluoren-2-yl)9,9'-spirobi[9H-fluoren]-2-amine, and N,N-bis(9,9-dimehtyl-9H-fluoren-2-yl)-9,9'-spirobi[9H-fluoren]-1-amine.

Note that it is further preferable that the material having a hole-transport property to be used in the composite material have a relatively deep HOMO level of greater than or equal to −5.7 eV and lower than or equal to −5.4 eV Using the hole-transport material with a relatively deep HOMO level in the composite material makes it easy to inject holes into the hole-transport layer 112 and to obtain a light-emitting device having a long lifetime.

Note that mixing the above composite material with a fluoride of an alkali metal or an alkaline earth metal (the proportion of fluorine atoms in a layer using the mixed material is preferably greater than or equal to 20%) can lower the refractive index of the layer. This also enables a layer with a low refractive index to be formed in the EL layer 103, leading to higher external quantum efficiency of the light-emitting device.

The formation of the hole-injection layer 111 can improve the hole-injection property, which allows the light-emitting device to be driven at a low voltage. In addition, the organic compound having an acceptor property is easy to use because it is easily deposited by vapor deposition.

The hole-transport layer 112 is formed using a material having a hole-transport property. The material having a hole-transport material preferably has a hole mobility higher than or equal to 1×10$^{-6}$ cm/Vs. Examples of the material having a hole-transport property include compounds having an aromatic amine skeleton such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP),4-phenyl-4'-(9-phenyl-9H-carbazol-3-yl)triphenylamine (abbreviation: PCBA1BP), 4,4'-diphenyl-4''-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4''-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), and N-phenyl-N-[4-(9-phenyl-9H-carbazol-3-yl)phenyl]-9,9'-spirobi[9H-fluoren]-2-amine (abbreviation: PCBASF); compounds having a carbazole skeleton such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), and 3,3'-bis(9-phenyl-9H-carbazole) (abbreviation: PCCP); compounds having a thiophene skeleton such as 4,4',4''-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV); and compounds having a furan skeleton such as 4,4',4''-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II). Among the above materials, the compound having an aromatic amine skeleton and the compound having a carbazole skeleton are preferable because these compounds are highly reliable and have high hole-transport properties to contribute to a reduction in driving voltage. Note that any of the substances given as examples of the material having a hole-transport property that is used in the composite material for the hole-injection layer 111 can also be suitably used as the material included in the hole-transport layer 112. The organic compound described in Embodiment 1 can be highly suitably used as a material of the hole-transport layer 112 because of its high hole-transport property. Furthermore, since the organic compound described in Embodiment 1 has a high hole-transport property, even when the hole-transport layer 112 is formed to have a large thickness of 100 nm or more, a light-emitting device with a small increase in driving voltage and favorable device characteristics can be provided. The large thickness of the hole-transport layer 112 facilitates appropriate formation of a microcavity structure because it allows the optical length between electrodes to be adjusted easily.

Since the organic compound described in Embodiment 1 has a low refractive index and includes a bulky alkyl group, a film with a low refractive index can be obtained. Thus, a light-emitting device including the organic compound can have high light extraction efficiency and high emission efficiency.

The light-emitting layer 113 includes a light-emitting substance and a host material. The light-emitting layer 113 may additionally include other materials. Alternatively, the light-emitting layer 113 may be a stack of two layers with different compositions.

The light-emitting substance may be a fluorescent substance, a phosphorescent substance, a substance exhibiting thermally activated delayed fluorescence (TADF), or any other light-emitting substance.

Examples of the fluorescent substance that can be used in the light-emitting layer 113 include 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N-diphenyl-N,N'-bis[4-(9-phenyl-9H-fluoren-9-yl)phenyl]pyrene-1,6-diamine (abbreviation: 1,6FLPAPm), N,N'-bis(3-methylphenyl)-N,N'-bis[3-(9-phenyl-9H-fluoren-9-yl)phenyl]pyrene-1,6-diamine (abbreviation: 1,6mMemFLPAPm), N,N-bis[4-(9H-carbazol-9-yl)phenyl]-N,N-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra(tert-butyl)perylene (abbreviation: TBP), 4-(10-phenyl-9-anthryl)-4'-(9-phenyl-9H-carbazol-3-yl)triphenylamine (abbreviation: PCBAPA), N,N'-(2-tert-butylanthracene-9,10-diyldi-4,1-phenylene)bis[N,N,N-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N,N-triphenyl-1,4-phenylenediamine (abbreviation: 2DPAPPA), N,N,N',N',N'',N'',N''',N'''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N,N-triphenyl-1,4-phenylenediamine (abbreviation: 2DPAPA), N-[9,10-bis(1,1'-biphenyl-2-yl)-2-anthryl]-N,N,N-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM), N,N'-(pyrene-1,6-diyl)bis[(6,N-diphenylbenzo[b]naphtho[1,2-d]furan)-8-amine] (abbreviation: 1,6BnfAPm-03), 3,10-bis[N-(9-phenyl-9H-carbazol-2-yl)-N-phenylamino]naphtho[2,3-b;6,7-b']bisbenzofuran (abbreviation: 3,10PCA2Nbf(IV)-02), and 3,10-bis[N-(dibenzofuran-3-yl)-N-phenylamino]naphtho[2,3-b;6,7-b']bisbenzofuran (abbreviation: 3,10FrA2Nbf(IV)-02). Condensed aromatic diamine compounds typified by pyrenediamine compounds such as 1,6FLPAPm, 1,6mMemFLPAPm, and 1,6BnfAPm-03 are particularly preferable because of their high hole-trapping properties, high emission efficiency, and high reliability. Other fluorescent substances can also be used.

The organic compound described in Embodiment 1 can also be used as the fluorescent substance. The light-emitting device of one embodiment of the present invention preferably includes the organic compound described in Embodiment 1. The organic compound described in Embodiment 1 is easy to purify and evaporate, and thus enables a highly reliable light-emitting device to be provided. Furthermore, the organic compound can have higher thermophysical properties while keeping high color purity, and thus enables a light-emitting device with high color purity and high reliability to be provided. Furthermore, a light-emitting device having a long driving lifetime at high temperature can be provided.

Examples of the material that can be used when a phosphorescent substance is used as the light-emitting substance in the light-emitting layer 113 are as follows: an organometallic iridium complex having a 4H-triazole skeleton, such as tris{2-[5-(2-methylphenyl)-4-(2,6-dimethylphenyl)-4H-1,2,4-triazol-3-yl-κN2]phenyl-κC}iridium(III) (abbreviation: [Ir(mpptz-dmp)$_3$]), tris(5-methyl-3,4-diphenyl-4H-1,2,4-triazolato)iridium(III) (abbreviation: [Ir(Mptz)$_3$]), and tris[4-(3-biphenyl)-5-isopropyl-3-phenyl-4H-1,2,4-triazolato]iridium(III) (abbreviation: [Ir(iPrptz-3b)$_3$]); an organometallic iridium complex having a 1H-triazole skeleton, such as tris[3-methyl-1-(2-methylphenyl)-5-phenyl-TH-1,2,4-triazolato]iridium(III) (abbreviation: [Ir(Mptz1-mp)$_3$]) and tris(1-methyl-5-phenyl-3-propyl-1H-1,2,4-triazolato)iridium(III) (abbreviation: [Ir(Prptz1-Me)$_3$]); an organometallic iridium complex having an imidazole skeleton, such as fac-tris[1-(2,6-diisopropylphenyl)-2-phenyl-1H-imidazole]iridium(III) (abbreviation: [Ir(iPrpmi)$_3$]) and tris[3-(2,6-dimethylphenyl)-7-methylimidazo[1,2-f]phenanthridinato]iridium(III) (abbreviation: [Ir(dmpimpt-Me)$_3$]); and an organometallic iridium complex in which a phenylpyridine derivative having an electron-withdrawing group is a ligand, such as bis[2-(4',6'-difluorophenyl)pyridinato-N,C$^{2'}$]iridium(III) tetrakis(1-pyrazolyl)borate (abbreviation: FIr6), bis[2-(4',6'-difluorophenyl)pyridinato-N,C$^{2'}$]iridium(III) picolinate (abbreviation: FIrpic), bis{2-[3',5'-bis(trifluoromethyl)phenyl]pyridinato-N,C$^{2'}$}iridium(III) picolinate (abbreviation: [Ir(CF$_3$ppy)$_2$(pic)]), and bis[2-(4',6'-difluorophenyl)pyridinato-N,C$^{2'}$]iridium(III) acetylacetonate (abbreviation: FIr(acac)). These compounds emit blue phosphorescence and have an emission spectrum peak at 440 nm to 520 nm.

Other examples include an organometallic iridium complex having a pyrimidine skeleton, such as tris(4-methyl-6-phenylpyrimidinato)iridium(III) (abbreviation: [Ir(mppm)$_3$]), tris(4-t-butyl-6-phenylpyrimidinato)iridium(III) (abbreviation: [Ir(tBuppm)$_3$]), (acetylacetonato)bis(6-methyl-4-phenylpyrimidinato)iridium(III) (abbreviation: [Ir(mppm)$_2$(acac)]), (acetylacetonato)bis(6-tert-butyl-4-phenylpyrimidinato)iridium(III) (abbreviation: [Ir(tBuppm)$_2$(acac)]), (acetylacetonato)bis[6-(2-norbornyl)-4-phenylpyrimidinato]iridium(III) (abbreviation: [Ir(nbppm)$_2$(acac)]), (acetylacetonato)bis[5-methyl-6-(2-methylphenyl)-4-phenylpyrimidinato]iridium(III) (abbreviation: [Ir(mpmppm)$_2$(acac)]), and (acetylacetonato)bis(4,6-diphenylpyrimidinato)iridium(III) (abbreviation: [Ir(dppm)$_2$(acac)]); an organometallic iridium complex having a pyrazine skeleton, such as (acetylacetonato)bis(3,5-dimethyl-2-phenylpyrazinato)iridium(III) (abbreviation: [Ir(mppr-Me)$_2$(acac)]) and (acetylacetonato)bis(5-isopropyl-3-methyl-2-phenylpyrazinato)iridium(III) (abbreviation: [Ir(mppr-iPr)$_2$(acac)]); an organometallic iridium complex having a pyridine skeleton, such as tris(2-phenylpyridinato-N,C$^{2'}$)iridium(III) (abbreviation: [Ir(ppy)$_3$]), bis(2-phenylpyridinato-N,C$^{2'}$)iridium(III) acetylacetonate (abbreviation: [Ir(ppy)$_2$(acac)]), bis(benzo[h]quinolinato)iridium(III) acetylacetonate (abbreviation: [Ir(bzq)$_2$(acac)]), tris(benzo[h]quinolinato)iridium(III) (abbreviation: [Ir(bzq)$_3$]), tris(2-phenylquinolinato-N,C$^{2'}$)iridium(III) (abbreviation: [Ir(pq)$_3$]), bis(2-phenylquinolinato-N,C$^{2'}$)iridium(III) acetylacetonate (abbreviation: [Ir(pq)$_2$(acac)]), [2-d3-methyl-8-(2-pyridinyl-κN)benzofuro[2,3-b]pyridine-κC]bis[2-(5-d3-methyl-2-pyridinyl-κN)phenyl-κC]iridium(III) (abbreviation: [Ir(5mppy-d3)$_2$(mbfpypy-d3)]), [2-d3-methyl-(2-pyridinyl-κN)benzofuro[2,3-b]pyridine-κC]bis[2-(2-pyridinyl-κN)phenyl-κC]iridium(III) (abbreviation: [Ir(ppy)$_2$(mbfpypy-d3)]); and a rare earth metal complex such as tris(acetylacetonato) (monophenanthroline)terbium(III) (abbreviation: [Tb(acac)$_3$(Phen)]). These are mainly compounds that exhibit green phosphorescence and have an emission spectrum peak at 500 nm to 600 nm. Note that an organometallic iridium complex having a pyrimidine skeleton has distinctively high reliability and emission efficiency and thus is particularly preferable.

Other examples include organometallic iridium complexes having a pyrimidine skeleton, such as (diisobutyrylmethanato)bis[4,6-bis(3-methylphenyl)pyrimidinato]iridium(III) (abbreviation: [Ir(5mdppm)$_2$(dibm)]), bis[4,6-bis(3-methylphenyl)pyrimidinato](dipivaloylmethanato)iridium(III) (abbreviation: [Ir(5mdppm)$_2$(dpm)]), and bis[4,6-di(naphthalen-1-yl)pyrimidinato(dipivaloylmethanato)iridium(III) (abbreviation: [Ir(d1npm)$_2$(dpm)]); organometallic iridium complexes having a pyrazine skeleton, such as (acetylacetonato)bis(2,3,5-triphenylpyrazinato)iridium(III) (abbreviation: [Ir(tppr)$_2$(acac)]), bis(2,3,5-triphenylpyrazinato)(dipivaloylmethanato)iridium(III) (abbreviation: [Ir(tppr)$_2$(dpm)]), and (acetylacetonato)bis[2,3-bis(4-fluorophenyl)quinoxalinato]iridium(III) (abbreviation: [Ir(Fdpq)$_2$(acac)]); organometallic iridium complexes having a pyridine skeleton, such as tris(1-phenylisoquinolinato-N,C$^2$)iridium(III) (abbreviation: [Ir(piq)$_3$]) and bis(1-phenylisoquinolinato-N,C$^2$)iridium(III) acetylacetonate (abbreviation: [Ir(piq)$_2$(acac)]); platinum complexes such as 2,3,7,8,12,13,17,18-octaethyl-21H,23H-porphyrinplatinum(II) (abbreviation: PtOEP); and rare earth metal complexes such as tris(1,3-diphenyl-1,3-propanedionato) (monophenanthroline)europium(III) (abbreviation: [Eu(DBM)$_3$(Phen)]) and tris[1-(2-thenoyl)-3,3,3-trifluoroacetonato(monophenanthroline)europium(III) (abbreviation: [Eu(TTA)$_3$(Phen)]). These compounds emit red phosphorescence having an emission spectrum peak at 600 nm to 700 nm. Furthermore, the organometallic iridium complexes having a pyrazine skeleton can provide red light emission with favorable chromaticity.

Besides the above phosphorescent compounds, known phosphorescent substances may be selected and used.

Examples of the TADF material include a fullerene, a derivative thereof, an acridine, a derivative thereof, and an eosin derivative. Furthermore, a metal-containing porphyrin, such as a porphyrin containing magnesium (Mg), zinc (Zn), cadmium (Cd), tin (Sn), platinum (Pt), indium (In), or palladium (Pd), can be given. Examples of the metal-containing porphyrin include a protoporphyrin-tin fluoride complex (SnF$_2$(Proto IX)), a mesoporphyrin-tin fluoride complex (SnF$_2$(Meso IX)), a hematoporphyrin-tin fluoride complex (SnF$_2$(Hemato IX)), a coproporphyrin tetramethyl ester-tin fluoride complex (SnF$_2$(Copro III-4Me)), an octaethylporphyrin-tin fluoride complex (SnF$_2$(OEP)), an etioporphyrin-tin fluoride complex (SnF$_2$(Etio I)), and an octaethylporphyrin-platinum chloride complex (PtCl$_2$OEP), which are represented by the following structural formulae.

[Chemical Formula 38]

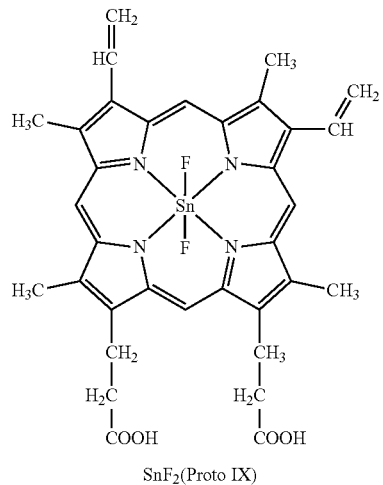

SnF$_2$(Proto IX)

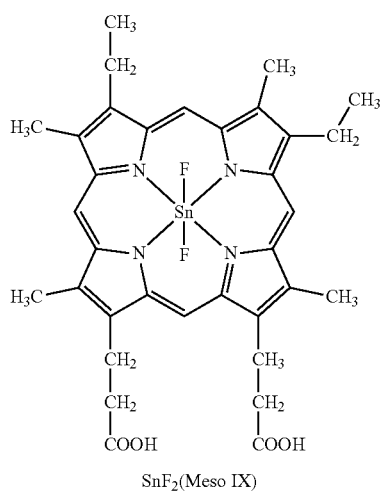

SnF$_2$(Meso IX)

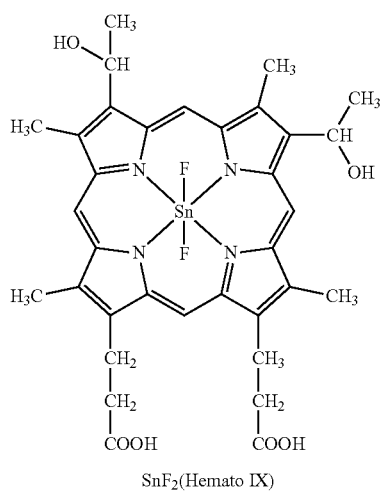

SnF$_2$(Hemato IX)

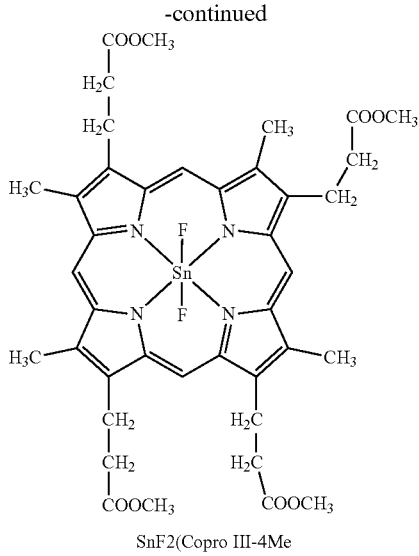

SnF2(Copro III-4Me)

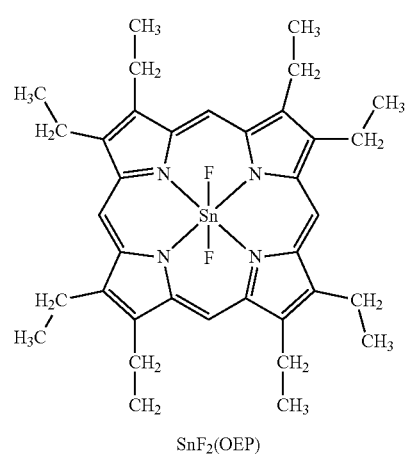

SnF2(OEP)

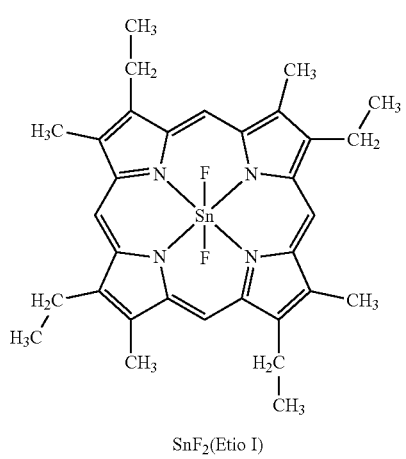

SnF2(Etio I)

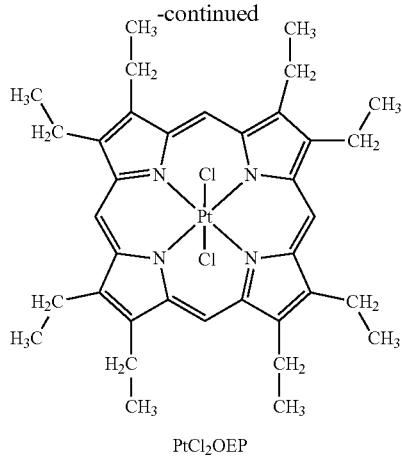

PtCl2OEP

It is also possible to use a heterocyclic compound having one or both of a π-electron rich heteroaromatic ring and a π-electron deficient heteroaromatic ring that is represented by the following structural formulae, such as 2-(biphenyl-4-yl)-4,6-bis(12-phenylindolo[2,3-a]carbazol-11-yl)-1,3,5-triazine (abbreviation: PIC-TRZ), 9-(4,6-diphenyl-1,3,5-triazin-2-yl)-9'-phenyl-9H,9'H-3,3'-bicarbazole (abbreviation: PCCzTzn), 2-{4-[3-(N-phenyl-9H-carbazol-3-yl)-9H-carbazol-9-yl]phenyl}-4,6-diphenyl-1,3,5-triazine (abbreviation: PCCzPTzn), 2-[4-(10H-phenoxazine-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), or 10-phenyl-10H,10'H-spiro[acridin-9,9'-anthracen]-10'-one (abbreviation: ACRSA). Such a heterocyclic compound is preferable because of having excellent electron-transport and hole-transport properties owing to a π-electron rich heteroaromatic ring and a π-electron deficient heteroaromatic ring. Among skeletons having the π-electron deficient heteroaromatic ring, a pyridine skeleton, a diazine skeleton (a pyrimidine skeleton, a pyrazine skeleton, and a pyridazine skeleton), and a triazine skeleton are preferred because of their high stability and reliability. In particular, a benzofuropyrimidine skeleton, a benzothienopyrimidine skeleton, a benzofuropyrazine skeleton, and a benzothienopyrazine skeleton are preferred because of their high accepting properties and high reliability. Among skeletons having the i-electron rich heteroaromatic ring, an acridine skeleton, a phenoxazine skeleton, a phenothiazine skeleton, a furan skeleton, a thiophene skeleton, and a pyrrole skeleton have high stability and reliability; therefore, at least one of these skeletons is preferably included. A dibenzofuran skeleton is preferable as a furan skeleton, and a dibenzothiophene skeleton is preferable as a thiophene skeleton. As a pyrrole skeleton, an indole skeleton, a carbazole skeleton, an indolocarbazole skeleton, a bicarbazole skeleton, and a 3-(9-phenyl-9H-carbazol-3-yl)-9H-carbazole skeleton are particularly preferable. Note that a substance in which the π-electron rich heteroaromatic ring is directly bonded to the π-electron deficient heteroaromatic ring is particularly preferred because the electron-donating property of the i-electron rich heteroaromatic ring and the electron-accepting property of the π-electron deficient heteroaromatic ring are both improved, the energy difference between the S1 level and the T1 level becomes small, and thus thermally activated delayed fluorescence can be obtained with high efficiency. Note that an aromatic ring to which an electron-withdrawing group such as a cyano group is bonded may be used instead of the π-electron deficient heteroaromatic ring. As a t-electron rich skeleton, an aromatic amine skeleton, a phenazine skeleton, or the like can be used. As a π-electron deficient skeleton, a xanthene skeleton, a thioxanthene dioxide skeleton, an oxadiazole skeleton, a triazole skeleton, an imidazole skeleton, an anthraquinone skeleton, a skeleton containing boron such as phenylborane or boranthrene, an aromatic ring or a heteroaromatic ring having a cyano group or a nitrile group such as benzonitrile or cyanobenzene, a carbonyl skeleton such as benzophenone, a phosphine oxide skeleton, a sulfone skeleton, or the like can be used. As described above, a π-electron deficient skeleton and a π-electron rich skeleton can be used instead of at least one of the π-electron deficient heteroaromatic ring and the π-electron rich heteroaromatic ring.

[Chemical Formula 39]

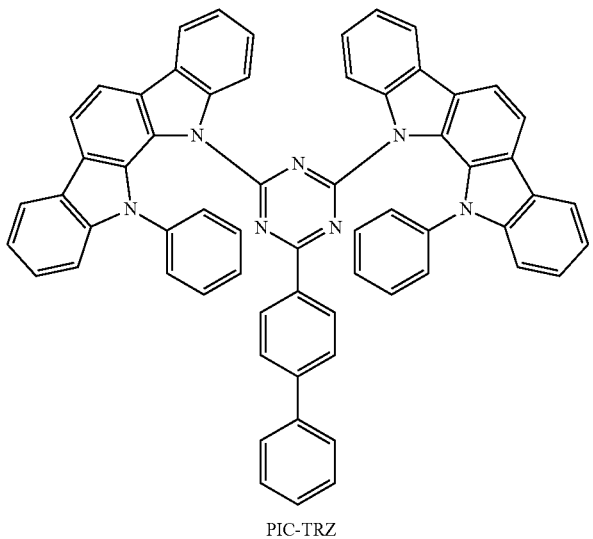

PIC-TRZ

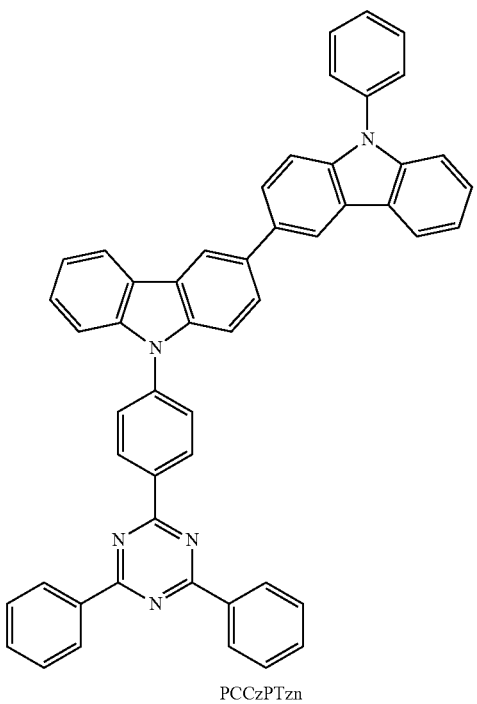

PCCzPTzn

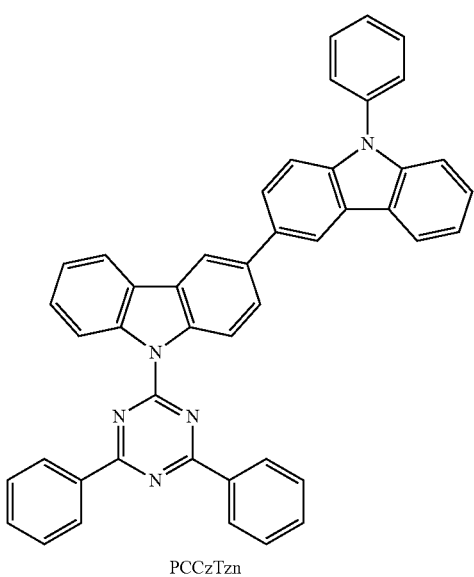

PCCzTzn

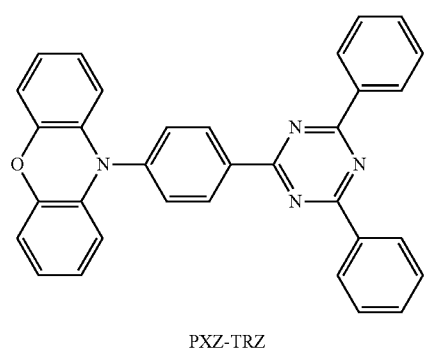

PXZ-TRZ

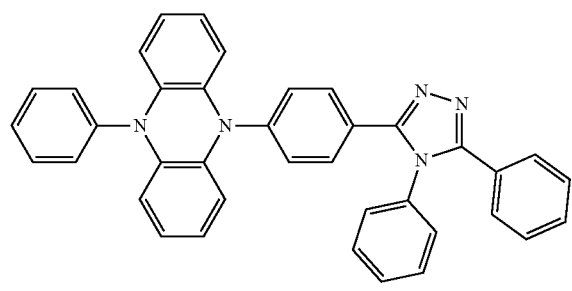

PPZ-3TPT

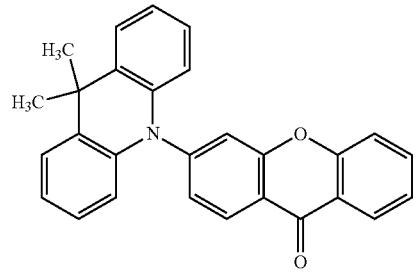

ACRXTN

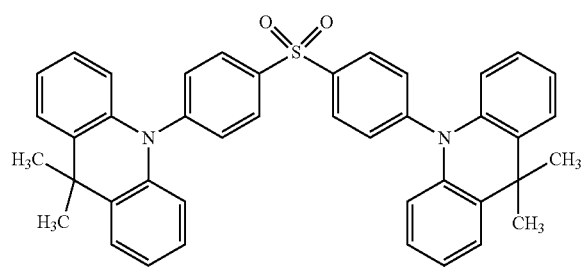

DMAC-DPS

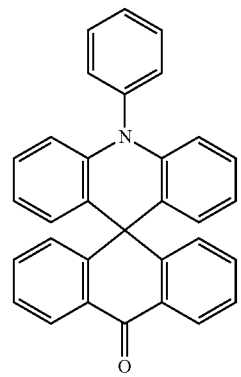

ACRSA

Note that the TADF material is a material having a small difference between the S1 level and the T1 level and a function of converting triplet excitation energy into singlet excitation energy by reverse intersystem crossing. Thus, the TADF material can upconvert triplet excitation energy into singlet excitation energy (i.e., reverse intersystem crossing) using a small amount of thermal energy and efficiently generate a singlet excited state. In addition, the triplet excitation energy can be converted into luminescence.

An exciplex whose excited state is formed of two kinds of substances has an extremely small difference between the S1 level and the T1 level and functions as a TADF material capable of converting triplet excitation energy into singlet excitation energy.

A phosphorescent spectrum observed at a low temperature (e.g., 77 K to 10 K) is used for an index of the T1 level. When the level of energy with a wavelength of the line obtained by extrapolating a tangent to the fluorescent spectrum at a tail on the short wavelength side is the S1 level and the level of energy with a wavelength of the line obtained by extrapolating a tangent to the phosphorescent spectrum at a tail on the short wavelength side is the T1 level, the difference between the S1 level and the T1 level of the TADF material is preferably smaller than or equal to 0.3 eV, further preferably smaller than or equal to 0.2 eV.

When a TADF material is used as the light-emitting substance, the S1 level of the host material is preferably higher than that of the TADF material. In addition, the T1 level of the host material is preferably higher than that of the TADF material.

As the host material in the light-emitting layer, various carrier-transport materials such as materials having an electron-transport property, materials having a hole-transport property, and the TADF materials can be used.

The material having a hole-transport property is preferably an organic compound having an amine skeleton or a π-electron rich heteroaromatic ring skeleton. Examples of the material include compounds having an aromatic amine skeleton such as 4,4'-bis[N-(1-naphthyl)-N-phenylamino]biphenyl (abbreviation: NPB), N,N-bis(3-methylphenyl)-N, N-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), and N-phenyl-N-[4-(9-phenyl-9H-carbazol-3-yl)phenyl]spiro-9,9'-bifluoren-2-amine (abbreviation: PCBASF); compounds having a carbazole skeleton such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), and 3,3'-bis(9-phenyl-9H-carbazole) (abbreviation: PCCP); compounds having a thiophene skeleton such as 4,4',4"-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV); and compounds having a furan skeleton such as 4,4',4"-(benzene-1,3,5-triyl)tri(dibenzofuran) (abbreviation: DBF3P-II) and 4-{3-[3-(9-phenyl-9H-fluoren-9-yl)

phenyl]phenyl}dibenzofuran (abbreviation: mmDBFFLBi-II). Among the above materials, the compound having an aromatic amine skeleton and the compound having a carbazole skeleton are preferable because these compounds are highly reliable and have high hole-transport properties to contribute to a reduction in driving voltage.

As the material having an electron-transport property, metal complexes such as bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ); or an organic compound having a π-electron deficient heteroaromatic ring skeleton is preferable. Examples of the organic compound having a π-electron deficient heteroaromatic ring skeleton include 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2',2"-(1,3,5-benzenetriyl)tris(1-phenyl-TH-benzimidazole) (abbreviation: TPBI), and 2-[3-(dibenzothiophen-4-yl)phenyl]-1-phenyl-1H-benzimidazole (abbreviation: mDBTBIm-II); heterocyclic compounds having a diazine skeleton, such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 4,6-bis[3-(phenanthren-9-yl)phenyl]pyrimidine (abbreviation: 4,6mPnP2Pm), 4,6-bis[3-(4-dibenzothienyl)phenyl]pyrimidine (abbreviation: 4,6mDBTP2Pm-II), and 4,8-bis[3-(dibenzothiophen-4-yl)phenyl]-benzo[h]quinazoline (abbreviation: 4,8mDBtP2Bqn); and heterocyclic compounds having a pyridine skeleton, such as 3,5-bis[3-(9H-carbazol-9-yl)phenyl]pyridine (abbreviation: 35DCzPPy) and 1,3,5-tri[3-(3-pyridyl)phenyl]benzene (abbreviation: TmPyPB). Among the above materials, the heterocyclic compound having a diazine skeleton and the heterocyclic compound having a pyridine skeleton have high reliability and thus are preferable. In particular, the heterocyclic compound having a diazine (pyrimidine or pyrazine) skeleton has a high electron-transport property to contribute to a reduction in driving voltage.

As the TADF material that can be used as the host material, the above materials mentioned as the TADF material can also be used. When the TADF material is used as the host material, triplet excitation energy generated in the TADF material is converted into singlet excitation energy by reverse intersystem crossing and transferred to the light-emitting substance, whereby the emission efficiency of the light-emitting device can be increased. Here, the TADF material functions as an energy donor, and the light-emitting substance functions as an energy acceptor.

This is very effective in the case where the light-emitting substance is a fluorescent substance. In that case, the S level of the TADF material is preferably higher than that of the fluorescent substance in order that high emission efficiency be achieved. Furthermore, the T1 level of the TADF material is preferably higher than the S1 level of the fluorescent substance. Therefore, the T1 level of the TADF material is preferably higher than that of the fluorescent substance.

It is also preferable to use a TADF material that emits light whose wavelength overlaps with the wavelength on a low-est-energy-side absorption band of the fluorescent substance. This enables smooth transfer of excitation energy from the TADF material to the fluorescent substance and accordingly enables efficient light emission, which is preferable.

In addition, in order to efficiently generate singlet excitation energy from the triplet excitation energy by reverse intersystem crossing, carrier recombination preferably occurs in the TADF material. It is also preferable that the triplet excitation energy generated in the TADF material not be transferred to the triplet excitation energy of the fluorescent substance. For that reason, the fluorescent substance preferably has a protective group around a luminophore (a skeleton which causes light emission) of the fluorescent substance. As the protective group, a substituent having no 7 bond and a saturated hydrocarbon are preferably used. Specific examples include an alkyl group having 3 to 10 carbon atoms, a substituted or unsubstituted cycloalkyl group having 3 to 10 carbon atoms, and a trialkylsilyl group having 3 to 10 carbon atoms. It is further preferable that the fluorescent substance have a plurality of protective groups. The substituents having no 7 bond are poor in carrier transport performance, whereby the TADF material and the luminophore of the fluorescent substance can be made away from each other with little influence on carrier transportation or carrier recombination. Here, the luminophore refers to an atomic group (skeleton) that causes light emission in a fluorescent substance. The luminophore is preferably a skeleton having a 7 bond, further preferably includes an aromatic ring, and still further preferably includes a condensed aromatic ring or a condensed heteroaromatic ring. Examples of the condensed aromatic ring or the condensed heteroaromatic ring include a phenanthrene skeleton, a stilbene skeleton, an acridone skeleton, a phenoxazine skeleton, and a phenothiazine skeleton. Specifically, a fluorescent substance having any of a naphthalene skeleton, an anthracene skeleton, a fluorene skeleton, a chrysene skeleton, a triphenylene skeleton, a tetracene skeleton, a pyrene skeleton, a perylene skeleton, a coumarin skeleton, a quinacridone skeleton, and a naphthobisbenzofuran skeleton is preferred because of its high fluorescence quantum yield.

In the case where a fluorescent substance is used as the light-emitting substance, a material having an anthracene skeleton is favorably used as the host material. The use of a substance having an anthracene skeleton as the host material for the fluorescent substance makes it possible to obtain a light-emitting layer with high emission efficiency and high durability. Among the substances having an anthracene skeleton, a substance having a diphenylanthracene skeleton, in particular, a substance having a 9,10-diphenylanthracene skeleton, is chemically stable and thus is preferably used as the host material. The host material preferably has a carbazole skeleton because the hole-injection and hole-transport properties are improved; further preferably, the host material has a benzocarbazole skeleton in which a benzene ring is further condensed to carbazole because the HOMO level thereof is shallower than that of carbazole by approximately 0.1 eV and thus holes enter the host material easily. In particular, the host material preferably has a dibenzocarbazole skeleton because the HOMO level thereof is shallower than that of carbazole by approximately 0.1 eV so that holes enter the host material easily, the hole-transport property is improved, and the heat resistance is increased. Accordingly, a substance that has both a 9,10-diphenylanthracene skeleton and a carbazole skeleton (or a benzocarbazole or dibenzocarbazole skeleton) is further preferable as the host material. Note that in terms of the hole-injection and hole-transport properties described above, instead of a carbazole skeleton, a benzofluorene skeleton or a dibenzo fluorene skeleton may be used. Examples of such a substance include 9-phenyl-3-[4-(10-phenyl-9-anthryl)phenyl]-9H-carbazole (abbreviation: PCzPA), 3-[4-(1-naphthyl)-phenyl]-9-phenyl-9H-carbazole (abbreviation: PCPN), 9-[4-(10-phenyl-9-anthracenyl)phenyl]-9H-carbazole (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d]furan (abbreviation: 2mBnfPPA), 9-phenyl-10-{4-(9-phenyl-9H-fluoren-9-yl)biphenyl-4'-yl}anthracene (abbreviation: FLPPA), and 9-(1-naphthyl)-10-[4-(2-naphthyl)phenyl]anthracene (abbreviation: αN-PNPAnth). In particular, CzPA, cgDBCzPA, 2mBnfPPA, and PCzPA have excellent characteristics and thus are preferably selected.

Note that the host material may be a mixture of a plurality of kinds of substances; in the case of using a mixed host material, it is preferable to mix a material having an electron-transport property with a material having a hole-transport property. By mixing the material having an electron-transport property with the material having a hole-transport property, the transport property of the light-emitting layer 113 can be easily adjusted and a recombination region can be easily controlled. The weight ratio of the content of the material having a hole-transport property to the content of the material having an electron-transport property may be 1:19 to 19:1. Note that the organic compounds described in Embodiment 1 can be suitably used as an electron-transport material in the mixed host material.

Note that a phosphorescent substance can be used as part of the mixed material. When a fluorescent substance is used as the light-emitting substance, a phosphorescent substance can be used as an energy donor for supplying excitation energy to the fluorescent substance.

An exciplex may be formed of these mixed materials. When these mixed materials are selected so as to form an exciplex that exhibits light emission whose wavelength overlaps with the wavelength on a lowest-energy-side absorption band of the light-emitting substance, energy can be transferred smoothly and light emission can be obtained efficiently, which is preferable. The use of such a structure is preferable because the driving voltage can also be reduced.

Note that at least one of the materials forming an exciplex may be a phosphorescent substance. In this case, triplet excitation energy can be efficiently converted into singlet excitation energy by reverse intersystem crossing.

In order to form an exciplex efficiently, a material having an electron-transport property and a material having a hole-transport property and a HOMO level higher than or equal to that of the material having an electron-transport property are preferably used in combination. In addition, the LUMO level of the material having a hole-transport property is preferably higher than or equal to the LUMO level of the material having an electron-transport property. Note that the LUMO levels and the HOMO levels of the materials can be derived from the electrochemical characteristics (the reduction potentials and the oxidation potentials) of the materials that are measured by cyclic voltammetry (CV).

The formation of an exciplex can be confirmed by a phenomenon in which the emission spectrum of the mixed film in which the material having a hole-transport property and the material having an electron-transport property are mixed is shifted to the longer wavelength side than the emission spectrum of each of the materials (or has another peak on the longer wavelength side) observed by comparison of the emission spectra of the material having a hole-transport property, the material having an electron-transport property, and the mixed film of these materials, for example. Alternatively, the formation of an exciplex can be confirmed by a difference in transient response, such as a phenomenon in which the transient PL lifetime of the mixed film has more long lifetime components or has a larger proportion of delayed components than that of each of the materials, observed by comparison of transient photoluminescence (PL) of the material having a hole-transport property, the material having an electron-transport property, and the mixed film of the materials. The transient PL can be rephrased as transient electroluminescence (EL). That is, the formation of an exciplex can also be confirmed by a difference in transient response observed by comparison of the transient EL of the material having a hole-transport property, the material having an electron-transport property, and the mixed film of the materials.

The electron-transport layer 114 contains a substance having an electron-transport property. As the substance having an electron-transport property, it is possible to use any of the above-listed substances having electron-transport properties that can be used as the host material.

The electron mobility of the material included in the electron-transport layer 114 in the case where the square root of the electric field strength [V/cm] is 600 is preferably higher than or equal to $1 \times 10$ cm$^2$/Vs and lower than or equal to $5 \times 10^{-5}$ cm$^2$/Vs. The amount of electrons injected into the light-emitting layer can be controlled by the reduction in the electron-transport property of the electron-transport layer 114, whereby the light-emitting layer can be prevented from having excess electrons. The electron-transport layer 114 preferably includes a material having an electron-transport property and an alkali metal, an alkaline earth metal, a compound thereof, or a complex thereof. It is particularly preferable that this structure be employed when the hole-injection layer is formed using a composite material that includes a material having a hole-transport property with a relatively deep HOMO level of −5.7 eV or higher and −5.4 eV or lower, in which case the light-emitting device can have a long lifetime. In this case, the material having an electron-transport property preferably has a HOMO level of −6.0 eV or higher. The material having an electron-transport property is preferably an organic compound having an anthracene skeleton and further preferably an organic compound having both an anthracene skeleton and a heterocyclic skeleton. The heterocyclic skeleton is preferably a nitrogen-containing five-membered ring skeleton or a nitrogen-containing six-membered ring skeleton, and particularly preferably a nitrogen-containing five-membered ring skeleton or a nitrogen-containing six-membered ring skeleton including two heteroatoms in the ring, such as a pyrazole ring, an imidazole ring, an oxazole ring, a thiazole ring, a pyrazine ring, a pyrimidine ring, or a pyridazine ring. In addition, it is preferable that the alkali metal, the alkaline earth metal, the compound thereof, or the complex thereof have a 8-hydroxyquinolinato structure. Specific examples include 8-hydroxyquinolinato-lithium (abbreviation: Liq) and 8-hydroxyquinolinato-sodium (abbreviation: Naq). In particular, a complex of a monovalent metal ion, especially a complex of lithium is preferable, and Liq is further preferable. Note that in the case where the 8-hydroxyquinolinato structure is included, a methyl-substituted product (e.g., a 2-methyl-substituted product or a 5-methyl-substituted product) of the alkali metal, the alkaline earth metal, the compound, or the complex can also be used. There is preferably a difference in the concentration (including 0) of the alkali metal, the alkaline earth metal, the compound thereof, or the complex thereof in the electron-transport layer in the thickness direction.

A layer containing an alkali metal, an alkaline earth metal, or a compound thereof such as lithium fluoride (LiF), cesium fluoride (CsF), calcium fluoride (CaF$_2$), or 8-hydroxyquinolinatolithium (Liq) may be provided as the electron-injection layer 115 between the electron-transport layer 114 and the second electrode 102. As the electron-injection layer 115, an electride or a layer that is formed using a substance having an electron-transport property and that includes an alkali metal, an alkaline earth metal, or a compound thereof can be used. Examples of the electride include a substance in which electrons are added at high concentration to calcium oxide-aluminum oxide.

Note that as the electron-injection layer 115, it is possible to use a layer that contains a substance having an electron-transport property (preferably an organic compound having a bipyridine skeleton) and contains a fluoride of the alkali metal or the alkaline earth metal at a concentration higher than that at which the electron-injection layer 115 becomes in a microcrystalline state (50 wt % or higher). Since the layer has a low refractive index, a light-emitting device including the layer can have high external quantum efficiency.

Figure 1B:
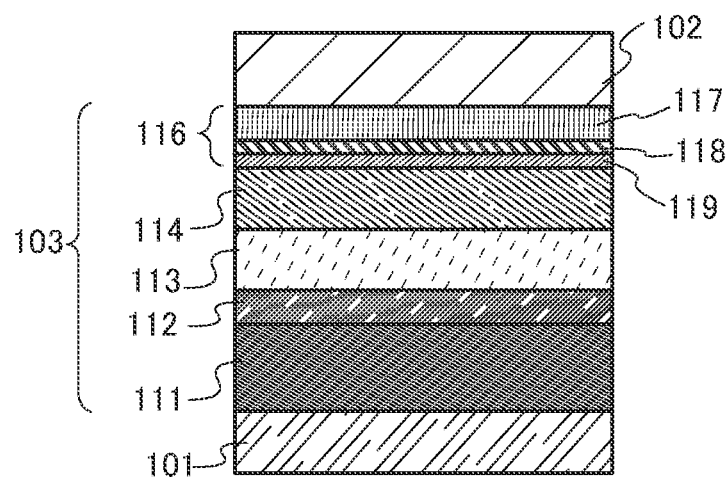

Instead of the electron-injection layer 115, the charge-generation layer 116 may be provided (FIG. 1B). The charge-generation layer 116 refers to a layer capable of injecting holes into a layer in contact with the cathode side of the charge-generation layer 116 and electrons into a layer in contact with the anode side thereof when a potential is applied. The charge-generation layer 116 includes at least a p-type layer 117. The p-type layer 117 is preferably formed using any of the composite materials given above as examples of materials that can be used for the hole-injection layer 111. The p-type layer 117 may be formed by stacking a film containing the above-described acceptor material as a material included in the composite material and a film containing a hole-transport material. When a potential is applied to the p-type layer 117, electrons are injected into the electron-transport layer 114 and holes are injected into the second electrode 102 serving as a cathode; thus, the light-emitting device operates. Since the organic compound of one embodiment of the present invention has a low refractive index, using the organic compound for the p-type layer 117 enables the light-emitting device to have high external quantum efficiency.

Note that the charge-generation layer 116 preferably includes an electron-relay layer 118 and/or an electron-injection buffer layer 119 in addition to the p-type layer 117.

The electron-relay layer 118 includes at least the substance having an electron-transport property and has a function of preventing an interaction between the electron-injection buffer layer 119 and the p-type layer 117 and smoothly transferring electrons. The LUMO level of the substance having an electron-transport property contained in the electron-relay layer 118 is preferably between the LUMO level of the acceptor substance in the p-type layer 117 and the LUMO level of a substance contained in a layer of the electron-transport layer 114 that is in contact with the charge-generation layer 116. As a specific value of the energy level, the LUMO level of the substance having an electron-transport property in the electron-relay layer 118 is preferably higher than or equal to −5.0 eV, more preferably higher than or equal to −5.0 eV and lower than or equal to −3.0 eV Note that as the substance having an electron-transport property in the electron-relay layer 118, a phthalocyanine-based material or a metal complex having a metal-oxygen bond and an aromatic ligand is preferably used.

A substance having a high electron-injection property can be used for the electron-injection buffer layer 119; for example, an alkali metal, an alkaline earth metal, a rare earth metal, or a compound thereof (an alkali metal compound (including an oxide such as lithium oxide, a halide, and a carbonate such as lithium carbonate and cesium carbonate), an alkaline earth metal compound (including an oxide, a halide, and a carbonate), or a rare earth metal compound (including an oxide, a halide, and a carbonate)) can be used.

In the case where the electron-injection buffer layer 119 contains the substance having an electron-transport property and a donor substance, an organic compound such as tetrathianaphthacene (abbreviation: TTN), nickelocene, or decamethylnickelocene can be used as the donor substance, as well as an alkali metal, an alkaline earth metal, a rare earth metal, a compound thereof (e.g., an alkali metal compound (including an oxide such as lithium oxide, a halide, and a carbonate such as lithium carbonate and cesium carbonate), an alkaline earth metal compound (including an oxide, a halide, and a carbonate), or a rare earth metal compound (including an oxide, a halide, and a carbonate)). As the substance having an electron-transport property, a material similar to the above-described material for the electron-transport layer 114 can be used.

For the second electrode 102, a metal, an alloy, an electrically conductive compound, or a mixture thereof each having a low work function (specifically, lower than or equal to 3.8 eV) or the like can be used. Specific examples of such a cathode material are elements belonging to Group 1 or 2 of the periodic table, such as alkali metals (e.g., lithium (Li) and cesium (Cs)), magnesium (Mg), calcium (Ca), and strontium (Sr), alloys containing these elements (e.g., MgAg and AlLi), rare earth metals such as europium (Eu) and ytterbium (Yb), and alloys containing these rare earth metals. However, when the electron-injection layer is provided between the second electrode 102 and the electron-transport layer, for the second electrode 102, a variety of conductive materials such as Al, Ag, ITO, or indium oxide-tin oxide containing silicon or silicon oxide can be used regardless of the work function. Films of these conductive materials can be formed by a dry process such as a vacuum evaporation method or a sputtering method, an ink-jet method, a spin coating method, or the like. Alternatively, a wet process using a sol-gel method or a wet process using a paste of a metal material may be employed.

Furthermore, any of a variety of methods can be used for forming the EL layer 103, regardless of a dry method or a wet method. For example, a vacuum evaporation method, a gravure printing method, an offset printing method, a screen printing method, an ink-jet method, a spin coating method, or the like may be used.

Different methods may be used to form the electrodes or the layers described above.

The structure of the layers provided between the first electrode 101 and the second electrode 102 is not limited to the above-described structure. Preferably, a light-emitting region where holes and electrons recombine is positioned away from the first electrode 101 and the second electrode 102 so as to prevent quenching due to the proximity of the light-emitting region and a metal used for electrodes and carrier-injection layers.

Furthermore, in order that transfer of energy from an exciton generated in the light-emitting layer can be suppressed, preferably, the hole-transport layer and the electron-transport layer which are in contact with the light-emitting layer 113, particularly a carrier-transport layer closer to the recombination region in the light-emitting layer 113, are formed using a substance having a wider band gap than the light-emitting material of the light-emitting layer or the light-emitting material included in the light-emitting layer.

Next, an embodiment of a light-emitting device with a structure in which a plurality of light-emitting units are stacked (this type of light-emitting device is also referred to as a stacked or tandem light-emitting device) is described with reference to FIG. 1C. This light-emitting device includes a plurality of light-emitting units between an anode and a cathode. One light-emitting unit has substantially the same structure as the EL layer 103 illustrated in FIG. TA. In other words, the light-emitting device illustrated in FIG. 1A or 1B includes a single light-emitting unit, and the light-emitting device illustrated in FIG. 1C includes a plurality of light-emitting units.

Figure 1C:
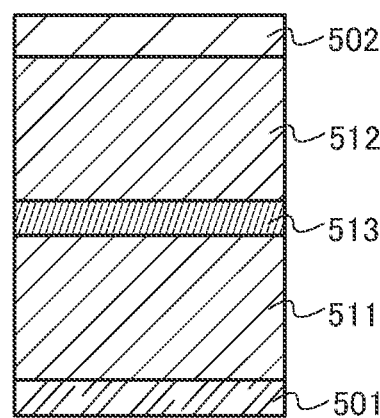

In FIG. 1C, a first light-emitting unit 511 and a second light-emitting unit 512 are stacked between an anode 501 and a cathode 502, and a charge-generation layer 513 is provided between the first light-emitting unit 511 and the second light-emitting unit 512. The anode 501 and the cathode 502 correspond, respectively, to the first electrode 101 and the second electrode 102 illustrated in FIG. TA, and the materials given in the description for FIG. TA can be used. Furthermore, the first light-emitting unit 511 and the second light-emitting unit 512 may have the same structure or different structures.

The charge-generation layer 513 has a function of injecting electrons into one of the light-emitting units and injecting holes into the other of the light-emitting units when a voltage is applied between the anode 501 and the cathode 502. That is, in FIG. 1C, the charge-generation layer 513 injects electrons into the first light-emitting unit 511 and holes into the second light-emitting unit 512 when a voltage is applied so that the potential of the anode becomes higher than the potential of the cathode.

The charge-generation layer 513 preferably has a structure similar to that of the charge-generation layer 116 described with reference to FIG. 1B. A composite material of an organic compound and a metal oxide has an excellent carrier-injection property and an excellent carrier-transport property; thus, low-voltage driving and low-current driving can be achieved. In the case where the anode-side surface of a light-emitting unit is in contact with the charge-generation layer 513, the charge-generation layer 513 can also function as a hole-injection layer of the light-emitting unit; therefore, a hole-injection layer is not necessarily provided in the light-emitting unit.

In the case where the charge-generation layer 513 includes the electron-injection buffer layer 119, the electron-injection buffer layer 119 functions as the electron-injection layer in the light-emitting unit on the anode side and thus, an electron-injection layer is not necessarily formed in the light-emitting unit on the anode side.

The light-emitting device having two light-emitting units is described with reference to FIG. 1C; however, one embodiment of the present invention can also be applied to a light-emitting device in which three or more light-emitting units are stacked. When a plurality of light-emitting units partitioned by the charge-generation layer 513 are provided between a pair of electrodes as in the light-emitting device of this embodiment, it is possible to provide a long-life device which can emit light with high luminance at a low current density. Alight-emitting apparatus which can be driven at a low voltage and has low power consumption can be provided.

When the emission colors of the light-emitting units are different, light emission of a desired color can be obtained from the light-emitting device as a whole. For example, in a light-emitting device having two light-emitting units, the emission colors of the first light-emitting unit may be red and green and the emission color of the second light-emitting unit may be blue, so that the light-emitting device can emit white light as the whole.

The above-described layers and electrodes such as the EL layer 103, the first light-emitting unit 511, the second light-emitting unit 512, and the charge-generation layer 513 can be formed by a method such as an evaporation method (including a vacuum evaporation method), a droplet discharge method (also referred to as an ink-jet method), a coating method, or a gravure printing method. A low molecular material, a middle molecular material (including an oligomer and a dendrimer), or a high molecular material may be included in the layers and electrodes.

Embodiment 3

In this embodiment, a light-emitting apparatus including the light-emitting device described in Embodiment 2 is described.

In this embodiment, the light-emitting apparatus manufactured using the light-emitting device described in Embodiment 2 is described with reference to FIGS. 2A and 2B. Note that FIG. 2A is a top view of the light-emitting apparatus and FIG. 2B is a cross-sectional view taken along the lines A-B and C-D in FIG. 2A. This light-emitting apparatus includes a driver circuit portion (source line driver circuit) 601, a pixel portion 602, and a driver circuit portion (gate line driver circuit) 603, which are to control light emission of a light-emitting device and illustrated with dotted lines. Reference numeral 604 denotes a sealing substrate; 605, a sealing material; and 607, a space surrounded by the sealing material 605.

Reference numeral 608 denotes a lead wiring for transmitting signals to be input to the source line driver circuit 601 and the gate line driver circuit 603 and receiving signals such as a video signal, a clock signal, a start signal, and a reset signal from a flexible printed circuit (FPC) 609 serving as an external input terminal. Although only the FPC is illustrated here, a printed wiring board (PWB) may be attached to the FPC. The light-emitting apparatus in the present specification includes, in its category, not only the light-emitting apparatus itself but also the light-emitting apparatus provided with the FPC or the PWB.

Next, a cross-sectional structure is described with reference to FIG. 2B. The driver circuit portions and the pixel portion are formed over an element substrate 610; here, the source line driver circuit 601, which is a driver circuit portion, and one pixel in the pixel portion 602 are illustrated.

The element substrate 610 may be a substrate containing glass, quartz, an organic resin, a metal, an alloy, or a semiconductor or a plastic substrate formed offiber reinforced plastic (FRP), poly(vinyl fluoride) (PVF), polyester, or acrylic resin.

The structure of transistors used in pixels and driver circuits is not particularly limited. For example, inverted staggered transistors may be used, or staggered transistors may be used. Furthermore, top-gate transistors or bottom-gate transistors may be used. A semiconductor material used for the transistors is not particularly limited, and for example, silicon, germanium, silicon carbide, gallium nitride, or the like can be used. Alternatively, an oxide semiconductor containing at least one of indium, gallium, and zinc, such as an In—Ga—Zn-based metal oxide, may be used.

There is no particular limitation on the crystallinity of a semiconductor material used for the transistors, and an amorphous semiconductor or a semiconductor having crystallinity (a microcrystalline semiconductor, a polycrystalline semiconductor, a single crystal semiconductor, or a semiconductor partly including crystal regions) may be used. A semiconductor having crystallinity is preferably used because deterioration of the transistor characteristics can be suppressed.

Here, an oxide semiconductor is preferably used for semiconductor devices such as the transistors provided in the pixels and driver circuits and transistors used for touch sensors described later, and the like. In particular, an oxide semiconductor having a wider band gap than silicon is preferably used. When an oxide semiconductor having a wider band gap than silicon is used, off-state current of the transistors can be reduced.

The oxide semiconductor preferably contains at least indium (In) or zinc (Zn). Further preferably, the oxide semiconductor contains an oxide represented by an In-M-Zn-based oxide (M represents a metal such as Al, Ti, Ga, Ge, Y, Zr, Sn, La, Ce, or Hf).

As a semiconductor layer, it is particularly preferable to use an oxide semiconductor film including a plurality of crystal parts whose c-axes are aligned perpendicular to a surface on which the semiconductor layer is formed or the top surface of the semiconductor layer and in which the adjacent crystal parts have no grain boundary.

The use of such materials for the semiconductor layer makes it possible to provide a highly reliable transistor in which a change in the electrical characteristics is suppressed.

Charge accumulated in a capacitor through a transistor including the above-described semiconductor layer can be held for a long time because of the low off-state current of the transistor. When such a transistor is used in a pixel, operation of a driver circuit can be stopped while a gray scale of an image displayed in each display region is maintained. As a result, an electronic device with extremely low power consumption can be obtained.

For stable characteristics of the transistor, a base film is preferably provided. The base film can be formed with a single layer or stacked layers using an inorganic insulating film such as a silicon oxide film, a silicon nitride film, a silicon oxynitride film, or a silicon nitride oxide film. The base film can be formed by a sputtering method, a chemical vapor deposition (CVD) method (e.g., a plasma CVD method, a thermal CVD method, or a metal organic CVD (MOCVD) method), an atomic layer deposition (ALD) method, a coating method, a printing method, or the like. Note that the base film is not necessarily provided.

Note that an FET 623 is illustrated as a transistor formed in the driver circuit portion 601. The driver circuit may be formed with any of a variety of circuits such as a CMOS circuit, a PMOS circuit, or an NMOS circuit. Although a driver integrated type in which the driver circuit is formed over the substrate is illustrated in this embodiment, the driver circuit is not necessarily formed over the substrate, and the driver circuit can be formed outside, not over the substrate.

The pixel portion 602 includes a plurality of pixels including a switching FET 611, a current controlling FET 612, and a first electrode 613 electrically connected to a drain of the current controlling FET 612. One embodiment of the present invention is not limited to the structure. The pixel portion 602 may include three or more FETs and a capacitor in combination.

Note that an insulator 614 is formed to cover an end portion of the first electrode 613. Here, the insulator 614 can be formed using a positive photosensitive acrylic resin film.

In order to improve the coverage with an EL layer or the like which is formed later, the insulator 614 is formed to have a curved surface with curvature at its upper or lower end portion. For example, in the case where positive photosensitive acrylic resin is used as a material of the insulator 614, only the upper end portion of the insulator 614 preferably has a curved surface with a curvature radius (0.2 m to 3 m). As the insulator 614, either a negative photosensitive resin or a positive photosensitive resin can be used.

An EL layer 616 and a second electrode 617 are formed over the first electrode 613. Here, as a material used for the first electrode 613 functioning as an anode, a material having a high work function is preferably used. For example, a single-layer film of an ITO film, an indium tin oxide film containing silicon, an indium oxide film containing zinc oxide at 2 wt % to 20 wt %, a titanium nitride film, a chromium film, a tungsten film, a Zn film, a Pt film, or the like, a stack of a titanium nitride film and a film containing aluminum as its main component, a stack of three layers of a titanium nitride film, a film containing aluminum as its main component, and a titanium nitride film, or the like can be used. The stacked-layer structure enables low wiring resistance, favorable ohmic contact, and a function as an anode.

The EL layer 616 is formed by any of a variety of methods such as an evaporation method using an evaporation mask, an inkjet method, and a spin coating method. The EL layer 616 has the structure described in Embodiment 2. As another material included in the EL layer 616, a low molecular compound or a high molecular compound (including an oligomer or a dendrimer) may be used.

As a material used for the second electrode 617, which is formed over the EL layer 616 and functions as a cathode, a material having a low work function (e.g., Al, Mg, Li, and Ca, or an alloy or a compound thereof, such as MgAg, MgIn, and AlLi) is preferably used. In the case where light generated in the EL layer 616 is transmitted through the second electrode 617, a stack of a thin metal film and a transparent conductive film (e.g., ITO, indium oxide containing zinc oxide at 2 wt % to 20 wt %, indium tin oxide containing silicon, or zinc oxide (ZnO)) is preferably used for the second electrode 617.

Note that the light-emitting device is formed with the first electrode 613, the EL layer 616, and the second electrode 617. The light-emitting device is the light-emitting device described in Embodiment 2. In the light-emitting apparatus of this embodiment, the pixel portion, which includes a plurality of light-emitting devices, may include both the light-emitting device described in Embodiment 2 and a light-emitting device having a different structure.

The sealing substrate 604 is attached to the element substrate 610 with the sealing material 605, so that a light-emitting device 618 is provided in the space 607 surrounded by the element substrate 610, the sealing substrate 604, and the sealing material 605. The space 607 may be filled with a filler, or may be filled with an inert gas (such as nitrogen or argon), or the sealing material. It is preferable that the sealing substrate be provided with a recessed portion and a drying agent be provided in the recessed portion, in which case deterioration due to influence of moisture can be suppressed.

An epoxy-based resin or glass frit is preferably used for the sealing material 605. It is preferable that such a material transmit moisture or oxygen as little as possible. As the sealing substrate 604, a glass substrate, a quartz substrate, or a plastic substrate formed of fiber reinforced plastic (FRP), poly(vinyl fluoride) (PVF), polyester, and acrylic resin can be used.

Although not illustrated in FIGS. 2A and 2B, a protective film may be provided over the second electrode. As the protective film, an organic resin film or an inorganic insulating film may be formed. The protective film may be formed so as to cover an exposed portion of the sealing material 605. The protective film may be provided so as to cover surfaces and side surfaces of the pair of substrates and exposed side surfaces of a sealing layer, an insulating layer, and the like.

The protective film can be formed using a material that does not easily transmit an impurity such as water. Thus, diffusion of an impurity such as water from the outside into the inside can be effectively suppressed.

As a material of the protective film, an oxide, a nitride, a fluoride, a sulfide, a ternary compound, a metal, a polymer, or the like can be used. For example, the material may contain aluminum oxide, hafnium oxide, hafnium silicate, lanthanum oxide, silicon oxide, strontium titanate, tantalum oxide, titanium oxide, zinc oxide, niobium oxide, zirconium oxide, tin oxide, yttrium oxide, cerium oxide, scandium oxide, erbium oxide, vanadium oxide, indium oxide, aluminum nitride, hafnium nitride, silicon nitride, tantalum nitride, titanium nitride, niobium nitride, molybdenum nitride, zirconium nitride, gallium nitride, a nitride containing titanium and aluminum, an oxide containing titanium and aluminum, an oxide containing aluminum and zinc, a sulfide containing manganese and zinc, a sulfide containing cerium and strontium, an oxide containing erbium and aluminum, an oxide containing yttrium and zirconium, or the like.

The protective film is preferably formed using a deposition method with favorable step coverage. One such method is an atomic layer deposition (ALD) method. A material that can be deposited by an ALD method is preferably used for the protective film. A dense protective film having reduced defects such as cracks or pinholes or a uniform thickness can be formed by an ALD method. Furthermore, damage caused to a process member in forming the protective film can be reduced.

By an ALD method, a uniform protective film with few defects can be formed even on, for example, a surface with a complex uneven shape or upper, side, and lower surfaces of a touch panel.

As described above, the light-emitting apparatus manufactured using the light-emitting device described in Embodiment 2 can be obtained.

The light-emitting apparatus in this embodiment is manufactured using the light-emitting device described in Embodiment 2 and thus can have favorable characteristics. Specifically, since the light-emitting device described in Embodiment 2 has high emission efficiency, the light-emitting apparatus can achieve low power consumption.

Figures 3A, 3B:
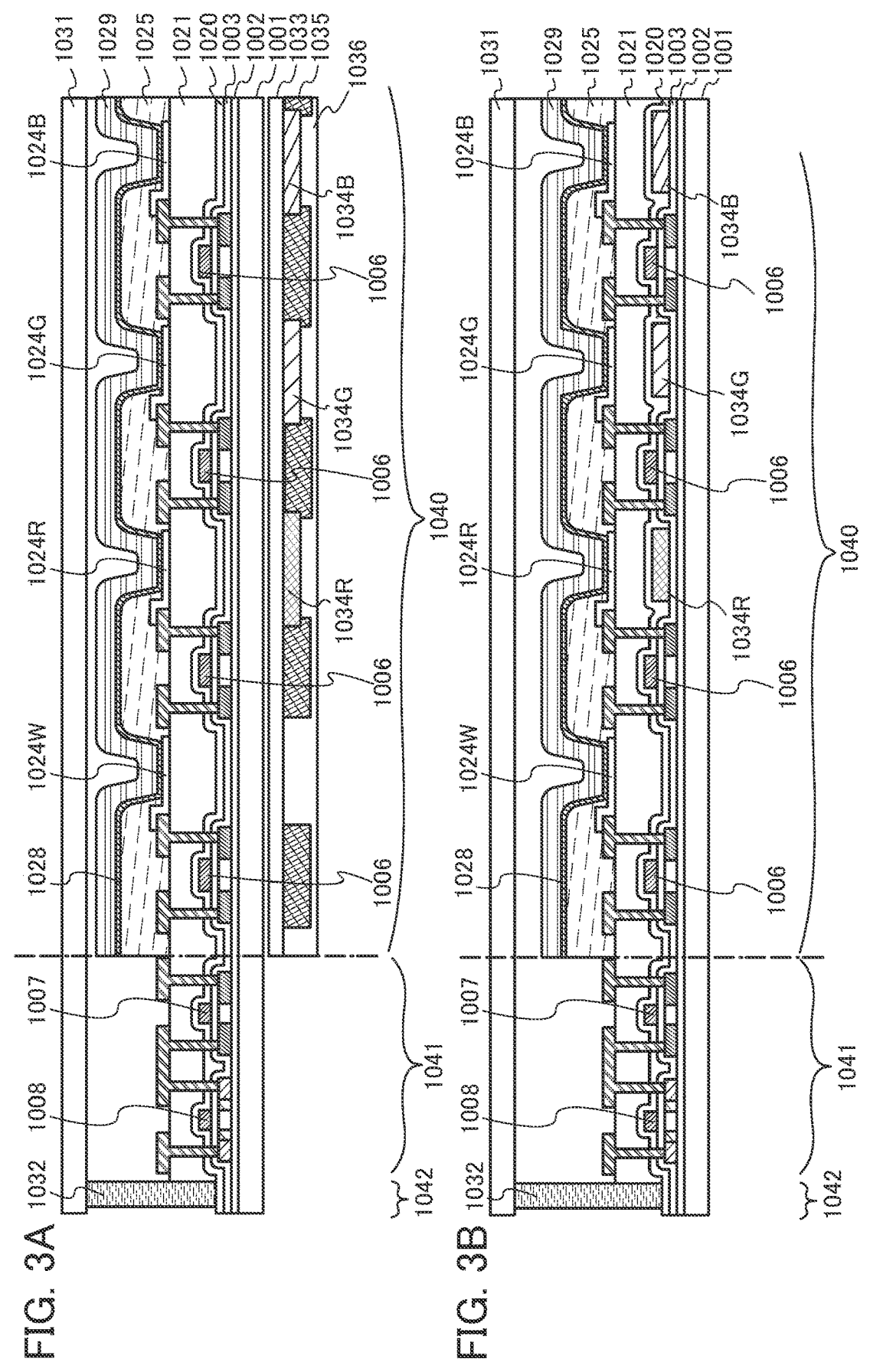

FIGS. 3A and 3B each illustrate an example of a light-emitting apparatus in which full color display is achieved by formation of a light-emitting device exhibiting white light emission and with the use of coloring layers (color filters) and the like. FIG. 3A illustrates a substrate 1001, a base insulating film 1002, a gate insulating film 1003, gate electrodes 1006, 1007, and 1008, a first interlayer insulating film 1020, a second interlayer insulating film 1021, a peripheral portion 1042, a pixel portion 1040, a driver circuit portion 1041, first electrodes 1024W, 1024R, 1024G, and 1024B of light-emitting devices, a partition 1025, an EL layer 1028, a second electrode 1029 of the light-emitting devices, a sealing substrate 1031, a sealing material 1032, and the like.

In FIG. 3A, coloring layers (a red coloring layer 1034R, a green coloring layer 1034G, and a blue coloring layer 1034B) are provided on a transparent base material 1033. A black matrix 1035 may be additionally provided. The transparent base material 1033 provided with the coloring layers and the black matrix is aligned and fixed to the substrate 1001. Note that the coloring layers and the black matrix 1035 are covered with an overcoat layer 1036. In FIG. 3A, light emitted from part of the light-emitting layer does not pass through the coloring layers, while light emitted from the other part of the light-emitting layer passes through the coloring layers. Since the light that does not pass through the coloring layers is white and the light that passes through any one of the coloring layers is red, green, or blue, an image can be displayed using pixels of the four colors.

FIG. 3B illustrates an example in which the coloring layers (the red coloring layer 1034R, the green coloring layer 1034G, and the blue coloring layer 1034B) are provided between the gate insulating film 1003 and the first interlayer insulating film 1020. As in the structure, the coloring layers may be provided between the substrate 1001 and the sealing substrate 1031.

Figure 4:
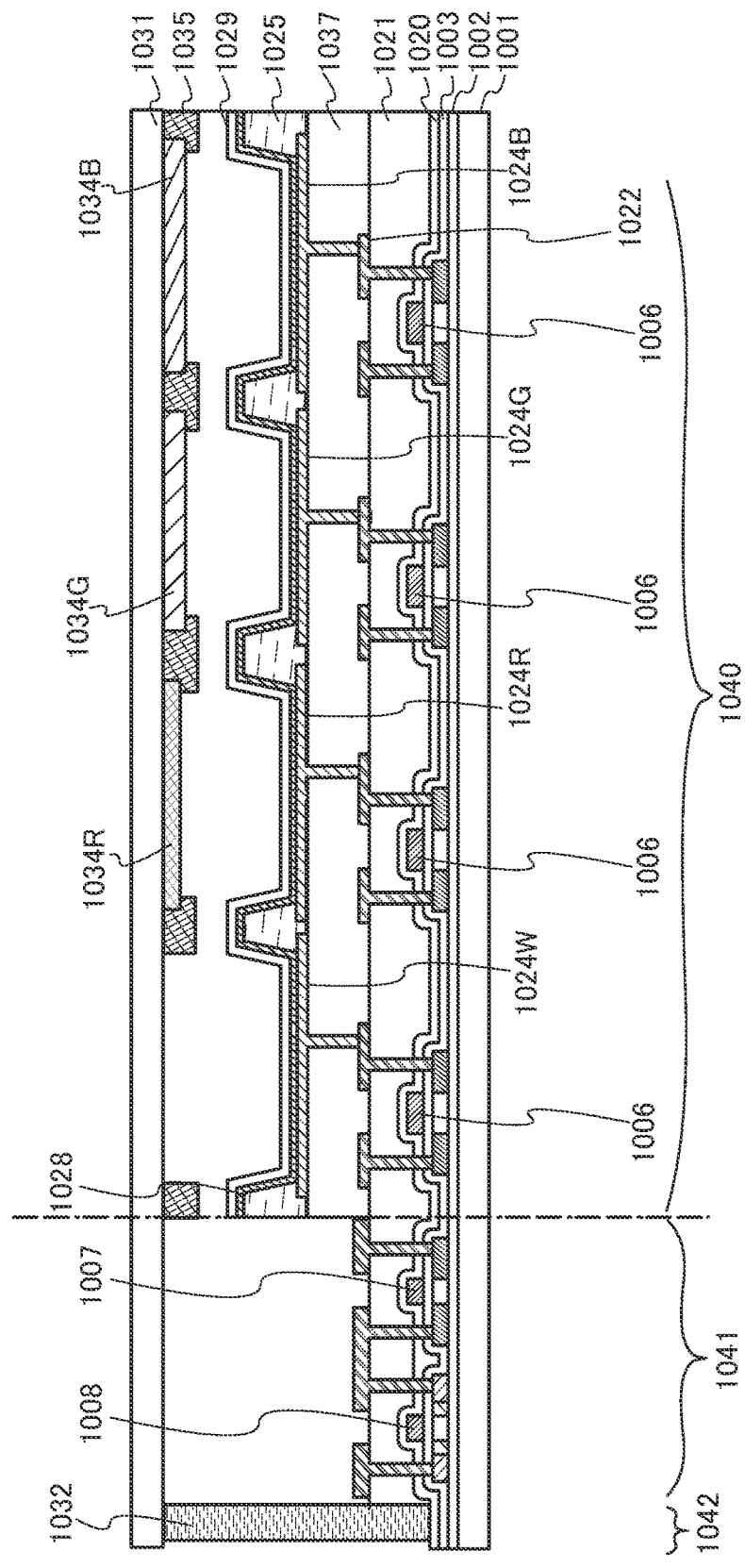
FIG. 4 is a conceptual view of an active matrix light-emitting apparatus.

The above-described light-emitting apparatus is a light-emitting apparatus having a structure in which light is extracted from the substrate 1001 side where FETs are formed (a bottom emission structure), but may be a light-emitting apparatus having a structure in which light is extracted from the sealing substrate 1031 side (a top emission structure). FIG. 4 is a cross-sectional view of a light-emitting apparatus having a top emission structure. In this case, a substrate that does not transmit light can be used as the substrate 1001. The process up to the step of forming a connection electrode which connects the FET and the anode of the light-emitting device is performed in a manner similar to that of the light-emitting apparatus having a bottom emission structure. Then, a third interlayer insulating film 1037 is formed to cover the electrode 1022. This insulating film may have a planarization function. The third interlayer insulating film 1037 can be formed using a material similar to that of the second interlayer insulating film, and can alternatively be formed using any of other known materials.

The first electrodes 1024W, 1024R, 1024G, and 1024B of the light-emitting devices each serve as an anode here, but may serve as a cathode. Furthermore, in the case of a light-emitting apparatus having a top emission structure as illustrated in FIG. 4, the first electrodes are preferably reflective electrodes. The EL layer 1028 is formed to have a structure similar to the structure of the EL layer 103, which is described in Embodiment 2, with which white light emission can be obtained.

In the case of a top emission structure as illustrated in FIG. 4, sealing can be performed with the sealing substrate 1031 on which the coloring layers (the red coloring layer 1034R, the green coloring layer 1034G, and the blue coloring layer 1034B) are provided. The sealing substrate 1031 may be provided with the black matrix 1035 which is positioned between pixels. The coloring layers (the red coloring layer 1034R, the green coloring layer 1034G, and the blue coloring layer 1034B) and the black matrix 1035 may be covered with the overcoat layer 1036. Note that a light-transmitting substrate is used as the sealing substrate 1031. Although an example in which full color display is performed using four colors of red, green, blue, and white is shown here, there is no particular limitation and full color display using four colors of red, yellow, green, and blue or three colors of red, green, and blue may be performed.

In the light-emitting apparatus having a top emission structure, a microcavity structure can be favorably employed. A light-emitting device with a microcavity structure is formed with the use of a reflective electrode as the first electrode and a transflective electrode as the second electrode. The light-emitting device with a microcavity structure includes at least an EL layer between the reflective electrode and the transflective electrode, which includes at least a light-emitting layer serving as a light-emitting region.

Note that the reflective electrode has a visible light reflectivity of 40% to 100%, preferably 70% to 100%, and a resistivity of $1\times10^{-2}$ Ωcm or lower. In addition, the transflective electrode has a visible light reflectivity of 20% to 80%, preferably 40% to 70%, and a resistivity of $1\times10^{-2}$ Ωcm or lower.

Light emitted from the light-emitting layer included in the EL layer is reflected and resonated by the reflective electrode and the transflective electrode.

In the light-emitting device, by changing thicknesses of the transparent conductive film, the composite material, the carrier-transport material, and the like, the optical path length between the reflective electrode and the transflective electrode can be changed. Thus, light with a wavelength that is resonated between the reflective electrode and the transflective electrode can be intensified while light with a wavelength that is not resonated therebetween can be attenuated.

Note that light that is reflected back by the reflective electrode (first reflected light) considerably interferes with light that directly enters the transflective electrode from the light-emitting layer (first incident light). For this reason, the optical path length between the reflective electrode and the light-emitting layer is preferably adjusted to $(2n-1)\lambda/4$ (n is a natural number of 1 or larger and $\lambda$ is a wavelength of light to be amplified). By adjusting the optical path length, the phases of the first reflected light and the first incident light can be aligned with each other and the light emitted from the light-emitting layer can be further amplified.

Note that in the above structure, the EL layer may include a plurality of light-emitting layers or may include a single light-emitting layer. The tandem light-emitting device described above may be combined with a plurality of EL layers; for example, a light-emitting device may have a structure in which a plurality of EL layers are provided, a charge-generation layer is provided between the EL layers, and each EL layer includes a plurality of light-emitting layers or a single light-emitting layer.

With the microcavity structure, emission intensity with a specific wavelength in the front direction can be increased, whereby power consumption can be reduced. Note that in the case of a light-emitting apparatus that displays images with subpixels of four colors, red, yellow, green, and blue, the light-emitting apparatus can have favorable characteristics because the luminance can be increased owing to yellow light emission and each subpixel can employ a microcavity structure suitable for wavelengths of the corresponding color.

The light-emitting apparatus in this embodiment is manufactured using the light-emitting device described in Embodiment 2 and thus can have favorable characteristics. Specifically, since the light-emitting device described in Embodiment 2 has high emission efficiency, the light-emitting apparatus can achieve low power consumption.

Figure 5A:
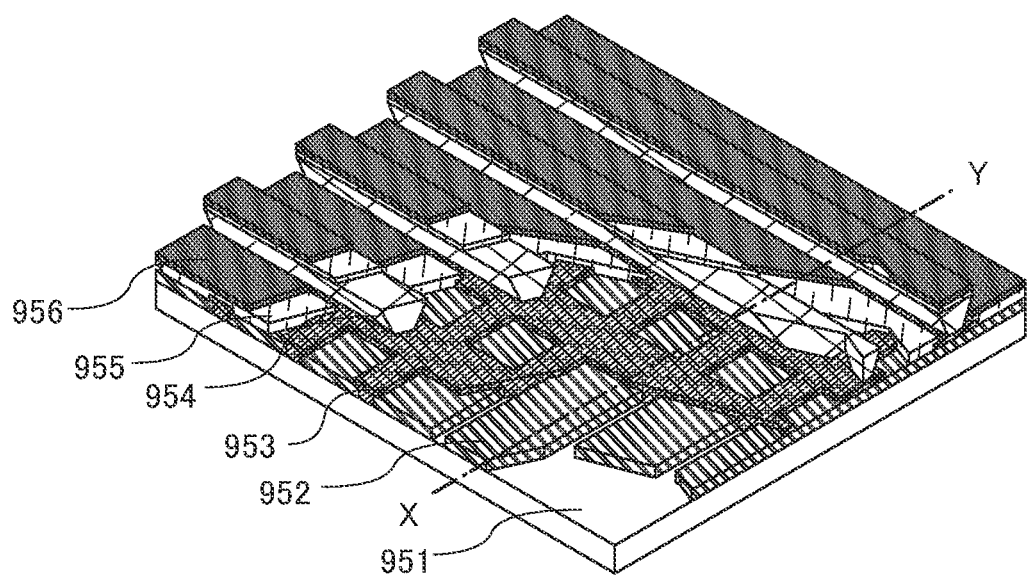
FIG. 5A and FIG. 5B are conceptual views of a passive matrix light-emitting apparatus.
Figure 5B:
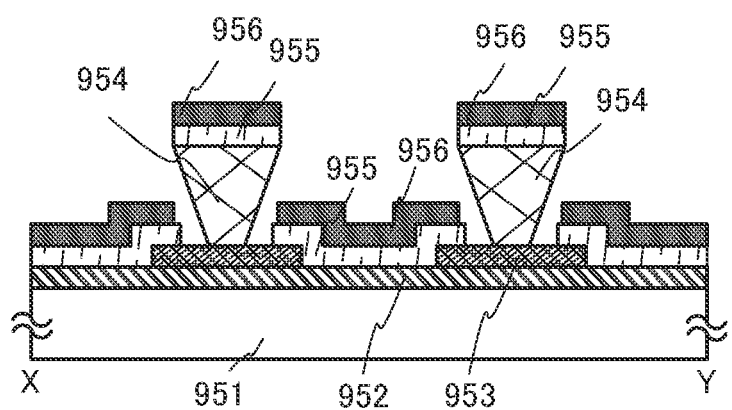

An active matrix light-emitting apparatus is described above, whereas a passive matrix light-emitting apparatus is described below. FIGS. 5A and 5B illustrate a passive matrix light-emitting apparatus manufactured using the present invention. Note that FIG. 5A is a perspective view of the light-emitting apparatus, and FIG. 5B is a cross-sectional view taken along the line X-Y in FIG. 5A. In FIGS. 5A and 5B, over a substrate 951, an EL layer 955 is provided between an electrode 952 and an electrode 956. An end portion of the electrode 952 is covered with an insulating layer 953. A partition layer 954 is provided over the insulating layer 953. The sidewalls of the partition layer 954 are aslope such that the distance between both sidewalls is gradually narrowed toward the surface of the substrate. In other words, a cross section taken along the direction of the short side of the partition layer 954 is trapezoidal, and the lower side (a side of the trapezoid that is parallel to the surface of the insulating layer 953 and is in contact with the insulating layer 953) is shorter than the upper side (a side of the trapezoid that is parallel to the surface of the insulating layer 953 and is not in contact with the insulating layer 953). The partition layer 954 thus provided can prevent defects in the light-emitting device due to static electricity or others. The passive-matrix light-emitting apparatus also includes the light-emitting device described in Embodiment 2; thus, the light-emitting apparatus can have high reliability or low power consumption.

In the light-emitting apparatus described above, many minute light-emitting devices arranged in a matrix can each be controlled; thus, the light-emitting apparatus can be suitably used as a display device for displaying images.

This embodiment can be freely combined with any of the other embodiments.

Embodiment 4

Figure 6A:
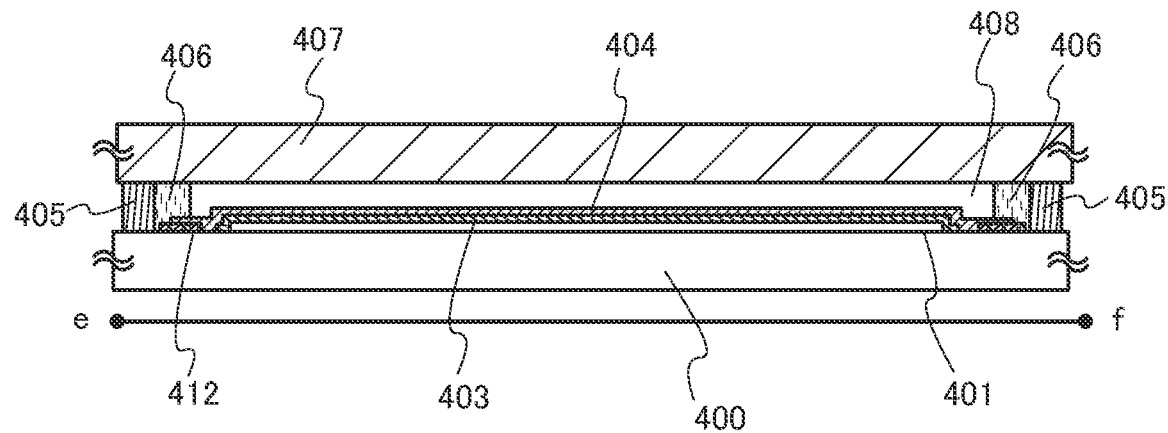
FIG. 6A and FIG. 6B illustrate a lighting device.
Figure 6B:
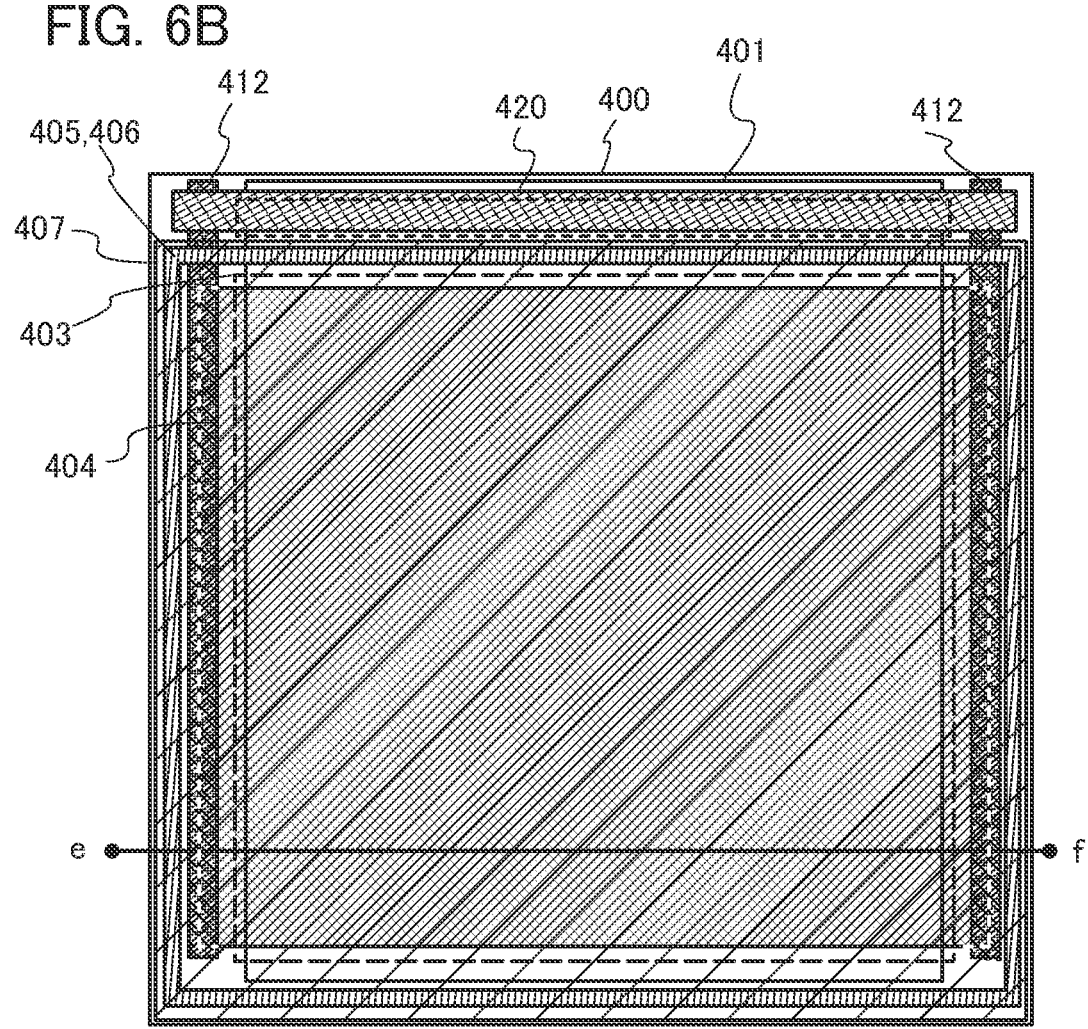

In this embodiment, an example in which the light-emitting device described in Embodiment 2 is used for a lighting device will be described with reference to FIGS. 6A and 6B. FIG. 6B is a top view of the lighting device, and FIG. 6A is a cross-sectional view taken along the line e-f in FIG. 6B.

In the lighting device in this embodiment, a first electrode 401 is formed over a substrate 400 which is a support with a light-transmitting property. The first electrode 401 corresponds to the first electrode 101 in Embodiment 2. When light is extracted through the first electrode 401 side, the first electrode 401 is formed using a material having a light-transmitting property.

A pad 412 for applying voltage to a second electrode 404 is provided over the substrate 400.

An EL layer 403 is formed over the first electrode 401. The structure of the EL layer 403 corresponds to, for example, the structure of the EL layer 103 in Embodiment 2, or the structure in which the light-emitting units 511 and 512 and the charge-generation layer 513 are combined. Refer to the descriptions for the structure.

The second electrode 404 is formed to cover the EL layer 403. The second electrode 404 corresponds to the second electrode 102 in Embodiment 2. The second electrode 404 is formed using a material having high reflectance when light is extracted through the first electrode 401 side. The second electrode 404 is connected to the pad 412, whereby voltage is applied.

As described above, the lighting device described in this embodiment includes a light-emitting device including the first electrode 401, the EL layer 403, and the second electrode 404. Since the light-emitting device is a light-emitting device with high emission efficiency, the lighting device in this embodiment can have low power consumption.

The substrate 400 provided with the light-emitting device having the above structure is fixed to a sealing substrate 407 with sealing materials 405 and 406 and sealing is performed, whereby the lighting device is completed. It is possible to use only either the sealing material 405 or the sealing material 406. The inner sealing material 406 (not shown in FIG. 6B) can be mixed with a desiccant which enables moisture to be adsorbed, increasing reliability.

When parts of the pad 412 and the first electrode 401 are extended to the outside of the sealing materials 405 and 406, the extended parts can serve as external input terminals. An IC chip 420 mounted with a converter or the like may be provided over the external input terminals.

The lighting device described in this embodiment includes as an EL element the light-emitting device described in Embodiment 2; thus, the lighting device can have low power consumption.

Embodiment 5

In this embodiment, examples of electronic devices each including the light-emitting device described in Embodiment 2 will be described. The light-emitting device described in Embodiment 2 has high emission efficiency and low power consumption. As a result, the electronic devices described in this embodiment can each include a light-emitting portion having low power consumption.

Examples of the electronic device including the above light-emitting device include television devices (also referred to as TV or television receivers), monitors for computers and the like, digital cameras, digital video cameras, digital photo frames, cellular phones (also referred to as mobile phones or mobile phone devices), portable game machines, portable information terminals, audio playback devices, and large game machines such as pachinko machines. Specific examples of these electronic devices are shown below.

Figure 7A:
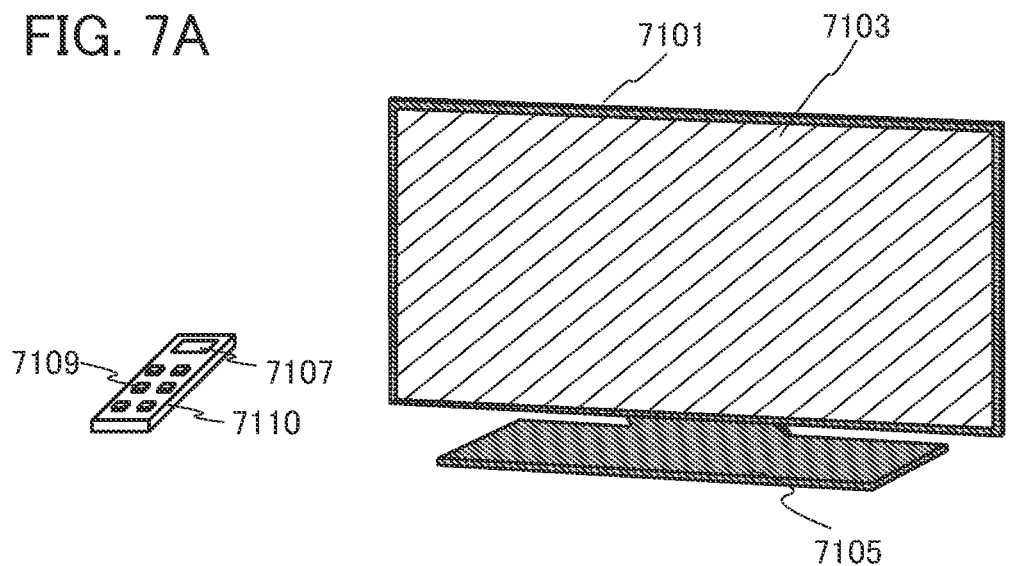
Figure 7A:
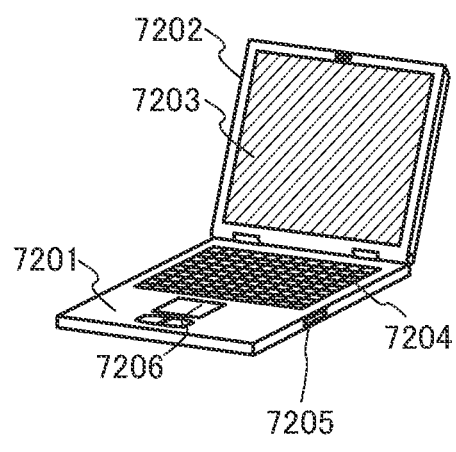
Figure 7A:
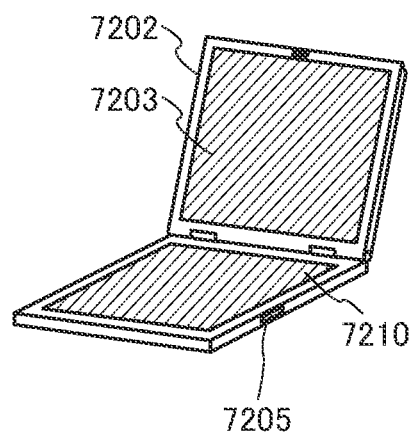

FIG. 7A illustrates an example of a television device. In the television device, a display portion 7103 is incorporated in a housing 7101. Here, the housing 7101 is supported by a stand 7105. Images can be displayed on the display portion 7103, and in the display portion 7103, the light-emitting devices described in Embodiment 2 are arranged in a matrix.

The television device can be operated with an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device is provided with a receiver, a modem, and the like. With the use of the receiver, a general television broadcast can be received. Moreover, when the television device is connected to a communication network with or without wires via the modem, one-way (from a sender to a receiver) or two-way (between a sender and a receiver or between receivers) data communication can be performed.

FIG. 7B1 illustrates a computer, which includes a main body 7201, a housing 7202, a display portion 7203, a keyboard 7204, an external connection port 7205, a pointing device 7206, and the like. Note that this computer is manufactured using the light-emitting devices described in Embodiment 2 and arranged in a matrix in the display portion 7203. The computer illustrated in FIG. 7B1 may have a structure illustrated in FIG. 7B2. A computer illustrated in FIG. 7B2 is provided with a second display portion 7210 instead of the keyboard 7204 and the pointing device 7206. The second display portion 7210 is a touch panel, and input operation can be performed by touching display for input on the second display portion 7210 with a finger or a dedicated pen. The second display portion 7210 can also display images other than the display for input. The display portion 7203 may also be a touch panel. Connecting the two screens with a hinge can prevent troubles; for example, the screens can be prevented from being cracked or broken while the computer is being stored or carried.

Figure 7C:
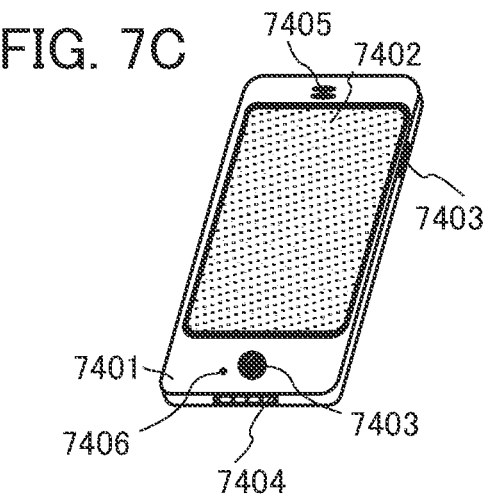

FIG. 7C illustrates an example of a portable terminal. A cellular phone is provided with a display portion 7402 incorporated in a housing 7401, operation buttons 7403, an external connection port 7404, a speaker 7405, a microphone 7406, and the like. Note that the cellular phone has the display portion 7402 including the light-emitting devices described in Embodiment 2 and arranged in a matrix.

When the display portion 7402 of the portable terminal illustrated in FIG. 7C is touched with a finger or the like, data can be input into the portable terminal. In this case, operations such as making a call and creating an e-mail can be performed by touching the display portion 7402 with a finger or the like.

The display portion 7402 has mainly three screen modes. The first mode is a display mode mainly for displaying images. The second mode is an input mode mainly for inputting data such as text. The third mode is a display-and-input mode in which the two modes, the display mode and the input mode, are combined.

For example, in the case of making a call or creating an e-mail, a text input mode mainly for inputting text is selected for the display portion 7402 so that text displayed on the screen can be input. In this case, it is preferable to display a keyboard or number buttons on almost the entire screen of the display portion 7402.

When a sensing device including a sensor such as a gyroscope sensor or an acceleration sensor for detecting inclination is provided inside the portable terminal, display on the screen of the display portion 7402 can be automatically changed in direction by determining the orientation of the portable terminal (whether the portable terminal is placed horizontally or vertically).

The screen modes are switched by touching the display portion 7402 or operating the operation buttons 7403 of the housing 7401. Alternatively, the screen modes can be switched depending on the kind of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, when input by touching the display portion 7402 is not performed for a certain period while a signal sensed by an optical sensor in the display portion 7402 is sensed, the screen mode may be controlled so as to be switched from the input mode to the display mode.

The display portion 7402 may also function as an image sensor. For example, an image of a palm print, a fingerprint, or the like is taken when the display portion 7402 is touched with the palm or the finger, whereby personal authentication can be performed. Furthermore, by providing a backlight or a sensing light source which emits near-infrared light in the display portion, an image of a finger vein, a palm vein, or the like can be taken.

Figure 8A:
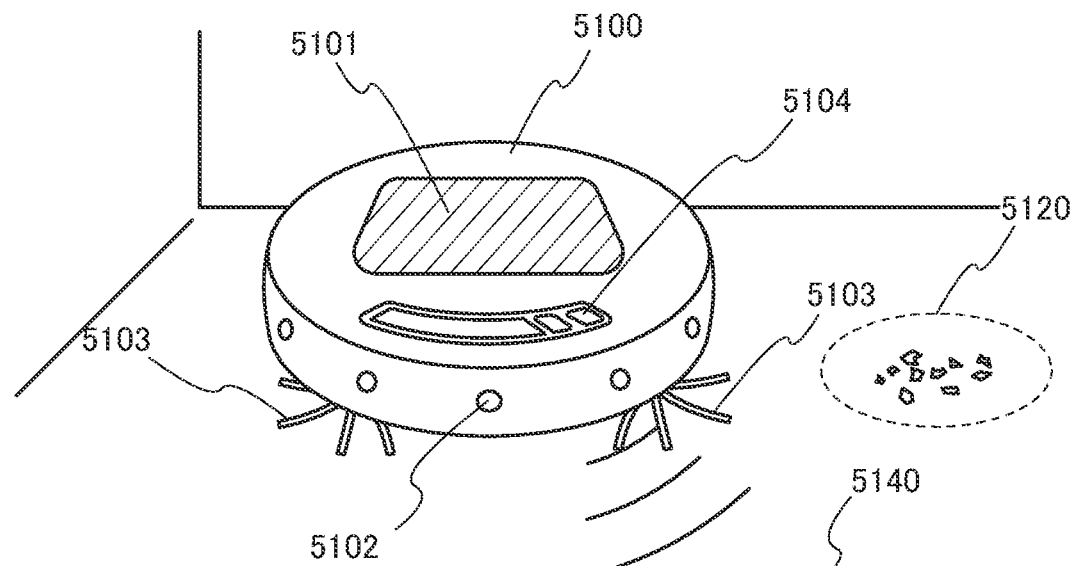
FIG. 8A, FIG. 8B, and FIG. 8C illustrate electronic devices.

FIG. 8A is a schematic view illustrating an example of a cleaning robot.

A cleaning robot 5100 includes a display 5101 on its top surface, a plurality of cameras 5102 on its side surface, a brush 5103, and operation buttons 5104. Although not illustrated, the bottom surface of the cleaning robot 5100 is provided with a tire, an inlet, and the like. Furthermore, the cleaning robot 5100 includes various sensors such as an infrared sensor, an ultrasonic sensor, an acceleration sensor, a piezoelectric sensor, an optical sensor, and a gyroscope sensor. The cleaning robot 5100 has a wireless communication means.

The cleaning robot 5100 is self-propelled, detects dust 5120, and sucks up the dust through the inlet provided on the bottom surface.

The cleaning robot 5100 can determine whether there is an obstacle such as a wall, furniture, or a step by analyzing images taken by the cameras 5102. When the cleaning robot 5100 detects an object that is likely to be caught in the brush 5103 (e.g., a wire) by image analysis, the rotation of the brush 5103 can be stopped.

The display 5101 can display the remaining capacity of a battery, the amount of collected dust, and the like. The display 5101 may display a path on which the cleaning robot 5100 has run. The display 5101 may be a touch panel, and the operation buttons 5104 may be provided on the display 5101.

The cleaning robot 5100 can communicate with a portable electronic device 5140 such as a smartphone. Images taken by the cameras 5102 can be displayed on the portable electronic device 5140. Accordingly, an owner of the cleaning robot 5100 can monitor his/her room even when the owner is not at home. The owner can also check the display on the display 5101 by the portable electronic device 5140 such as a smartphone.

The light-emitting apparatus of one embodiment of the present invention can be used for the display 5101.

Figure 8B:
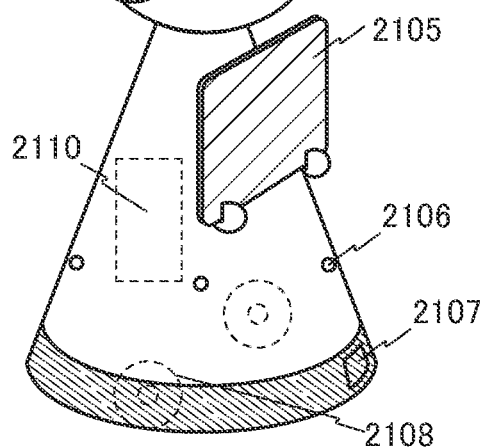

A robot 2100 illustrated in FIG. 8B includes an arithmetic device 2110, an illuminance sensor 2101, a microphone 2102, an upper camera 2103, a speaker 2104, a display 2105, a lower camera 2106, an obstacle sensor 2107, and a moving mechanism 2108.

The microphone 2102 has a function of detecting a speaking voice of a user, an environmental sound, and the like. The speaker 2104 also has a function of outputting sound. The robot 2100 can communicate with a user using the microphone 2102 and the speaker 2104.

The display 2105 has a function of displaying various kinds of information. The robot 2100 can display information desired by a user on the display 2105. The display 2105 may be provided with a touch panel. Moreover, the display 2105 may be a detachable information terminal, in which case charging and data communication can be performed when the display 2105 is set at the home position of the robot 2100.

The upper camera 2103 and the lower camera 2106 each have a function of taking an image of the surroundings of the robot 2100. The obstacle sensor 2107 can detect an obstacle in the direction where the robot 2100 advances with the moving mechanism 2108. The robot 2100 can move safely by recognizing the surroundings with the upper camera 2103, the lower camera 2106, and the obstacle sensor 2107. The light-emitting apparatus of one embodiment of the present invention can be used for the display 2105.

Figure 8C:
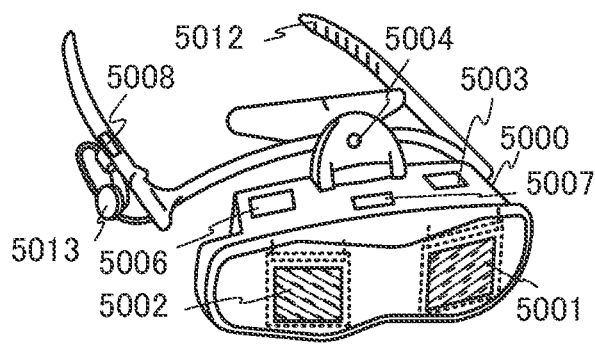

FIG. 8C illustrates an example of a goggle-type display. The goggle-type display includes, for example, a housing 5000, a display portion 5001, a speaker 5003, an LED lamp 5004, a connection terminal 5006, a sensor 5007 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared ray), a microphone 5008, a display portion 5002, a support 5012, and an earphone 5013.

The light-emitting apparatus of one embodiment of the present invention can be used for the display portion 5001 and the display portion 5002.

Figure 9:
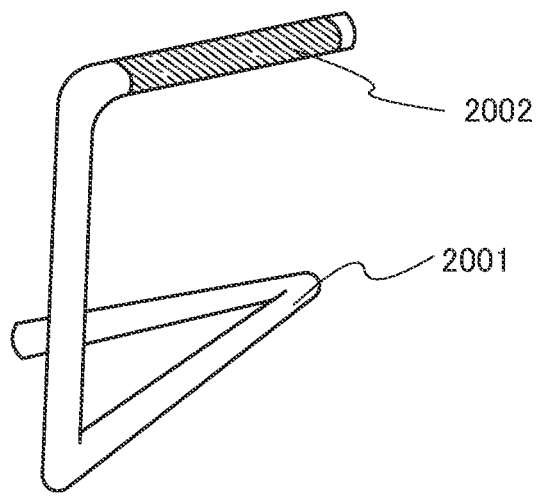
FIG. 9 illustrates a lighting device.

FIG. 9 illustrates an example in which the light-emitting device described in Embodiment 2 is used for a table lamp which is a lighting device. The table lamp illustrated in FIG. 9 includes a housing 2001 and a light source 2002, and the lighting device described in Embodiment 3 may be used for the light source 2002.

Figure 10:
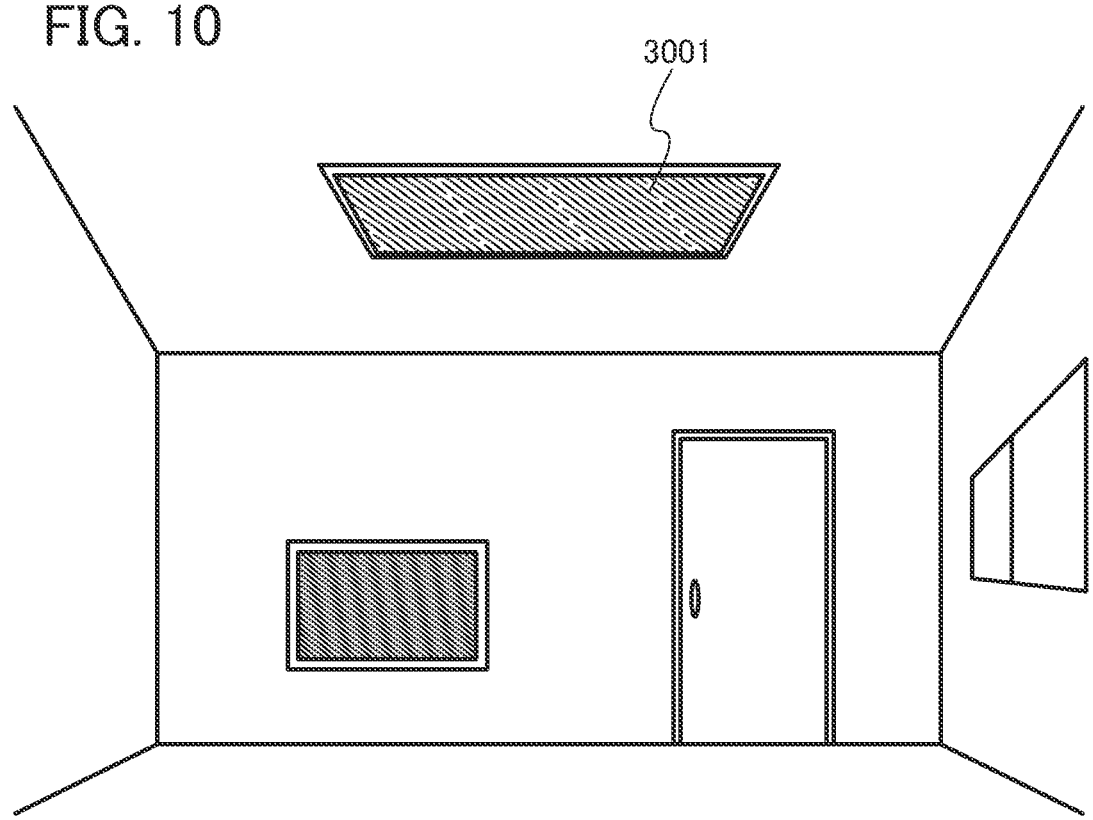
FIG. 10 illustrates a lighting device.

FIG. 10 illustrates an example in which the light-emitting device described in Embodiment 2 is used for an indoor lighting device 3001. Since the light-emitting device described in Embodiment 2 has high emission efficiency, the lighting device can have low power consumption. Furthermore, since the light-emitting device described in Embodiment 2 can have a large area, the light-emitting device can be used for a large-area lighting device. Furthermore, since the light-emitting device described in Embodiment 2 is thin, the light-emitting device can be used for a lighting device having a reduced thickness.

Figure 11:
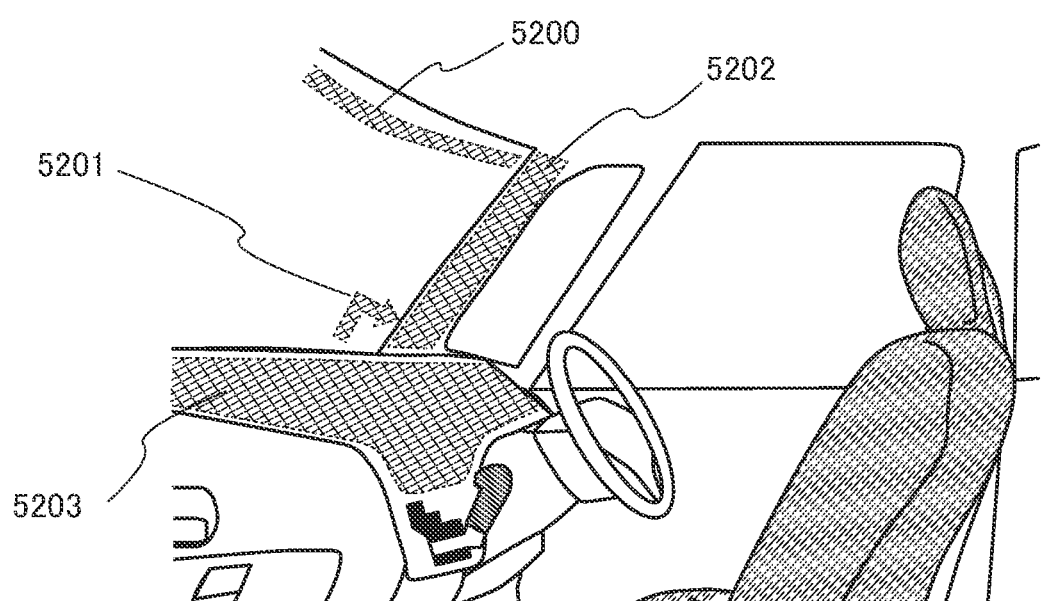
FIG. 11 illustrates in-vehicle display devices and lighting devices.

The light-emitting device described in Embodiment 2 can also be used for an automobile windshield or an automobile dashboard. FIG. 11 illustrates one mode in which the light-emitting devices described in Embodiment 2 are used for an automobile windshield and an automobile dashboard. Display regions 5200 to 5203 each include the light-emitting device described in Embodiment 2.

The display regions 5200 and 5201 are display devices which are provided in the automobile windshield and include the light-emitting device described in Embodiment 2. The light-emitting device described in Embodiment 2 can be formed into what is called a see-through display device, through which the opposite side can be seen, by including a first electrode and a second electrode formed of light-transmitting electrodes. Such see-through display devices can be provided even in the automobile windshield without hindering the view. In the case where a driving transistor or the like is provided, a transistor having a light-transmitting property, such as an organic transistor including an organic semiconductor material or a transistor including an oxide semiconductor, is preferably used.

The display region 5202 is a display device which is provided in a pillar portion and includes the light-emitting device described in Embodiment 2. The display region 5202 can compensate for the view hindered by the pillar by displaying an image taken by an imaging unit provided in the car body. Similarly, the display region 5203 provided in the dashboard portion can compensate for the view hindered by the car body by displaying an image taken by an imaging unit provided on the outside of the automobile. Thus, blind areas can be eliminated to enhance the safety. Images that compensate for the areas which a driver cannot see enable the driver to ensure safety easily and comfortably.

The display region 5203 can provide a variety of kinds of information such as navigation data, speed, the number of revolutions, and the like. The content or layout of the display can be changed freely by a user as appropriate. Note that such information can also be displayed on the display regions 5200 to 5202. The display regions 5200 to 5203 can also be used as lighting devices.

Figure 12A:
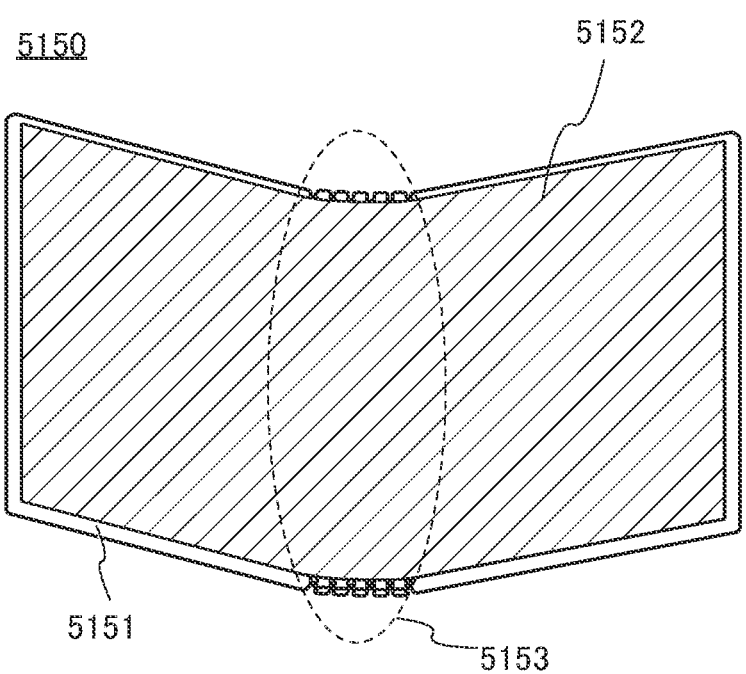
FIGS. 12A and 12B illustrate an electronic device.
Figure 12B:
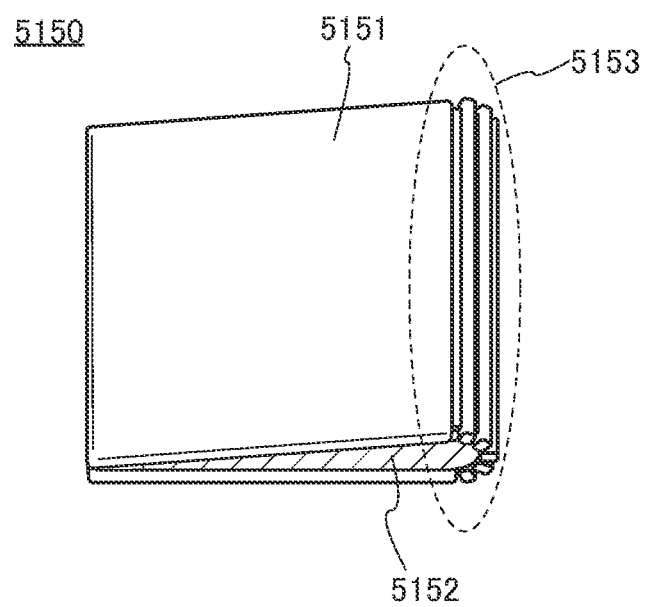

FIGS. 12A and 12B illustrate a foldable portable information terminal 5150. The foldable portable information terminal 5150 includes a housing 5151, a display region 5152, and a bend portion 5153. FIG. 12A illustrates the portable information terminal 5150 that is opened. FIG. 12B illustrates the portable information terminal 5150 that is folded. Despite its large display region 5152, the portable information terminal 5150 is compact in size and has excellent portability when folded.

The display region 5152 can be folded in half with the bend portion 5153. The bend portion 5153 includes a flexible member and a plurality of supporting members. When the display region is folded, the flexible member expands and the bend portion 5153 has a radius of curvature of greater than or equal to 2 mm, preferably greater than or equal to 3 mm.

Note that the display region 5152 may be a touch panel (an input/output device) including a touch sensor (an input device). The light-emitting apparatus of one embodiment of the present invention can be used for the display region 5152.

Figure 13A:
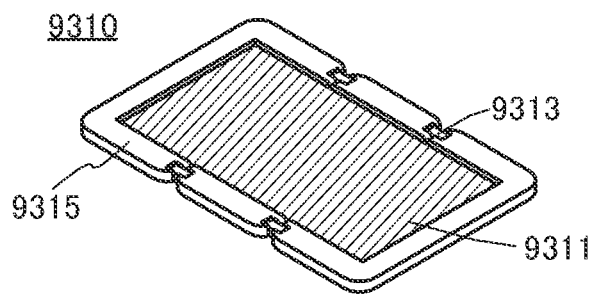
FIG. 13A, FIG. 13B, and FIG. 13C illustrate an electronic device.
Figure 13B:
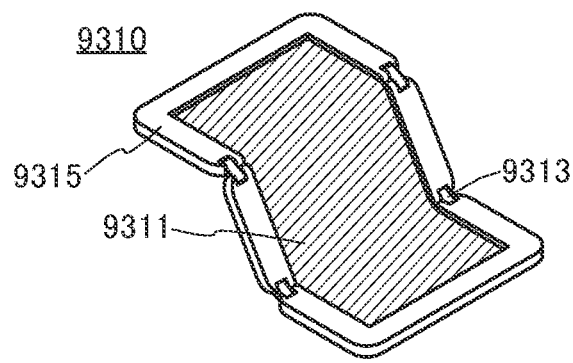
Figure 13C:
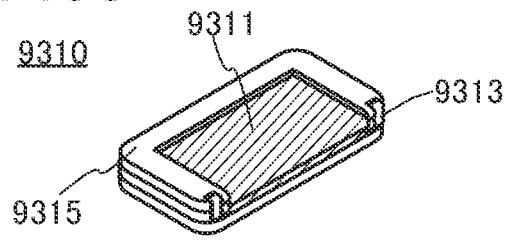

FIGS. 13A to 13C illustrate a foldable portable information terminal 9310. FIG. 13A illustrates the portable information terminal 9310 that is opened. FIG. 13B illustrates the portable information terminal 9310 that is being opened or being folded. FIG. 13C illustrates the portable information terminal 9310 that is folded. The portable information terminal 9310 is highly portable when folded. The portable information terminal 9310 is highly browsable when opened because of a seamless large display region.

A display panel 9311 is supported by three housings 9315 joined together by hinges 9313. Note that the display panel 9311 may be a touch panel (an input/output device) including a touch sensor (an input device). By folding the display panel 9311 at the hinges 9313 between two housings 9315, the portable information terminal 9310 can be reversibly changed in shape from the opened state to the folded state. The light-emitting apparatus of one embodiment of the present invention can be used for the display panel 9311.

Note that the structure described in this embodiment can be combined with any of the structures described in Embodiments 1 to 4 as appropriate.

As described above, the application range of the light-emitting apparatus including the light-emitting device described in Embodiment 2 is wide so that this light-emitting apparatus can be applied to electronic devices in a variety of fields. By using the light-emitting device described in Embodiment 2, an electronic device with low power consumption can be obtained.

Example 1

Synthesis Example 1

In this synthesis example, a synthesis method of N,N-bis[9-(3,5-di-tert-butylphenyl)-9H-carbazol-2-yl]-N,N-diphenyl-naphtho[2,3-b;6,7-b']bisbenzofuran-3,10-diamine (abbreviation: 3,10mmtBuPCA2Nbf(IV)-02), which is represented by Structural Formula 100 in Embodiment 1, will be described. The structural formula of 3,10mmtBuPCA2Nbf(IV)-02 is shown below.

[Chemical Formula 40]

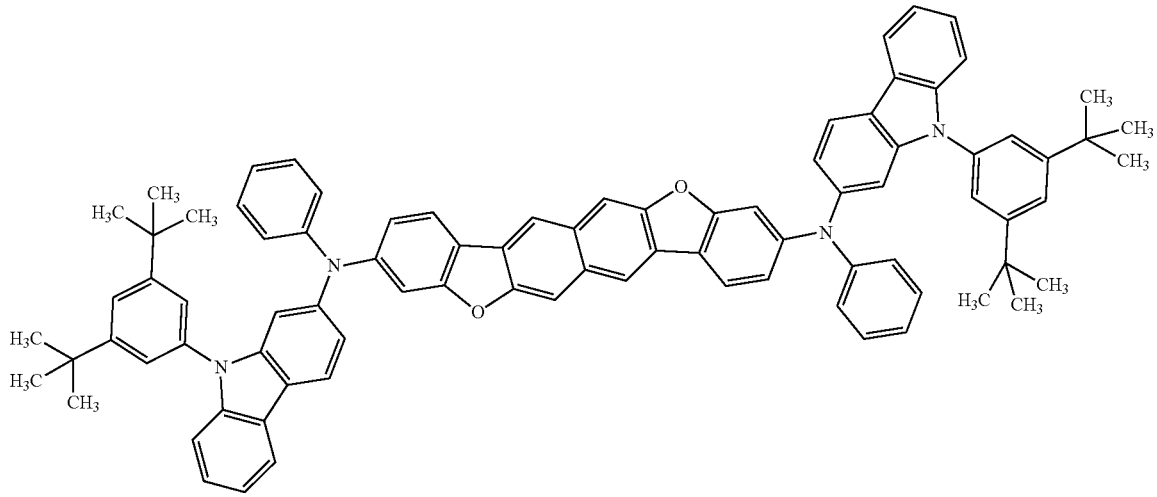

3,10mmtBuPCA2Nbf(IV)-02

Step 1: Synthesis of N-phenyl-9-(3,5-di-tert-butylphenyl)-9H-carbazol-2-amine

Into a 200-mL three-neck flask, 5.5 g (14 mmol) of 2-chloro-9-(3,5-di-tert-butylphenyl)-9H-carbazole, 1.9 g (21 mmol) of aniline, 4.0 g (41 mmol) of sodium tert-butoxide, and 0.25 g (0.69 mmol) of di(1-adamantyl)-n-butylphosphine were put. Then, 90 mL of xylene was added to this mixture, and the mixture was degassed by being stirred while the pressure was reduced. To this mixture, 79 mg (0.14 mmol) of bis(dibenzylideneacetone)palladium(0)

was added, and the mixture was heated and stirred under a nitrogen stream at 150° C. for 6 hours. After the stirring, toluene was added to the mixture, and the resulting mixture was suction-filtered through Florisil, Celite, and alumina, and the filtrate was concentrated to give a solid. This solid was purified by silica gel column chromatography (toluene and hexane at 3:7 in the developing solvent). Ethanol was added to the obtained solid, and the mixture was irradiated with ultrasonic waves and then filtered to give 5.2 g of a white solid in 83% yield. The synthesis scheme of Step 1 is shown below.

Figure 14A:
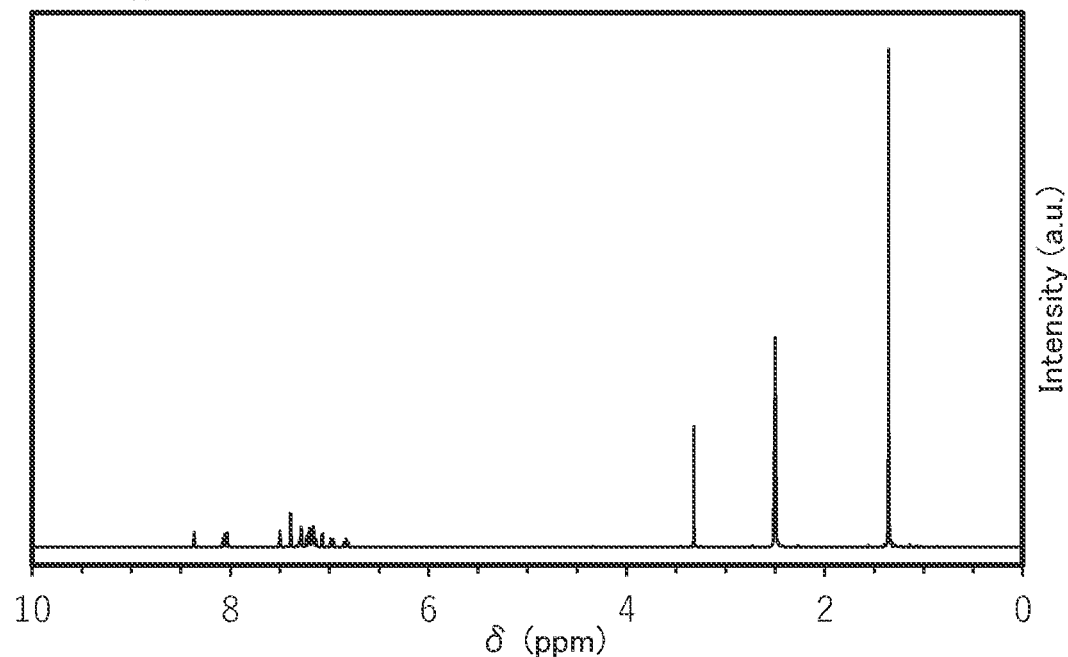
FIG. 14A and FIG. 14B are $^1$H-NMR charts of A-phenyl-9-(3,5-di-tert-butlphenyl)-9H-carbazol-2-amine.
Figure 14B:
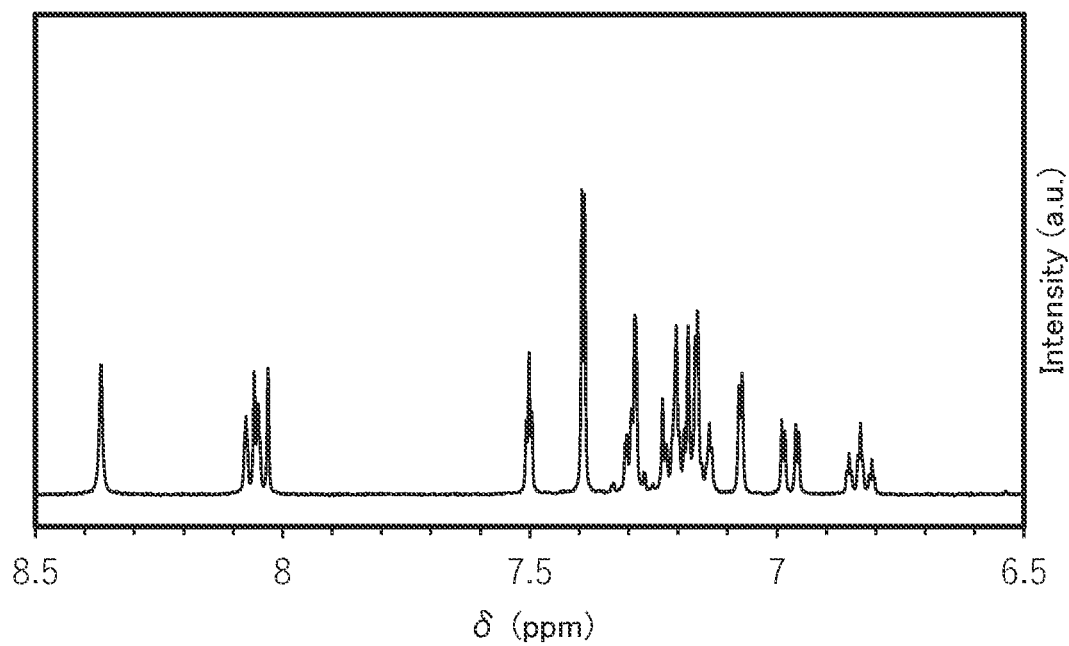

Measurement results by nuclear magnetic resonance ($^1$H-NMR) spectroscopy of the white solid obtained in Step 1 are shown in FIGS. 14A and 14B. In addition, numerical data is shown below. This indicates that N-phenyl-9-(3,5-di-tert-butylphenyl)-9H-carbazol-2-amine was obtained in Step 1.

$^1$H NMR (DMSO-$d_6$, 300 MHz): δ=1.36 (s, 18H), 6.83 (tt, J1=6.9 Hz, J2=1.5 Hz, 1H), 6.97 (dd, J1=8.4 Hz, J2=1.8 Hz, 1H), 7.07 (d, J1=1.8 Hz, 1H), 7.13-7.33 (m, 7H), 7.39 (d, J1=1.8 Hz, 2H), 7.50 (t, J1=1.8 Hz, 1H), 8.03-8.07 (m, 2H), 8.37 (s, 1H).

Step 2: Synthesis of 3,10mmtBuPCA2Nbf(IV)-02

Into a 200-mL three-neck flask, 0.79 g (2.1 mmol) of 3,10-dichloronaphtho[2,3-b;6,7-b']bisbenzofuran, 2.2 g (6.4 mmol) of N-phenyl-9-(3,5-di-tert-butylphenyl)-9H-carbazol-2-amine, 75 mg (0.21 mmol) of di(1-adamantyl)-n-butylphosphine, and 1.2 g (13 mmol) of sodium tert-butoxide were put. To the mixture, 20 mL of xylene was added. This mixture was degassed by being stirred while the pressure was reduced. To this mixture, 24 mg (42 µmol) of bis(dibenzylideneacetone)palladium(0) was added, and stirring was performed under a nitrogen stream at 150° C. for 14 hours. After the stirring, the mixture was filtered to collect a solid. The obtained solid was washed with ethanol and water. The washed solid was purified by silica gel column chromatography (toluene and hexane at 1:4 and then at 3:7 in the developing solvent) to give a solid. The obtained solid was recrystallized with toluene to give 1.6 g of a yellow solid in 66% yield. By a train sublimation method, 1.0 g of the obtained solid was purified. The purification by sublimation was performed by heating at 375° C. under a pressure of 2.2×10$^{-2}$ Pa with an argon flow rate of 0 mL/min to give 0.94 g of a yellow solid at a collection rate of 91%. The synthesis scheme of Step 2 is shown below.

[Chemical Formula 41]

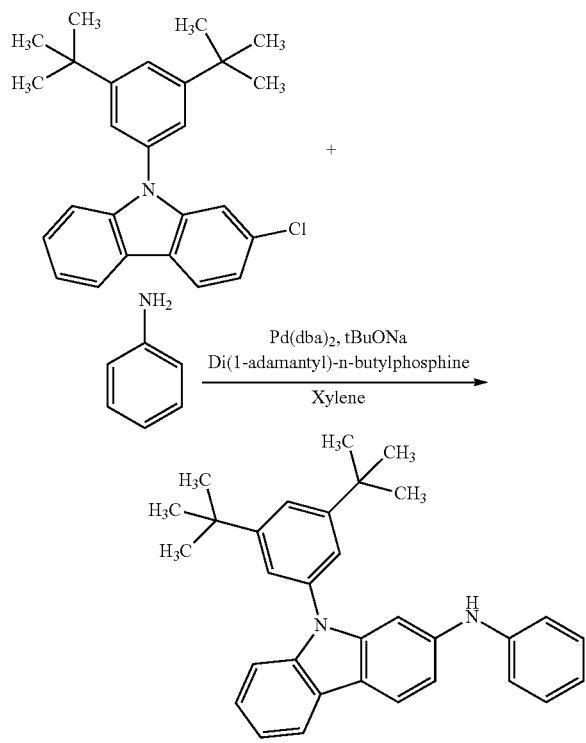

[Chemical Formula 42]

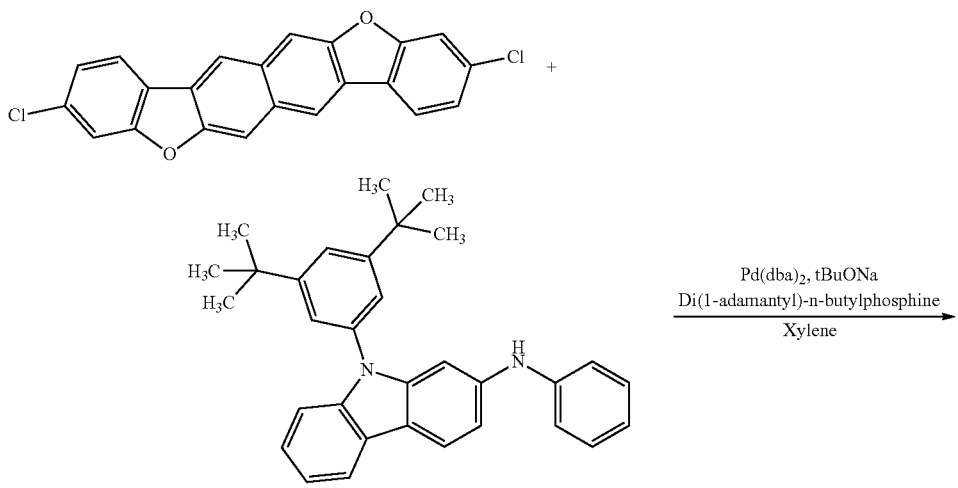

-continued

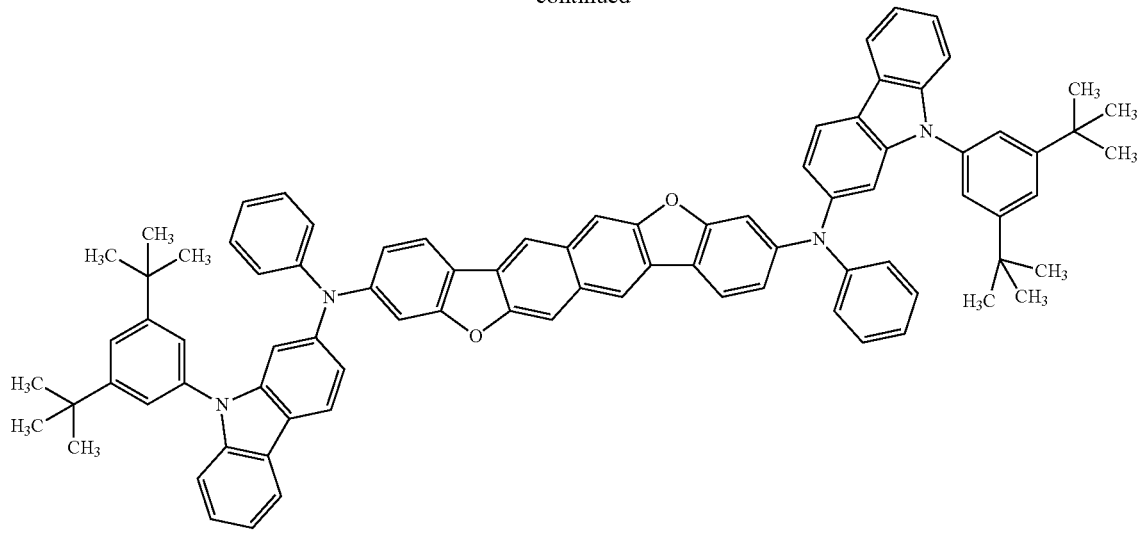

Figure 15A:
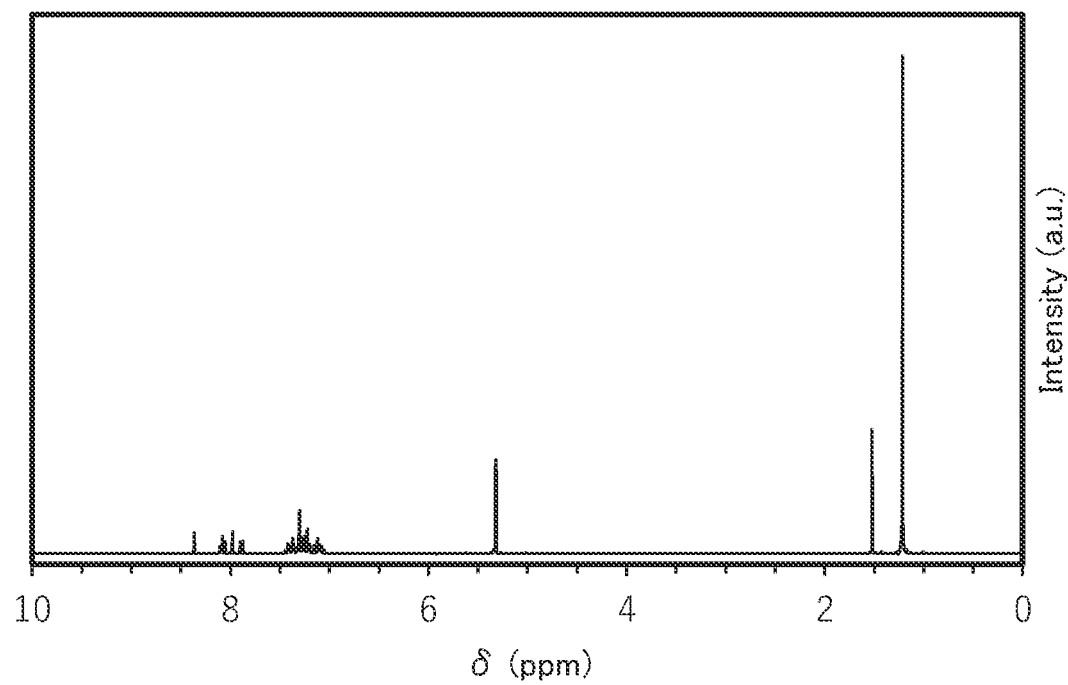
FIG. 15A and FIG. 15B are $^1$H-NMR charts of 3,10mmtBuPCA2Nbf(IV)-02.
Figure 15B:
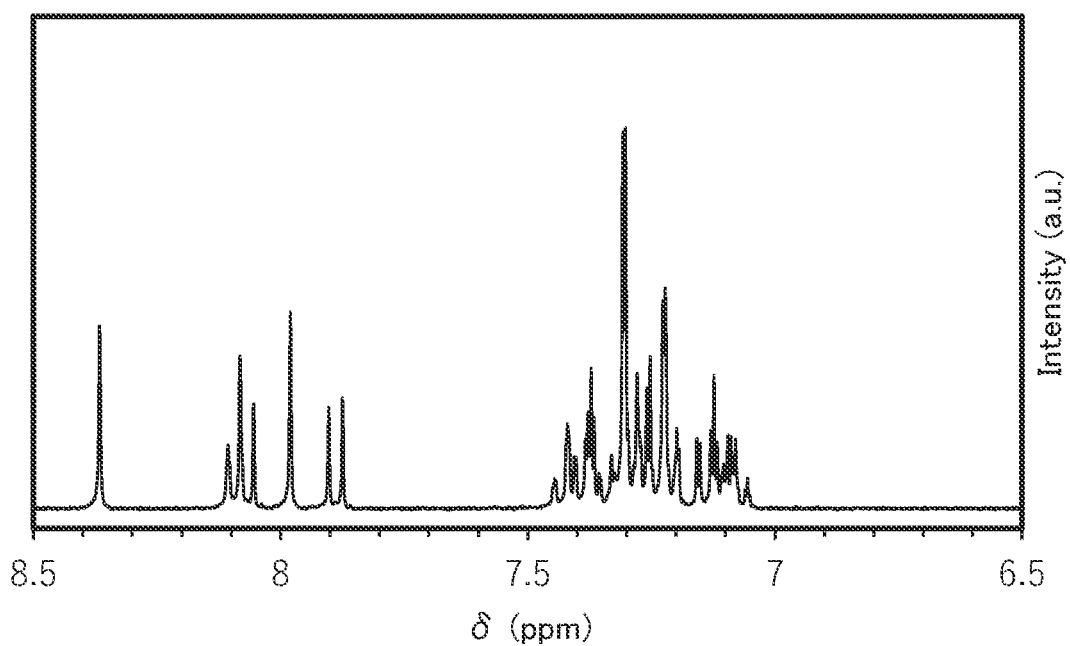

¹H-NMR numerical data of the resulting solid are as follows. FIGS. 15A and 15B show the H-NMR chart. This shows that 3,10mmtBuPCA2Nbf(IV)-02 was obtained in this synthesis example.

¹H NMR (CD$_2$Cl$_2$, 300 MHz): δ=1.21 (s, 36H), 7.05-7.16 (m, 6H), 7.19-7.33 (m, 18H), 7.35-7.45 (m, 6H), 7.89 (d, J1=8.4 Hz, 2H), 7.98 (s, 2H), 8.05-8.11 (m, 4H), 8.37 (s, 2H).

Figure 16:
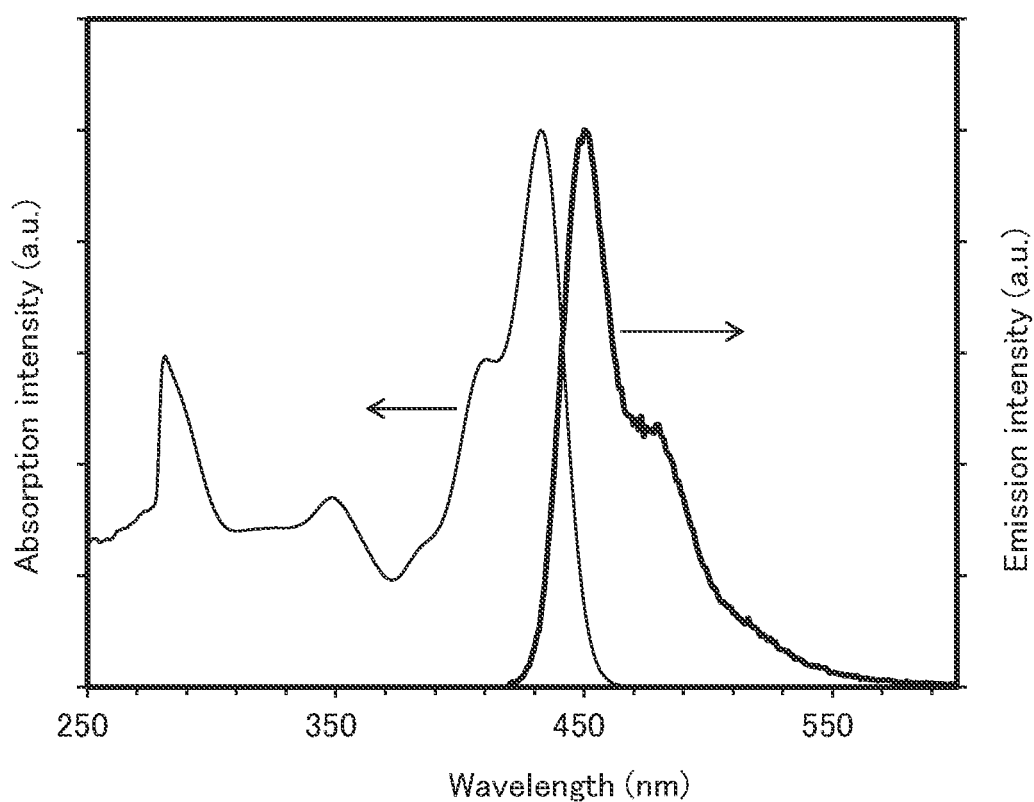
FIG. 16 shows an absorption spectrum and an emission spectrum of 3,10mmtBuPCA2Nbf(IV)-02 in a toluene solution.
Figure 17:
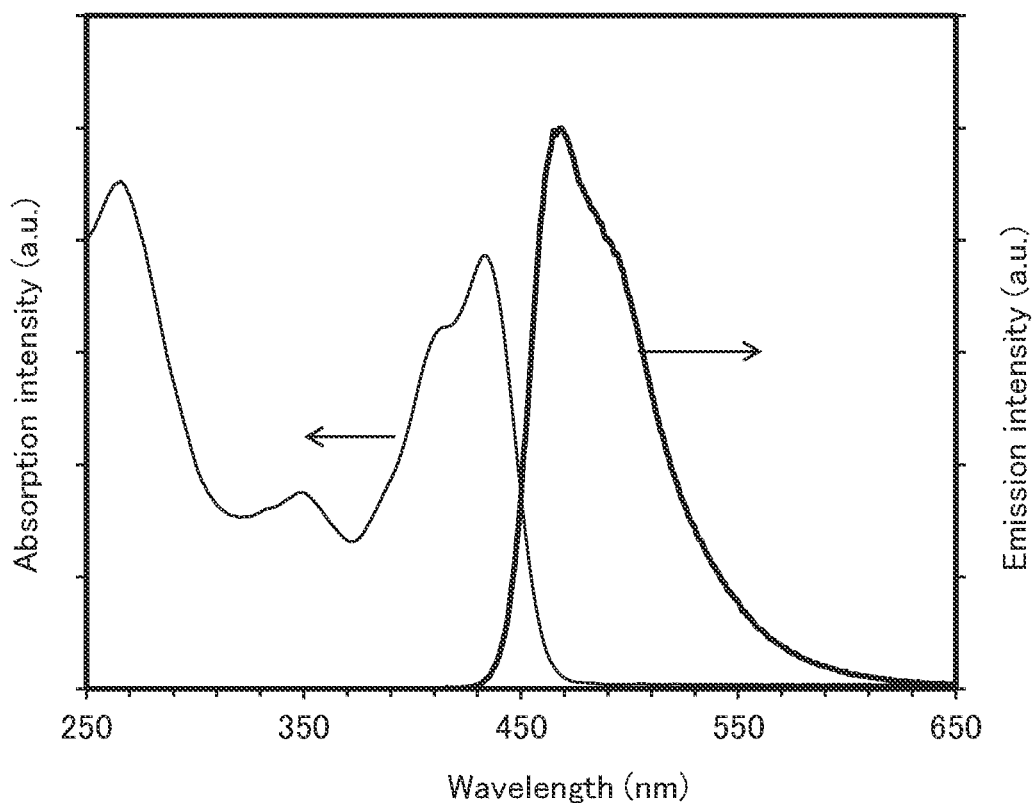
FIG. 17 shows an absorption spectrum and an emission spectrum of 3,10mmtBuPCA2Nbf(IV)-02 in a thin film state.

Next, the measurement results of the absorption and emission spectra of 3,10mmtBuPCA2Nbf(IV)-02 in a toluene solution are shown in FIG. 16. Furthermore, the absorption and emission spectra of the thin film are shown in FIG. 17. The absorption spectrum of the toluene solution was measured with an ultraviolet-visible light spectrophotometer (V550, manufactured by JASCO Corporation), and the spectrum of toluene alone in a quartz cell was subtracted. The thin film was formed over a quartz substrate by a vacuum evaporation method. The absorption spectrum of the thin film was measured with a spectrophotometer (U-4100 Spectrophotometer, manufactured by Hitachi High-Technologies Corporation). The emission spectrum was measured with a fluorescence spectrophotometer (FS920, produced by Hamamatsu Photonics K.K.). Quantum yields were measured with an absolute PL quantum yield measurement system (Quantaurus-QY, manufactured by Hamamatsu Photonics K. K.).

As can be seen in FIG. 16, 3,10mmtBuPCA2Nbf(IV)-02 in the toluene solution has absorption peaks at 433 nm, 411 nm, 384 nm, and 348 nm, and emission spectrum peaks at 450 nm and 479 nm (excitation wavelength: 410 nm). As can be seen in FIG. 17, 3,10mmtBuPCA2Nbf(IV)-02 in the thin film has absorption peaks at 434 nm, 414 nm, 350 nm, and 266 nm, and emission spectrum peaks at 468 nm and 494 nm (excitation wavelength: 410 nm). These results indicate that 3,10mmtBuPCA2Nbf(IV)-02 emits blue light and can be used as a host for a light-emitting substance or a substance which emits fluorescence in the visible region.

The measured quantum yield of 3,10mmtBuPCA2Nbf (IV)-02 in the toluene solution was as high as 90%, which indicates that 3,10mmtBuPCA2Nbf(IV)-02 is suitable for a light-emitting material.

Example 2

In this example, a light-emitting device which uses the organic compound of one embodiment of the present invention and comparative light-emitting devices which do not use the organic compound are described. Structural formulae of organic compounds used for a light-emitting device 1, a comparative light-emitting device 1-1, and a comparative light-emitting device 1-2 are shown below.

[Chemical Formula 43]
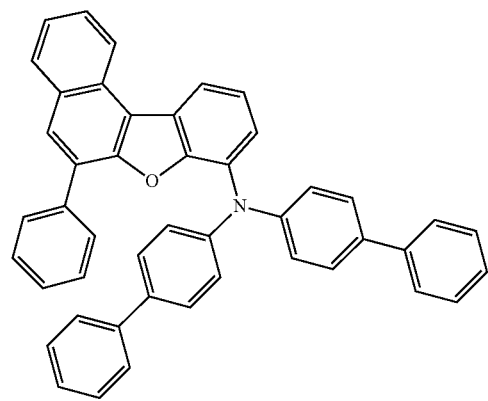
BBABnf
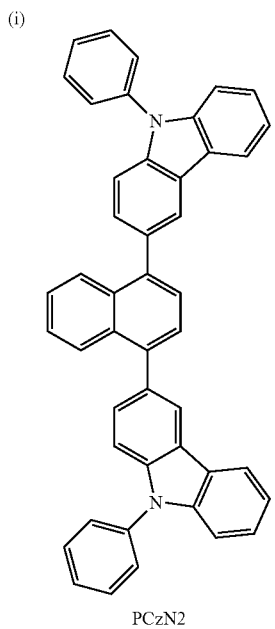
PCzN2
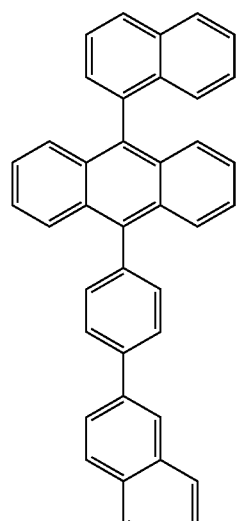
αN-βNPAnth
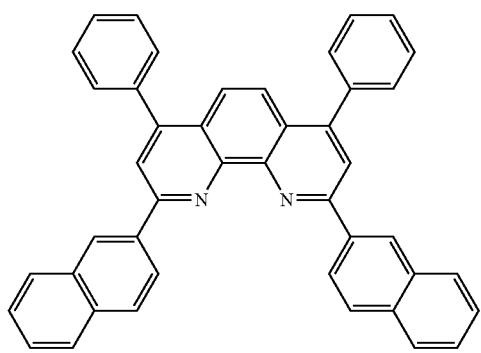
NBPhen
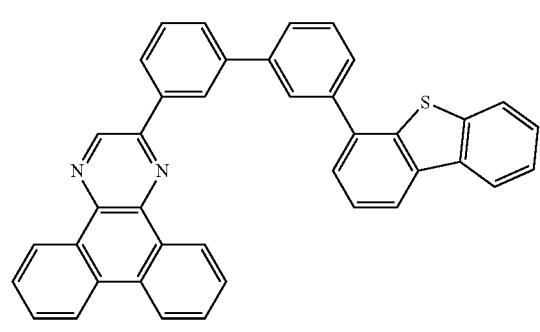
2mDBTBPDBq-II -continued

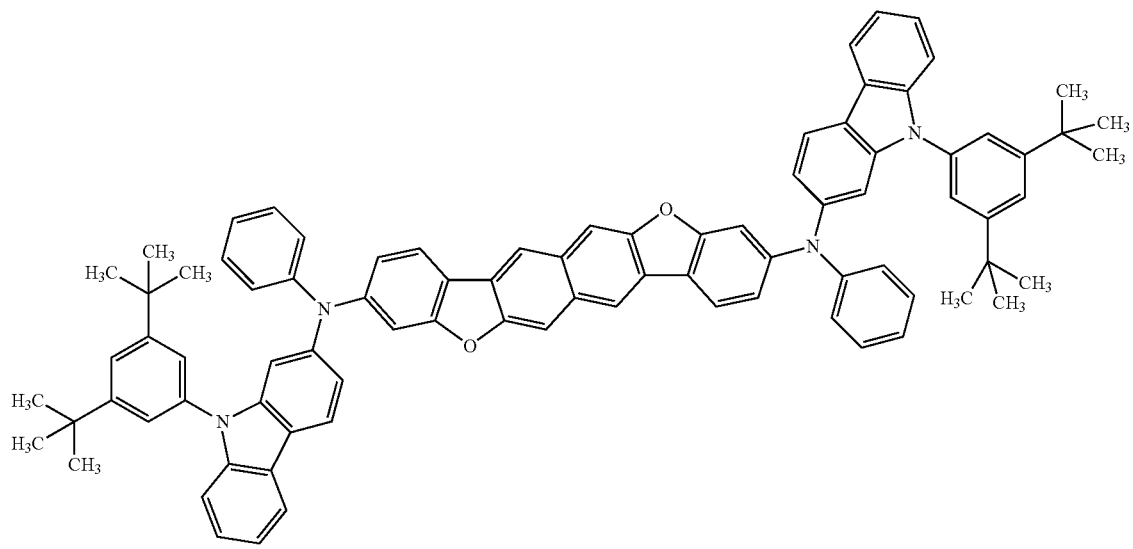

3,10mmtBuPCA2Nbf(IV)-02

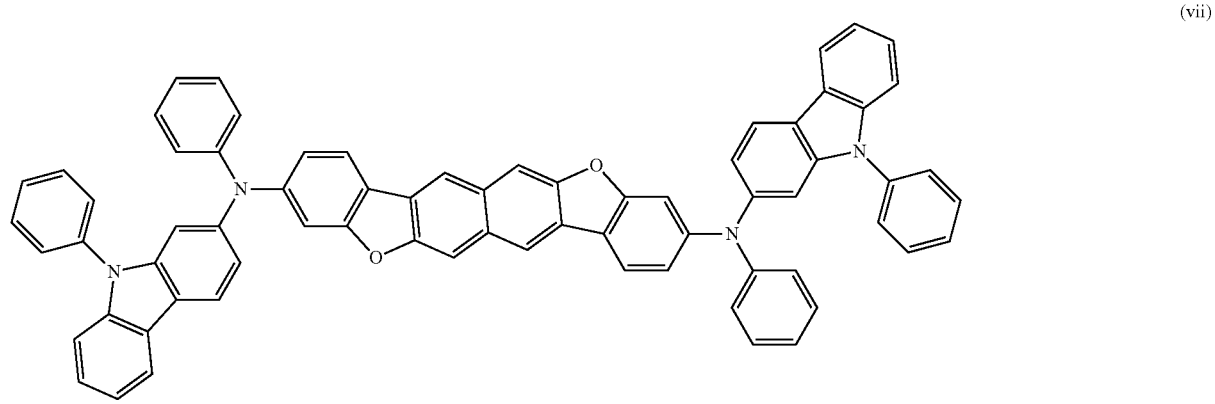

3,10PCA2Nbf(IV)-02

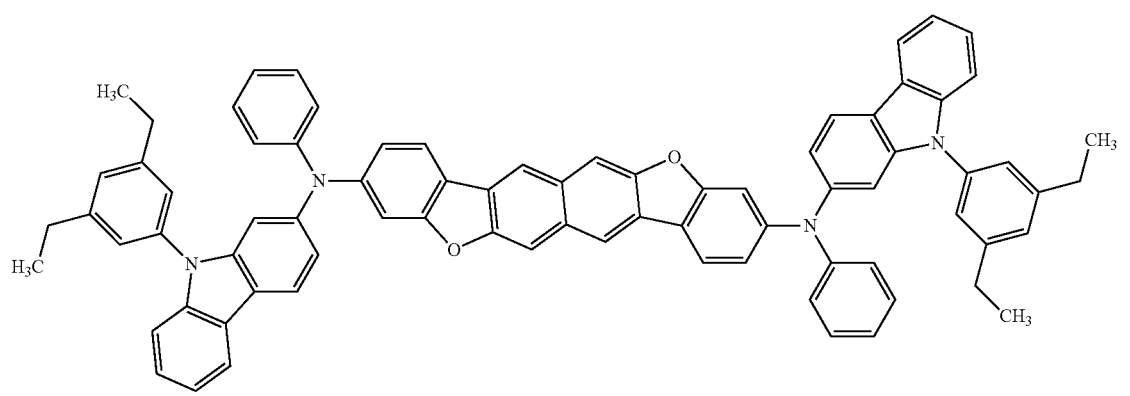

3,10mmEtPCA2Nbf(IV)-02

(Fabrication Method of Light-Emitting Device 1)

First, indium tin oxide containing silicon oxide (ITSO) was deposited over a glass substrate by a sputtering method to form the first electrode 101. The thickness of the first electrode 101 was 70 nm and the electrode area was 2 mm×2 mm.

Next, in pretreatment for forming the light-emitting device over a substrate, a surface of the substrate was washed with water and baked at 200° C. for 1 hour, and then UV ozone treatment was performed for 370 seconds.

After that, the substrate was transferred into a vacuum evaporation apparatus where the pressure was reduced to approximately 104 Pa, vacuum baking was performed at 170° C. for 30 minutes in a heating chamber of the vacuum evaporation apparatus, and then the substrate was cooled down for approximately 30 minutes.

Next, the substrate provided with the first electrode 101 was fixed to a substrate holder provided in the vacuum evaporation apparatus such that the side on which the first electrode 101 was formed faced downward. Then, N,N-bis(4-biphenyl)-6-phenylbenzo[b]naphtho[1,2-d]furan-8-amine (abbreviation: BBABnf) represented by Structural Formula (i) above and an electron acceptor material (OCHD-001) were deposited on the first electrode 101 to a thickness of 10 nm by a co-evaporation method using resistance heating such that the weight ratio of BBABnf to OCHD-001 was 1:0.1, whereby the hole-injection layer 111 was formed.

Next, over the hole-injection layer 111, BBABnf was deposited by evaporation to a thickness of 20 nm, and then 3,3'-(naphthalene-1,4-diyl)bis(9-phenyl-9H-carbazole) (abbreviation: PCzN2) represented by Structural Formula (ii) above was deposited by evaporation to a thickness of 10 nm, whereby the hole-transport layer 112 was formed.

Then, 9-(1-naphthyl)-10-[4-(2-naphthyl)phenyl]anthracene (abbreviation: αN-PNPAnth) represented by Structural Formula (iii) above and N,N'-bis[9-(3,5-di-tert-butylphenyl)-9H-carbazol-2-yl]-N,N'-diphenyl-naphtho[2,3-b;6,7-b']bisbenzofuran-3,10-diamine (abbreviation: 3,10mmtBuPCA2Nbf(IV)-02) represented by Structural Formula (iv) above were deposited by co-evaporation to a thickness of 25 nm such that the weight ratio of αN-βNPAnth to 3,10mmtBuPCA2Nbf(IV)-02 was 1:0.015, whereby the light-emitting layer 113 was formed.

Then, over the light-emitting layer 113, 2-[3'-(dibenzothiophen-4-yl)biphenyl-3-yl]dibenzo[f,h]quinoxaline (abbreviation: 2mDBTBPDBq-II) represented by Structural formula (v) above was deposited to a thickness of 15 nm, and then 2,9-di(2-naphthyl)-4,7-diphenyl-1,10-phenanthroline (abbreviation: NBPhen) represented by Structural Formula (vi) above was deposited to a thickness of 10 nm by evaporation, whereby the electron-transport layer 114 was formed.

After the formation of the electron-transport layer 114, lithium fluoride (LiF) was deposited by evaporation to a thickness of 1 nm to form the electron-injection layer 115. Then, aluminum was deposited by evaporation to a thickness of 200 nm to form the second electrode 102. Thus, the light-emitting device 1 of this example was fabricated.

(Fabrication Method of Comparative Light-Emitting Device 1-1)

The comparative light-emitting device 1-1 was fabricated in the same manner as the light-emitting device 1 except that 3,10-bis[N-(9-phenyl-9H-carbazol-2-yl)-N-phenylamino]naphtho[2,3-b;6,7-b']bisbenzofuran (abbreviation: 3,10PCA2Nbf(IV)-02) represented by Structural Formula (vii) was used instead of 3,10mmtBuPCA2Nbf(IV)-02 used for the light-emitting device 1.

(Fabrication Method of Comparative Light-Emitting Device 1-2)

The comparative light-emitting device 1-2 was fabricated in the same manner as the light-emitting device 1 except that N,N-bis[9-(3,5-diethylphenyl)-9H-carbazol-2-yl]-N,N-diphenyl-naphtho[2,3-b;6,7-b']bisbenzofuran-3,10-diamine (abbreviation: 3,10mmEtPCA2Nbf(IV)-02) represented by Structural Formula (viii) above was used instead of 3,10mmtBuPCA2Nbf(IV)-02 used for the light-emitting device 1.

The structures of the light-emitting devices are listed in the following table.

TABLE 1

| | Hole-injection layer 10 nm | Hole-transport layer | | Light-emitting layer 25 nm | Electron-transport layer | |
|---|---|---|---|---|---|---|
| | | 1 20 nm | 2 10 nm | | 1 15 nm | 2 10 nm |
| Light-emitting device 1 | BBABnf:OCHD-001 (1:0.1) | BBABnf | PCzN2 | *1 | 2mDBTBPDBq-II | NBPhen |
| Comparative light-emitting device 1-1 | | | | *2 | | |
| Comparative light-emitting device 1-2 | | | | *3 | | |

*1 αN-βNPAnth:3,10mmtBuPCA2Nbf(IV)-02 (1:0.015)
*2 αN-βNPAnth:3,10PCA2Nbf(IV)-02 (1:0.015)
*3 αN-βNPAnth:3,10mmEtPCA2Nbf(IV)-02 (1:0.015)

The light-emitting devices were sealed using a glass substrate in a glove box containing a nitrogen atmosphere so as not to be exposed to the air (a sealing material was applied to surround the device and UV treatment and heat treatment at 80° C. for 1 hour were performed at the time of sealing). Then, the initial characteristics of the light-emitting devices were measured.

Figure 18:
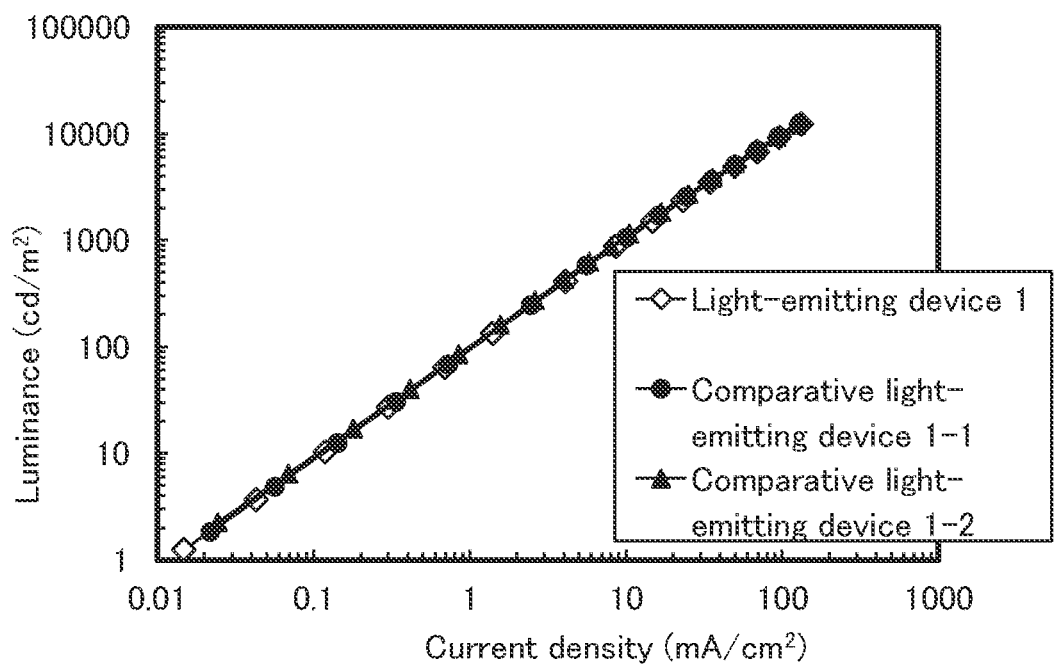
FIG. 18 shows luminance-current density characteristics of a light-emitting device 1, a comparative light-emitting device 1-1, and a comparative light-emitting device 1-2.
Figure 19:
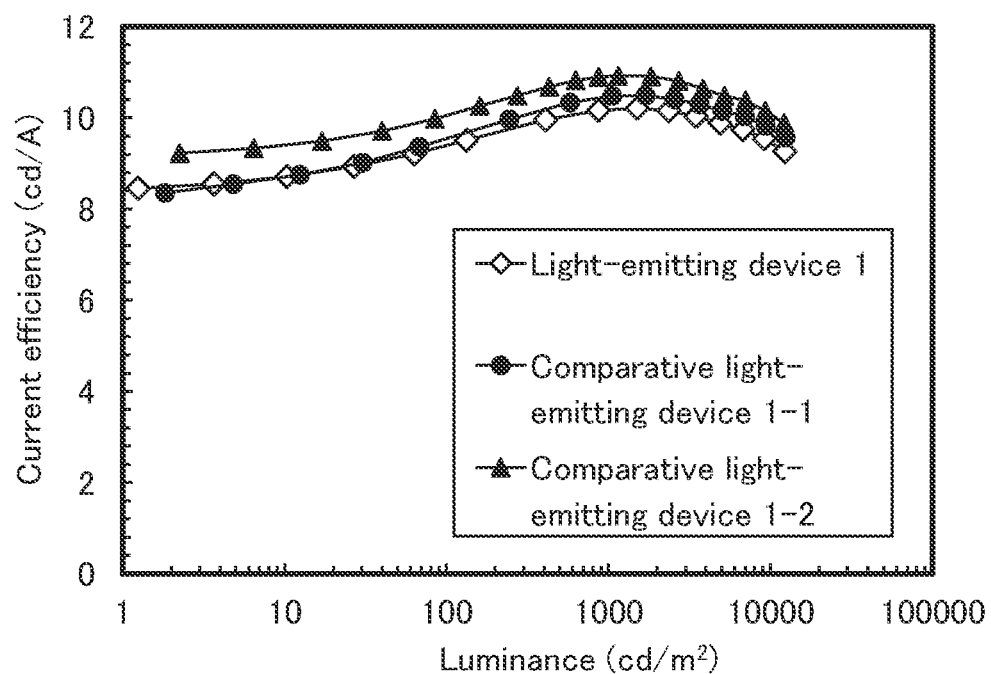
FIG. 19 shows current efficiency-luminance characteristics of the light-emitting device 1, the comparative light-emitting device 1-1, and the comparative light-emitting device 1-2.
Figure 20:
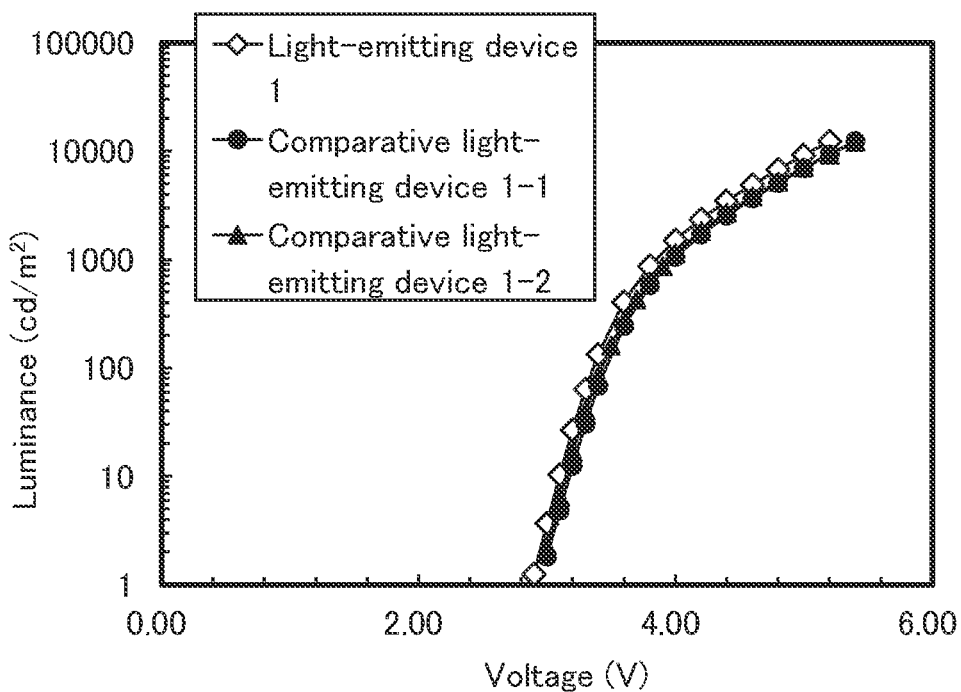
FIG. 20 shows luminance-voltage characteristics of the light-emitting device 1, the comparative light-emitting device 1-1, and the comparative light-emitting device 1-2.
Figure 21:
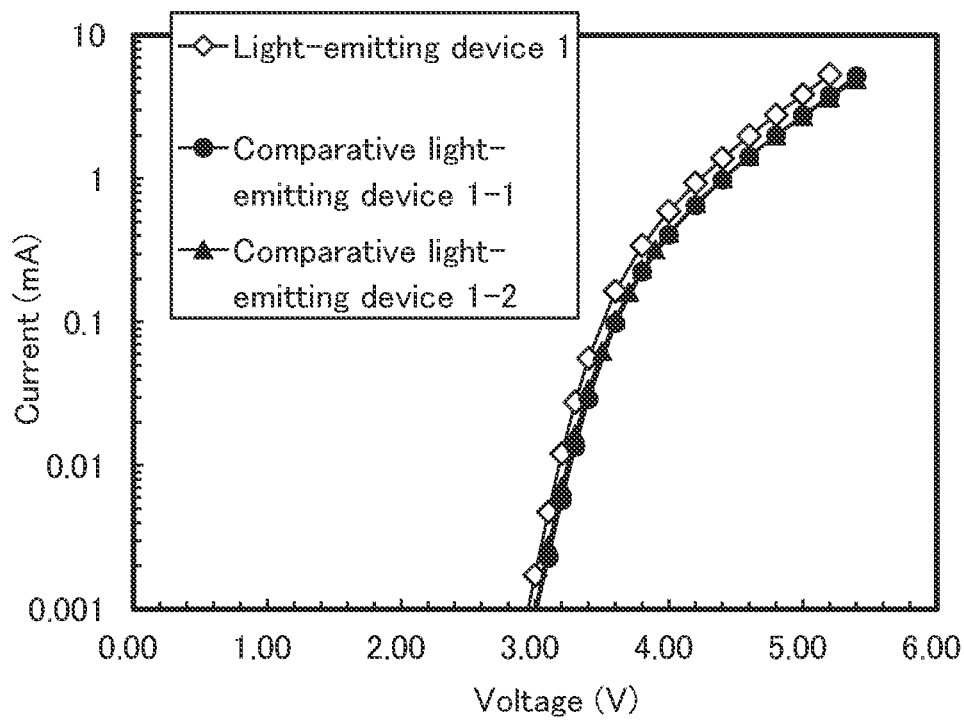
FIG. 21 shows current-voltage characteristics of the light-emitting device 1, the comparative light-emitting device 1-1, and the comparative light-emitting device 1-2.
Figure 22:
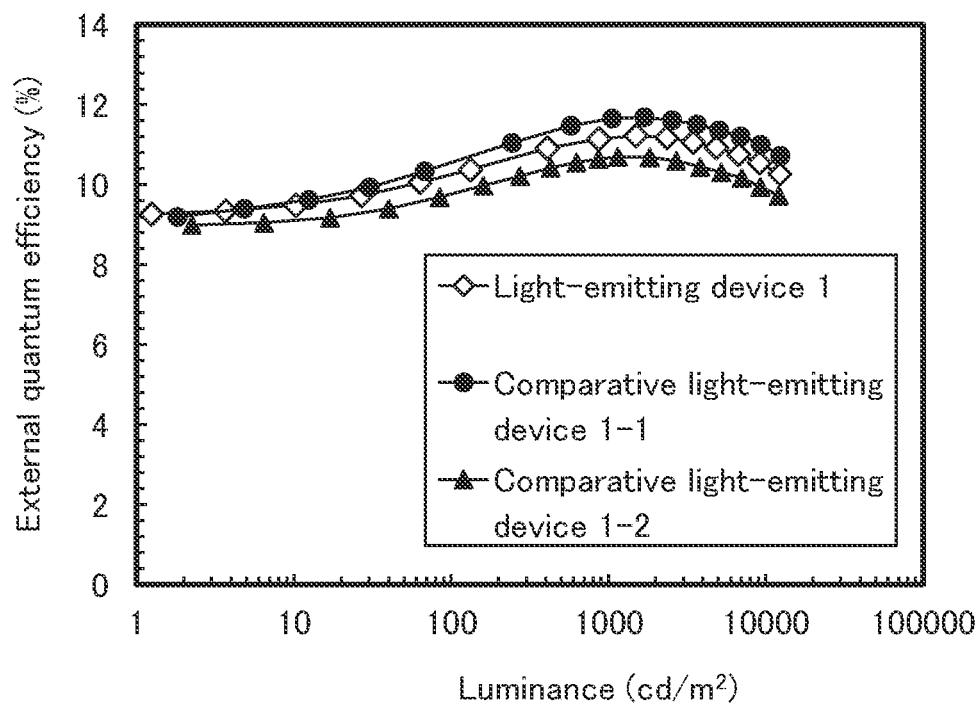
FIG. 22 shows external quantum efficiency-luminance characteristics of the light-emitting device 1, the comparative light-emitting device 1-1, and the comparative light-emitting device 1-2.
Figure 23:
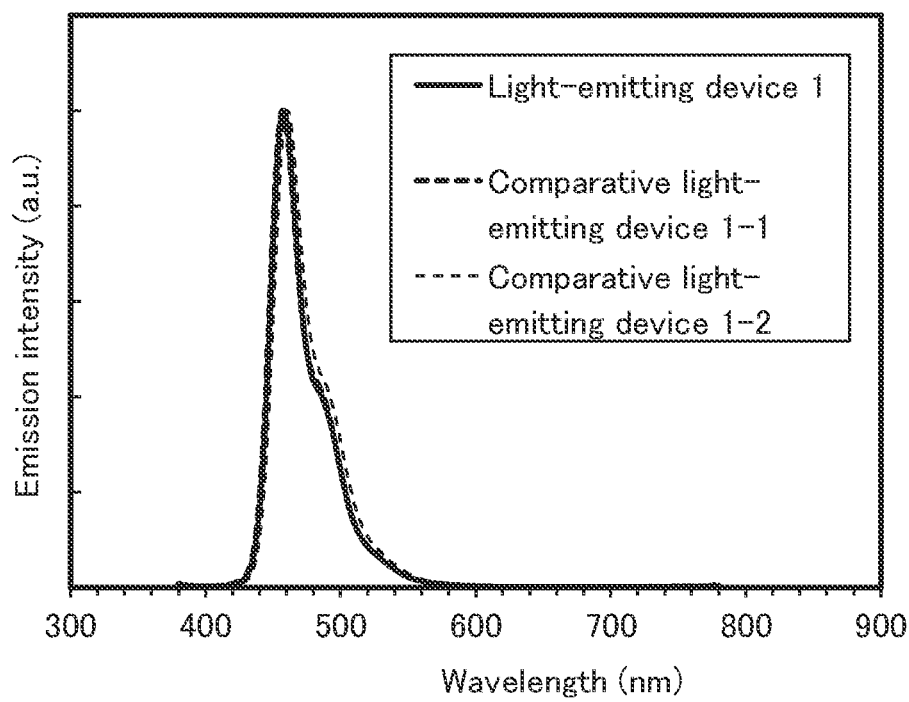
FIG. 23 shows emission spectra of the light-emitting device 1, the comparative light-emitting device 1-1, and the comparative light-emitting device 1-2.

FIG. 18 shows the luminance-current density characteristics of the light-emitting device 1, the comparative light-emitting device 1-1, and the comparative light-emitting device 1-2. FIG. 19 shows the current efficiency-luminance characteristics thereof. FIG. 20 shows the luminance-voltage characteristics thereof. FIG. 21 shows the current-voltage characteristics thereof. FIG. 22 shows the external quantum efficiency-luminance characteristics thereof. FIG. 23 shows the emission spectra thereof. The main characteristics of the light-emitting devices at a luminance of approximately 1000 cd/m$^2$ are shown below.

TABLE 2

| | Voltage (V) | Current (mA) | Current density (mA/cm$^2$) | Chromaticity x | Chromaticity y | Current efficiency (cd/A) | External quantum efficiency (%) |
|---|---|---|---|---|---|---|---|
| Light-emitting device 1 | 3.8 | 0.34 | 8.6 | 0.14 | 0.10 | 10.2 | 11.2 |

TABLE 2-continued

| | Voltage (V) | Current (mA) | Current density (mA/cm$^2$) | Chromaticity x | Chromaticity y | Current efficiency (cd/A) | External quantum efficiency (%) |
|---|---|---|---|---|---|---|---|
| Comparative light-emitting device 1-1 | 4.0 | 0.40 | 10.1 | 0.14 | 0.10 | 10.5 | 11.7 |
| Comparative light-emitting device 1-2 | 3.9 | 0.32 | 8.0 | 0.13 | 0.12 | 10.9 | 10.6 |

FIG. 18 to FIG. 23 show that the light-emitting device 1 of one embodiment of the present invention, the comparative light-emitting device 1-1, and the comparative light-emitting device 1-2 are each an EL device having high emission efficiency.

Here, emission spectra and thermophysical properties of 3,10mmtBuPCA2Nbf(IV)-02, which is the organic compound of one embodiment of the present invention used as the light-emitting material of the light-emitting device 1, 3,10PCA2Nbf(IV)-02 used as the light-emitting material of the comparative light-emitting device 1-1, 3,10mmEtPCA2Nbf(IV)-02 used as the light-emitting material of the comparative light-emitting device 1-2, and N,N-bis[9-(3,5-dihexylphenyl)-9H-carbazol-2-yl]-N,N-diphenyl-naphtho[2,3-b;6,7-b']bisbenzofuran-3,10-diamine (abbreviation: 3,10mmHexPCA2Nbf(IV)-02) represented by Structural Formula (ix) below were examined.

four substances have their emission spectrum peaks at substantially the same position and also have alike spectrum shapes. This means introduction of the above-described substituents to the phenyl group that is substituted at the 9-position of the carbazolyl group in these four substances does not influence the conjugation of the substances themselves nor the emission colors.

In other words, 3,10PCA2Nbf(IV)-02 exhibits blue light emission with favorable color purity; the emission and absorption spectra of 3,10mmtBuPCA2Nbf(IV)-02, 3,10mmEtPCA2Nbf(IV)-02, and 3,10mmHexPCA2Nbf(IV)-02 are hardly influenced by introduction of substituents; and they are each an organic compound which exhibits blue light emission with favorable color purity. It should be noted that 3,10PCA2Nbf(IV)-02 includes arylamine bonded to the main skeleton, which is a luminophore, and introduction of the same substituents to the phenyl group included in

[Chemical Formula 44]

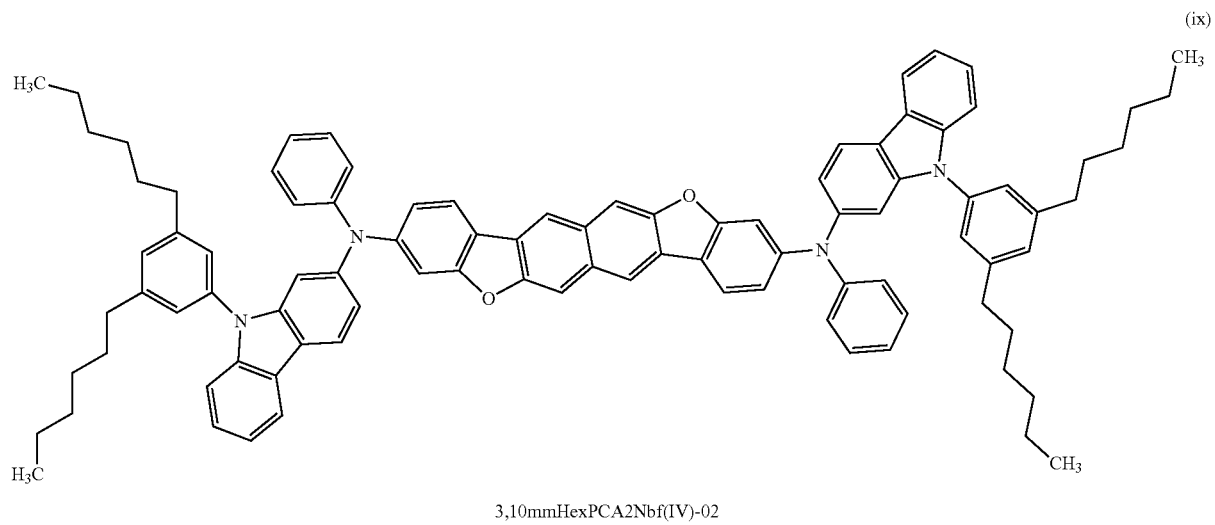

(ix)

3,10mmHexPCA2Nbf(IV)-02

Note that 3,10mmtBuPCA2Nbf(IV)-02, which is the organic compound represented by Structural Formula (iv) above, is a substance having two tert-butyl groups substituted at meta-positions of a phenyl group that is substituted at the 9-position of a carbazolyl group included in 3,10PCA2Nbf(IV)-02, which is the organic compound represented by Structural Formula (vii) above. Furthermore, 3,10mmEtPCA2Nbf(IV)-02, which is the organic compound represented by Structural Formula (viii) above, is a substance having ethyl groups substituted at the same positons as the above, and 3,10mmHexPCA2Nbf(IV)-02, which is the organic compound represented by Structural Formula (ix) above, is a substance having n-hexyl groups substituted at the same positons as the above.

Figure 24:
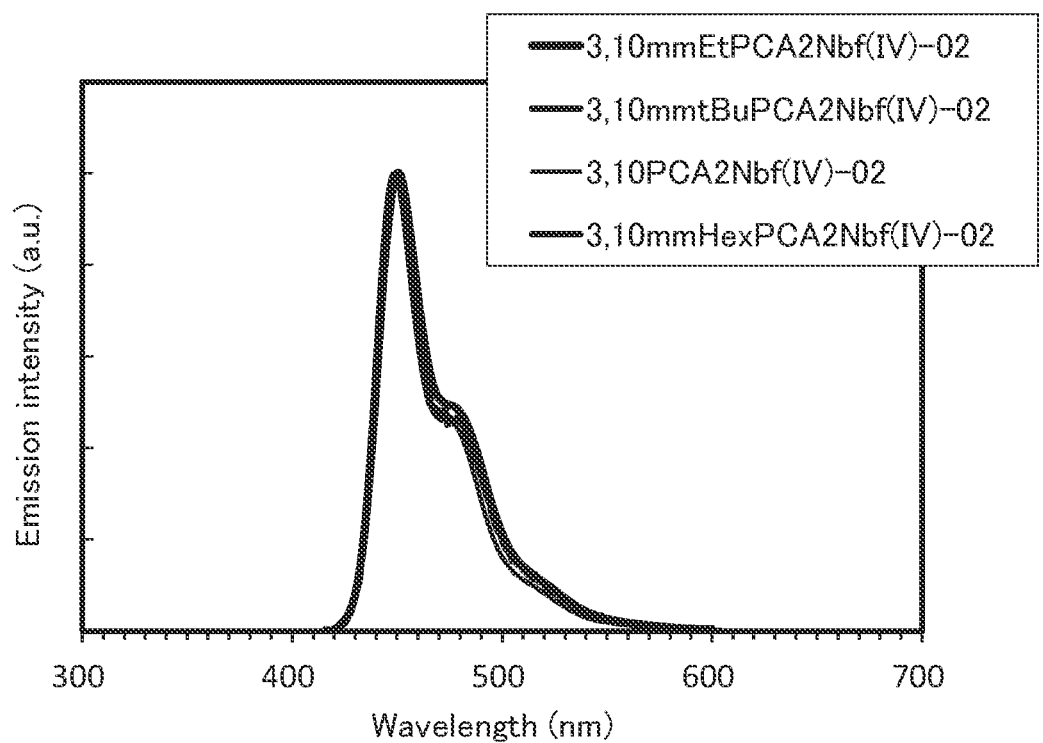
FIG. 24 shows emission spectra of 3,10mmtBuPCA2Nbf(IV)-02; 3,10mmEtPCA2Nbf(IV)-02; 3,10mmHexPCA2Nbf(IV)-02; and 3,10PCA2Nbf(IV)-02 in the solution state.

FIG. 24 shows emission spectra of these four substances in a toluene solution. As can be found from FIG. 24, these the arylamine shifts the emission spectrum to the longer wavelength side and lowers the color purity.

Figure 25:
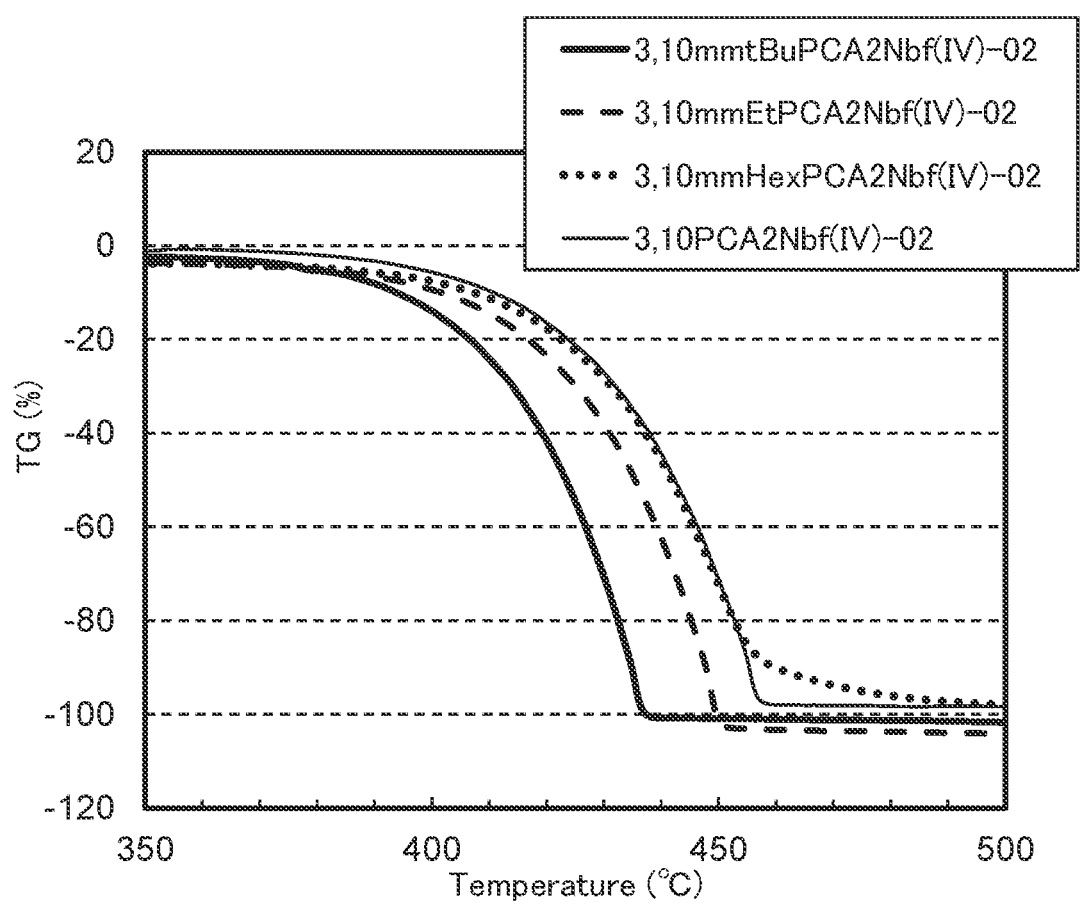
FIG. 25 shows the relationship between the weight and the temperature in thermogravimetry-differential thermal analysis of 3,10mmtBuPCA2Nbf(IV)-02; 3,10mmEtPCA2Nbf(IV)-02; 3,10mmHexPCA2Nbf(IV)-02; and 3,10PCA2Nbf(IV)-02.

The thermogravimetry-differential thermal analysis (TG-DTA) of these four substances was performed. The measurement was performed with a high vacuum differential type differential thermal balance (TG-DTA2410SA, produced by Bruker AXS K.K.). FIG. 25 shows the relationship between weight reduction and temperature under measurement conditions of 10 Pa and the temperature rising rate of 10° C./min. The temperatures of the time when the weight of the organic compounds is reduced from the initial weight by 5%, 10%, and 50% (weight reduction temperature) are shown in Table 3.

TABLE 3

| | | TG [%] | | |
|---|---|---|---|---|
| | | −5 | −10 | −50 |
| Temperature [° C.] | (vii) 3,10PCA2Nbf(IV)-02 | 398 | 411 | 442 |
| | (iv) 3,10mmtBuPCA2Nbf(IV)-02 | 378 | 394 | 423 |
| | (viii) 3,10mmEtPCA2Nbf(IV)-02 | 380 | 402 | 436 |
| | (ix) 3,10mmHexPCA2Nbf(IV)-02 | 384 | 407 | 442 |

According to Table 3, the substances having two alkyl groups both substituted at meta-positions of the phenyl group that is substituted at the 9-position of the carbazolyl group included in 3,10PCA2Nbf(IV)-02 each have a tendency for weight reduction temperature to become lower and have improved sublimability. In particular, 3,10mmtBuPCA2Nbf(IV)-02 in which two tert-butyl groups are substituted at the meta-positions exhibited the highest sublimability.

Figure 26:
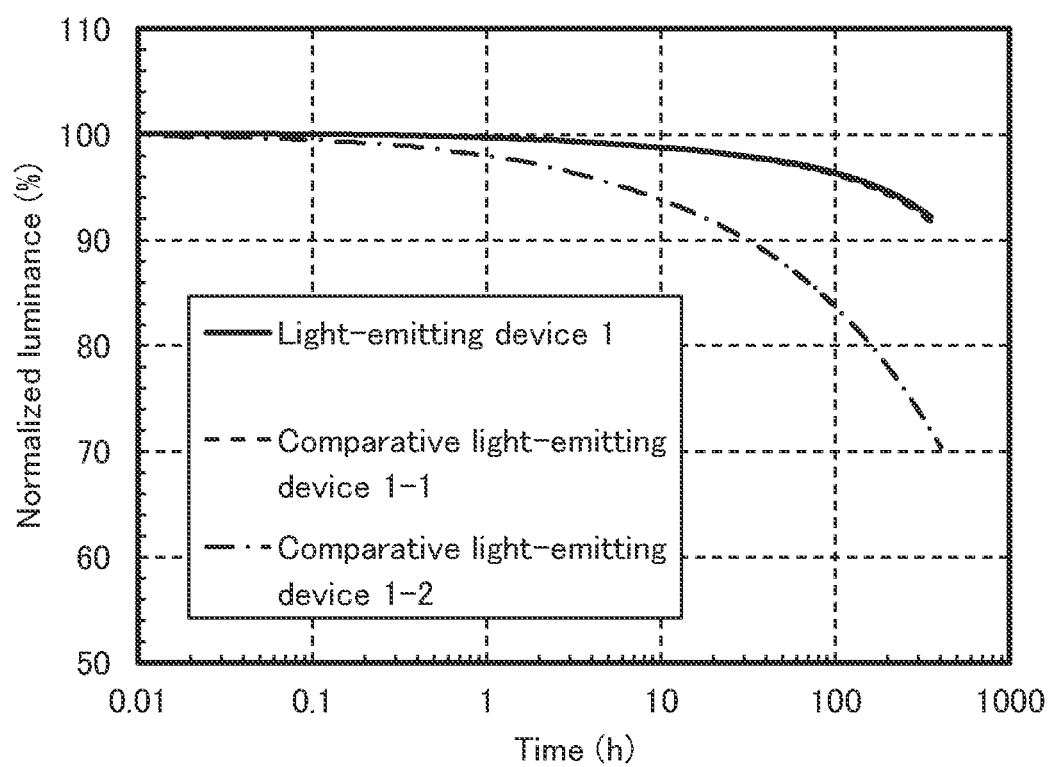
FIG. 26 is a graph showing a change in luminance over driving time of the light-emitting device 1, the comparative light-emitting device 1-1, and the comparative light-emitting device 1-2.

FIG. 26 is a graph showing a change in luminance over driving time at a current density of 50 mA/cm². As shown in FIG. 26, the comparative light-emitting device 1-1 and the light-emitting device 1, which is the light-emitting device of one embodiment of the present invention, both show more favorable characteristics than the comparative light-emitting element 1-2.

Note that the light-emitting device which uses 3,10mmHexPCA2Nbf(IV)-02 was not able to be fabricated and thus data for the device does not exist because 3,10mmHexPCA2Nbf(IV)-02 was decomposed at the time of sublimation purification.

As described above, to each of the meta-positions of the phenyl group bonded to the 9-position of the carbazolyl group in the organic compound of one embodiment of the present invention, the secondary or tertiary alkyl group having a branched carbon atom which is bonded to the phenyl group is bonded. This enables favorable sublimability and fabrication of a highly reliable light-emitting device.

The measurement results on the solubility of 3,10PCA2Nbf(IV)-02 and 3,10mmtBuPCA2Nbf(IV)-02 in a solvent are shown below. The solubility in the table are that in toluene at 25° C. Consequently, the organic compound of one embodiment of the present invention has improved solubility in a solvent owing to the bonding of the secondary or tertiary alkyl groups having 3 to 6 carbon atoms and having a branched carbon atom which is bonded to the phenyl group to the two meta-positions of the phenyl group bonded to the 9-position of the carbazolyl group. Thus, the organic compound of one embodiment of the present invention can be easily produced owing to the easy purification.

[Chemical Formula 45]

TABLE 4

| | Solubility | | |
|---|---|---|---|
| Material | 1M | 0.1M | 0.01M |
| (vii) 3,10PCA2Nbf(IV)-02 | x | x | x |
| (iv) 3,10mmtBuPCA2Nbf(IV)-02 | x | ○ | ○ |
| | Solubility in toluene | | |
| | Temperature: 25° C. | | |

The melting point and the glass transition temperature of 3,10mmtBuPCA2Nbf(IV)-02 and 3,10PCA2Nbf(IV)-02 were measured with a differential scanning calorimeter (Pyris 1 DSC, manufactured by Perkin Elmer Co., Ltd.). The measurement results show that the melting point of 3,10mmtBuPCA2Nbf(IV)-02 was 391° C. and the glass transition temperature thereof was 201° C. The melting point of 3,10PCA2Nbf(IV)-02 was 366° C. and the glass transition temperature thereof was 184° C. Consequently, the organic compound of one embodiment of the present invention has a high melting point and a high glass transition temperature owing to the bonding of the secondary or tertiary alkyl groups having 3 to 6 carbon atoms and having a branched carbon atom which is bonded to the phenyl group to the two meta-positions of the phenyl group bonded to the 9-position of the carbazolyl group. Thus, the organic compound of one embodiment of the present invention can have favorable heat resistance.

Example 3

In this example, a light-emitting device 2 which uses the organic compound of one embodiment of the present invention and a comparative light-emitting device 2 which does not use the organic compound are described. Structural formulae of organic compounds used for the light-emitting device 2 and the comparative light-emitting device 2 are shown below.

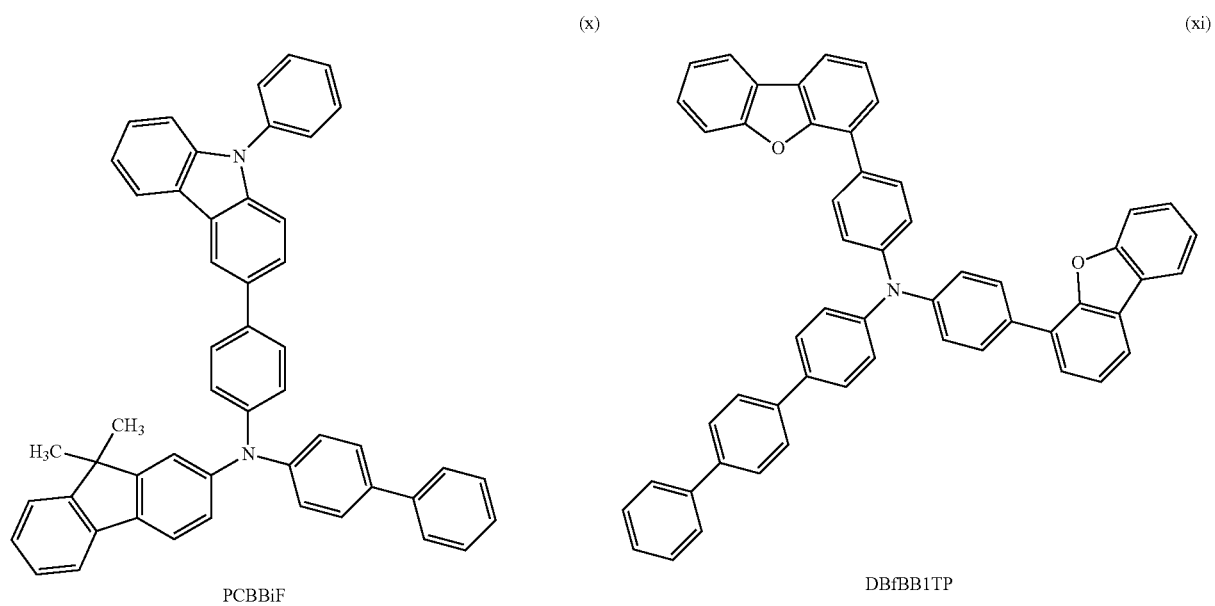

(x) PCBBiF (xi) DBfBB1TP

-continued
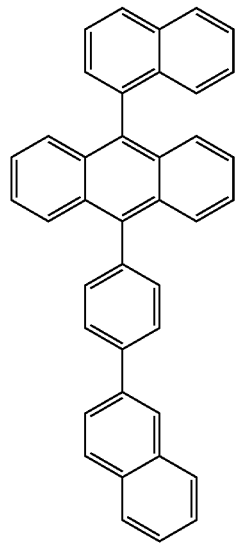
αN-βNPAnth
(iii)
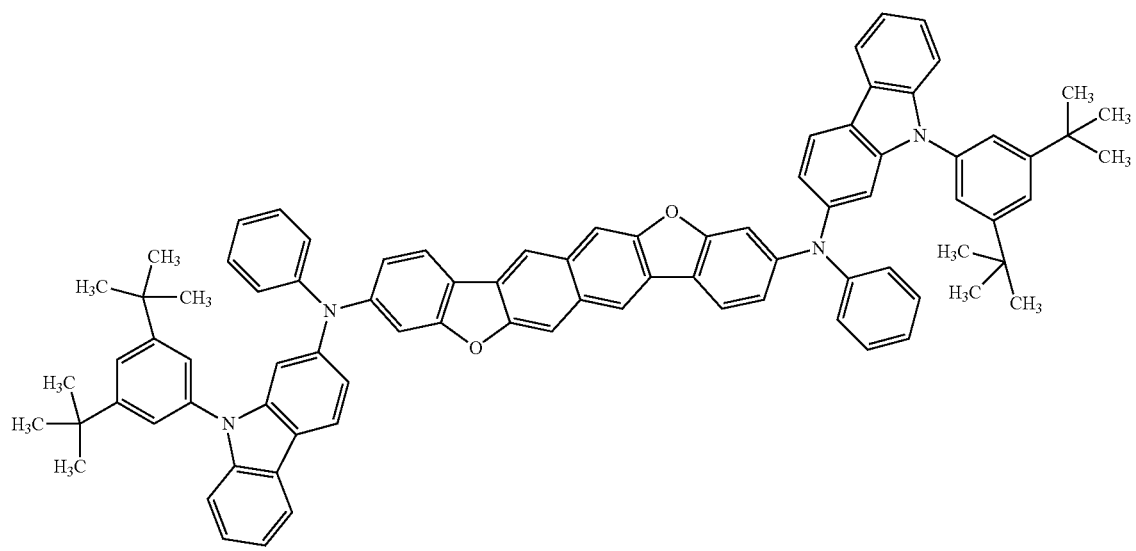
3,10mmtBuPCA2Nbf(IV)-02
(iv)

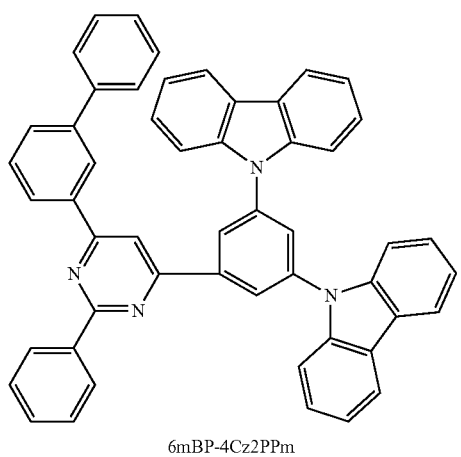

6mBP-4Cz2PPm

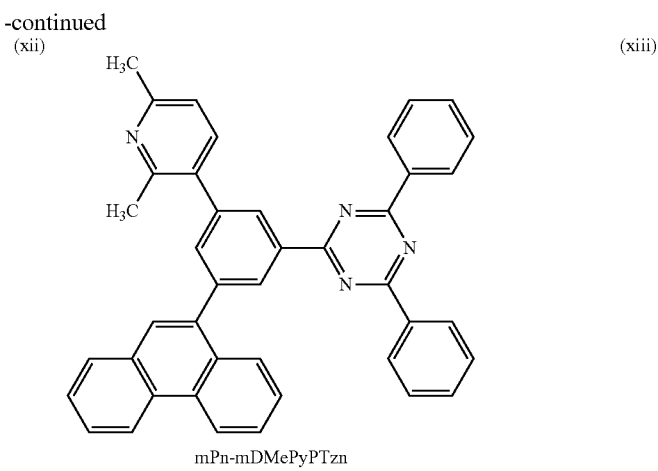

mPn-mDMePyPTzn

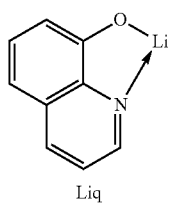

Liq

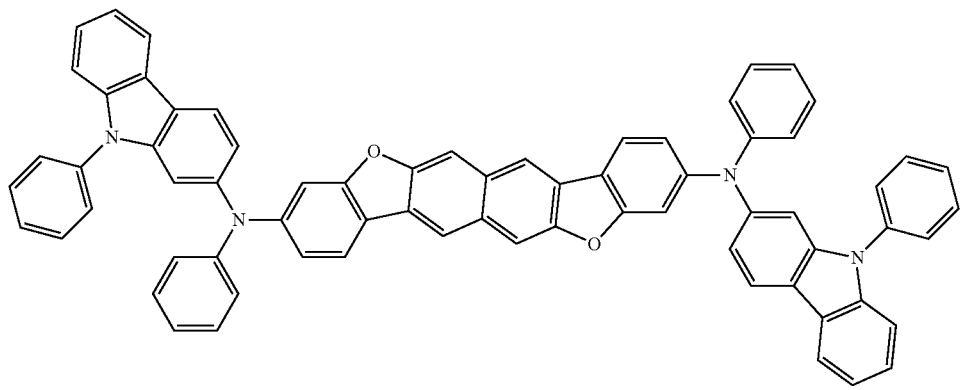

3,10PCA2Nbf(IV)-02

(Fabrication Method of Light-Emitting Device 2)

First, indium tin oxide containing silicon oxide (ITSO) was deposited over a glass substrate by a sputtering method to form the first electrode 101. The thickness of the first electrode 101 was 70 nm and the electrode area was 2 mm×2 mm.

Next, in pretreatment for forming the light-emitting device over a substrate, a surface of the substrate was washed with water and baked at 200° C. for 1 hour, and then UV ozone treatment was performed for 370 seconds.

After that, the substrate was transferred into a vacuum evaporation apparatus where the pressure was reduced to approximately 104 Pa, vacuum baking was performed at 170° C. for 30 minutes in a heating chamber of the vacuum evaporation apparatus, and then the substrate was cooled down for approximately 30 minutes.

Next, the substrate provided with the first electrode 101 was fixed to a substrate holder provided in the vacuum evaporation apparatus such that the side on which the first electrode 101 was formed faced downward. Then, N-(1,1'-biphenyl-4-yl)-N-[4-(9-phenyl-9H-carbazol-3-yl)phenyl]-9,9-dimethyl-9H-fluoren-2-amine (abbreviation: PCBBiF) represented by Structural Formula (x) above and an electron acceptor material (OCHD-001) were deposited on the first electrode 101 to a thickness of 10 nm by a co-evaporation method using resistance heating such that the weight ratio of PCBBiF to OCHD-001 was 1:0.03, whereby the hole-injection layer 111 was formed.

Next, over the hole-injection layer 111, PCBBiF was deposited by evaporation to a thickness of 20 nm, and then N,N-bis[4-(dibenzofuran-4-yl)phenyl]-4-amino-p-terphenyl (abbreviation: DBfBB1TP) represented by Structural Formula (xi) above was deposited by evaporation to a thickness of 10 nm, whereby the hole-transport layer 112 was formed.

Then, 9-(1-naphthyl)-10-[4-(2-naphthyl)phenyl]anthracene (abbreviation: αN-PNPAnth) represented by Structural Formula (iii) above and N,N-bis[9-(3,5-di-tert-butylphenyl)-9H-carbazol-2-yl]-N,N-diphenyl-naphtho[2,3-b;6,7-b']bisbenzofuran-3,10-diamine (abbreviation: 3,10mmtBuPCA2Nbf(IV)-02) represented by Structural Formula (iv) above were deposited by co-evaporation to a thickness of 25 nm such that the weight ratio of αN-βNPAnth to 3,10mmtBuPCA2Nbf(IV)-02 was 1:0.015, whereby the light-emitting layer 113 was formed.

Then, over the light-emitting layer 113, 6-(1,1'-biphenyl-3-yl)-4-[3,5-bis(9H-carbazol-9-yl)phenyl]-2-phenylpyrimidine (abbreviation: 6mBP-4Cz2PPm) represented by Structural formula (xii) above was deposited to a thickness of 10 nm, and then 2-[3-(2,6-dimethyl-3-pyridinyl)-5-(9-phenanthrenyl)phenyl]-4,6-diphenyl-1,3,5-triazine (abbreviation: mPn-mDMePyPTzn) represented by Structural Formula (xiii) above and 8-hydroxyquinolinato-lithium (abbreviation: Liq) represented by Structural Formula (xiv) above were deposited by co-evaporation to a thickness of 15 nm such that the weight ratio of mPn-mDMePyPTzn to Liq was 1:1, whereby the electron-transport layer 114 was formed.

After the formation of the electron-transport layer 114, Liq was deposited by evaporation to a thickness of 1 nm to form the electron-injection layer 115. Then, aluminum was deposited by evaporation to a thickness of 200 nm to form the second electrode 102. Thus, the light-emitting device 2 of this example was fabricated.

(Fabrication Method of Comparative Light-Emitting Device 2)

The comparative light-emitting device 2 was fabricated in the same manner as the light-emitting device 2 except that 3,10-bis[N-(9-phenyl-9H-carbazol-2-yl)-N-phenylamino]naphtho[2,3-b;6,7-b']bisbenzofuran (abbreviation: 3,10PCA2Nbf(IV)-02) represented by Structural Formula (vii) was used instead of 3,10mmtBuPCA2Nbf(IV)-02 used for the light-emitting device 2.

Figure 30:
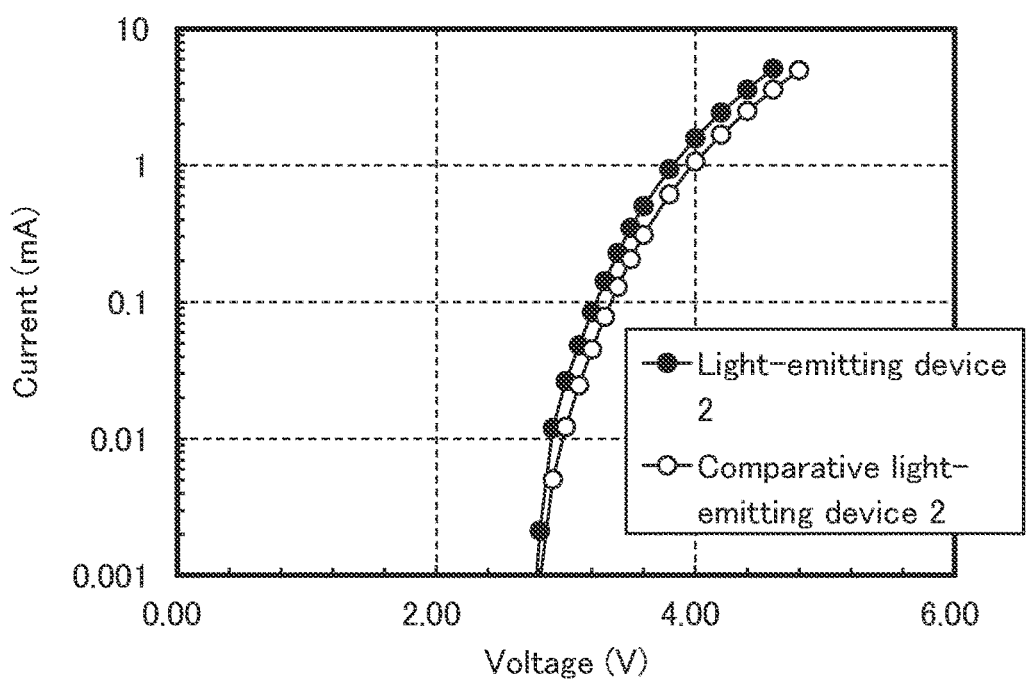
FIG. 30 shows current-voltage characteristics of the light-emitting device 2 and the comparative light-emitting device 2.
Figure 31:
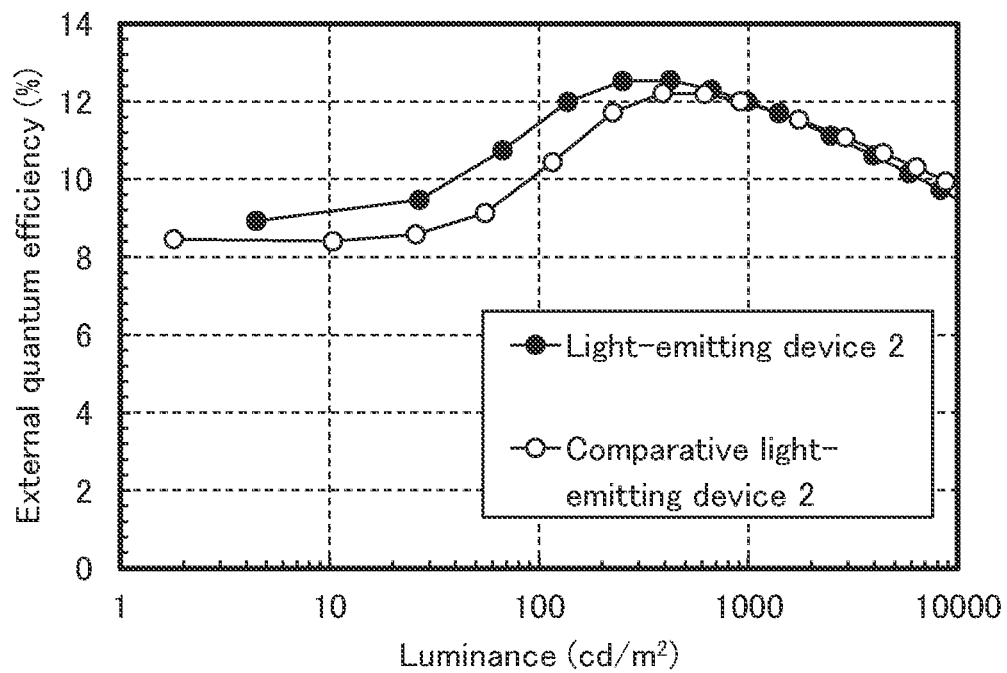
FIG. 31 shows external quantum efficiency-luminance characteristics of the light-emitting device 2 and the comparative light-emitting device 2.
Figure 32:
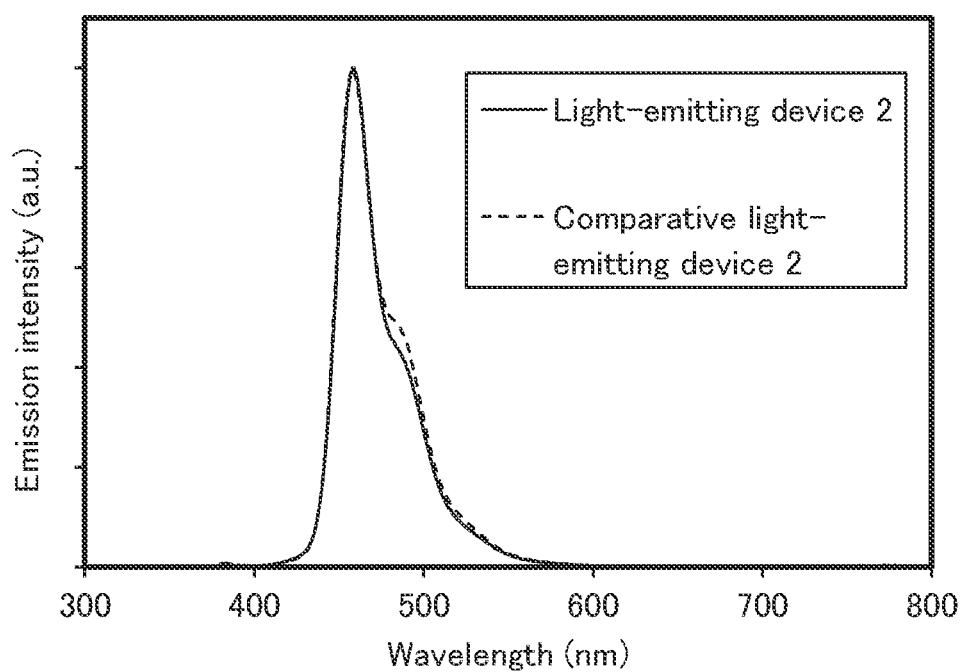
FIG. 32 shows emission spectra of the light-emitting device 2 and the comparative light-emitting device 2.

The structures of the light-emitting devices are listed in the following table.

luminance-voltage characteristics thereof. FIG. 30 shows the current-voltage characteristics thereof. FIG. 31 shows the external quantum efficiency-luminance characteristics thereof. FIG. 32 shows the emission spectra thereof. The main characteristics of the light-emitting devices at a luminance of approximately 1000 cd/m² are shown below.

TABLE 6

|  | Voltage (V) | Current (mA) | Current density (mA/cm²) | Chromaticity x | Chromaticity y | Current efficiency (cd/A) | External quantum efficiency (%) |
|---|---|---|---|---|---|---|---|
| Light-emitting device 2 | 3.5 | 0.35 | 8.7 | 0.14 | 0.11 | 11.4 | 12.0 |
| Comparative light-emitting device 2 | 3.6 | 0.31 | 7.7 | 0.13 | 0.12 | 11.9 | 12.0 |

FIG. 27 to FIG. 32 show that the light-emitting device 2 of one embodiment of the present invention and the comparative light-emitting device 2 are each an EL device having favorable characteristics.

Figure 33:
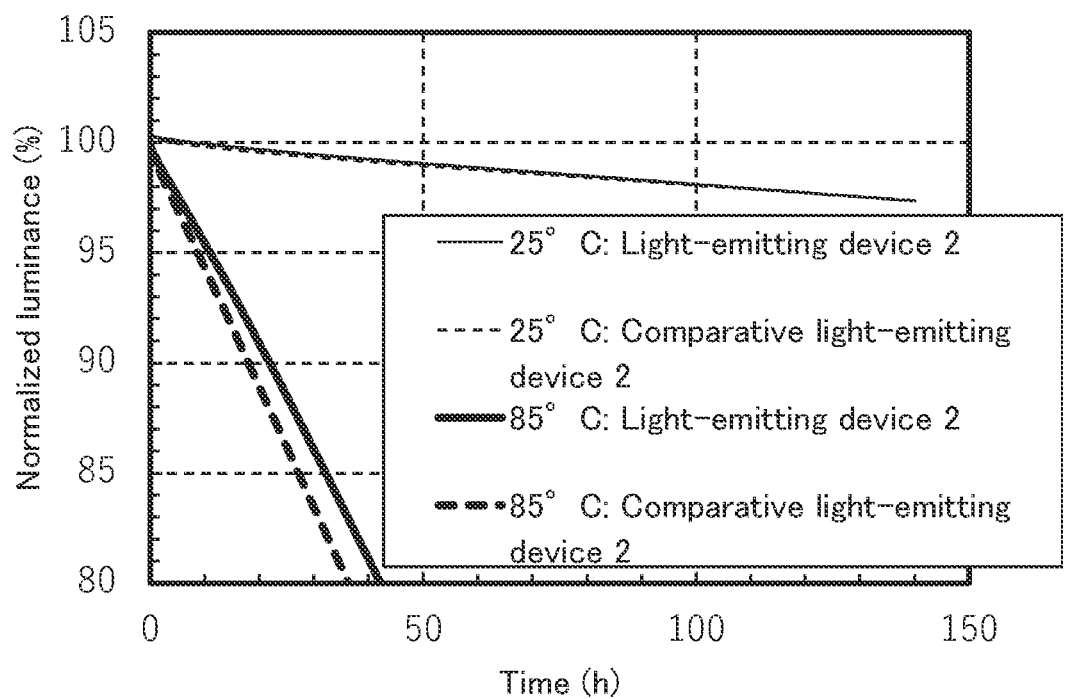
FIG. 33 is a graph showing a change in luminance over driving time of the light-emitting device 2 and the comparative light-emitting device 2.

Moreover, changes in luminance of the light-emitting devices having the same structures as the light-emitting device 2 and the comparative light-emitting device 2 over driving time at a current density of 50 mA/cm² were measured. The results are shown in FIG. 33. Note that the measurement was conducted under two temperature conditions, 25° C. and 85° C., and FIG. 33 shows the results under both conditions. As shown in FIG. 33, the light-emitting device 2 and the comparative light-emitting device 2 had similar favorable reliability at 25° C. On the other hand, the light-emitting device 2 and the comparative light-emitting device 2 showed apparently different results at 85° C.: the light-emitting device 2, which is one embodiment of the present invention, had more favorable reliability.

These results show that the light-emitting device which uses the organic compound of one embodiment of the present invention is highly reliable at high temperatures.

TABLE 5

|  | Hole-injection layer 10 nm | Hole-transport layer 1 20 nm | Hole-transport layer 2 10 nm | Light-emitting layer 25 nm | Electron-transport layer 1 10 nm | Electron-transport layer 2 15 nm | Electron-injection layer 1 nm |
|---|---|---|---|---|---|---|---|
| Light-emitting device 2 | PCBBiF:OCHD-001 (1:0.03) | PCBBiF | DBfBB1TP | *4 | 6mBP-4Cz2PPm | mPn-mDMePyPTzn:Liq (1:1) | Liq |
| Comparative light-emitting device 2 |  |  |  | *5 |  |  |  |

*4 αN-βNPAnth:3,10mmtBuPCA2Nbf(IV)-02 (1:0.015)
*5 αN-βNPAnth:3,10PCA2Nbf(IV)-02 (1:0.015)

The light-emitting devices were sealed using a glass substrate in a glove box containing a nitrogen atmosphere so as not to be exposed to the air (a sealing material was applied to surround the device and UV treatment and heat treatment at 80° C. for 1 hour were performed at the time of sealing). Then, the initial characteristics of the light-emitting devices were measured.

Figure 27:
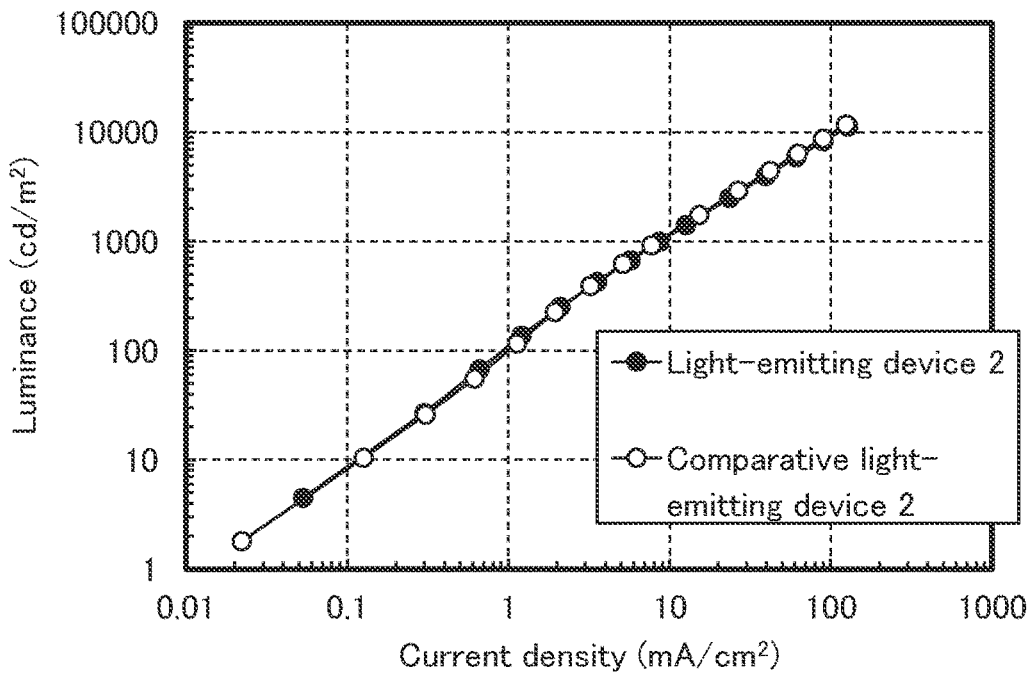
FIG. 27 shows luminance-current density characteristics of a light-emitting device 2 and a comparative light-emitting device 2.
Figure 28:
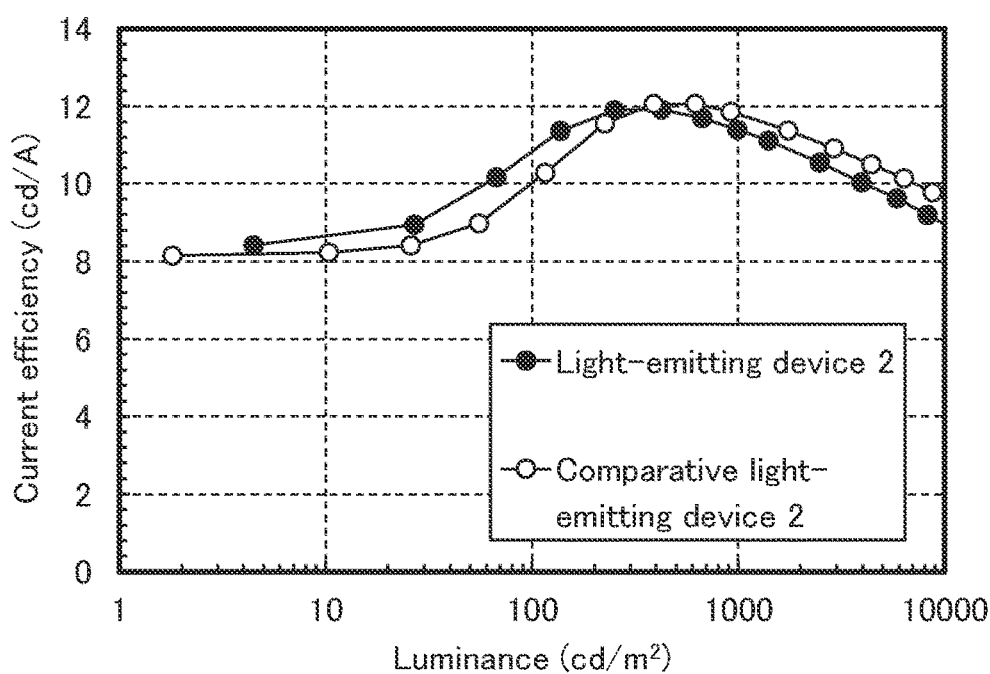
FIG. 28 shows current efficiency-luminance characteristics of the light-emitting device 2 and the comparative light-emitting device 2.
Figure 29:
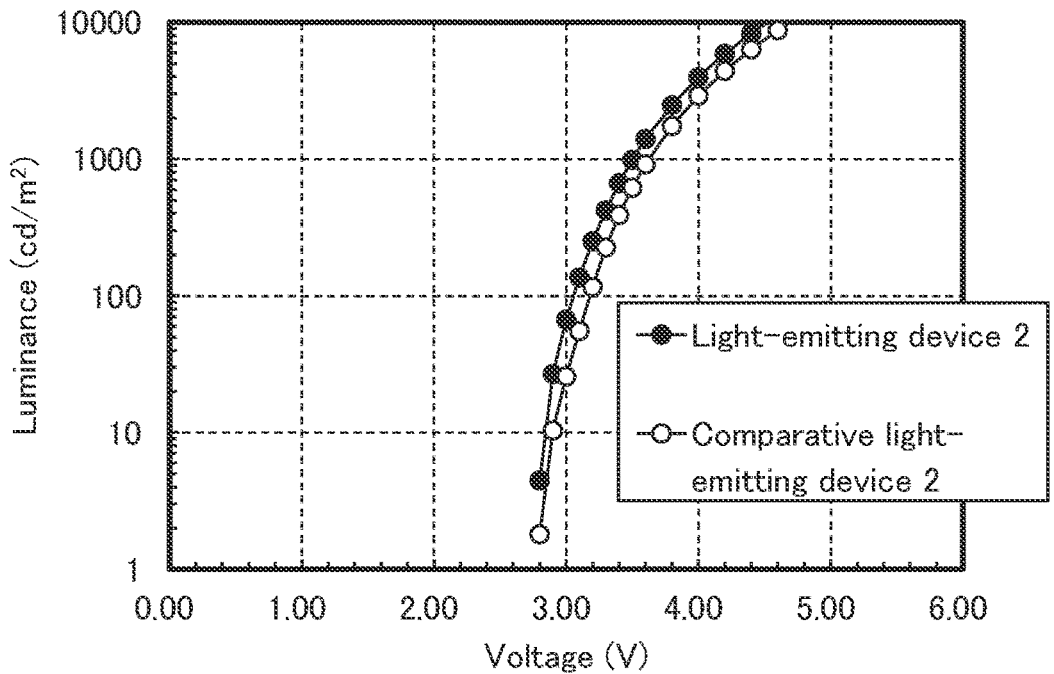
FIG. 29 shows luminance-voltage characteristics of the light-emitting device 2 and the comparative light-emitting device 2.

FIG. 27 shows the luminance-current density characteristics of the light-emitting device 2 and the comparative light-emitting device 2. FIG. 28 shows the current efficiency-luminance characteristics thereof. FIG. 29 shows the Therefore, it was found that the organic compound of one embodiment of the present invention has high heat resistance.

Example 4

In this example, a light-emitting device 3 which uses the organic compound of one embodiment of the present invention is described. Structural formulae of organic compounds used for the light-emitting device 3 are shown below.

[Chemical Formula 46]
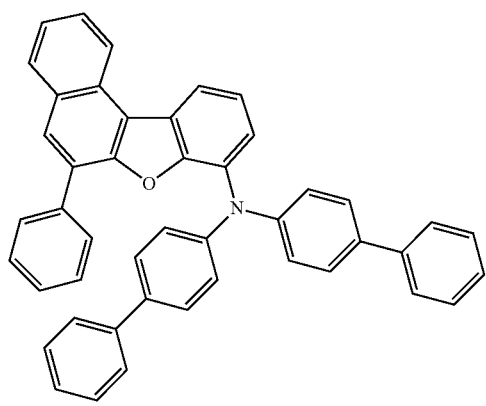
BBABnf
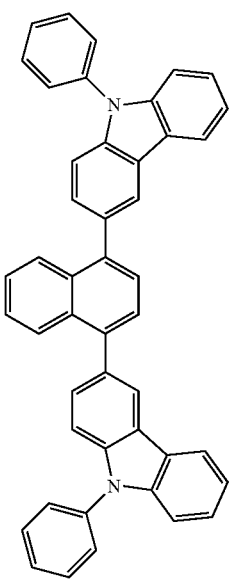
PCzN2
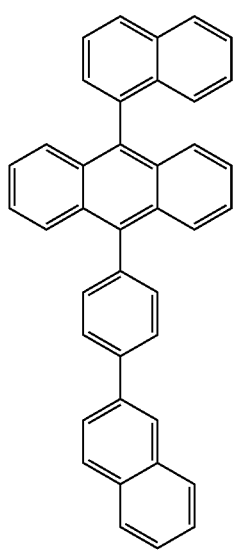
αN-βNPAnth
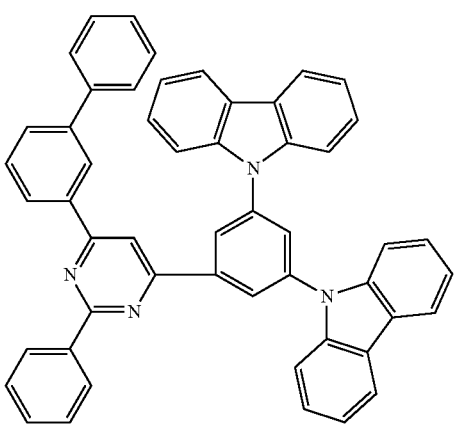
6mBP-4Cz2PPm
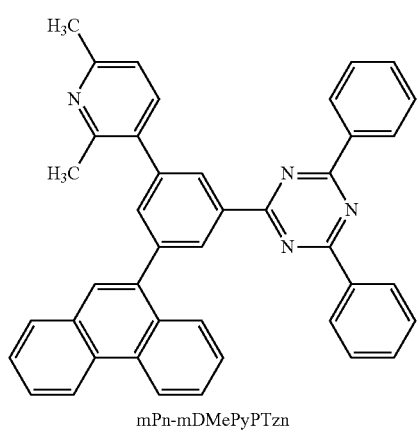
mPn-mDMePyPTzn
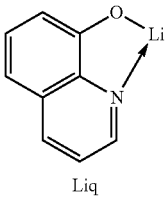
Liq

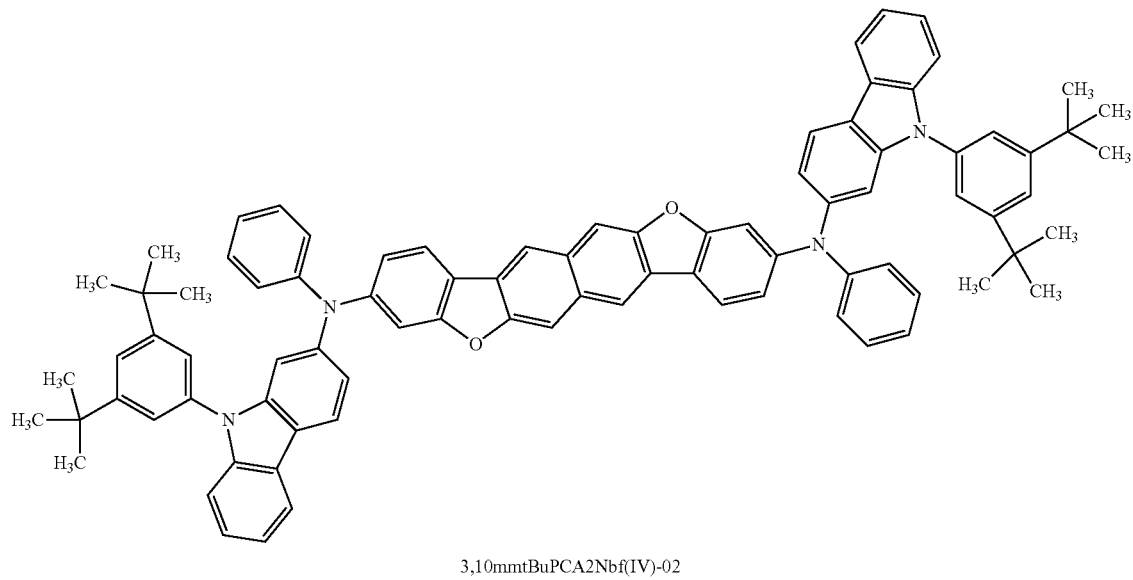

3,10mmtBuPCA2Nbf(IV)-02

(iv)

(Fabrication Method of Light-Emitting Device 3)

First, indium tin oxide containing silicon oxide (ITSO) was deposited over a glass substrate by a sputtering method to form the first electrode 101. The thickness of the first electrode 101 was 70 nm and the electrode area was 2 mm×2 mm.

Next, in pretreatment for forming the light-emitting device over a substrate, a surface of the substrate was washed with water and baked at 200° C. for 1 hour, and then UV ozone treatment was performed for 370 seconds.

After that, the substrate was transferred into a vacuum evaporation apparatus where the pressure was reduced to approximately 104 Pa, vacuum baking was performed at 170° C. for 30 minutes in a heating chamber of the vacuum evaporation apparatus, and then the substrate was cooled down for approximately 30 minutes.

Next, the substrate provided with the first electrode 101 was fixed to a substrate holder provided in the vacuum evaporation apparatus such that the side on which the first electrode 101 was formed faced downward. Then, N,N-bis (4-biphenyl)-6-phenylbenzo[b]naphtho[1,2-d]furan-8-amine (abbreviation: BBABnf) represented by Structural Formula (i) above and an electron acceptor material (OCHD-001) were deposited on the first electrode 101 to a thickness of 10 nm by a co-evaporation method using resistance heating such that the weight ratio of BBABnf to OCHD-001 was 1:0.1, whereby the hole-injection layer 111 was formed.

Next, over the hole-injection layer 111, BBABnf was deposited by evaporation to a thickness of 20 nm, and then 3,3'-(naphthalene-1,4-diyl)bis(9-phenyl-9H-carbazole) (abbreviation: PCzN2) represented by Structural Formula (ii) above was deposited by evaporation to a thickness of 10 nm, whereby the hole-transport layer 112 was formed.

Then, 9-(1-naphthyl)-10-[4-(2-naphthyl)phenyl]anthracene (abbreviation: αN-PNPAnth) represented by Structural Formula (iii) above and N,N'-bis[9-(3,5-di-tert-butylphenyl)-9H-carbazol-2-yl]-N,N'-diphenyl-naphtho[2,3-b;6,7-b']bisbenzofuran-3,10-diamine (abbreviation: 3,10mmtBuPCA2Nbf(IV)-02) represented by Structural Formula (iv) above were deposited by co-evaporation to a thickness of 25 nm such that the weight ratio of αN-βNPAnth to 3,10mmtBuPCA2Nbf(IV)-02 was 1:0.015, whereby the light-emitting layer 113 was formed.

Then, over the light-emitting layer 113, 6-(1,1'-biphenyl-3-yl)-4-[3,5-bis(9H-carbazol-9-yl)phenyl]-2-phenylpyrimidine (abbreviation: 6mBP-4Cz2PPm) represented by Structural formula (xii) above was deposited to a thickness of 10 nm, and then 2-[3-(2,6-dimethyl-3-pyridinyl)-5-(9-phenanthrenyl)phenyl]-4,6-diphenyl-1,3,5-triazine (abbreviation: mPn-mDMePyPTzn) represented by Structural Formula (xiii) above and 8-hydroxyquinolinato-lithium (abbreviation: Liq) represented by Structural Formula (xiv) above were deposited by co-evaporation to a thickness of 15 nm such that the weight ratio of mPn-mDMePyPTzn to Liq was 1:1, whereby the electron-transport layer 114 was formed.

After the formation of the electron-transport layer 114, Liq was deposited by evaporation to a thickness of 1 nm to form the electron-injection layer 115. Then, aluminum was deposited by evaporation to a thickness of 200 nm to form the second electrode 102. Thus, the light-emitting device 3 of this example was fabricated.

The structures of the light-emitting device are listed in the following table.

TABLE 7

| | Hole-injection layer 10 nm | Hole-transport layer 1 20 nm | Hole-transport layer 2 10 nm | Light-emitting layer 25 nm | Electron-transport layer 1 10 nm | Electron-transport layer 2 15 nm | Electron-injection layer 1 nm |
|---|---|---|---|---|---|---|---|
| Light-emitting device 3 | BBABnf:OCHD-001 (1:0.1) | BBABnf | PCzN2 | *6 | 6mBP-4Cz2PPm | mPn-mDMePyPTzn:Liq (1:1) | Liq |

*6 αN-βNPAnth:3,10mmtBuPCA2Nbf(IV)-02 (1:0.015)

The above-described light-emitting device was sealed using a glass substrate in a glove box containing a nitrogen atmosphere so as not to be exposed to the air (a sealing material was applied to surround the device and UV treatment and heat treatment at 80° C. for 1 hour were performed at the time of sealing). Then, the initial characteristics of the light-emitting device were measured.

Figure 34:
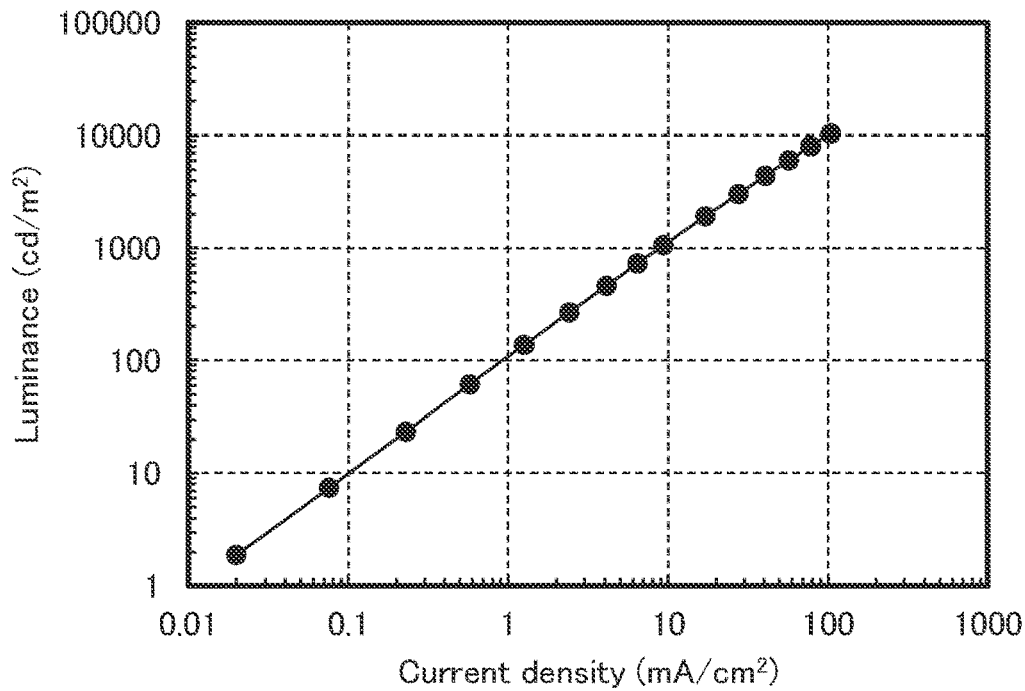
FIG. 34 shows luminance-current density characteristics of a light-emitting device 3.
Figure 35:
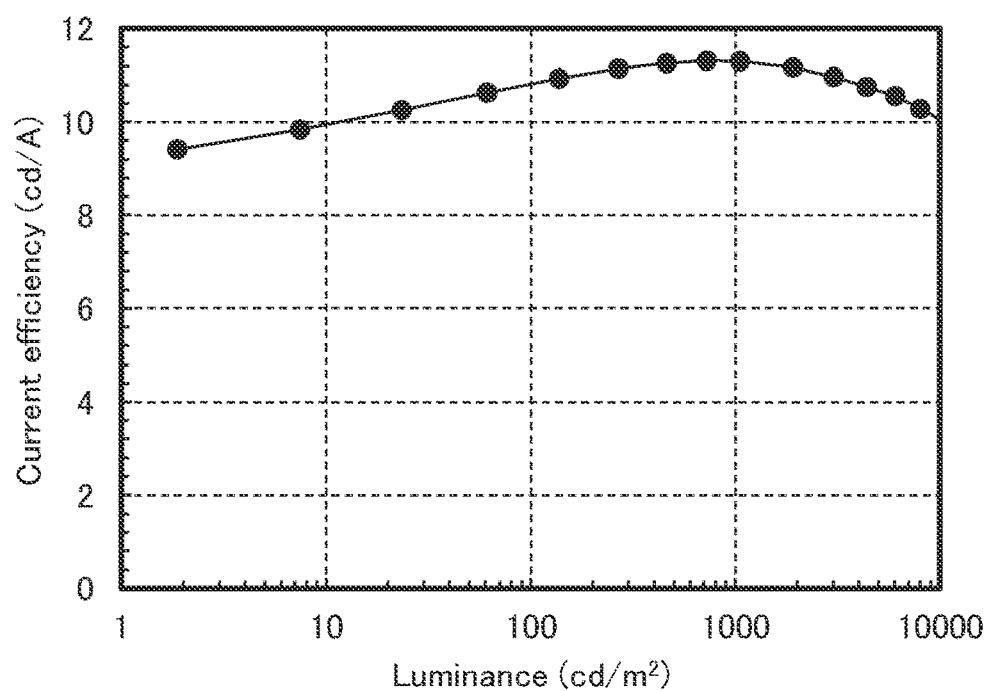
FIG. 35 shows current efficiency-luminance characteristics of the light-emitting device 3.
Figure 36:
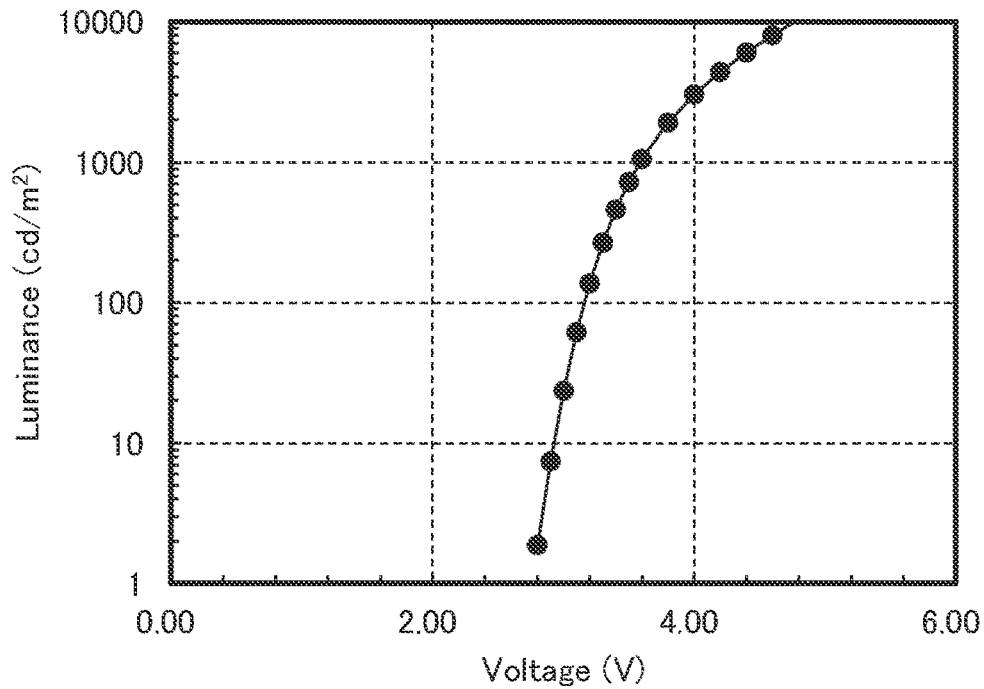
FIG. 36 shows luminance-voltage characteristics of the light-emitting device 3.
Figure 37:
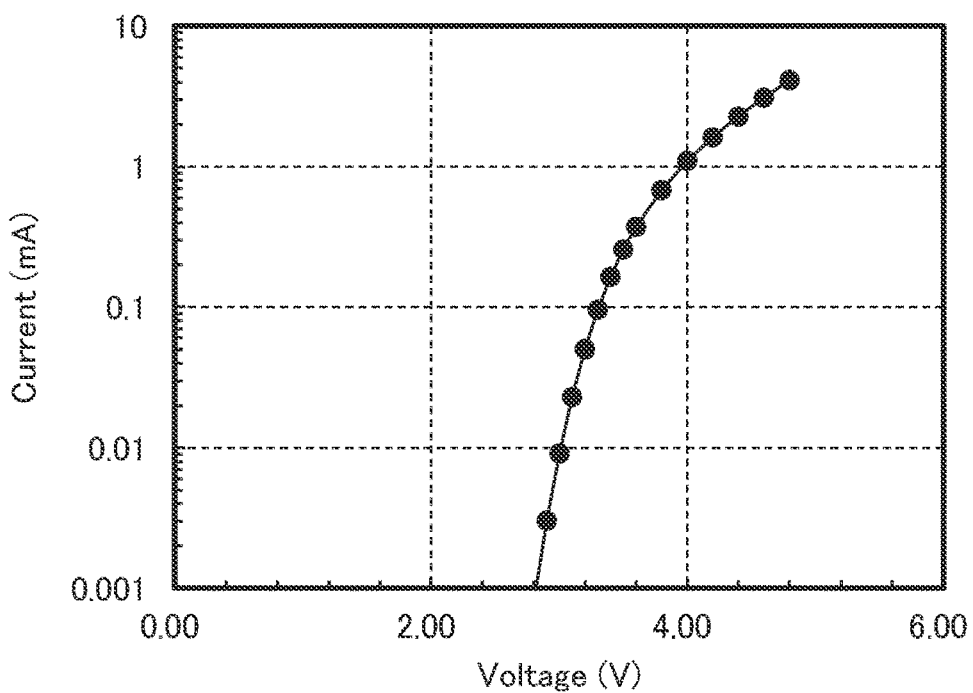
FIG. 37 shows current-voltage characteristics of the light-emitting device 3.
Figure 38:
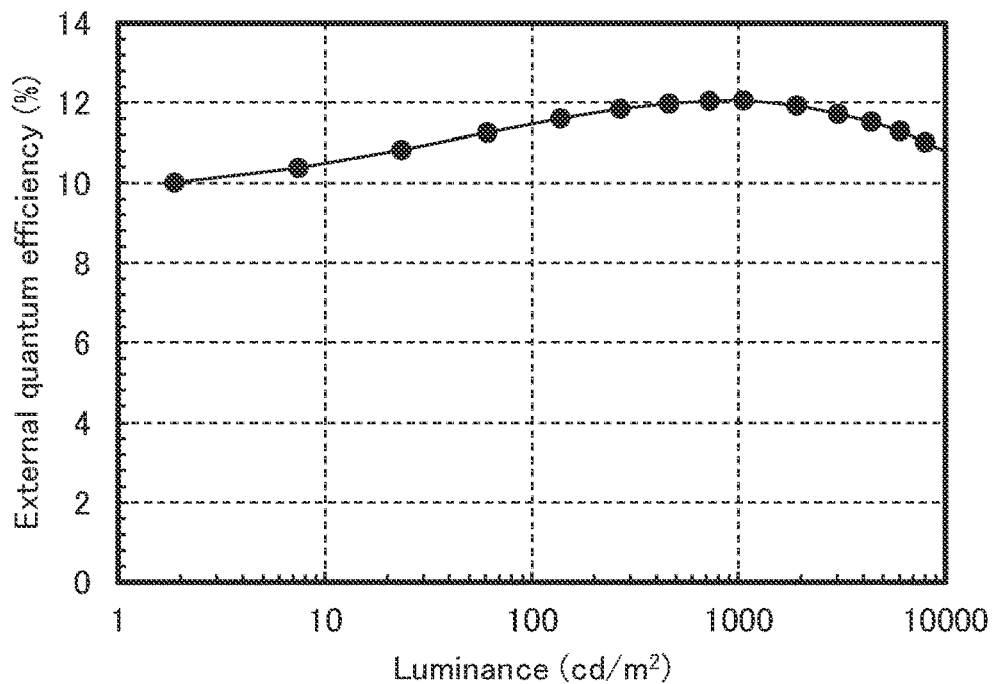
FIG. 38 shows external quantum efficiency-luminance characteristics of the light-emitting device 3.
Figure 39:
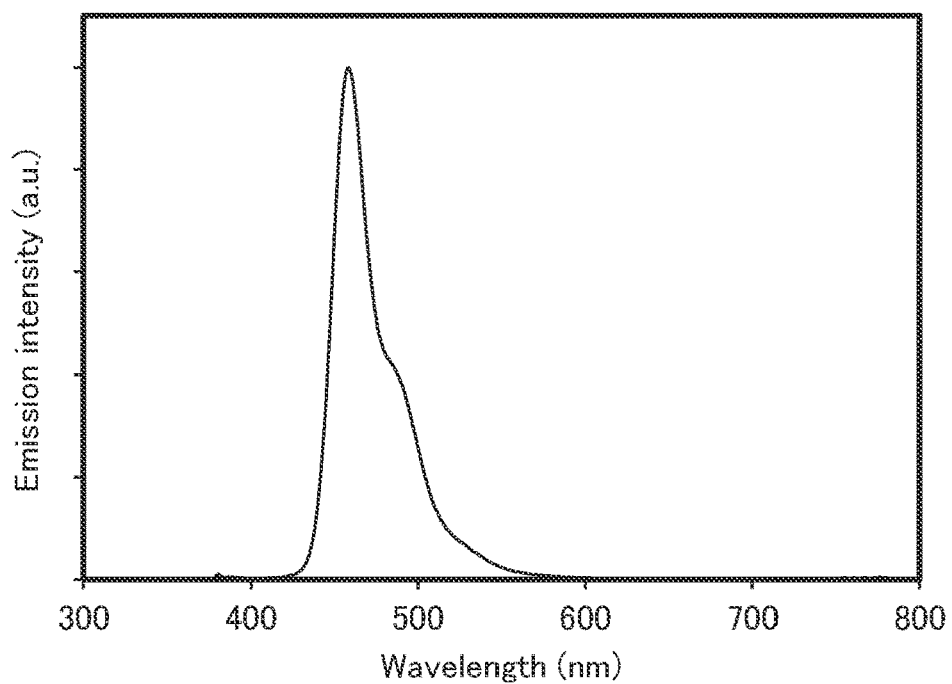
FIG. 39 shows an emission spectrum of the light-emitting device 3.

FIG. 34 shows the luminance-current density characteristics of the light-emitting device 3. FIG. 35 shows the current efficiency-luminance characteristics thereof. FIG. 36 shows the luminance-voltage characteristics thereof. FIG. 37 shows the current-voltage characteristics thereof. FIG. 38 shows the external quantum efficiency-luminance characteristics thereof. FIG. 39 shows the emission spectrum thereof. The main characteristics of the light-emitting device at a luminance of approximately 1000 cd/m$^2$ are shown below.

TABLE 8

| | Voltage (V) | Current (mA) | Current density (mA/cm$^2$) | Chromaticity x | Chromaticity y | Current efficiency (cd/A) | External quantum efficiency (%) |
|---|---|---|---|---|---|---|---|
| Light-emitting device 3 | 3.6 | 0.37 | 9.4 | 0.14 | 0.11 | 11.3 | 12.1 |

FIG. 34 to FIG. 39 show that the light-emitting device 3 of one embodiment of the present invention is an EL device having favorable characteristics.

Figure 40:
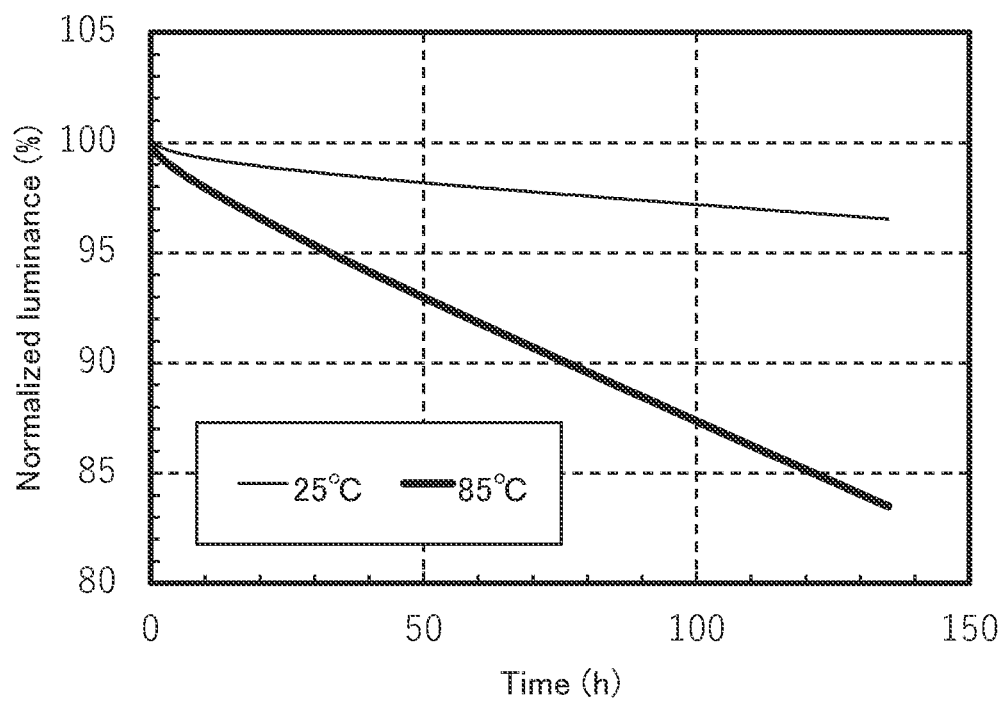
FIG. 40 is a graph showing a change in luminance over driving time of the light-emitting device 3.

Moreover, changes in luminance of the light-emitting device having the same structures as the light-emitting device 3 over driving time at a current density of 50 mA/cm$^2$ were measured. The results are shown in FIG. 40. Note that the measurement was conducted under two temperature conditions, 25° C. and 85° C., and FIG. 40 shows the results under both conditions. As shown in FIG. 40, the light-emitting device 3 had significantly favorable reliability at both temperatures.

These results show that the light-emitting device which uses the organic compound of one embodiment of the present invention is highly reliable.

Example 5

Synthesis Example 2

In this synthesis example, a synthesis method of N,N-bis[9-(3,5-di-tert-butylphenyl)-9H-carbazol-4-yl]-N,N-diphenyl-pyrene-1,6-diamine (abbreviation: 1,6mmtBuPCAPrn-03), which is an organic compound of one embodiment of the present invention, will be described. The structural formula of 1,6mmtBuPCAPrn-03 is shown below.

[Chemical Formula 47]

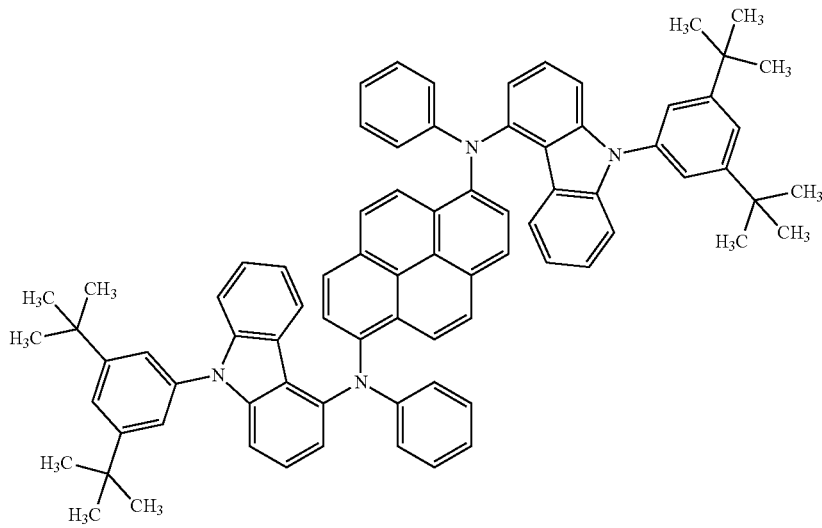

1,6mmtBuPCAPrn-03

Step 1: Synthesis of 4-bromo-9-(3,5-di-tert-butylphenyl)-9H-carbazole

Into a 200-mL three-neck flask, 10 g (41 mmol) of 4-bromo-9H-carbazole, 20 g (73 mmol) of 1-bromo-3,5-di-tert-butylbenzene, 0.77 g (4.1 mmol) of copper(I) iodide, 11 g (81 mmol) of potassium carbonate, 0.32 g (1.2 mmol) of 18-crown-6-ether, and 10 mL of 1,3-dimethyl-3,4,5,6-tetrahydro-2(1H)pyrimidinone (abbreviation: DMPU) were put. This mixture was stirred under a nitrogen stream at 180° C. for 7 hours. After the stirring, 100 mL of toluene was added to this mixture, the precipitate was removed by suction filtration, and the obtained filtrate was washed with a dilute hydrochloric acid, water, and a saturated aqueous solution of sodium hydrogen carbonate in this order. Separation into an organic layer and an aqueous layer was performed, and the organic layer was dried with magnesium sulfate. This mixture was filtered, and the obtained filtrate was concentrated to give an oily substance. The oily substance was purified by silica gel column chromatography (developing solvent: hexane). Methanol was added to the obtained solid. After irradiation with ultrasonic waves was performed, the solid was collected; thus, 19 g of a white solid was obtained. The synthesis scheme of Step 1 is shown below.

[Chemical Formula 48]

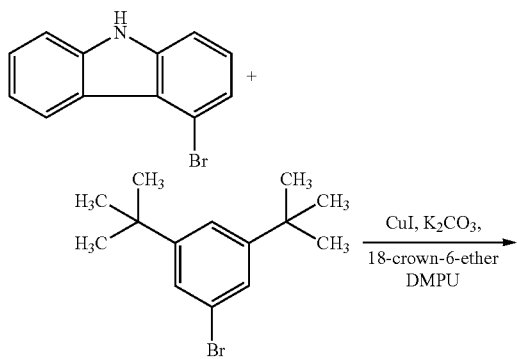

-continued

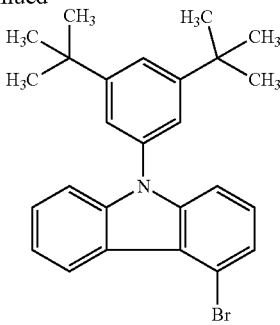

Step 2: Synthesis of N-phenyl-9-(3,5-di-tert-butylphenyl)-9H-carbazol-4-amine (abbreviation: mmtBuPCA-03

Into a 200-mL three-neck flask, 6.0 g (14 mmol) of 4-bromo-9-(3,5-di-tert-butylphenyl)-9H-carbazole, 1.9 g (21 mmol) of aniline, and 4.0 g (15 mmol) of sodium tert-butoxide were put. Then, 70 mL of toluene and 0.2 mL of tri(tert-butyl)phosphine (a 10% hexane solution) were added to this mixture, and the mixture was degassed by being stirred while the pressure was reduced. To this mixture, 79 mg (0.14 mmol) of bis(dibenzylideneacetone)palladium(0) was added, and the mixture was heated and stirred under a nitrogen stream at 120° C. for 7 hours. After the stirring, toluene was added to the mixture, the resulting mixture was suction-filtered through Florisil, Celite, and alumina, and the filtrate was concentrated to give a solid. This solid was purified by silica gel column chromatography (toluene and hexane at 1:5 and then at 1:3 in the developing solvent) to give 5.1 g of a white solid in 82% yield. The synthesis scheme of Step 2 is shown below.

[Chemical Formula 49]

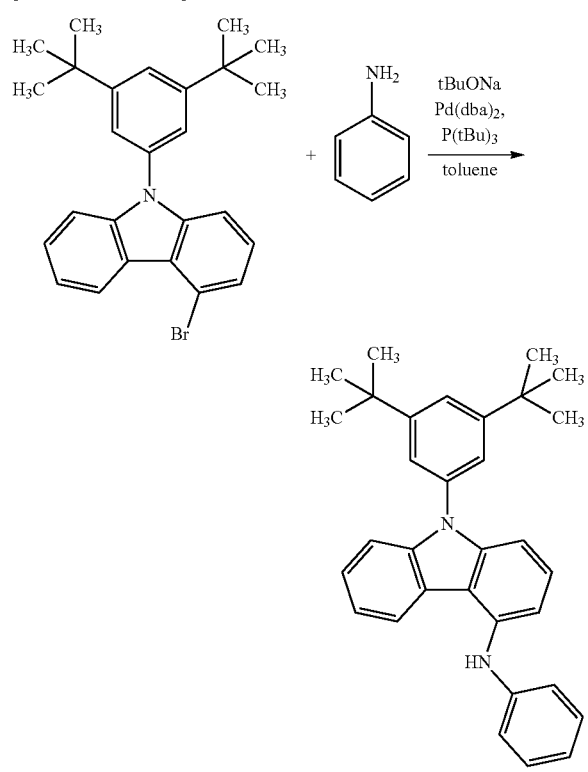

Figure 43A:
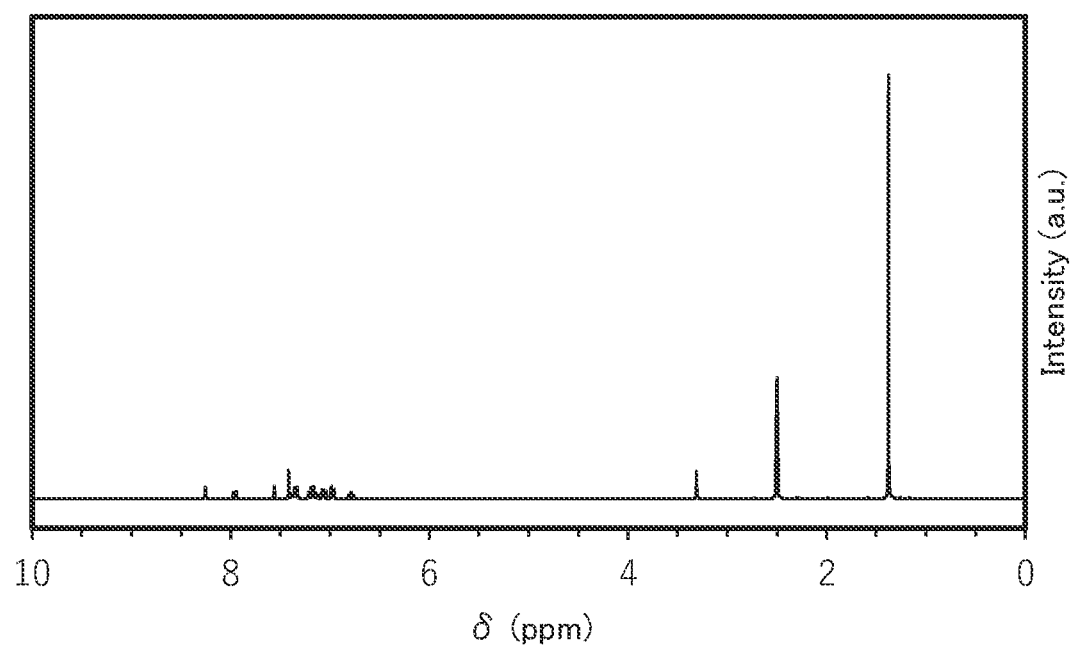
FIG. 43A and FIG. 43B are $^1$H-NMR charts of mmt-BuPCA-03.
Figure 43B:
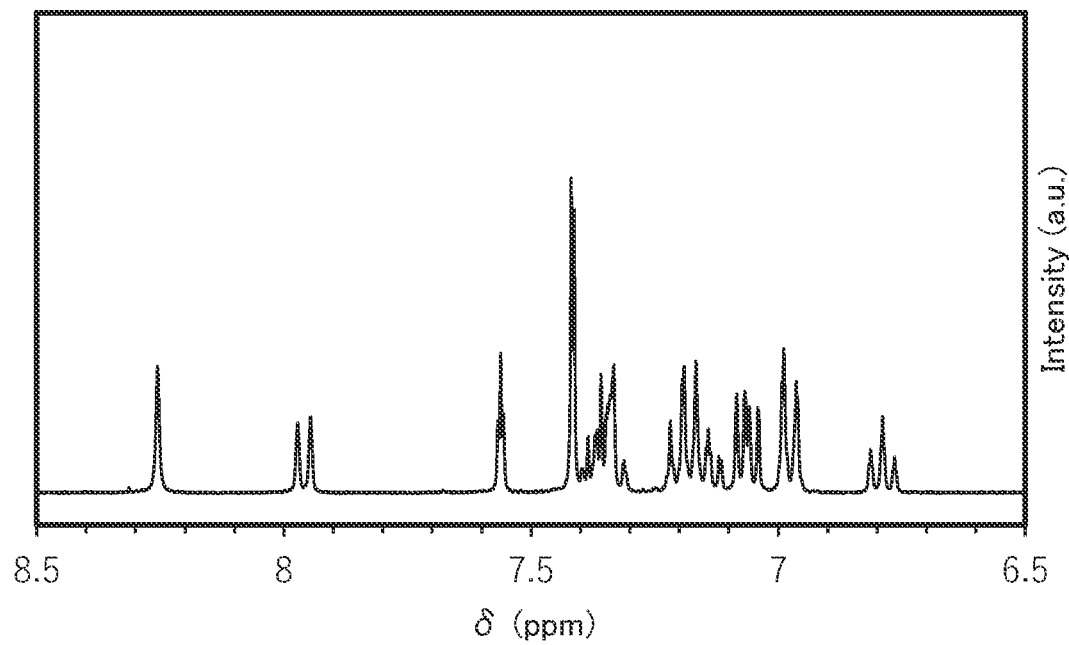

Measurement results by nuclear magnetic resonance ($^1$H-NMR) spectroscopy of the white solid obtained in Step 2 are shown in FIGS. 43A and 43B. Note that FIG. 43B is an enlarged chart of FIG. 43A in the range of 6.5 ppm to 8.5 ppm. In addition, numerical data is shown below. This indicates that N-phenyl-9-(3,5-di-tert-butylphenyl)-9H-carbazol-4-amine was obtained in Step 2.

$^1$H NMR (DMSO-$d_6$, 300 MHz): δ=1.38 (s, 18H), 6.79 (tt, J1=7.2 Hz, 1H), 6.98 (d, J1=7.8 Hz, 2H), 7.06 (dd, J1=5.1 Hz, J2=7.8 Hz, 2H), 7.11-7.22 (m, 3H), 7.31-7.42 (m, 5H), 7.56 (t, J1=1.8 Hz, 1H), 7.96 (d, J1=7.8 Hz, 1H), 8.26 (s, 1H).

Step 3: Synthesis of 1,6mmtBuPCAPrn-03

Into a 200-mL three-neck flask, 0.99 g (2.8 mmol) of 1,6-dibromopyrene, 3.1 g (6.9 mmol) of N-phenyl-9-(3,5-di-tert-butylphenyl)-9H-carbazol-4-amine, and 1.9 g (19 mmol) of sodium tert-butoxide were put. To this mixture, 30 mL of toluene and 0.2 mL of tri(tert-butyl)phosphine (a 10% hexane solution) were added, and this mixture was degassed by being stirred while the pressure was reduced. To this mixture, 32 mg (55 mol) of bis(dibenzylideneacetone)palladium(0) was added, and stirring was performed under a nitrogen stream at 120° C. for 20.5 hours. After the stirring, toluene was added to the mixture, and the resulting mixture was suction-filtered through Florisil, Celite, and alumina to give a filtrate. The obtained filtrate was concentrated to give a solid. This solid was purified by silica gel column chromatography (hexane and toluene at 7:3 in the developing solvent) to give a solid. The obtained solid was recrystallized with toluene to give 1.1 g of a yellow solid in 38% yield. By a train sublimation method, 1.1 g of the obtained solid was purified at 355° C. under a pressure of 4.0×10$^{-2}$ Pa with an argon flow rate of 0 mL/min. After the sublimation purification, 1.0 g of a yellow solid was obtained at a collection rate of 88%. The synthesis scheme of Step 3 is shown below.

[Chemical Formula 50]

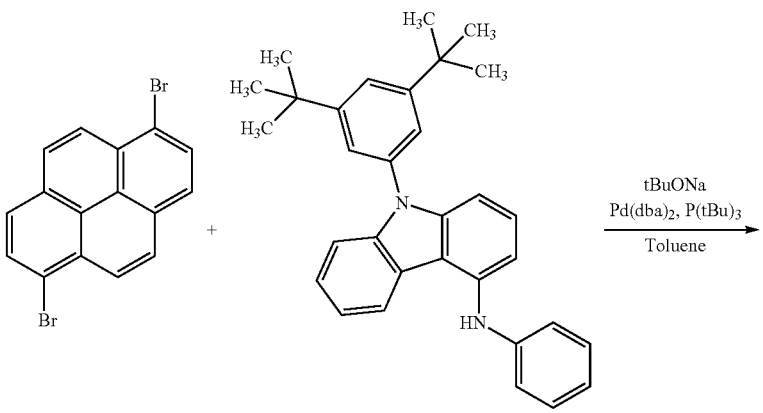

-continued

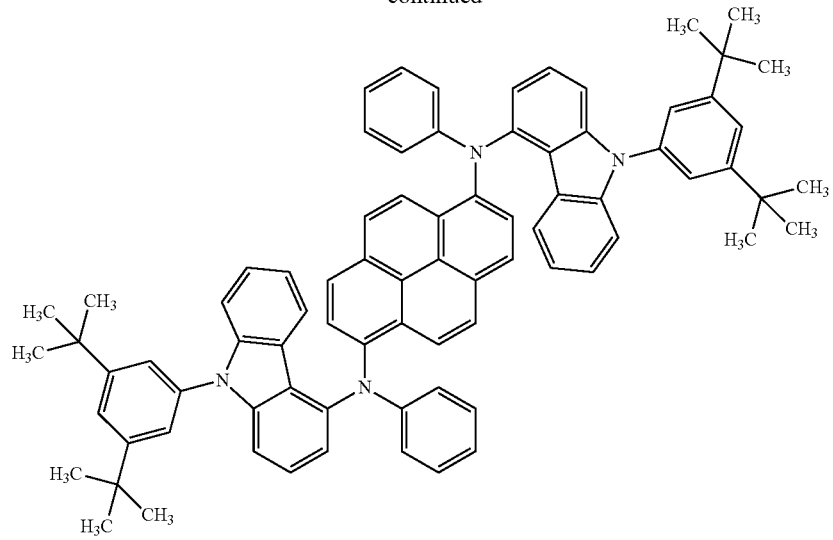

Figure 44A:
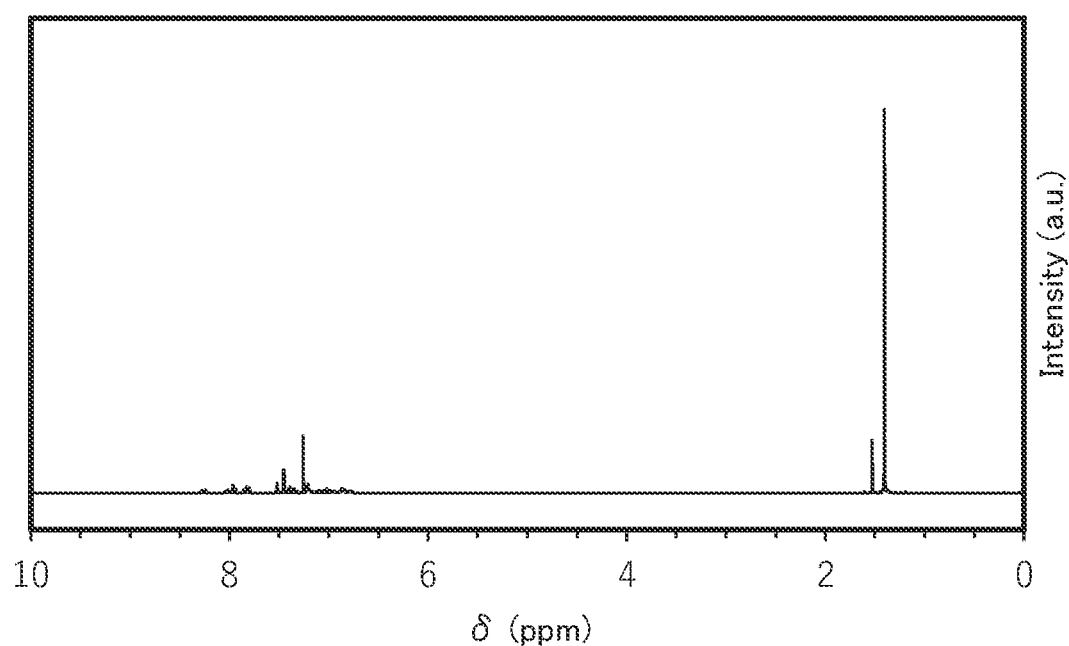
FIG. 44A and FIG. 44B are $^1$H-NMR charts of 1,6mmt-BuPCAPm-03.
Figure 44B:
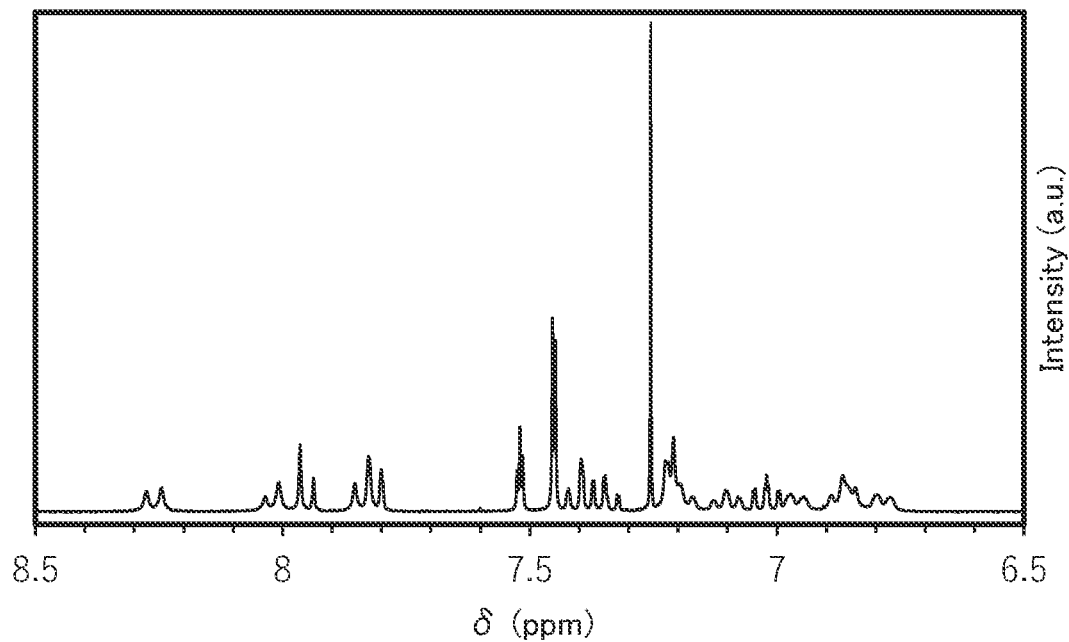

Measurement results by nuclear magnetic resonance ($^1$H-NMR) spectroscopy of the yellow solid obtained in Step 3 above are shown in FIGS. 44A and 44B. Note that FIG. 44B is an enlarged chart of FIG. 44A in the range of 6.5 ppm to 8.5 ppm. In addition, numerical data is shown below. This indicates that 1,6mmtBuPCAPm-03 was obtained in this synthesis example.

$^1$H NMR (CDCl$_3$, 300 MHz): δ=1.41 (s, 36H), 6.77-6.89 (m, 6H), 6.96-7.05 (m, 4H), 7.10 (t, J1=7.8 Hz, 2H), 7.17-7.23 (m, 6H), 7.32-7.42 (m, 4H), 7.45 (d, J1=1.8 Hz, 4H), 7.52 (t, J1=1.8 Hz, 2H), 7.80-7.85 (m, 4H), 7.95 (d, J1=7.8 Hz, 2H), 8.02 (d, J1=8.1 Hz, 2H), 8.26 (d, J1=9.3 Hz, 2H).

Figure 45:
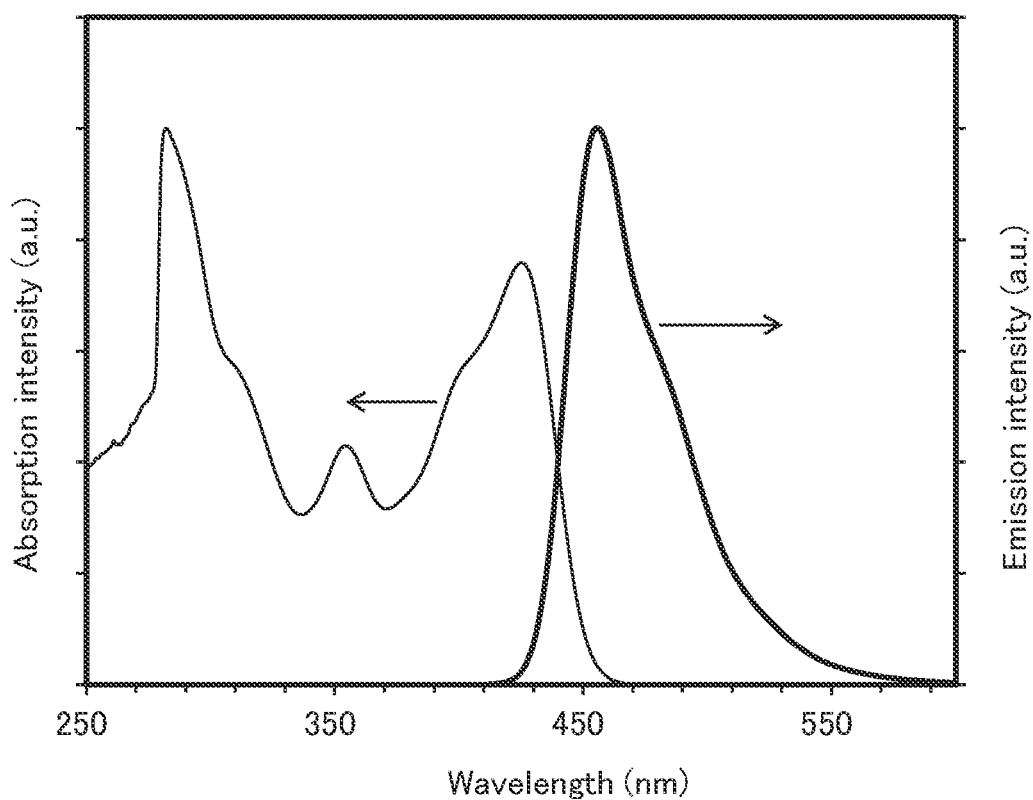
FIG. 45 shows an absorption spectrum and an emission spectrum of 1,6mmtBuPCAPm-03 in a toluene solution.
Figure 46:
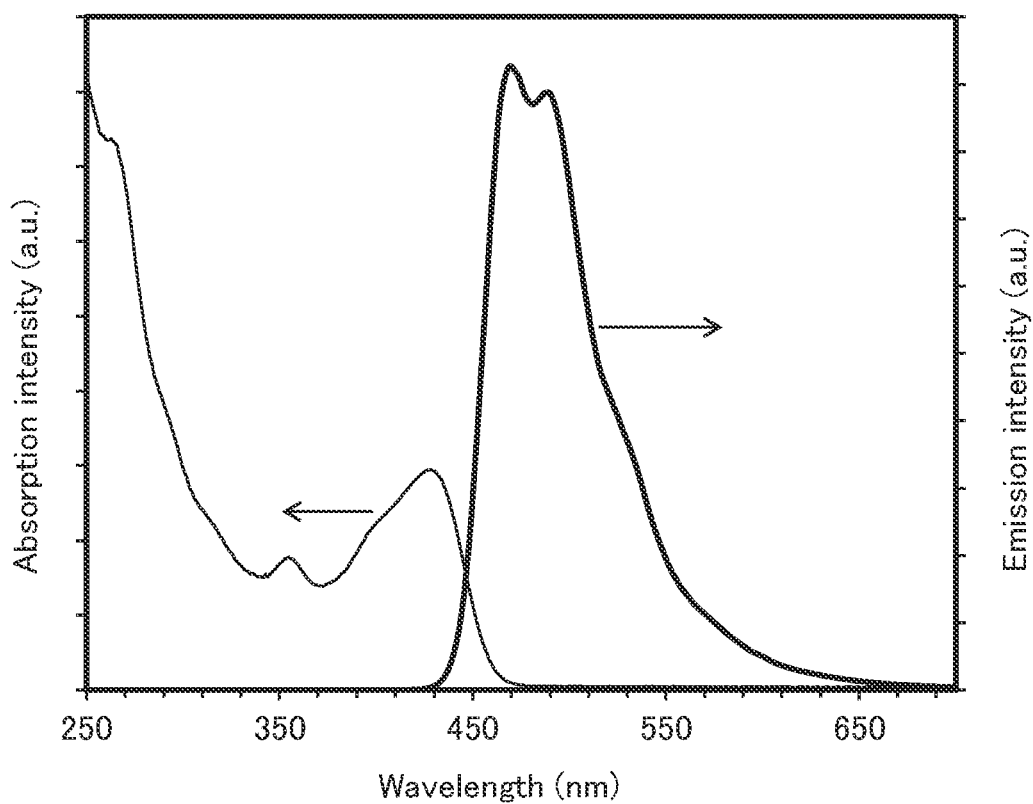
FIG. 46 shows an absorption spectrum and an emission spectrum of 1,6mmtBuPCAPm-03 in a thin film state.

Next, the measurement results of the absorption and emission spectra of 1,6mmtBuPCAPrn-03 in a toluene solution are shown in FIG. 45. Furthermore, the absorption and emission spectra of the thin film are shown in FIG. 46. The solid thin film was formed over a quartz substrate by a vacuum evaporation method. The absorption spectrum of the toluene solution was measured with an ultraviolet-visible light spectrophotometer (V550, manufactured by JASCO Corporation), and the spectrum of toluene alone in a quartz cell was subtracted. The absorption spectrum of the thin film was measured with a spectrophotometer (U-4100 Spectrophotometer, manufactured by Hitachi High-Technologies Corporation). The emission spectrum was measured with a fluorescence spectrophotometer (FP-8600, produced by JASCO Corporation). Quantum yields were measured with an absolute PL quantum yield measurement system (Quantaurus-QY, manufactured by Hamamatsu Photonics K. K.).

As can be seen in FIG. 45, 1,6mmtBuPCAPm-03 in the toluene solution has absorption peaks at 425 nm, 355 nm, and 282 nm, and an emission spectrum peak at 456 nm (excitation wavelength: 400 nm). As can be seen in FIG. 46, 1,6mmtBuPCAPm-03 in the thin film has absorption peaks at 430 nm, 398 nm, 335 nm, 315 nm, 295 nm, and 265 nm, and emission spectrum peaks at 470 nm, 491 nm, and 535 nm (excitation wavelength: 400 nm). These results indicate that 1,6mmtBuPCAPm-03 emits blue light and can be used as a host for a light-emitting substance or a substance which emits fluorescence in the visible region.

The measured quantum yield in the toluene solution was as high as 86%, which indicates that 1,6mmtBuPCAPm-03 is suitable for a light-emitting material.

Example 6

Synthesis Example 3

In this synthesis example, a synthesis method of N,N-bis[9-(3,5-di-tert-butylphenyl)-9H-carbazol-4-yl]-N,N-diphenyl-7-phenyl-7H-dibenzo[c,g]carbazole-5,9-diamine (abbreviation: 5,9mmtBuPCA2PcgDBC-03), which is an organic compound of one embodiment of the present invention, will be described. The structural formula of 5,9mmtBuPCA2PcgDBC-03 is shown below.

[Chemical Formula 51]

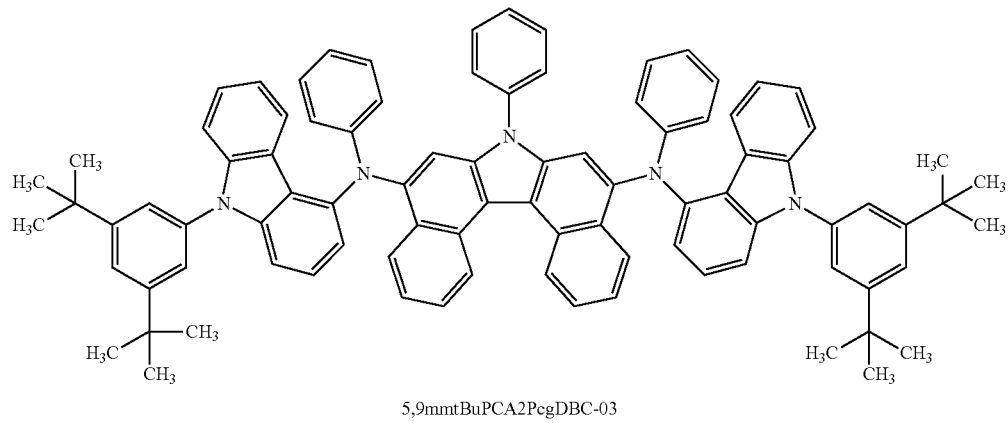

5,9mmtBuPCA2PcgDBC-03

Step 1: Synthesis of 4-bromo-9-(3,5-di-tert-butylphenyl)-9H-carbazole

The synthesis was performed in a manner similar to Step 1 of the synthesis example 2 in Example 5.

Step 2: Synthesis of N-phenyl-9-(3,5-di-tert-butylphenyl)-9H-carbazol-4-amine

The synthesis was performed in a manner similar to Step 2 of the synthesis example 2 in Example 5.

Step 3: Synthesis of 5,9mmtBuPCA2PcgDBC-03

Into a 200-mL three-neck flask, 0.81 g (1.6 mmol) of 5,9-dibromo-7-phenyldibenzo[c,g]carbazole, 1.7 g (3.9 mmol) of N-phenyl-9-(3,5-di-tert-butylphenyl)-9H-carbazol-4-amine, and 0.93 g (9.7 mmol) of sodium tert-butoxide were put. To this mixture, 20 mL of toluene and 0.2 mL of tri(tert-butyl)phosphine (a 10% hexane solution) were added, and this mixture was degassed by being stirred while the pressure was reduced. To this mixture, 19 mg (32 μmol) of bis(dibenzylideneacetone)palladium(0) was added, and stirring was performed under a nitrogen stream at 110° C. for 14.5 hours. After the stirring, toluene was added to the mixture, and the resulting mixture was suction-filtered through Florisil, Celite, and alumina to give a filtrate. The obtained filtrate was concentrated to give a solid. This solid was purified by silica gel column chromatography (hexane and toluene at 3:1 and then at 3:2 in the developing solvent) to give a solid. The obtained solid was recrystallized with ethyl acetate/ethanol to give 1.7 g of a yellow solid in 83% yield. By a train sublimation method, 1.4 g of the obtained solid was purified. The purification by sublimation was performed by heating at 350° C. under a pressure of 4.2× $10^{-2}$ Pa with an argon flow rate of 0 mL/min. After the sublimation purification, 1.2 g of a yellow solid was obtained at a collection rate of 86%. The synthesis scheme of Step 3 is shown below.

[Chemical Formula 52]

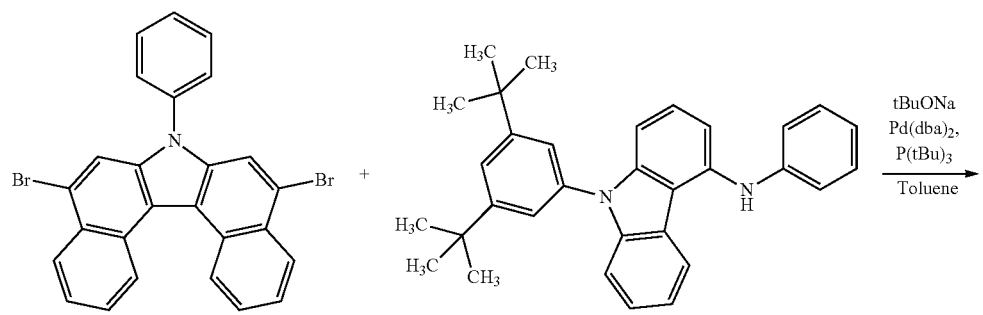

-continued

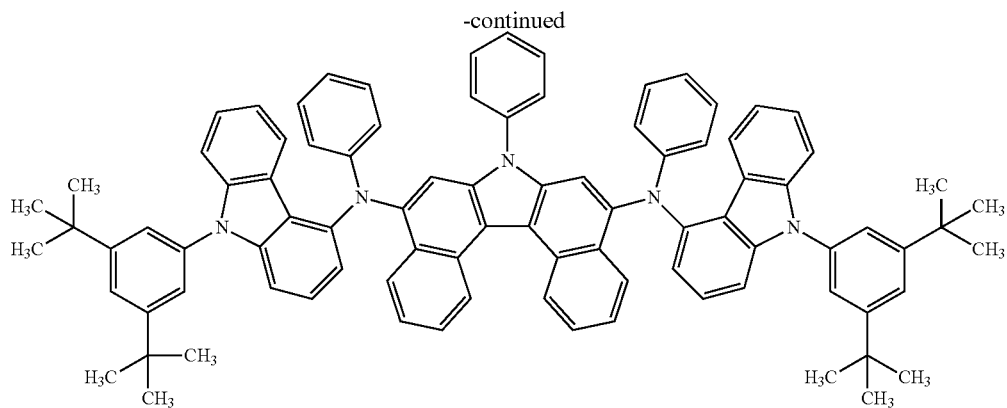

Figure 47A:
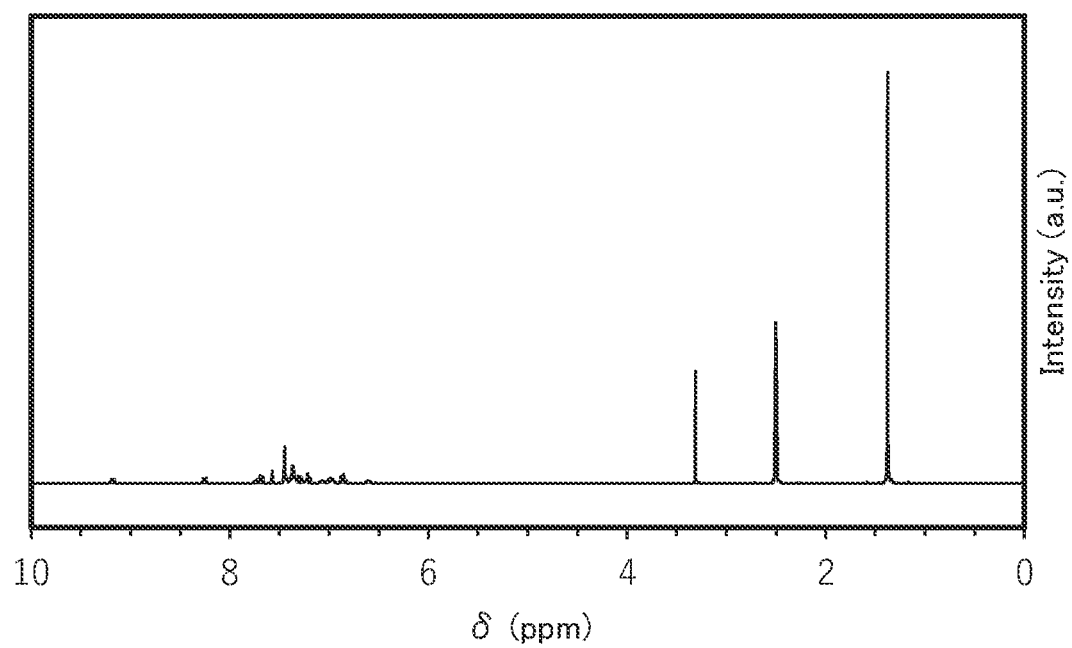
FIG. 47A and FIG. 47B are $^1$H-NMR charts of 5,9mmtBuPCA2PcgDBC-03.
Figure 47B:
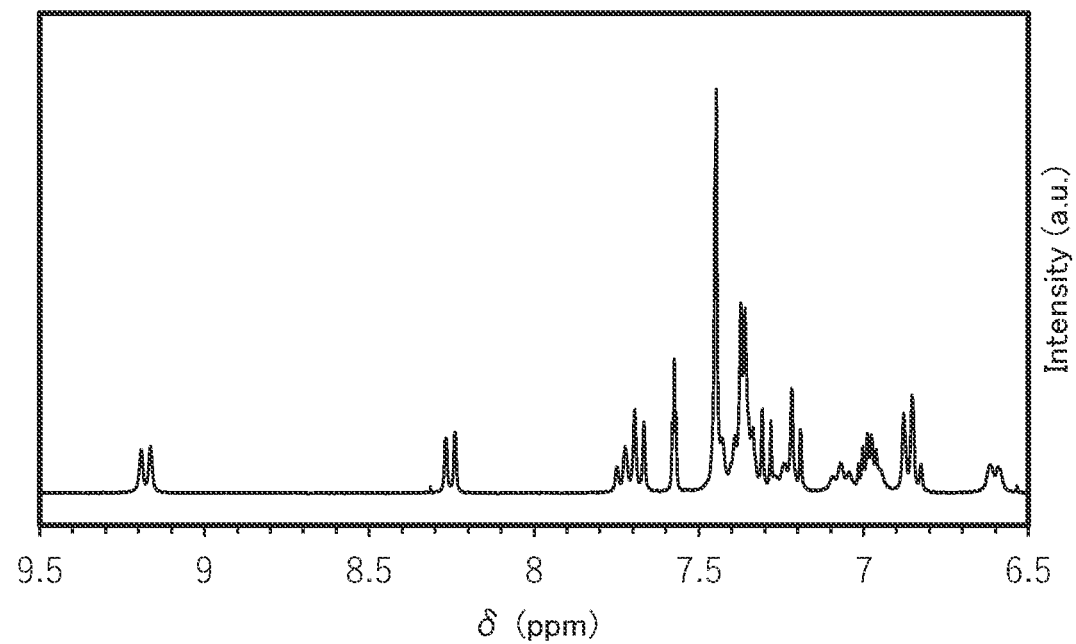

Measurement results by nuclear magnetic resonance ($^1$H-NMR) spectroscopy of the yellow solid obtained in Step 3 above are shown in FIGS. 47A and 47B. Note that FIG. 47B is an enlarged chart of FIG. 47A in the range of 6.5 ppm to 9.5 ppm. In addition, numerical data is shown below. This indicates that 5,9mmtBuPCA2PcgDBC-03 was obtained in this synthesis example.

$^1$H NMR (DMSO-d$_6$, 300 MHz): δ=1.38 (s, 36H), 6.60 (d, J1=6.9 Hz, 2H), 6.83-6.88 (m, 4H), 6.95-7.09 (m, 6H), 7.19-7.45 (m, 23H), 7.57 (t, J1=1.5 Hz, 2H), 7.67-7.75 (m, 4H), 8.26 (d, J1=8.4 Hz, 2H), 9.18 (d, J1=8.4 Hz, 2H).

Figure 48:
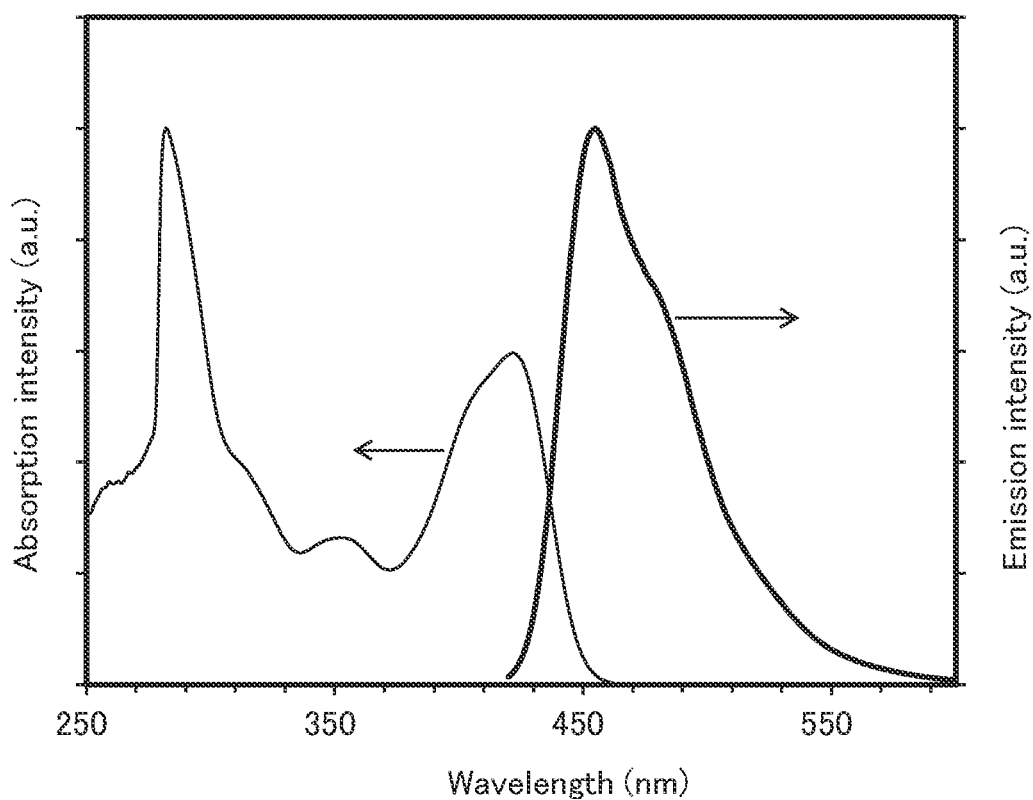
FIG. 48 shows an absorption spectrum and an emission spectrum of 5,9mmtBuPCA2PcgDBC-03 in a toluene solution.
Figure 49:
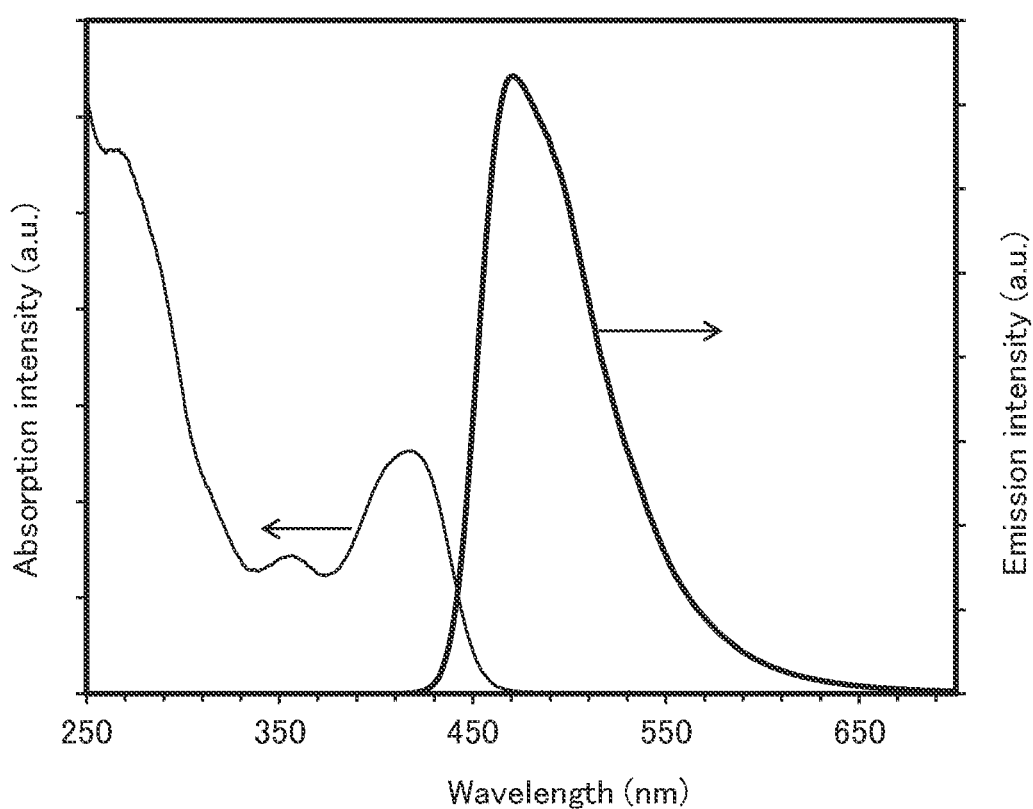
FIG. 49 shows an absorption spectrum and an emission spectrum of 5,9mmtBuPCA2PcgDBC-03 in a thin film state.

Next, the measurement results of the absorption and emission spectra of 5,9mmtBuPCA2PcgDBC-03 in a toluene solution are shown in FIG. 48. Furthermore, the absorption and emission spectra of the thin film are shown in FIG. 49. The solid thin film was formed over a quartz substrate by a vacuum evaporation method. The absorption spectrum of the toluene solution was measured with an ultraviolet-visible light spectrophotometer (V550, manufactured by JASCO Corporation), and the spectrum of toluene alone in a quartz cell was subtracted. The absorption spectrum of the thin film was measured with a spectrophotometer (U-4100 Spectrophotometer, manufactured by Hitachi High-Technologies Corporation). The emission spectrum was measured with a fluorescence spectrophotometer (FP-8600, produced by JASCO Corporation). Quantum yields were measured with an absolute PL quantum yield measurement system (Quantaurus-QY, manufactured by Hamamatsu Photonics K. K.).

As can be seen in FIG. 48, 5,9mmtBuPCA2PcgDBC-03 in the toluene solution has absorption peaks at 422 nm, 352 nm, and 282 nm, and emission spectrum peaks at 455 nm and 480 nm (excitation wavelength: 422 nm). As can be seen in FIG. 49, 5,9mmtBuPCA2PcgDBC-03 in the thin film has absorption peaks at 422 nm, 356 nm, and 275 nm, and emission spectrum peaks at 471 nm and 495 nm (excitation wavelength: 400 nm). These results indicate that 5,9mmtBuPCA2PcgDBC-03 emits blue light and can be used as a host for a light-emitting substance or a substance which emits fluorescence in the visible region.

The measured quantum yield in the toluene solution was as high as 82%, which indicates that 5,9mmtBuPCA2PcgDBC-03 is suitable for a light-emitting material.

Example 7

Synthesis Example 4

In this synthesis example, a synthesis method of N-(dibenzofuran-4-yl)-N-(9,9-dimetyl-9H-fluoren-2-yl)-9-(3,5-di-tert-butylphenyl)-9H-carbazole-3-amine (abbreviation: FrFAmmtBuPC), which is an organic compound of one embodiment of the present invention represented by Structural Formula (166) in Embodiment 1, will be described. The structural formula of FrFAmmtBuPC is shown below.

[Chemical Formula 53]

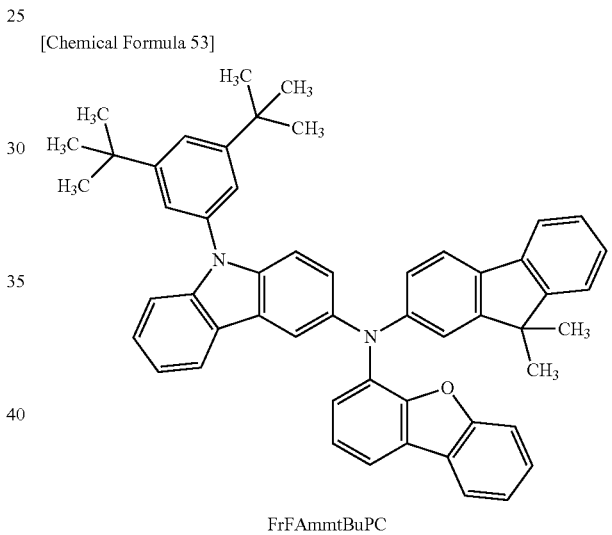

FrFAmmtBuPC

Step 1: Synthesis of N-(9,9-dimethylfluoren-2-yl)-9-(3,5-di-tert-butylphenyl)-9H-carbazol-3-amine Into a 1000-mL three-neck flask, 15 g (35 mmol) of 3-bromo-9-(3,5-di-tert-butylphenyl)-9H-carbazole, 11 g (52 mmol) of 2-amino-9,9-dimethylfluorene, and 10 g (0.10 mol) of sodium tert-butoxide were put. Then, 175 mL of toluene and 0.4 mL of tri(tert-butyl)phosphine (a 10% hexane solution) were added to this mixture, and the mixture was degassed by being stirred while the pressure was reduced. To this mixture, 0.20 g (0.35 mmol) of bis(dibenzylideneacetone)palladium(0) was added, and the mixture was heated and stirred under a nitrogen stream at 110° C. for 7 hours. After the stirring, toluene was added to the mixture, and the resulting mixture was suction-filtered through Florisil, Celite, and alumina to give a filtrate. The obtained filtrate was concentrated to give an oily substance. This oily substance was purified by silica gel column chromatography (hexane and toluene at 2:1 and then at 3:2 in the developing solvent) to give 4.0 g of a light brown solid in 21% yield.

The solid which has not purified was purified by silica gel column chromatography (hexane and ethyl acetate at 100:1 in the developing solvent) to give 3.6 g of a light brown solid in 18% yield. The synthesis scheme of Step 1 is shown below.

[Chemical Formula 54]

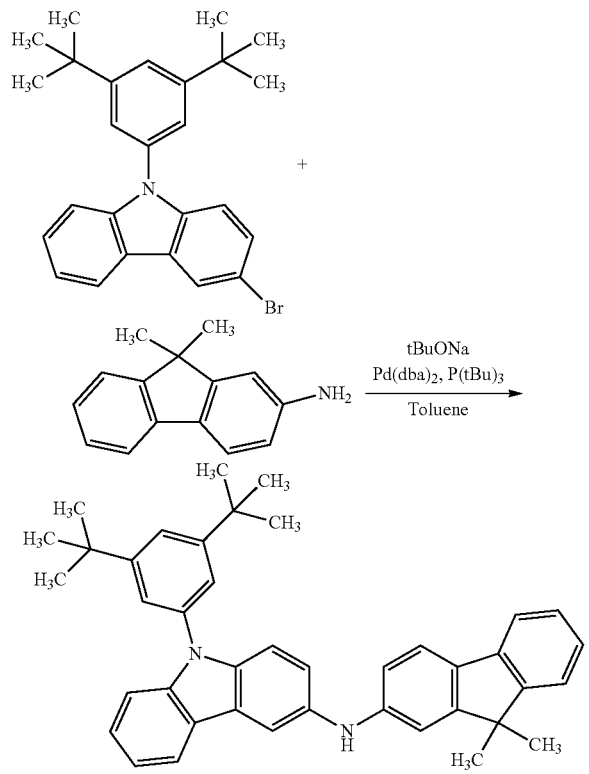

Figure 50A:
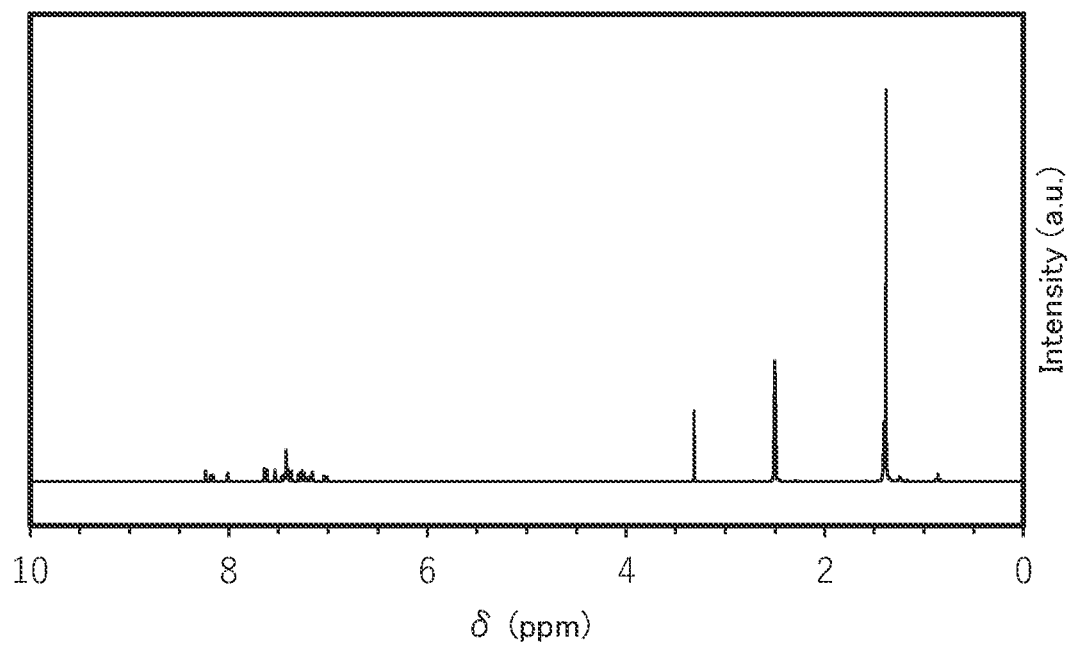
FIG. 50A and FIG. 50B are $^1$H-NMR charts of mmt-BuPCFA.
Figure 50B:
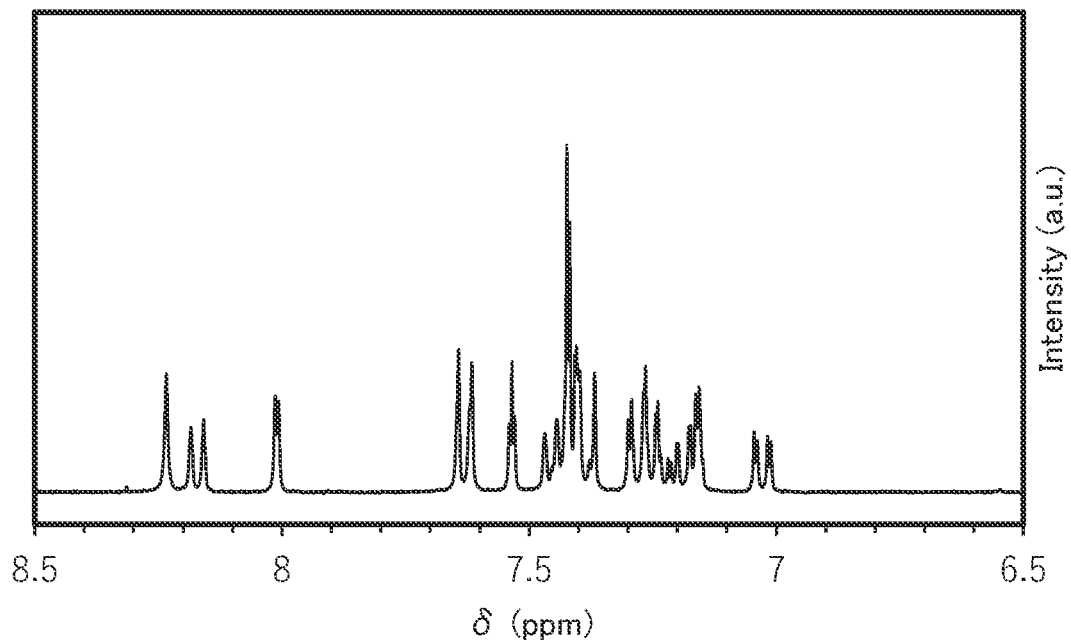

Measurement results by nuclear magnetic resonance ($^1$H-NMR) spectroscopy of the light brown solid obtained in Step 2 above are shown in FIGS. 50A and 50B. Note that FIG. 50B is an enlarged chart of FIG. 50A in the range of 6.5 ppm to 8.5 ppm. In addition, numerical data is shown below. This indicates that N-(9,9-dimethylfluoren-2-yl)-9-(3,5-di-tert-butylphenyl)-9H-carbazol-3-amine was obtained in Step 1.

$^1$H NMR (DMSO-d$_6$, 300 MHz): δ=1.38 (s, 18H), 1.41 (s, 6H), 7.03 (dd, J1=8.4 Hz, J2=2.1 Hz, 1H), 7.16-7.30 (m, 5H), 7.37-7.47 (m, 6H), 7.54 (t, J1=1.5 Hz, 1H), 7.63 (d, J1=8.1 Hz, 2H), 8.01 (d, J1=1.8 Hz, 1H), 8.17 (d, J1=7.8 Hz, 1H), 8.23 (s, 1H).

Step 2: Synthesis of FrFAmmtBuPC

Into a 200-mL three-neck flask, 3.7 g (6.2 mmol) of N-(9,9-dimethylfluoren-2-yl)-9-(3,5-di-tert-butylphenyl)-9H-carbazol-3-amine, 1.1 g (4.1 mmol) of 4-bromodibenzofuran, and 1.2 g (12 mmol) of sodium tert-butoxide were put. To this mixture, 20 mL of toluene and 0.2 mL of tri(tert-butyl)phosphine (a 10% hexane solution) were added, and this mixture was degassed by being stirred while the pressure was reduced. To this mixture, 35 mg (67 mol) of bis(dibenzylideneacetone)palladium(0) was added, and the mixture was heated and stirred under a nitrogen stream at 110° C. for 6.5 hours. After the stirring, toluene was added to the mixture, and the resulting mixture was suction-filtered through Florisil, Celite, and alumina to give a filtrate. The obtained filtrate was concentrated to give a solid. This solid was purified by silica gel column chromatography (hexane and toluene at 3:1 in the developing solvent). The obtained solid was recrystallized with ethyl acetate/ethanol to give 2.2 g of a white solid in 72% yield. The filtrate obtained by recrystallization was concentrated, and the resulting solid was recrystallized with ethyl acetate/ethanol to give 0.51 g of a white solid in 17% yield. By a train sublimation method, 2.6 g of the obtained solid was purified. The purification by sublimation was performed by heating at 265° C. under a pressure of 3.7 Pa with an argon flow rate of 15 mL/min. After the sublimation purification, 2.3 g of a white solid was obtained at a collection rate of 89%. The synthesis scheme of Step 2 is shown below.

[Chemical Formula 55]

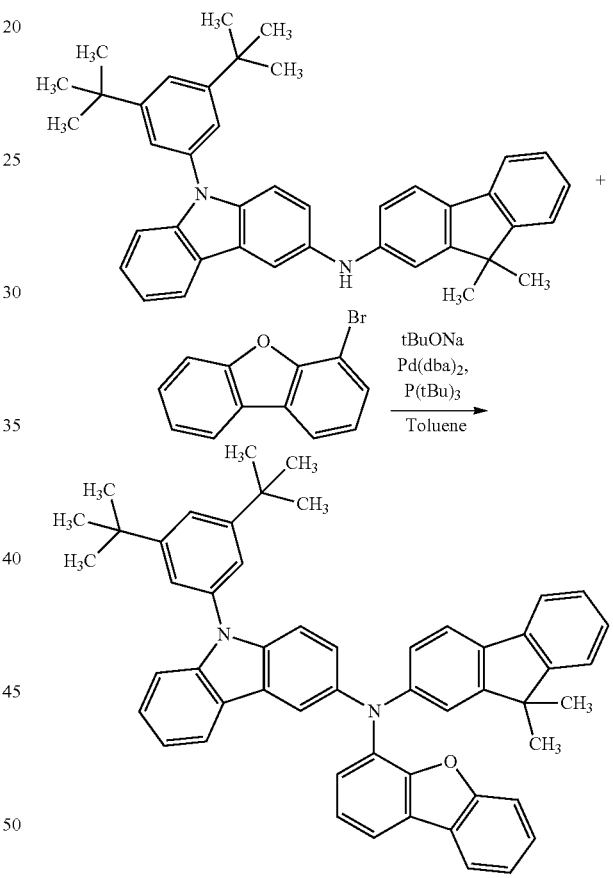

Figure 51A:
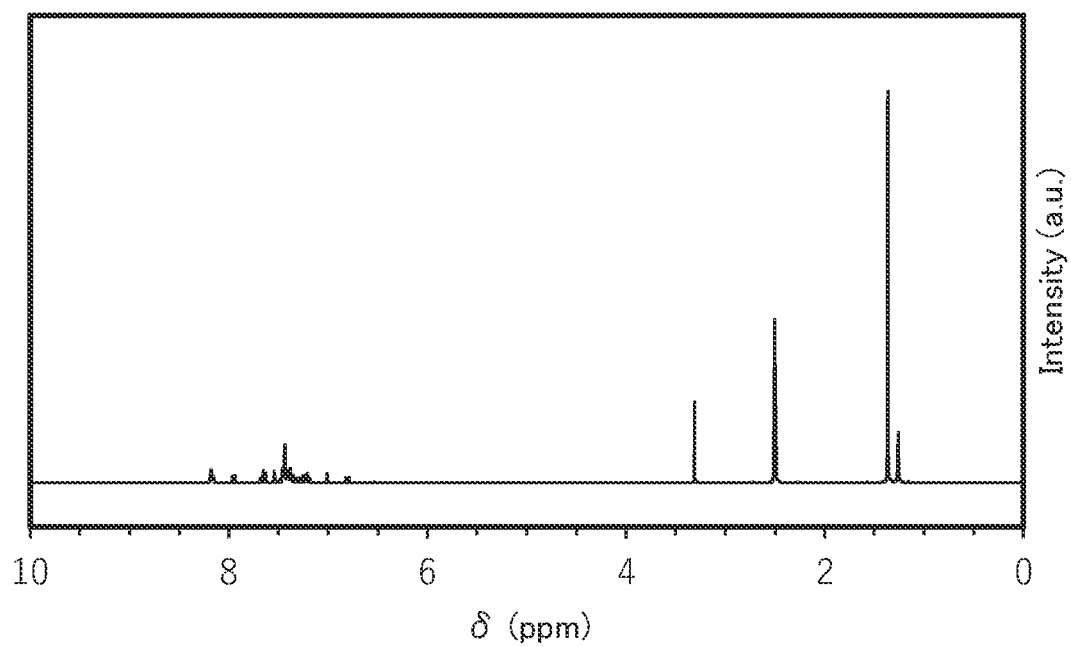
FIG. 51A and FIG. 51B are $^1$H-NMR charts of FrFAmmt-BuPC.
Figure 51B:
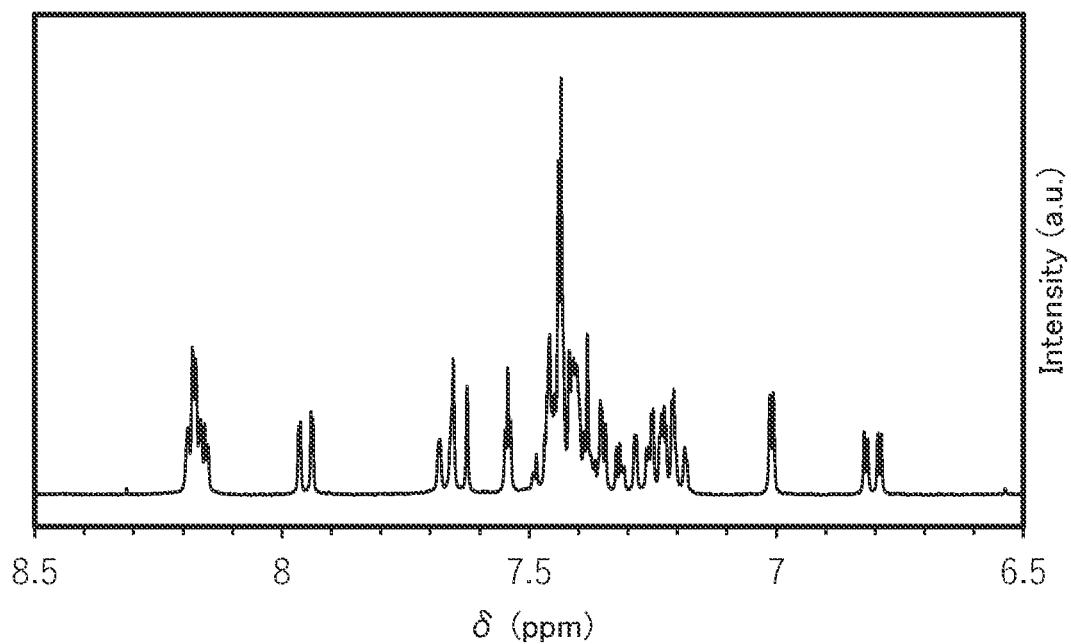

Measurement results by nuclear magnetic resonance ($^1$H-NMR) spectroscopy of the white solid obtained in Step 2 above are shown in FIGS. 51A and 51B. Note that FIG. 51B is an enlarged chart of FIG. 51A in the range of 6.5 ppm to 8.5 ppm. In addition, numerical data is shown below. This indicates that FrFAmmtBuPC was obtained in this synthesis example.

$^1$H NMR (DMSO-d$_6$, 300 MHz): δ=1.26 (s, 6H), 1.37 (s, 18H), 6.81 (dd, J1=8.4 Hz, J2=2.4 Hz, 1H), 7.01 (d, J1=1.8 Hz, 1H), 7.18-7.49 (m, 15H), 7.54 (t, J1=1.8 Hz, 1H), 7.63-7.68 (m, 2H), 7.95 (dd, J1=7.8 Hz, J2=1.2 Hz, 1H), 8.15-8.19 (m, 3H).

Figure 52:
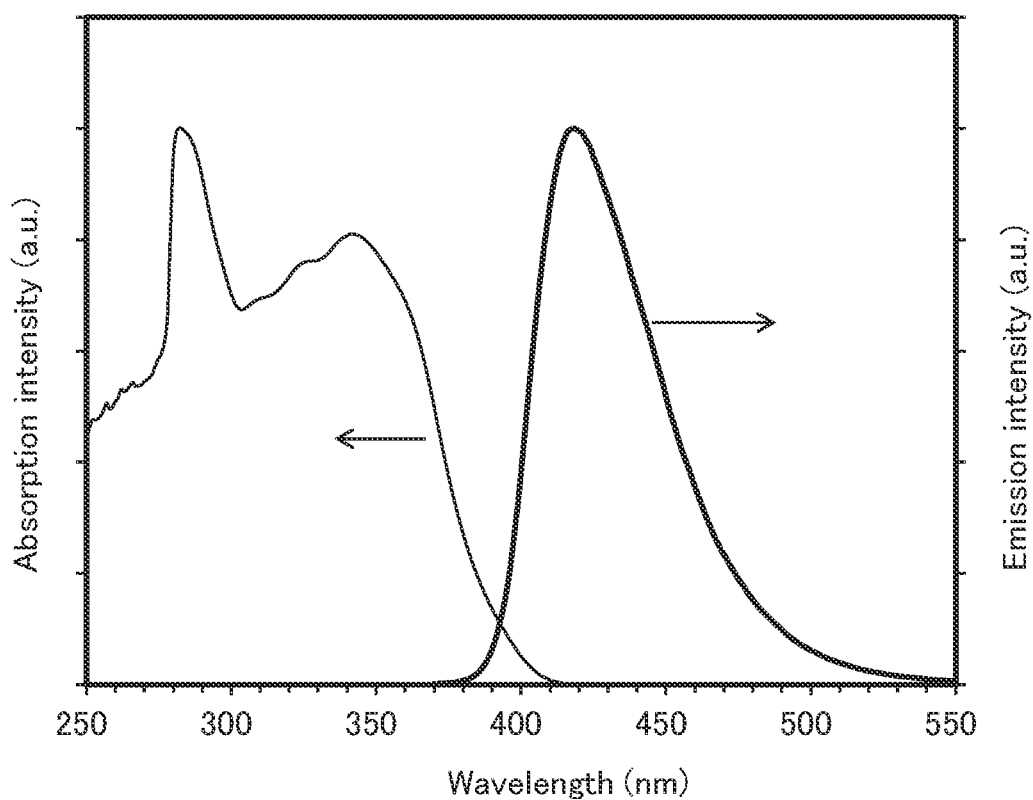
FIG. 52 shows an absorption spectrum and an emission spectrum of FrFAmmtBuPC in a toluene solution.
Figure 53:
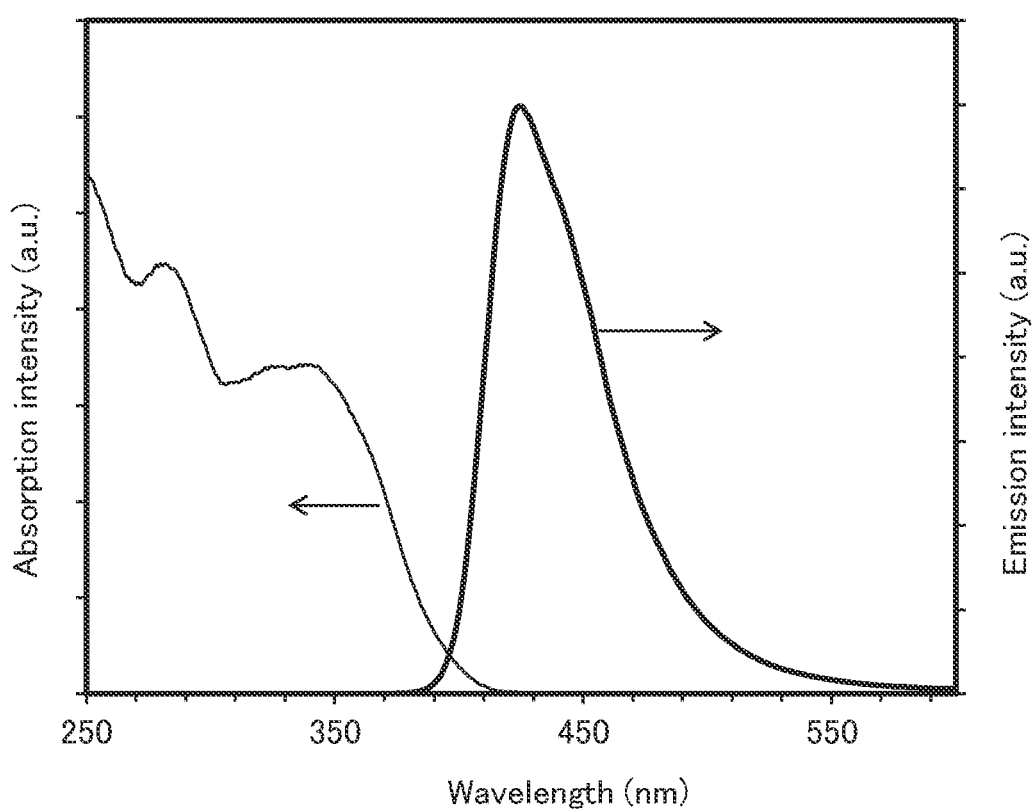
FIG. 53 shows an absorption spectrum and an emission spectrum of FrFAmmtBuPC in a thin film state.

Next, the measurement results of the absorption and emission spectra of FrFAmmtBuPC in a toluene solution are shown in FIG. 52. Furthermore, the absorption and emission spectra of the thin film are shown in FIG. 53. The solid thin film was formed over a quartz substrate by a vacuum evaporation method. The absorption spectrum of the toluene solution was measured with an ultraviolet-visible light spectrophotometer (V550, manufactured by JASCO Corporation), and the spectrum of toluene alone in a quartz cell was subtracted. The absorption spectrum of the thin film was measured with a spectrophotometer (U-4100 Spectrophotometer, manufactured by Hitachi High-Technologies Corporation). The emission spectrum was measured with a fluorescence spectrophotometer (FP-8600, produced by JASCO Corporation).

As can be seen in FIG. 52, FrFAmmtBuPC in the toluene solution has absorption peaks at 342 nm, 325 nm, 310 nm, and 282 nm, and an emission spectrum peak at 418 nm (excitation wavelength: 325 nm). As can be seen in FIG. 53, FrFAmmtBuPC in the thin film has absorption peaks at 384 nm, 340 nm, and 280 nm, and an emission spectrum peak at 425 nm (excitation wavelength: 340 nm).

Example 8

Synthesis Example 5

In this synthesis example, a synthesis method of N-(9,9-dimethyl-9H-fluoren-2-yl)-bis[9-(3,5-di-tert-buthylphenyl)-9H-carbazole]-3,3'-amine (abbreviation: mmtBuPCzPCFL), which is an organic compound of one embodiment of the present invention represented by Structural Formula (174) in Embodiment 1, will be described. The structural formula of mmtBuPCzPCFL is shown below.

[Chemical Formula 56]

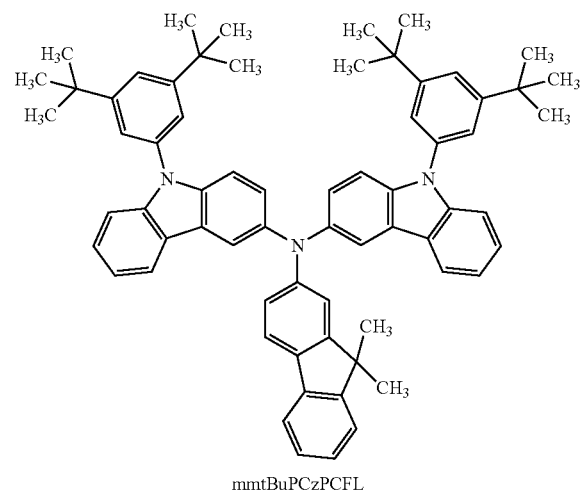

mmtBuPCzPCFL

Step 1: Synthesis of N-(9,9-dimethylfluoren-2-yl)-9-(3,5-di-tert-butylphenyl)-9H-carbazol-3-amine The synthesis was performed in a manner similar to Step 1 of the synthesis example 4 in Example 7.

Step 2: Synthesis of mmtBuPCzPCFL

Into a 200-mL three-neck flask, 2.8 g (4.9 mmol) of N-(9,9-dimethylfluoren-2-yl)-9-(3,5-di-tert-butylphenyl)-9H-carbazol-3-amine, 1.4 g (3.3 mmol) of 3-bromo-9-(3,5-di-tert-butylphenyl)-9H-carbazole, and 0.94 g (9.8 mmol) of sodium tert-butoxide were put. To this mixture, 20 mL of toluene and 0.2 mL of tri(tert-butyl)phosphine (a 10% hexane solution) were added, and this mixture was degassed by being stirred while the pressure was reduced. To this mixture, 19 mg (33 μmol) of bis(dibenzylideneacetone) palladium(0) was added, and the mixture was heated and stirred under a nitrogen stream at 110° C. for 6.5 hours. After the stirring, toluene was added to the mixture, and the resulting mixture was suction-filtered through Florisil, Celite, and alumina to give a filtrate. The obtained filtrate was concentrated to give a solid. This solid was purified by silica gel column chromatography (hexane and toluene at 3:1 in the developing solvent). The obtained solid was recrystallized with ethyl acetate/ethanol to give 2.7 g of a white solid in 91% yield. By a train sublimation method, 2.7 g of the obtained solid was purified. The purification by sublimation was performed by heating at 305° C. under a pressure of 3.3 Pa with an argon flow rate of 15 m/min. After the sublimation purification, 2.6 g of a light yellow solid was obtained at a collection rate of 95%. The synthesis scheme of Step 2 is shown below.

[Chemical Formula 57]

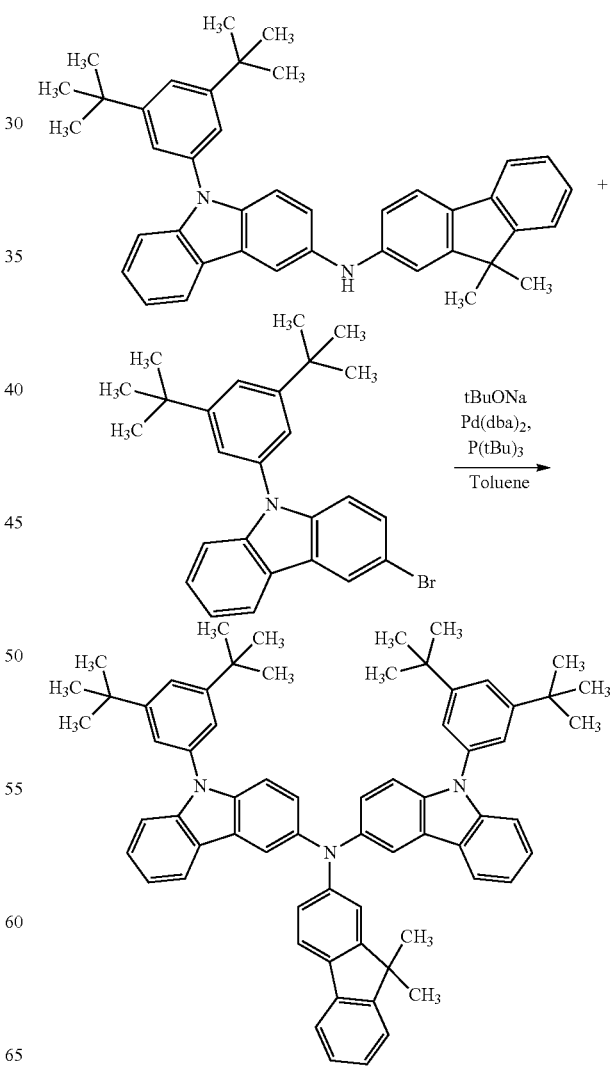

Figure 54A:
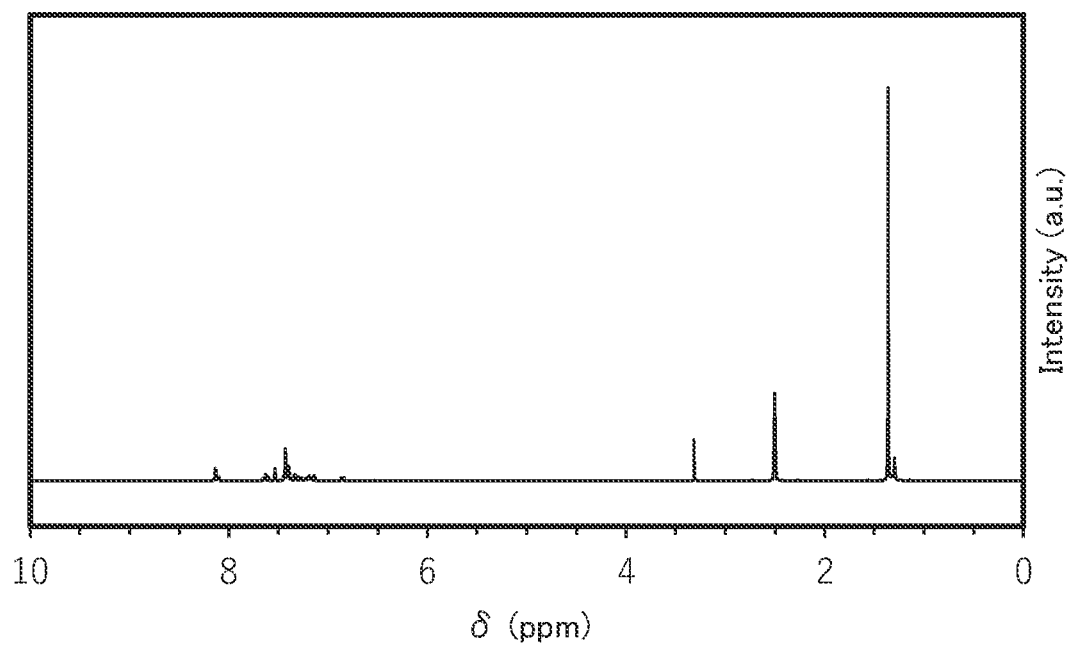
FIG. 54A and FIG. 54B are $^1$H-NMR charts of mmt-BuPCzPCFL.
Figure 54B:
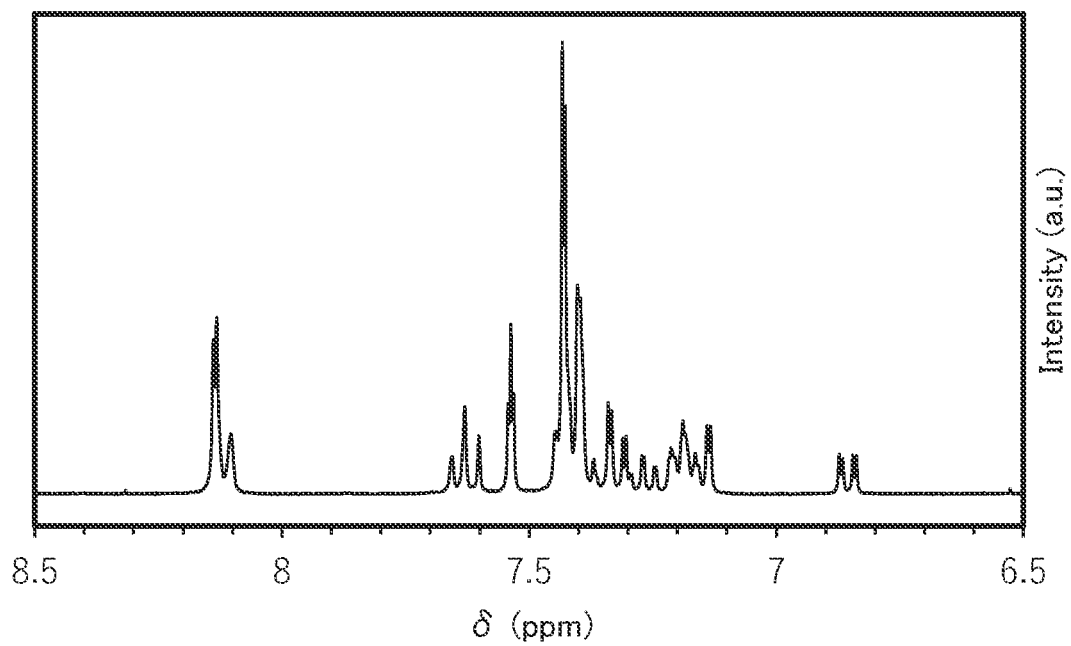

Measurement results by nuclear magnetic resonance ($^1$H-NMR) spectroscopy of the white solid obtained in Step 2 above are shown in FIGS. 54A and 54B. Note that FIG. 54B is an enlarged chart of FIG. 54A in the range of 6.5 ppm to 8.5 ppm. In addition, numerical data is shown below. This indicates that mmtBuPCzPCFL was obtained in this synthesis example.

$^1$H NMR (DMSO-d$_6$, 300 MHz): δ=1.30 (s, 6H), 1.36 (s, 36H), 6.86 (dd, J1=8.4 Hz, J2=2.1 Hz, 1H), 7.14 (d, J1=2.1 Hz, 1H), 7.16-7.23 (m, 3H), 7.24-7.34 (m, 3H), 7.36-7.45 (m, 11H), 7.54 (t, J1=1.8 Hz, 2H), 7.60-7.66 (m, 2H), 8.01-8.14 (m, 4H).

Figure 55:
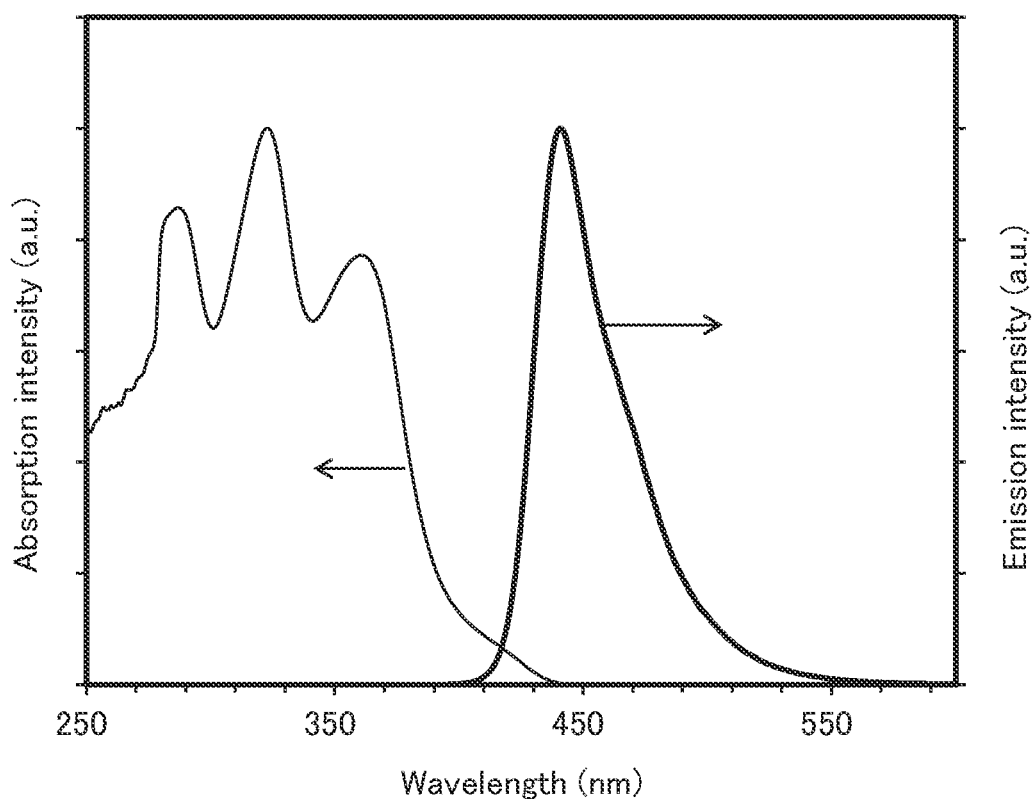
FIG. 55 shows an absorption spectrum and an emission spectrum of mmtBuPCzPCFL in a toluene solution.
Figure 56:
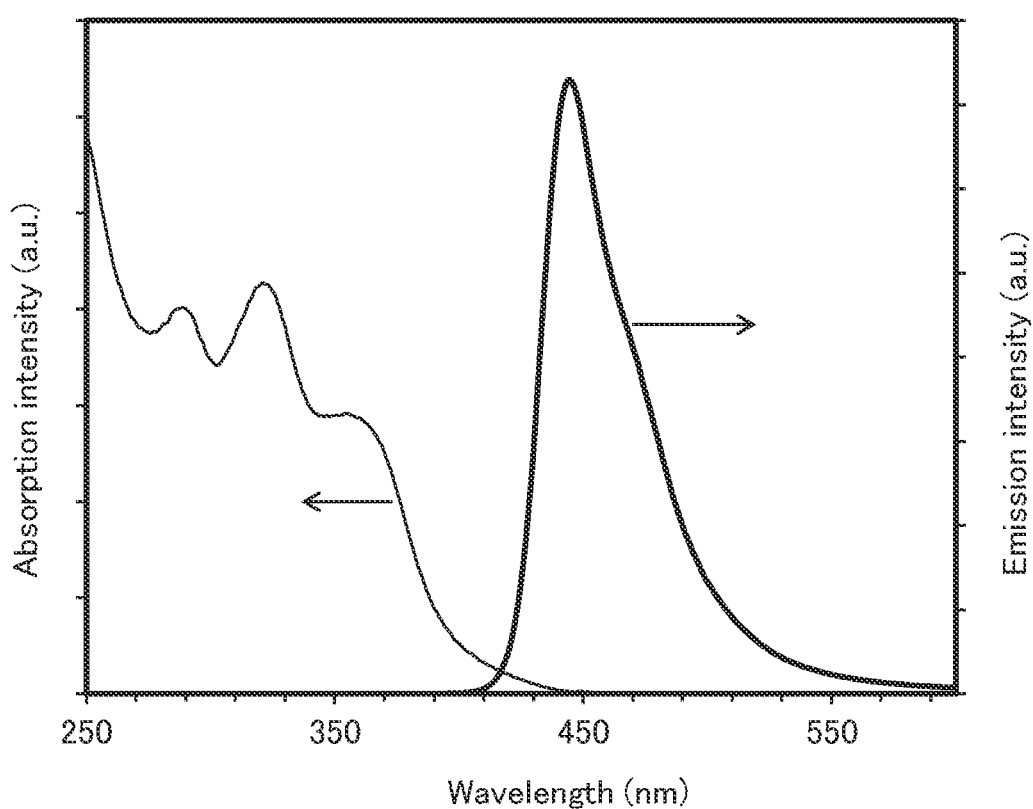
FIG. 56 shows an absorption spectrum and an emission spectrum of mmtBuPCzPCFL in a thin film state.

Next, the measurement results of the absorption and emission spectra of mmtBuPCzPCFL in a toluene solution are shown in FIG. 55. Furthermore, the absorption and emission spectra of the thin film are shown in FIG. 56. The solid thin film was formed over a quartz substrate by a vacuum evaporation method. The absorption spectrum of the toluene solution was measured with an ultraviolet-visible light spectrophotometer (V550, manufactured by JASCO Corporation), and the spectrum of toluene alone in a quartz cell was subtracted. The absorption spectrum of the thin film was measured with a spectrophotometer (U-4100 Spectrophotometer, manufactured by Hitachi High-Technologies Corporation). The emission spectrum was measured with a fluorescence spectrophotometer (FP-8600, produced by JASCO Corporation).

As can be seen in FIG. 55, mmtBuPCzPCFL in the toluene solution has absorption peaks at 361 nm, 323 nm, and 287 nm, and an emission spectrum peak at 441 nm (excitation wavelength: 323 nm). As can be seen in FIG. 56, mmtBuPCzPCFL in the thin film has absorption peaks at 420 nm, 365 nm, 324 nm, and 294 nm, and an emission spectrum peak at 444 nm (excitation wavelength: 360 nm).

Example 9

In this example, a light-emitting device 4 which uses the organic compound of one embodiment of the present invention is described. Structural formulae of organic compounds used for the light-emitting device 4 are shown below.

[Chemical Formula 58]

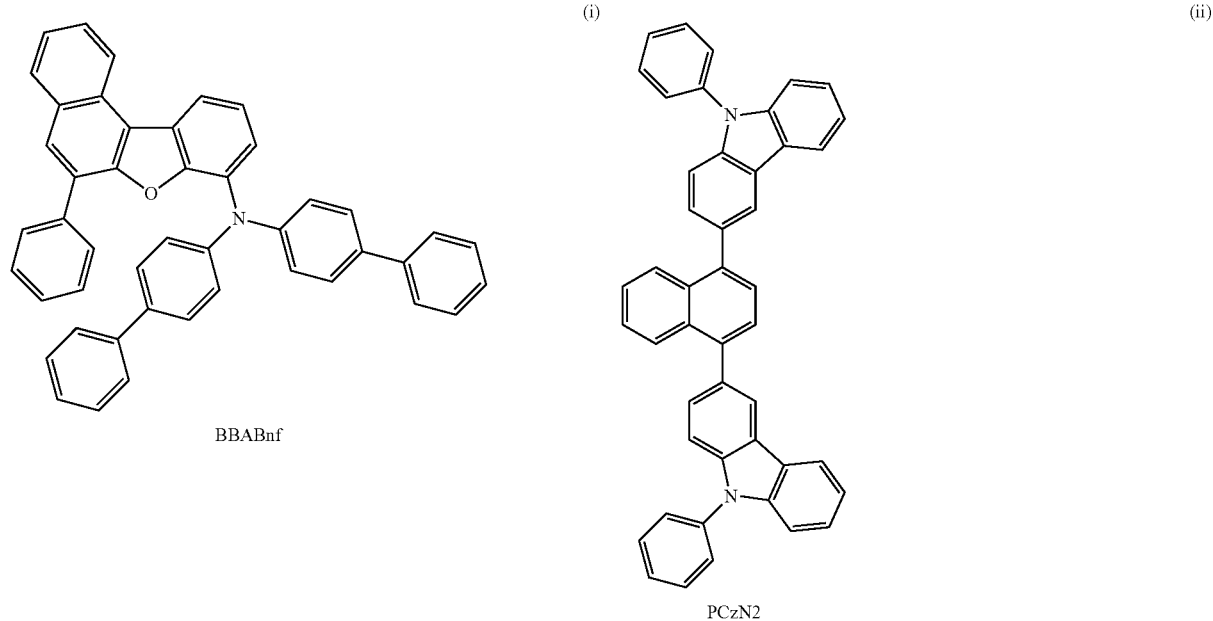

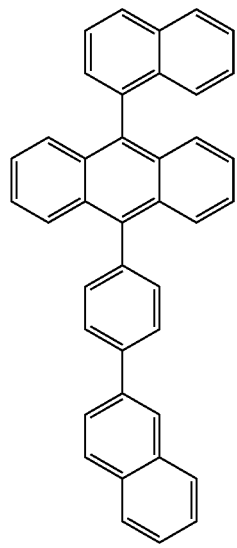
αN-βNPAnth
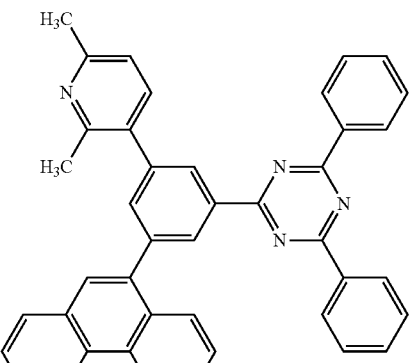
mPn-mDMePyPTzn
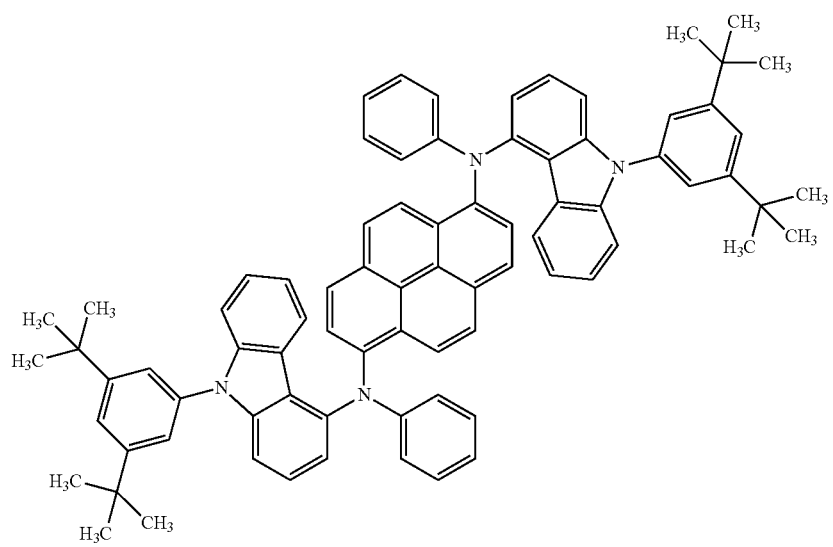
1,6mmtBuPCAPrn-03
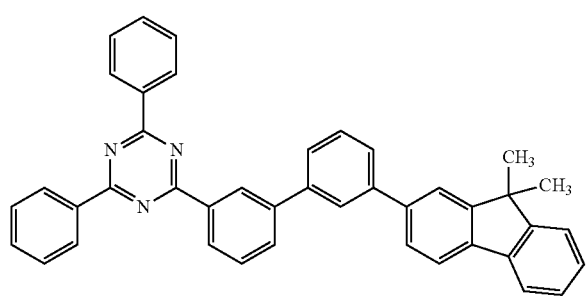
mFBPTzn
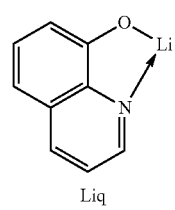
Liq (Fabrication Method of Light-Emitting Device 4)

First, indium tin oxide containing silicon oxide (ITSO) was deposited over a glass substrate by a sputtering method to form the first electrode 101. The thickness of the first electrode 101 was 70 nm and the electrode area was 2 mm×2 mm.

Next, in pretreatment for forming the light-emitting device over a substrate, a surface of the substrate was washed with water and baked at 200° C. for 1 hour, and then UV ozone treatment was performed for 370 seconds.

After that, the substrate was transferred into a vacuum evaporation apparatus where the pressure was reduced to approximately 104 Pa, vacuum baking was performed at 170° C. for 30 minutes in a heating chamber of the vacuum evaporation apparatus, and then the substrate was cooled down for approximately 30 minutes.

Next, the substrate provided with the first electrode 101 was fixed to a substrate holder provided in the vacuum evaporation apparatus such that the side on which the first electrode 101 was formed faced downward. Then, N,N-bis(4-biphenyl)-6-phenylbenzo[b]naphtho[1,2-d]furan-8-amine (abbreviation: BBABnf) represented by Structural Formula (i) above and an electron acceptor material (OCHD-001) were deposited on the first electrode 101 to a thickness of 10 nm by a co-evaporation method using resistance heating such that the weight ratio of BBABnf to OCHD-001 was 1:0.1, whereby the hole-injection layer 111 was formed.

Next, over the hole-injection layer 111, BBABnf was deposited by evaporation to a thickness of 20 nm, and then 3,3'-(naphthalene-1,4-diyl)bis(9-phenyl-9H-carbazole) (abbreviation: PCzN2) represented by Structural Formula (ii) above was deposited by evaporation to a thickness of 10 nm, whereby the hole-transport layer 112 was formed.

Then, 9-(1-naphthyl)-10-[4-(2-naphthyl)phenyl]anthracene (abbreviation: αN-βNPAnth) represented by Structural Formula (iii) above and N,N'-bis[9-(3,5-di-tert-butylphenyl)-9H-carbazol-4-yl]-N,N-diphenyl-pyrene-1,6-diamine (abbreviation: 1,6mmtBuPCAPrn-03) represented by Structural Formula (xv) above were deposited by co-evaporation to a thickness of 25 nm such that the weight ratio of αN-βNPAnth to 1,6mmtBuPCAPrn-03 was 1:0.03, whereby the light-emitting layer 113 was formed.

Then, over the light-emitting layer 113, 2-[3'-(9,9-dimethyl-9H-fluorene-2-yl)-1,1'-biphenyl-3-yl]-4,6-diphenyl-1,3,5-triazine (abbreviation: mFBPTzn) represented by Structural formula (xvi) above was deposited to a thickness of 10 nm, and then 2-[3-(2,6-dimethyl-3-pyridinyl)-5-(9-phenanthrenyl)phenyl]-4,6-diphenyl-1,3,5-triazine (abbreviation: mPn-mDMePyPTzn) represented by Structural Formula (xiii) above and 8-hydroxyquinolinato-lithium (abbreviation: Liq) represented by Structural Formula (xiv) above were deposited by co-evaporation to a thickness of 15 nm such that the weight ratio of mPn-mDMePyPTzn to Liq was 1:1, whereby the electron-transport layer 114 was formed.

After the formation of the electron-transport layer 114, Liq was deposited by evaporation to a thickness of 1 nm to form the electron-injection layer 115. Then, aluminum was deposited by evaporation to a thickness of 200 nm to form the second electrode 102. Thus, the light-emitting device 4 of this example was fabricated.

The structures of the light-emitting device are listed in the following table.

TABLE 9

| Hole-injection layer 10 nm | Hole-transport layer | | Light-emitting layer 25 nm | Electron-transport layer | | Electron-injection layer 1 nm |
|---|---|---|---|---|---|---|
| | 1 20 nm | 2 10 nm | | 1 10 nm | 2 15 nm | |
| BBABnf:OCHD-001 (1:0.1) | BBABnf | PCzN2 | αN-bNPAnth:1,6mmtBuPCAPrn-03 (1:0.03) | mFBPTzn | mPn-mDMePyPTzn:Liq (1:1) | Liq |

The light-emitting device was sealed using a glass substrate in a glove box containing a nitrogen atmosphere so as not to be exposed to the air (a sealing material was applied to surround the device and UV treatment and heat treatment at 80° C. for 1 hour were performed at the time of sealing). Then, the initial characteristics were measured.

Figure 57:
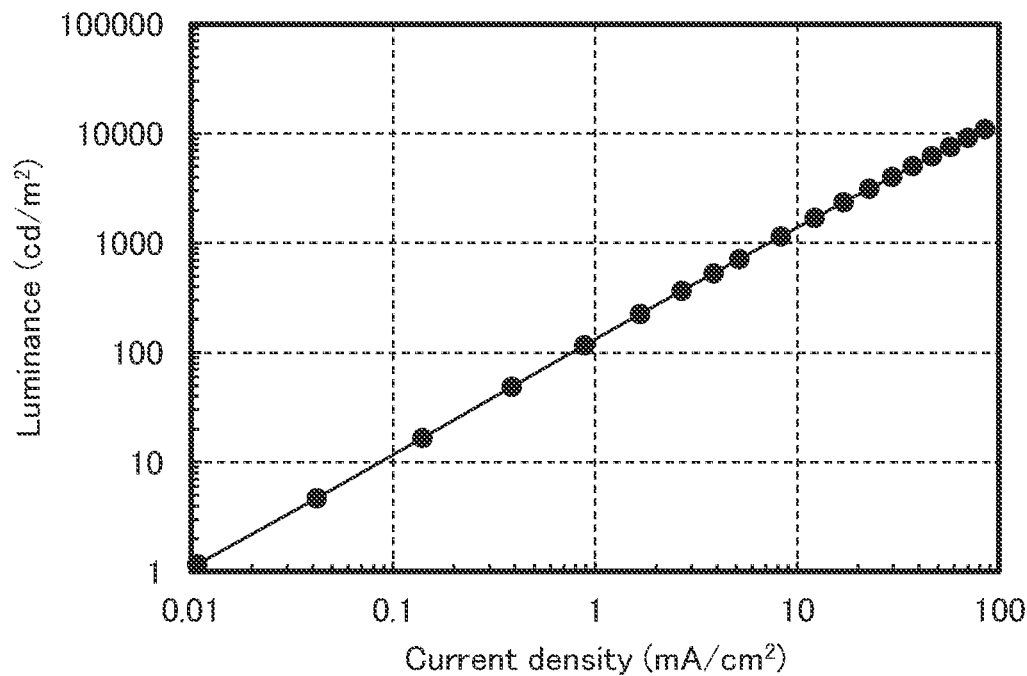
FIG. 57 shows luminance-current density characteristics of a light-emitting device 4.
Figure 58:
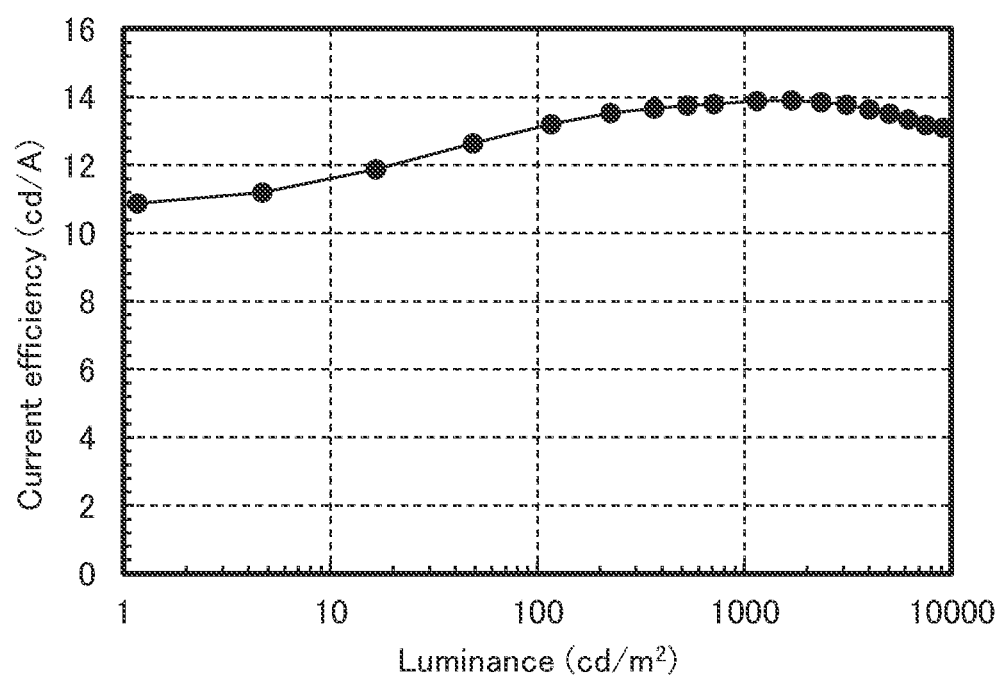
FIG. 58 shows current efficiency-luminance characteristics of the light-emitting device 4.
Figure 59:
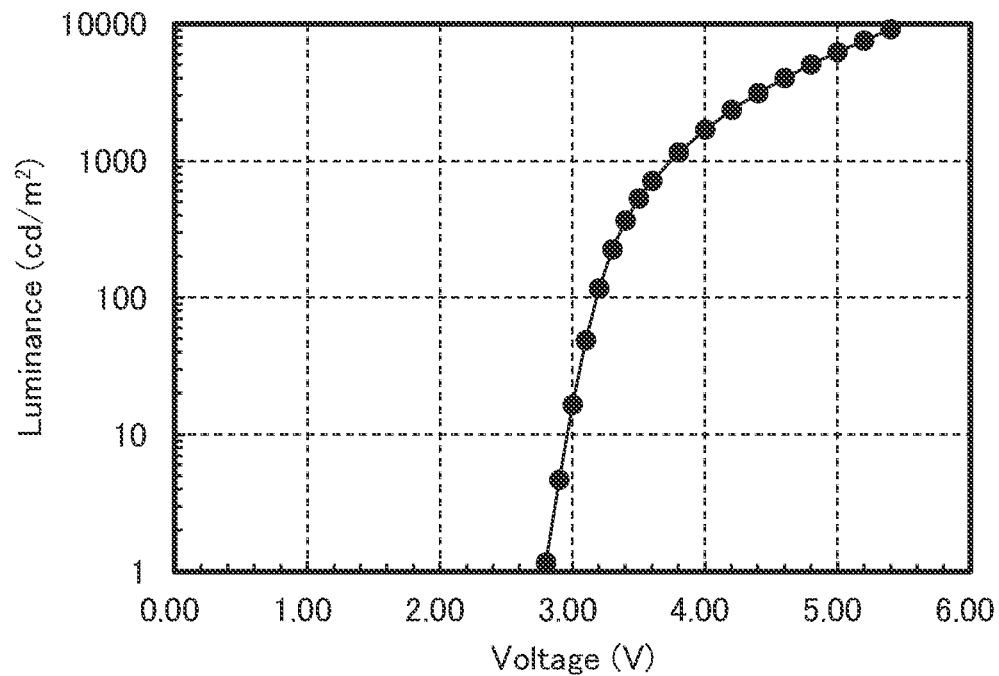
FIG. 59 shows luminance-voltage characteristics of the light-emitting device 4.
Figure 60:
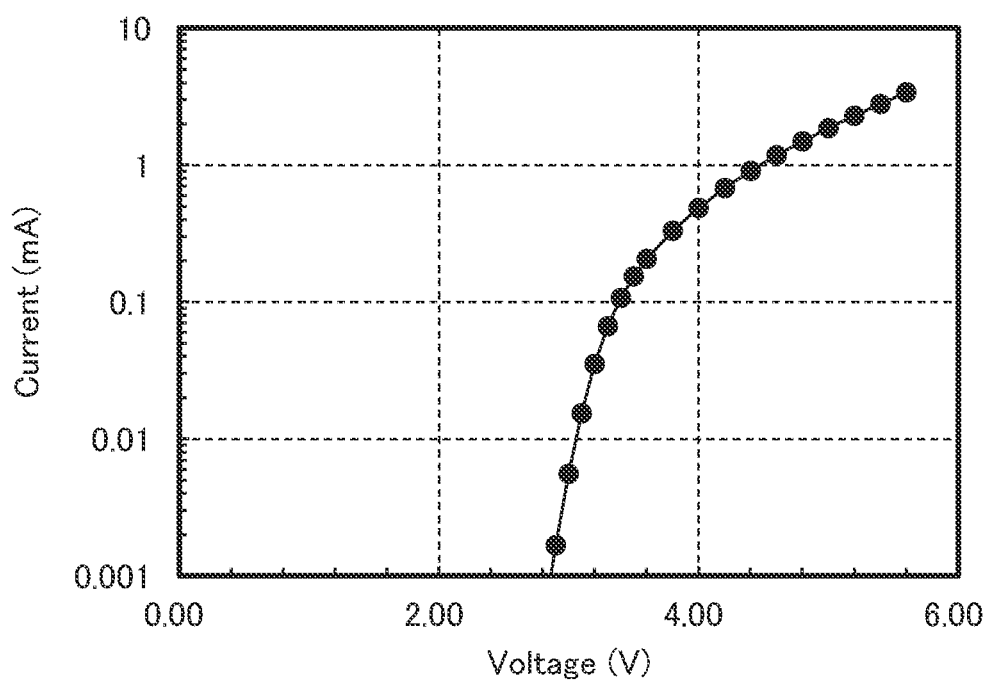
FIG. 60 shows current-voltage characteristics of the light-emitting device 4.
Figure 61:
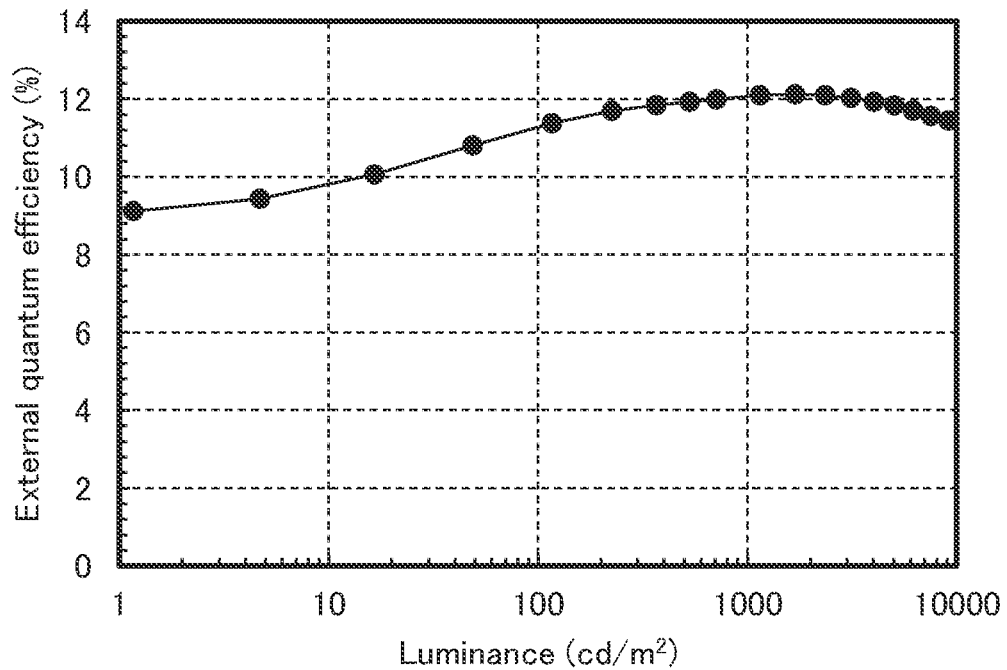
FIG. 61 shows external quantum efficiency-luminance characteristics of the light-emitting device 4.
Figure 62:
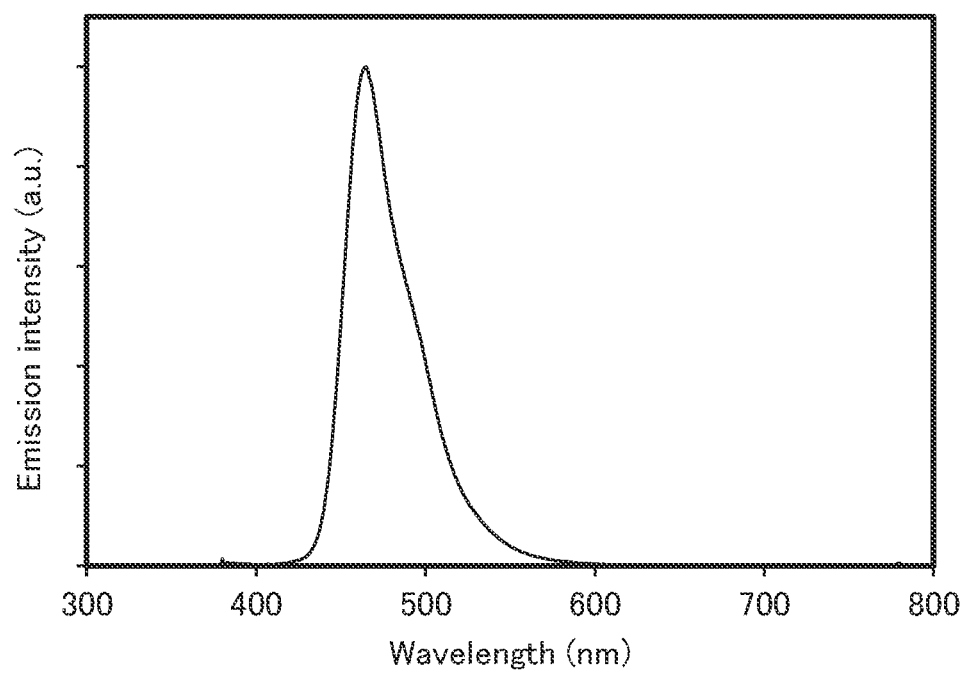
FIG. 62 shows an emission spectrum of the light-emitting device 4.

FIG. 57 shows the luminance-current density characteristics of the light-emitting device 4. FIG. 58 shows the current efficiency-luminance characteristics thereof. FIG. 59 shows the luminance-voltage characteristics thereof. FIG. 60 shows the current-voltage characteristics thereof. FIG. 61 shows the external quantum efficiency-luminance characteristics thereof. FIG. 62 shows the emission spectrum thereof. The main characteristics of the light-emitting device at a luminance of approximately 1000 cd/m² are shown below.

TABLE 10

| | Voltage (V) | Current (mA) | Current density (mA/cm²) | Chromaticity x | Chromaticity y | Current efficiency (cd/A) | External quantum efficiency (%) |
|---|---|---|---|---|---|---|---|
| Light-emitting device 4 | 3.8 | 0.33 | 8.3 | 0.13 | 0.15 | 13.9 | 12.1 |

FIG. 57 to FIG. 62 show that the light-emitting device 4 of one embodiment of the present invention is an EL device having favorable characteristics.

Example 10

In this example, a light-emitting device 5 which uses the organic compound of one embodiment of the present invention is described. Structural formulae of organic compounds used for the light-emitting device 5 are shown below.

[Chemical Formula 59]
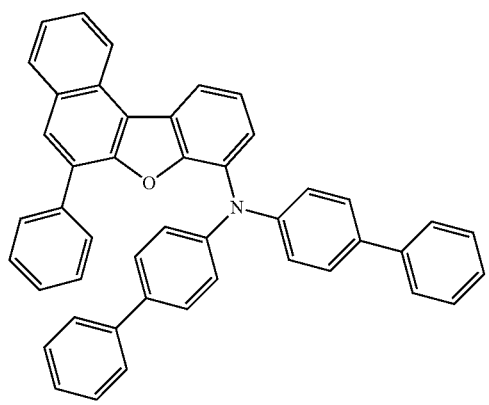
BBABnf (i)
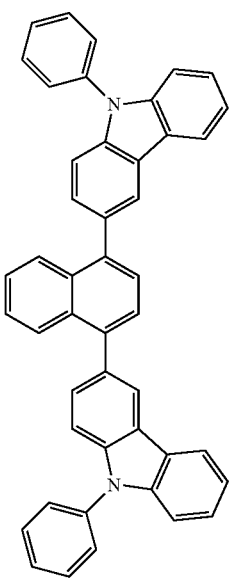
PCzN2 (ii)
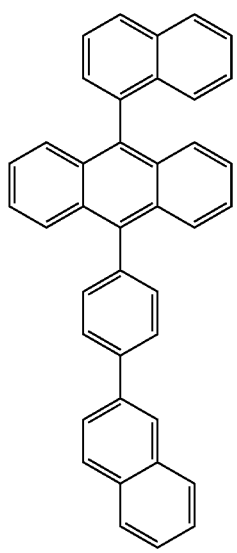
αN-βNPAnth (iii)
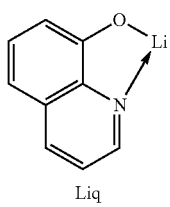
Liq (xiv)
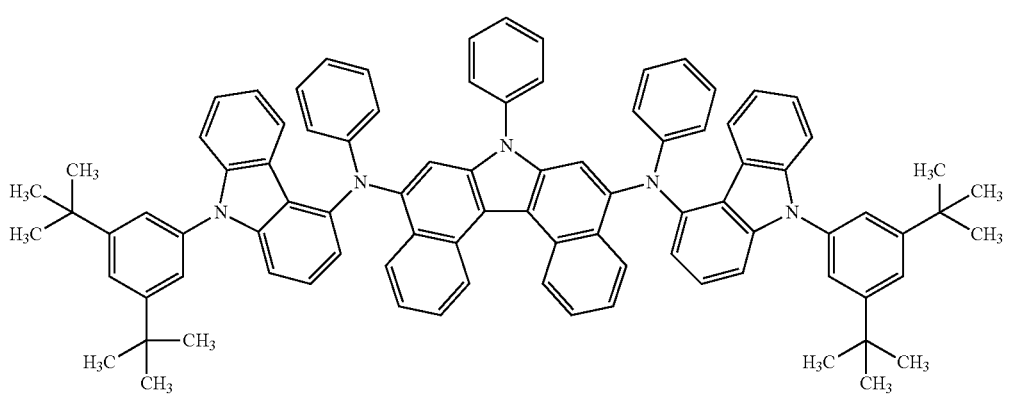
5,9mmtBuPCA2PcgDBC-03 (xvii)

(xvi)

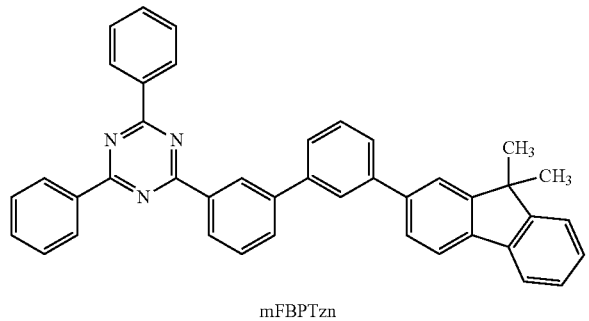

mFBPTzn (xiii)

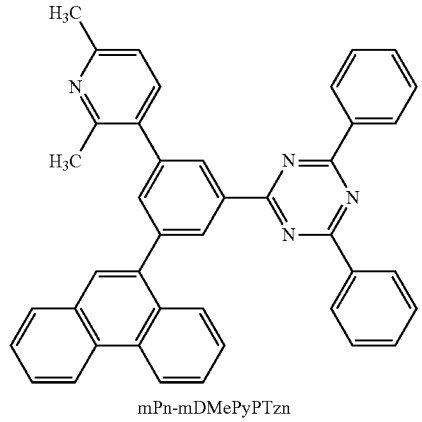

mPn-mDMePyPTzn (Fabrication Method of Light-Emitting Device 5)

First, indium tin oxide containing silicon oxide (ITSO) was deposited over a glass substrate by a sputtering method to form the first electrode 101. The thickness of the first electrode 101 was 70 nm and the electrode area was 2 mm×2 mm.

Next, in pretreatment for forming the light-emitting device over a substrate, a surface of the substrate was washed with water and baked at 200° C. for 1 hour, and then UV ozone treatment was performed for 370 seconds.

After that, the substrate was transferred into a vacuum evaporation apparatus where the pressure was reduced to approximately 10-4 Pa, vacuum baking was performed at 170° C. for 30 minutes in a heating chamber of the vacuum evaporation apparatus, and then the substrate was cooled down for approximately 30 minutes.

Next, the substrate provided with the first electrode 101 was fixed to a substrate holder provided in the vacuum evaporation apparatus such that the side on which the first electrode 101 was formed faced downward. Then, N,N-bis (4-biphenyl)-6-phenylbenzo[b]naphtho[1,2-d]furan-8-amine (abbreviation: BBABnf) represented by Structural Formula (i) above and an electron acceptor material (OCHD-001) were deposited on the first electrode 101 to a thickness of 10 nm by a co-evaporation method using resistance heating such that the weight ratio of BBABnf to OCHD-001 was 1:0.1, whereby the hole-injection layer 111 was formed.

Next, over the hole-injection layer 111, BBABnf was deposited by evaporation to a thickness of 20 nm, and then 3,3'-(naphthalene-1,4-diyl)bis(9-phenyl-9H-carbazole) (abbreviation: PCzN2) represented by Structural Formula (ii) above was deposited by evaporation to a thickness of 10 nm, whereby the hole-transport layer 112 was formed.

Then, 9-(1-naphthyl)-10-[4-(2-naphthyl)phenyl]anthracene (abbreviation: αN-PNPAnth) represented by Structural Formula (iii) above and N,N'-bis[9-(3,5-di-tert-butylphenyl)-9H-carbazol-4-yl]-N,N'-diphenyl-7-phenyl-7H-dibenzo[c,g]carbazole-5,9-diamine (abbreviation: 5,9mmtBuPCA2PcgDBC-03) represented by Structural Formula (xvii) above were deposited by co-evaporation to a thickness of 25 nm such that the weight ratio of αN-βNPAnth to 5,9mmtBuPCA2PcgDBC-03 was 1:0.03, whereby the light-emitting layer 113 was formed.

Then, over the light-emitting layer 113, 2-[3'-(9,9-dimethyl-9H-fluoren-2-yl)-1,1'-biphenyl-3-yl]-4,6-diphenyl-1,3,5-triazine (abbreviation: mFBPTzn) represented by Structural formula (xvi) above was deposited to a thickness of 10 nm, and then 2-[3-(2,6-dimethyl-3-pyridinyl)-5-(9-phenanthrenyl)phenyl]-4,6-diphenyl-1,3,5-triazine (abbreviation: mPn-mDMePyPTzn) represented by Structural Formula (xiii) above and 8-hydroxyquinolinato-lithium (abbreviation: Liq) represented by Structural Formula (xiv) above were deposited by co-evaporation to a thickness of 15 nm such that the weight ratio of mPn-mDMePyPTzn to Liq was 1:1, whereby the electron-transport layer 114 was formed.

After the formation of the electron-transport layer 114, Liq was deposited by evaporation to a thickness of 1 nm to form the electron-injection layer 115. Then, aluminum was deposited by evaporation to a thickness of 200 nm to form the second electrode 102. Thus, the light-emitting device 5 of this example was fabricated.

The structures of the light-emitting device 5 are listed in the following table.

TABLE 11

| Hole-injection layer 10 nm | Hole-transport layer | | Light-emitting layer 25 nm | Electron-transport layer | | Electron-injection layer 1 nm |
|---|---|---|---|---|---|---|
| | 1 20 nm | 2 10 nm | | 1 10 nm | 2 15 nm | |
| BBABnf:OCHD-001 (1:0.1) | BBABnf | PCzN2 | aN-bNPAnth:5,9mmtBuPCA2PcgDBC-03 (1:0.03) | mFBPTzn | mPn-mDMePyPTzn:Liq (1:1) | Liq |

The light-emitting device 5 was sealed using a glass substrate in a glove box containing a nitrogen atmosphere so as not to be exposed to the air (a sealing material was applied to surround the device and UV treatment and heat treatment at 80° C. for 1 hour were performed at the time of sealing). Then, the initial characteristics were measured.

Figure 63:
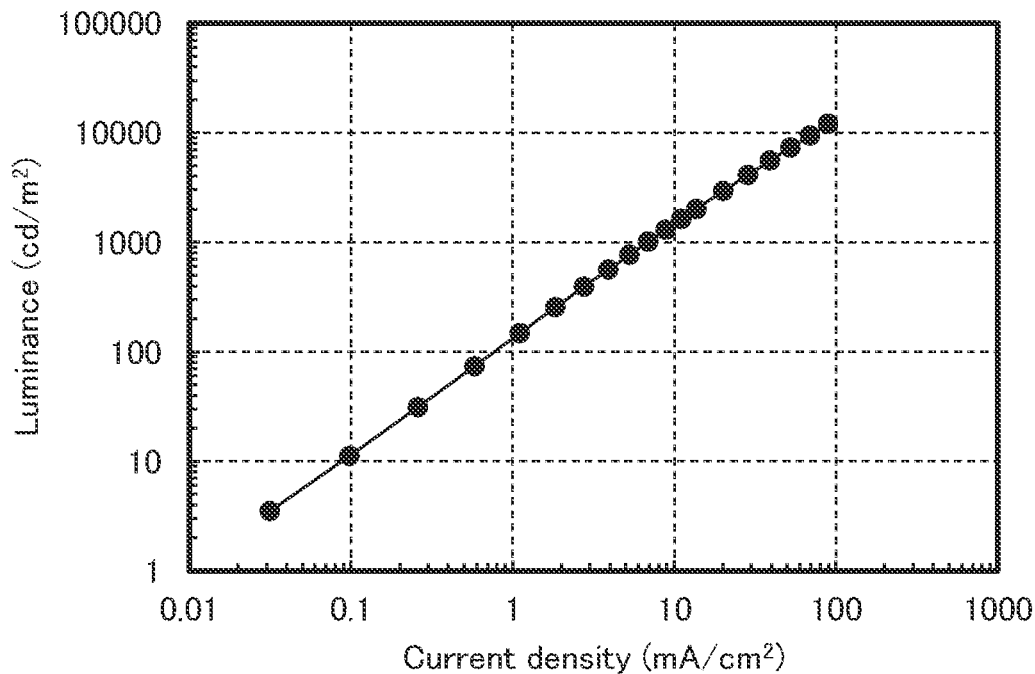
FIG. 63 shows luminance-current density characteristics of a light-emitting device 5.
Figure 64:
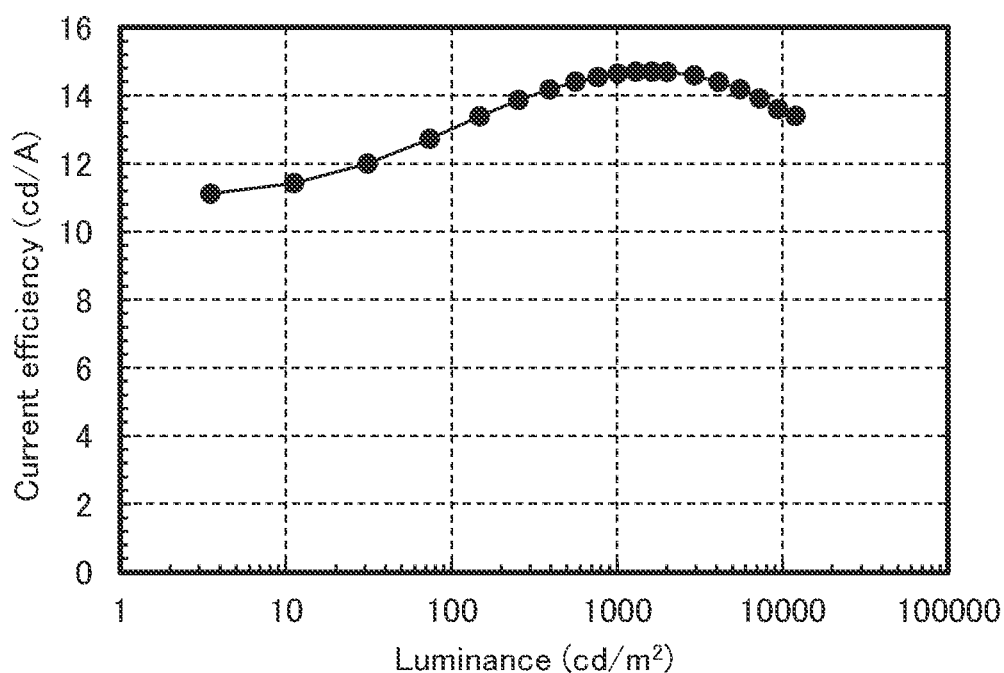
FIG. 64 shows current efficiency-luminance characteristics of the light-emitting device 5.
Figure 65:
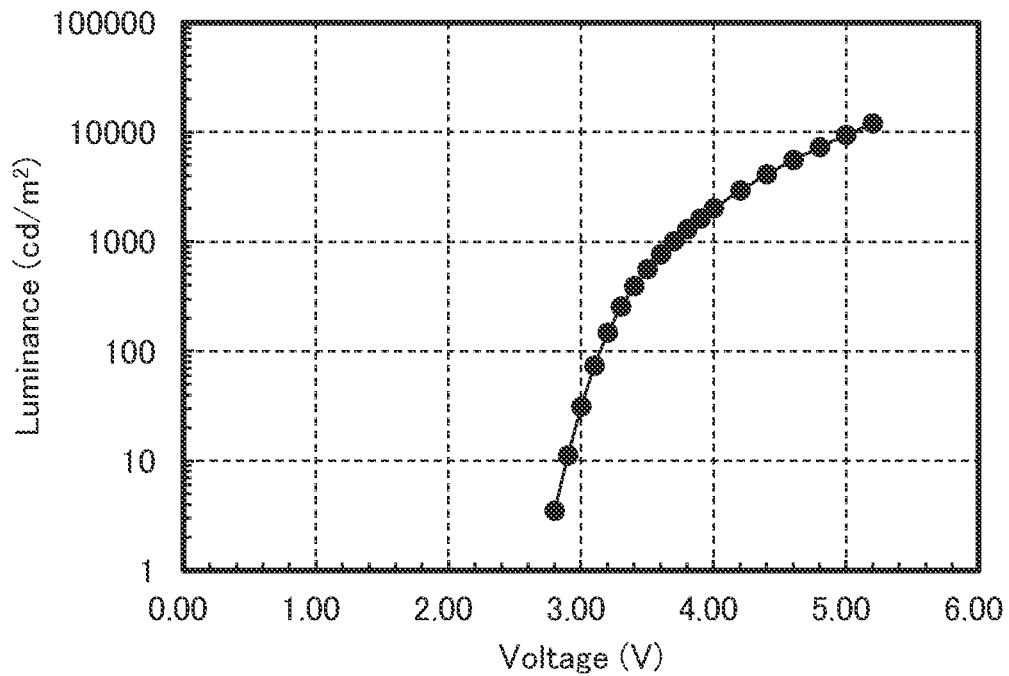
FIG. 65 shows luminance-voltage characteristics of the light-emitting device 5.
Figure 66:
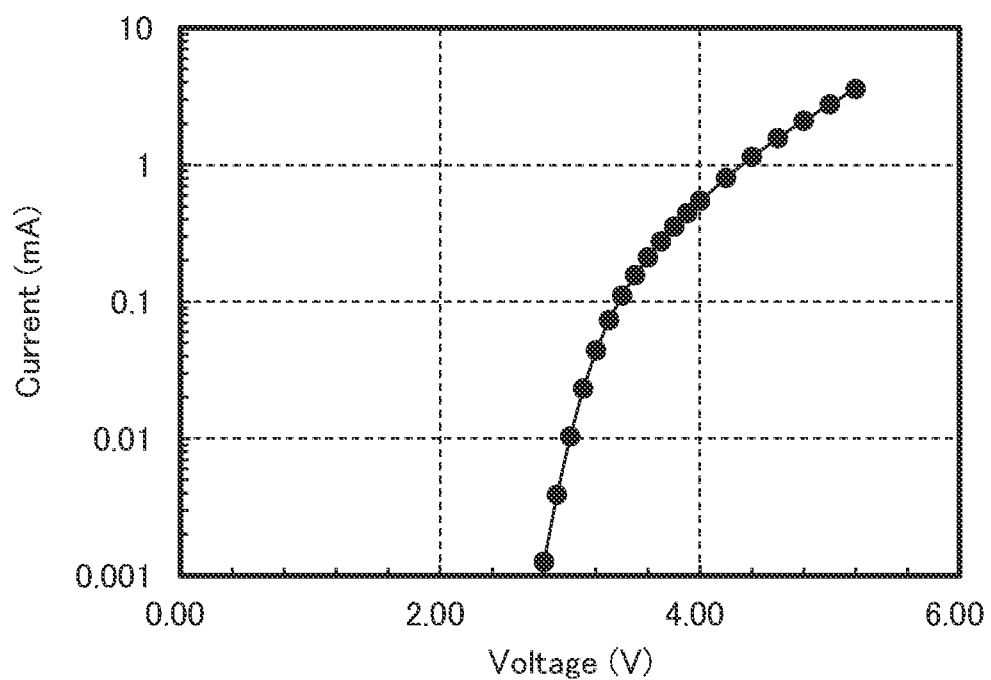
FIG. 66 shows current-voltage characteristics of the light-emitting device 5.
Figure 67:
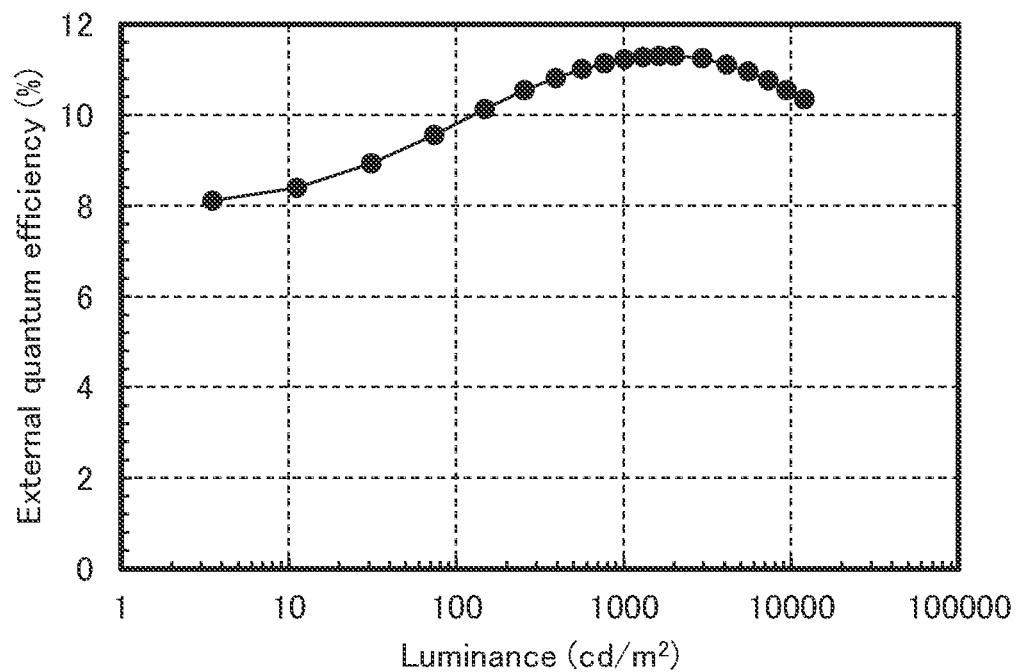
FIG. 67 shows external quantum efficiency-luminance characteristics of the light-emitting device 5.
Figure 68:
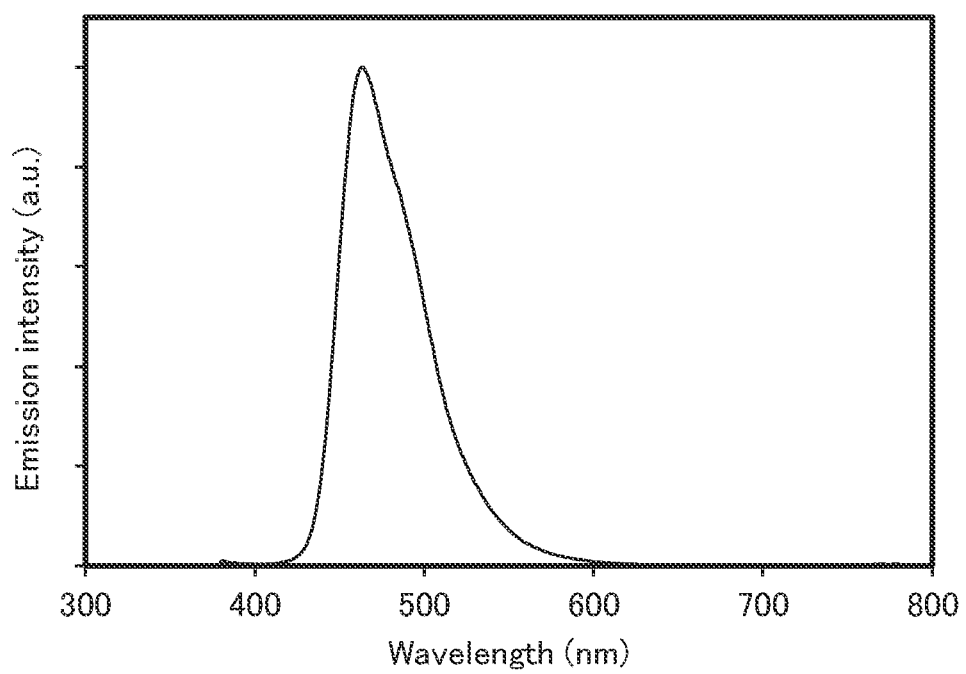
FIG. 68 shows an emission spectrum of the light-emitting device 5.

FIG. 63 shows the luminance-current density characteristics of the light-emitting device 5. FIG. 64 shows the current efficiency-luminance characteristics thereof. FIG. 65 shows the luminance-voltage characteristics thereof. FIG. 66 shows the current-voltage characteristics thereof. FIG. 67 shows the external quantum efficiency-luminance characteristics thereof. FIG. 68 shows the emission spectrum thereof. The main characteristics of the light-emitting device at a luminance of approximately 1000 cd/m² are shown below.

TABLE 12

| | Voltage (V) | Current (mA) | Current density (mA/cm²) | Chromaticity x | Chromaticity y | Current efficiency (cd/A) | External quantum efficiency (%) |
|---|---|---|---|---|---|---|---|
| Light-emitting device 5 | 3.7 | 0.28 | 6.9 | 0.13 | 0.17 | 14.6 | 11.2 |

FIG. 63 to FIG. 68 show that the light-emitting device 5 of one embodiment of the present invention is an EL device having favorable characteristics.

Example 11

In this example, a light-emitting device 6 and a light-emitting device 7 which use the organic compounds of embodiments of the present invention are described. Structural formulae of organic compounds used for the light-emitting device 6 and the light-emitting device 7 are shown below.

[Chemical Formula 60]

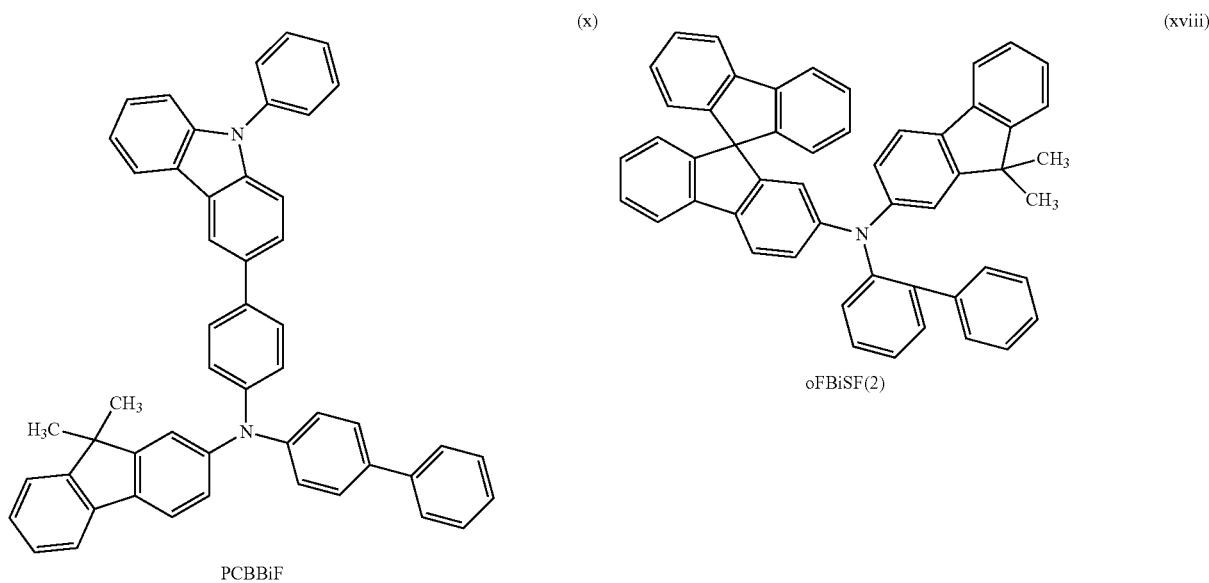

-continued (xix)
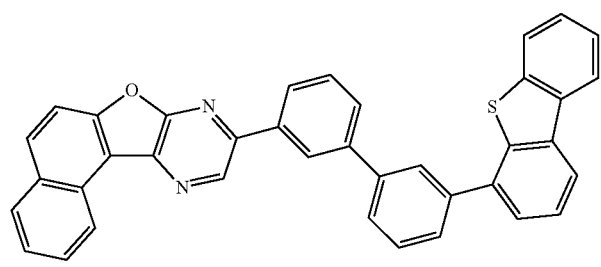
9mDBtBPNfpr (xx)
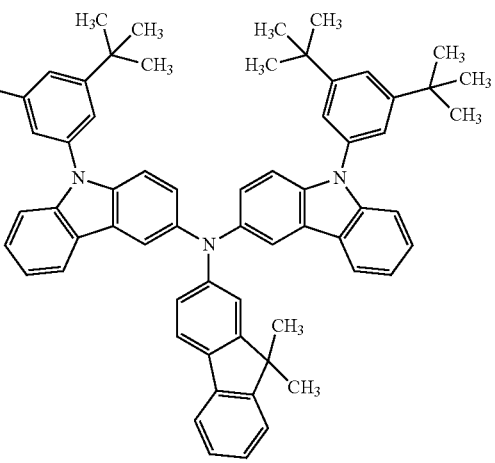
mmtBuPCzPCFL (xxi)
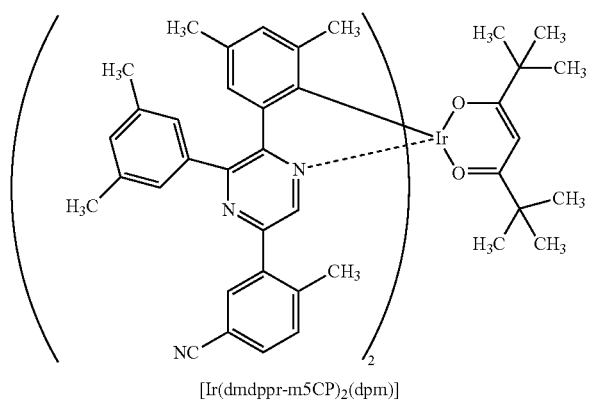
[Ir(dmdppr-m5CP)₂(dpm)]

(xvi)
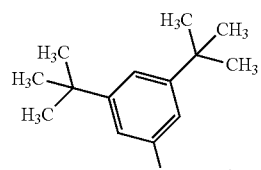
mFBPTzn (xiii)
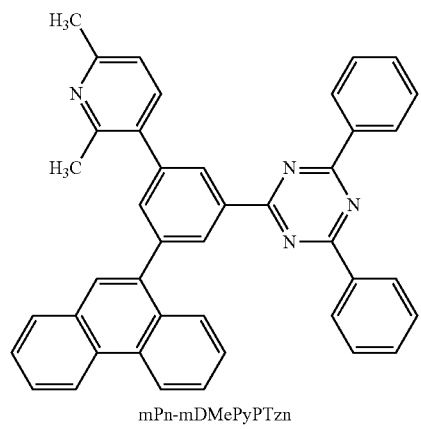
mPn-mDMePyPTzn (xxii)
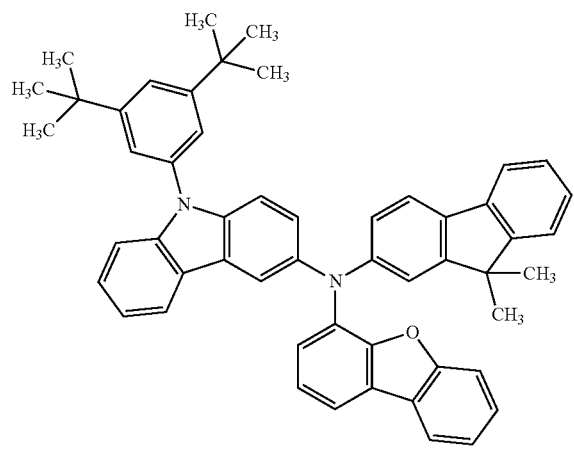
FrFAmmtBuPC (Fabrication Method of Light-Emitting Device 6)

First, indium tin oxide containing silicon oxide (ITSO) was deposited over a glass substrate by a sputtering method to form the first electrode 101. The thickness of the first electrode 101 was 110 nm and the electrode area was 2 mm×2 mm.

Next, in pretreatment for forming the light-emitting device over a substrate, a surface of the substrate was washed with water and baked at 200° C. for 1 hour, and then UV ozone treatment was performed for 370 seconds.

After that, the substrate was transferred into a vacuum evaporation apparatus where the pressure was reduced to approximately 104 Pa, vacuum baking was performed at 170° C. for 30 minutes in a heating chamber of the vacuum evaporation apparatus, and then the substrate was cooled down for approximately 30 minutes.

Next, the substrate provided with the first electrode 101 was fixed to a substrate holder provided in the vacuum evaporation apparatus such that the side on which the first electrode 101 was formed faced downward. Then, N-(1,1'-biphenyl-4-yl)-N-[4-(9-phenyl-9H-carbazol-3-yl)phenyl]-9,9-dimethyl-9H-fluoren-2-amine (abbreviation: PCBBiF) represented by Structural Formula (x) above and an electron acceptor material (OCHD-001) were deposited on the first electrode 101 to a thickness of 10 nm by a co-evaporation method using resistance heating such that the weight ratio of PCBBiF to OCHD-001 was 1:0.03, whereby the hole-injection layer 111 was formed.

Next, over the hole-injection layer 111, PCBBiF was deposited by evaporation to a thickness of 100 nm, and then N-(1,1'-biphenyl-2-yl)-N-(9,9-dimethylfluoren-2-yl)-9,9'-spirobi[9H-fluoren]-2-amine (abbreviation: oFBiSF(2)) represented by Structural Formula (xviii) above was deposited by evaporation to a thickness of 90 nm, whereby the hole-transport layer 112 was formed.

Then, 9-[3'-(dibenzothiophen-4-yl)bipheny-3-yl]naphtho[1',2':4,5]furo[2,3-b]pyrazine (abbreviation: 9mDBtBPNfpr) represented by Structural Formula (xix) above, N-(9,9-dimethyl-9H-fluoren-2-yl)-bis[9-(3,5-di-tert-buthylphenyl)-9H-carbazole]-3,3'-amine (abbreviation: mmtBuPCzPCFL), which is the organic compound of one embodiment of the present invention represented by Structural Formula (xx) above, and bis{4,6-dimethyl-2-[5-(5-cyano-2-methylphenyl)-3-(3,5-dimethylphenyl)-2-pyrazinyl-κN]phenyl-κC}(2,2,6,6-tetramethyl-3,5-heptanedionato-κ$^2$O,O')iridium(III) (abbreviation: [Ir(dmdppr-m5CP)$_2$(dpm)]) represented by Structural Formula (xxi) above were deposited by co-evaporation to a thickness of 50 nm such that the weight ratio of 9mDBtBPNfpr to mmtBuPCzPCFL and [Ir(dmdppr-m5CP)$_2$(dpm)] was 0.6:0.4:0.1, whereby the light-emitting layer 113 was formed.

Then, over the light-emitting layer 113, 2-[3'-(9,9-dimethyl-9H-fluorene-2-yl)-1,1'-biphenyl-3-yl]-4,6-diphenyl-1,3,5-triazine (abbreviation: mFBPTzn) represented by Structural Formula (xvi) above was deposited to a thickness of 10 nm, and then 2-[3-(2,6-dimethyl-3-pyridinyl)-5-(9-phenanthrenyl)phenyl]-4,6-diphenyl-1,3,5-triazine (abbreviation: mPn-mDMePyPTzn) represented by Structural formula (xiii) above and 8-hydroxyquinolinato-lithium (abbreviation: Liq) represented by Structural Formula (xiv) above were deposited by co-evaporation to a thickness of 25 nm such that the weight ratio of mPn-mDMePyPTzn to Liq was 1:1, whereby the electron-transport layer 114 was formed.

After the formation of the electron-transport layer 114, Liq was deposited by evaporation to a thickness of 1 nm to form the electron-injection layer 115. Then, aluminum was deposited by evaporation to a thickness of 200 nm to form the second electrode 102. Thus, the light-emitting device 6 of this example was fabricated.

(Fabrication Method of Light-Emitting Device 7)

The light-emitting device 7 was fabricated in the same manner as the light-emitting device 6 except that N-(dibenzofuran-4-yl)-N-(9,9-dimetyl-9H-fluoren-2-yl)-9-(3,5-di-tert-butylphenyl)-9H-carbazole-3-amine (abbreviation: FrFAmmtBuPC), which is the organic compound of one embodiment of the present invention represented by Structural Formula (xxii) above, was used instead of mmtBuPCzPCFL used for the light-emitting device 6.

The structures of the light-emitting devices 6 and 7 are listed in the following table.

TABLE 13

|  | Hole-injection layer 10 nm | Hole-transport layer 1 100 nm | Hole-transport layer 2 90 nm | Light-emitting layer 50 nm | Electron-transport layer 1 10 nm | Electron-transport layer 2 25 nm | Electron-injection layer 1 nm |
|---|---|---|---|---|---|---|---|
| Light-emitting device 6 | PCBBiF:OCHD-001 (1:0.03) | PCBBiF | oFBiSF(2) | *7 | mFBPTzn | mPn-mDMePyPTzn:Liq (1:1) | Liq |
| Light-emitting device 7 |  |  |  | *8 |  |  |  |

*7 9mDBtBPNfpr:mmtBuPCzPCFL:Ir(dmdppr-m5CP)$_2$(dpm) (0.6:0.4:0.1)
*8 9mDBtBPNfpr:FrFAmmtBuPC:Ir(dmdppr-m5CP)$_2$(dpm) (0.6:0.4:0.1)

The light-emitting devices 6 and 7 were sealed using a glass substrate in a glove box containing a nitrogen atmosphere so as not to be exposed to the air (a sealing material was applied to surround the device and UV treatment and heat treatment at 80° C. for 1 hour were performed at the time of sealing). Then, the initial characteristics were measured.

Figure 69:
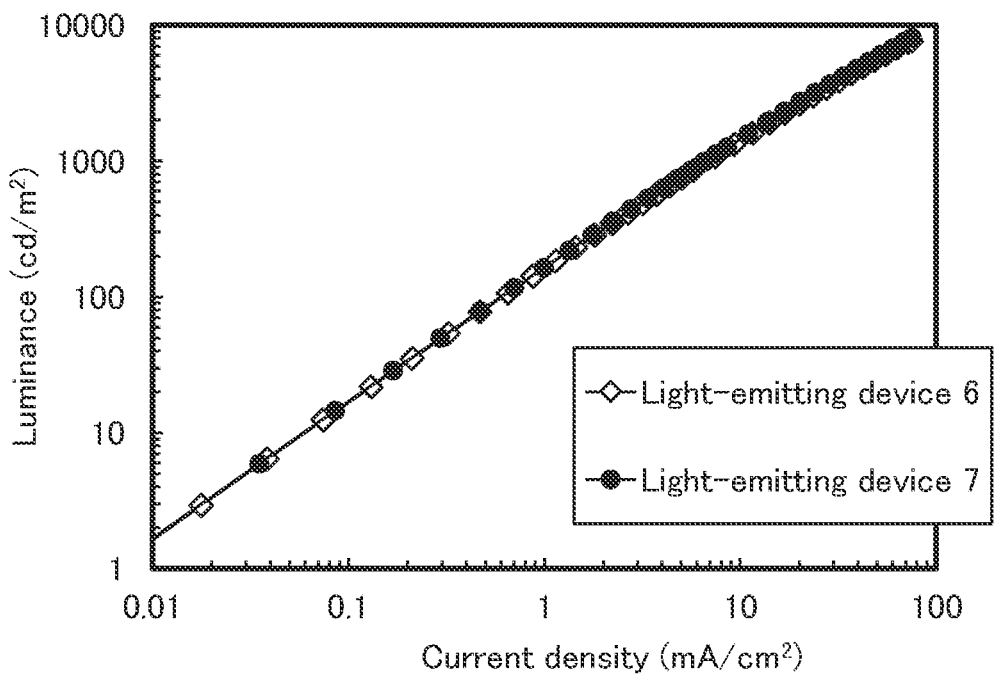
FIG. 69 shows luminance-current density characteristics of a light-emitting device 6 and a light-emitting device 7.
Figure 70:
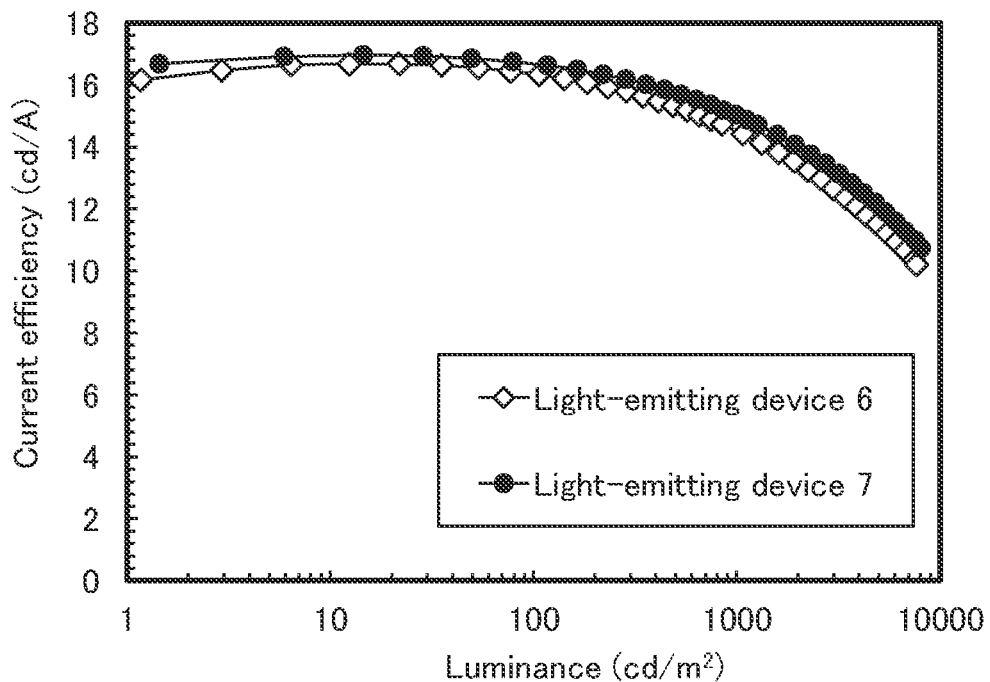
FIG. 70 shows current efficiency-luminance characteristics of the light-emitting device 6 and the light-emitting device 7.
Figure 71:
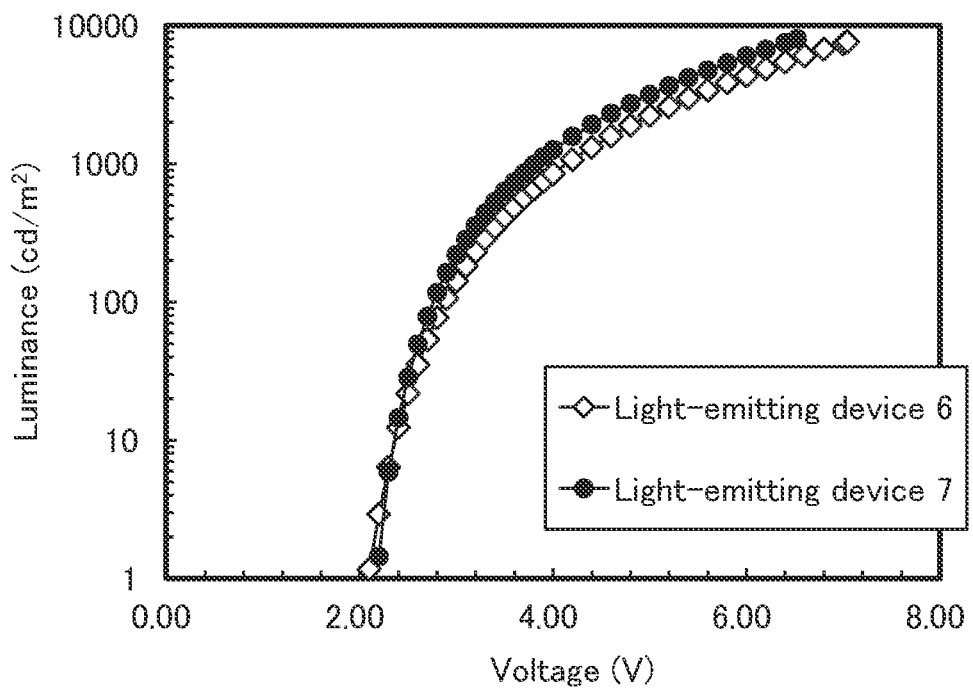
FIG. 71 shows luminance-voltage characteristics of the light-emitting device 6 and the light-emitting device 7.
Figure 72:
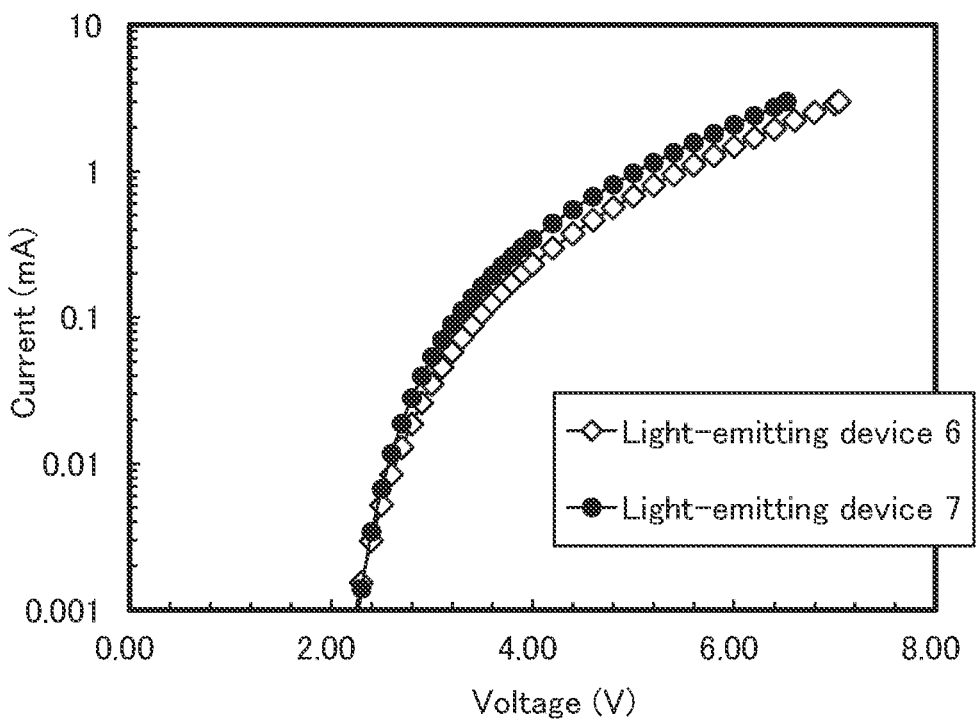
FIG. 72 shows current-voltage characteristics of the light-emitting device 6 and the light-emitting device 7.
Figure 73:
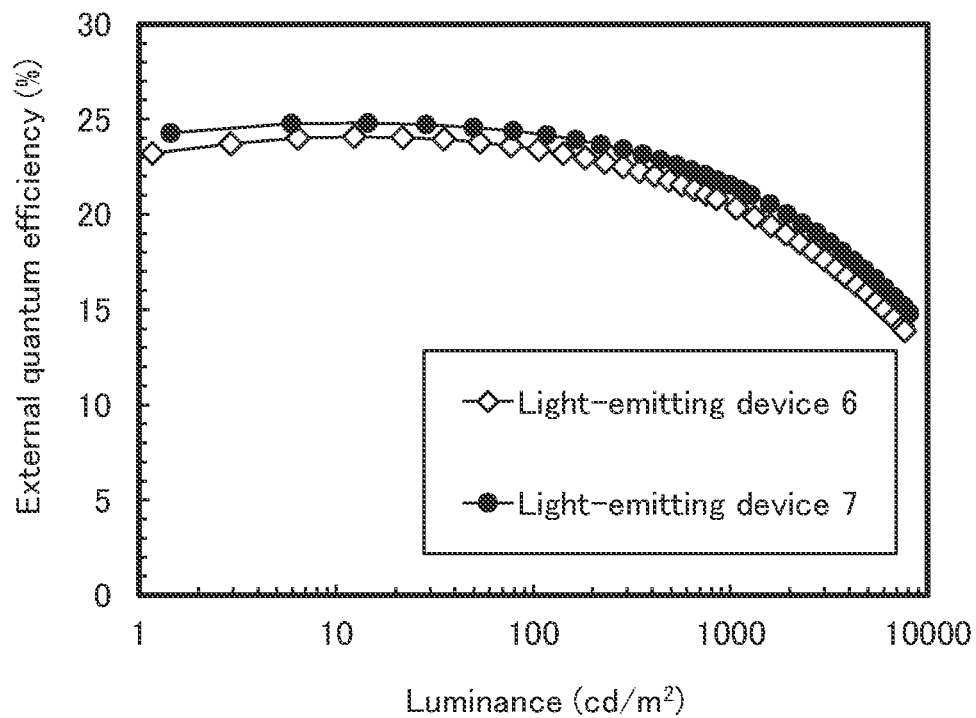
FIG. 73 shows external quantum efficiency-luminance characteristics of the light-emitting device 6 and the light-emitting device 7.
Figure 74:
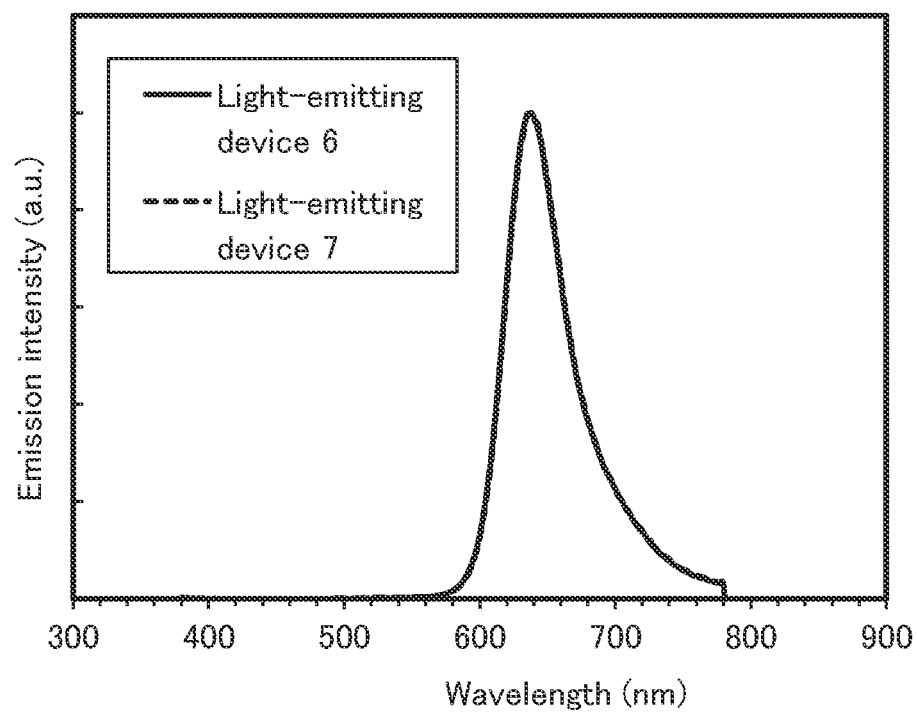
FIG. 74 shows emission spectra of the light-emitting device 6 and the light-emitting device 7.

FIG. 69 shows the luminance-current density characteristics of the light-emitting devices 6 and 7. FIG. 70 shows the current efficiency-luminance characteristics thereof. FIG. 71 shows the luminance-voltage characteristics thereof. FIG. 72 shows the current-voltage characteristics thereof. FIG. 73 shows the external quantum efficiency-luminance characteristics thereof. FIG. 74 shows the emission spectra thereof. The main characteristics of the light-emitting devices at a luminance of approximately 1000 cd/m$^2$ are shown below.

TABLE 14

|  | Voltage (V) | Current (mA) | Current density (mA/cm$^2$) | Chromaticity x | Chromaticity y | Current efficiency (cd/A) | External quantum efficiency (%) |
|---|---|---|---|---|---|---|---|
| Light-emitting device 6 | 4.2 | 0.30 | 7.4 | 0.69 | 0.31 | 14.4 | 20.3 |
| Light-emitting device 7 | 3.8 | 0.26 | 6.6 | 0.69 | 0.31 | 15.0 | 21.6 |

FIG. 69 to FIG. 74 show that the light-emitting devices 6 and 7 of embodiments of the present invention are EL devices having favorable characteristics.

Reference Example 1

Reference Synthesis Example 1

In this reference synthesis example, a synthesis method of N,N-bis[9-(3,5-diethylphenyl)-9H-carbazol-2-yl]-N,N-diphenyl-naphtho[2,3-b;6,7-b']bisbenzofuran-3,10-diamine (abbreviation: 3,10mmEtPCA2Nbf(IV)-02), which is used in Example 2, will be described. The structural formula of 3,10mmEtPCA2Nbf(IV)-02 is shown below.

[Chemical Formula 61]

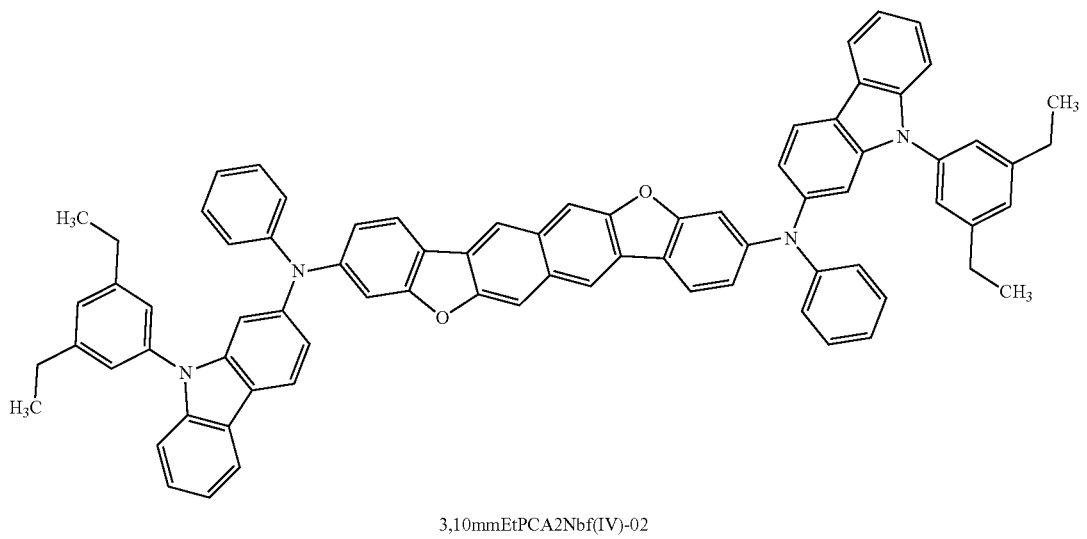

3,10mmEtPCA2Nbf(IV)-02

Step 1: Synthesis of 2-chloro-9-(3,5-diethylphenyl)-9H-carbazole

Into a 300-mL three-neck flask, 3.2 g (16 mmol) of 2-chloro-9H-carbazole, 5.0 g (23 mmol) of 1-bromo-3,5-diethylbenzene, and 4.5 g (47 mmol) of sodium tert-butoxide were put. To this mixture, 80 mL of xylene and 0.2 mL of tri(tert-butyl)phosphine (a 10% hexane solution) were added, and this mixture was degassed by being stirred while the pressure was reduced. Then, 90 mg (0.16 mmol) of bis(dibenzylideneacetone)palladium(0) was added to this mixture, and the mixture was heated and stirred under a nitrogen stream at 150° C. for 7 hours. After the stirring, toluene was added to the mixture, and the resulting mixture was suction-filtered through Florisil, Celite, and alumina. The obtained filtrate was concentrated to give an oily substance. This oily substance was purified by silica gel column chromatography (developing solvent: hexane) to give 4.8 g of a colorless transparent oily substance in 93% yield. The synthesis scheme of Step 1 is shown below.

[Chemical Formula 62]

Measurement results by nuclear magnetic resonance ($^1$H-NMR) spectroscopy of the colorless transparent oily substance obtained in Step 1 above are shown below. This indicates that 2-chloro-9-(3,5-diethylphenyl)-9H-carbazole was obtained in Step 1.

$^1$H NMR (CDCl$_3$, 300 MHz): δ=1.31 (t, J1=7.5 Hz, 6H), 2.75 (q, J1=7.5 Hz, 4H), 7.12 (s, 3H), 7.22-7.31 (m, 2H), 7.36-7.44 (m, 3H), 8.03 (dd, J1=8.1 Hz, J2=0.3 Hz, 1H), 8.25 (ddd, J1=7.8 Hz, J2=1.2 Hz, J3=0.9 Hz, 1H).

Step 2: Synthesis of N-[9-(3,5-diethylphenyl)-9H-carbazol-2-yl]-N-phenylamine Into a 300-mL three-neck flask, 4.8 g (14 mmol) of 2-chloro-9-(3,5-diethylphenyl)-9H-carbazole, 2.0 g (22 mmol) of aniline, 4.2 g (43 mmol) of sodium tert-butoxide, and 0.26 g (0.72 mmol) of di(1-adamantyl)-n-butylphosphine were put. Then, 75 mL of xylene was added to this mixture, and the mixture was degassed by being stirred while the pressure was reduced. To this mixture, 83 mg (0.14 mmol) of bis(dibenzylideneacetone)palladium(0) was added, and the mixture was heated and stirred under a nitrogen stream at 150° C. for 7 hours. After the stirring, toluene was added to the mixture, the resulting mixture was suction-filtered through Florisil, Celite, and alumina, and the filtrate was concentrated to give a solid. This solid was purified by silica gel column chromatography (toluene and hexane at 3:7 and then at 2:3 in the developing solvent). Ethanol and hexane were added to the obtained oily substance, and the mixture was irradiated with ultrasonic waves. The precipitated solid was collected to give 3.9 g of a white solid in 69% yield. The synthesis scheme of Step 2 is shown below.

[Chemical Formula 63]

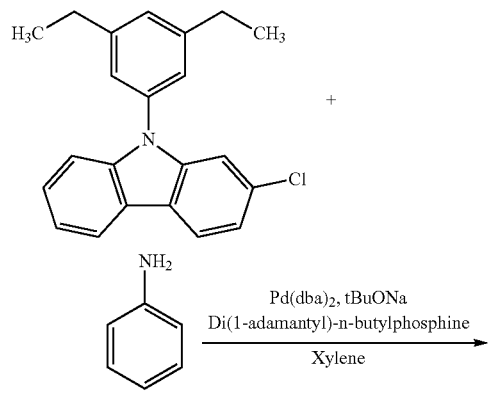

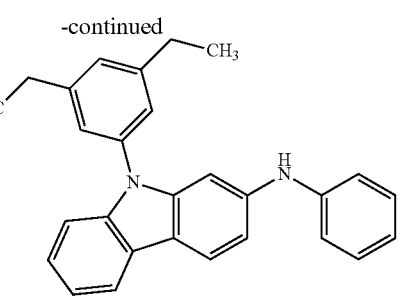

Measurement results by nuclear magnetic resonance ($^1$H-NMR) spectroscopy of the white solid obtained in Step 2 above are shown below. This indicates that N-[9-(3,5-diethylphenyl)-9H-carbazol-2-yl]-N-phenylamine was obtained in Step 2.

$^1$H NMR (DMSO-$d_6$, 300 MHz): δ=1.25 (t, J1=7.8 Hz, 6H), 2.70 (q, J1=7.8 Hz, 4H), 6.82 (t, J1=7.2 Hz, 1H), 7.00 (dd, J1=8.4 Hz, J2=1.8 Hz, 1H), 7.07 (d, J1=1.8 Hz, 1H), 7.12-7.31 (m, 10H), 8.02-8.07 (m, 2H), 8.37 (s, 1H).

Step 3: Synthesis of 3,10mmEtPCA2Nbf(IV)-02

Into a 200-mL three-neck flask, 0.87 g (2.3 mmol) of 3,10-dichloronaphtho[2,3-b;6,7-b']bisbenzofuran, 2.2 g (5.5 mmol) of N-[9-(3,5-diethylphenyl)-9H-carbazol-2-yl]-N-phenylamine, 82 mg (0.23 mmol) of di(1-adamantyl)-n-butylphosphine, and 1.3 g (14 mmol) of sodium tert-butoxide were put. To the mixture, 25 mL of xylene was added. This mixture was degassed by being stirred while the pressure was reduced. To this mixture, 26 mg (46 μmol) of bis(dibenzylideneacetone)palladium(0) was added, and stirring was performed under a nitrogen stream at 150° C. for 14 hours. After the stirring, toluene was added to this mixture, the mixture was suction-filtered through Florisil, Celite, and alumina, and the filtrate was concentrated to give a solid. The obtained solid was purified by silica gel column chromatography (toluene and hexane at 1:2 in the developing solvent) to give a solid. The obtained solid was recrystallized with toluene/ethyl acetate to give 1.88 g of a yellow solid in 75% yield. By a train sublimation method, 1.2 g of the obtained solid was purified. The purification by sublimation was performed by heating at 385° C. under a pressure of 2.2×10$^{-2}$ Pa with an argon flow rate of 0 mL/min. After the purification by sublimation, 0.93 g of a yellow solid was obtained at a collection rate of 78%. The synthesis scheme of Step 3 is shown below.

[Chemical Formula 64]

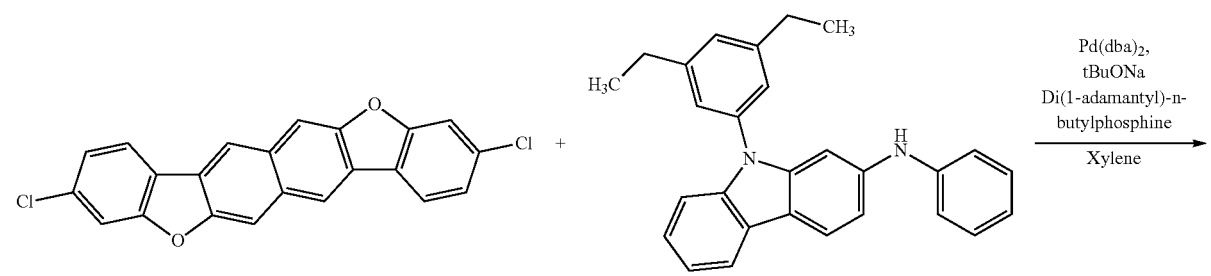

-continued

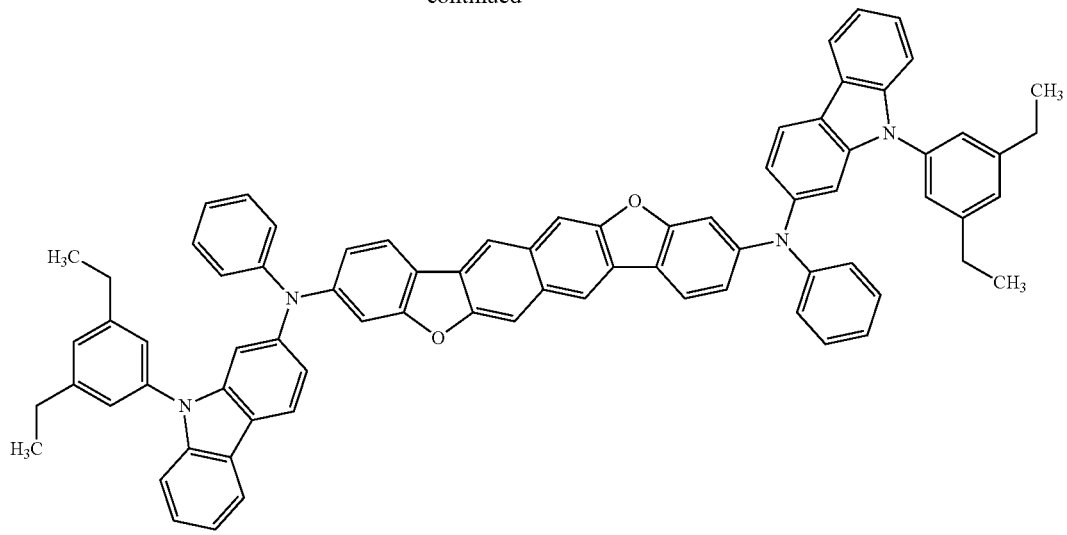

Measurement results by nuclear magnetic resonance ($^1$H-NMR) spectroscopy of the yellow solid obtained in Step 3 above are shown below. This indicates that 3,10mmEtPCA2Nbf(IV)-02 was obtained in Step 3.

$^1$H NMR (CD$_2$Cl$_2$, 300 MHz): δ=1.12 (t, J1=7.8 Hz, 12H), 2.60 (q, J1=7.8 Hz, 8H), 7.01 (s, 2H), 7.06-7.13 (m, 10H), 7.20-7.44 (m, 18H), 7.89 (d, J1=8.4 Hz, 2H), 7.97 (s, 2H), 8.04-8.10 (m, 4H), 8.36 (s, 2H).

Figure 41:
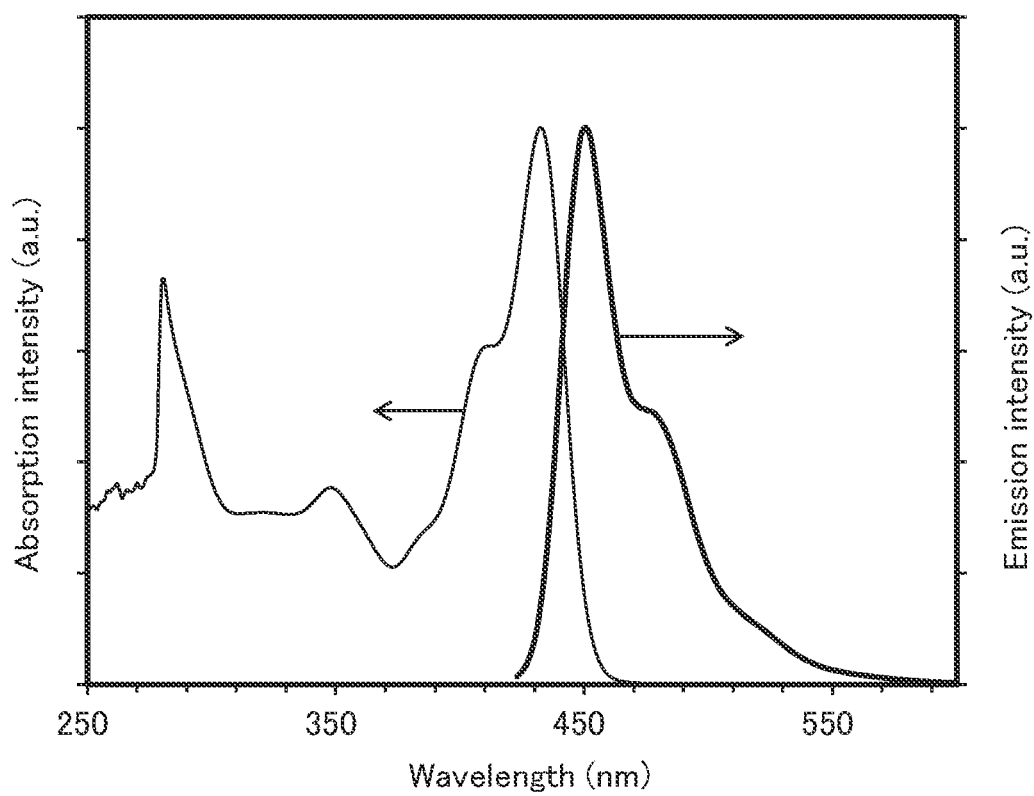
FIG. 41 shows an absorption spectrum and an emission spectrum of 3,10mmEtPCA2Nbf(IV)-02 in a toluene solution.
Figure 42:
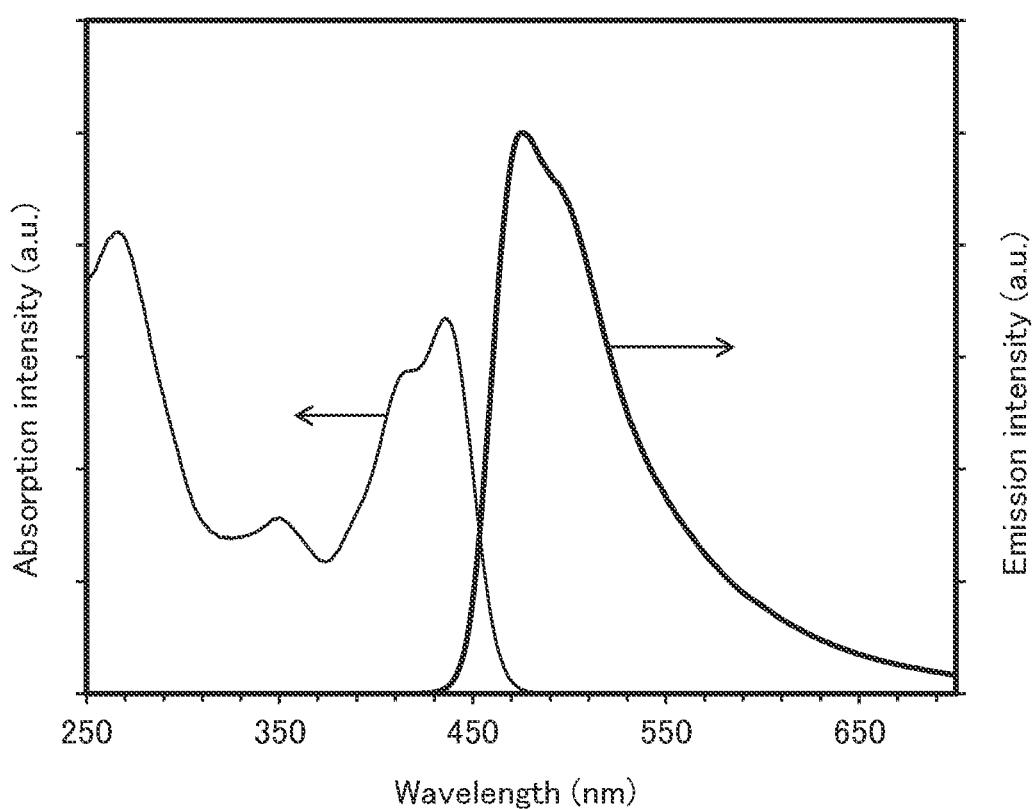
FIG. 42 shows an absorption spectrum and an emission spectrum of 3,10mmEtPCA2Nbf(IV)-02 in a thin film state.

Next, the measurement results of the absorption and emission spectra of 3,10mmEtPCA2Nbf(IV)-02 in a toluene solution are shown in FIG. 41. Furthermore, the absorption and emission spectra of the thin film are shown in FIG. 42. The solid thin film was formed over a quartz substrate by a vacuum evaporation method. The absorption spectrum of the toluene solution was measured with an ultraviolet-visible light spectrophotometer (V550, manufactured by JASCO Corporation), and the spectrum of toluene alone in a quartz cell was subtracted. The absorption spectrum of the thin film was measured with a spectrophotometer (U-4100 Spectrophotometer, manufactured by Hitachi High-Technologies Corporation). The emission spectrum was measured with a fluorescence spectrophotometer (FP-8600, produced by JASCO Corporation). Quantum yields were measured with an absolute PL quantum yield measurement system (Quantaurus-QY, manufactured by Hamamatsu Photonics K. K.).

As can be seen in FIG. 41, 3,10mmEtPCA2Nbf(IV)-02 in the toluene solution has absorption peaks at 433 nm, 411 nm, 348 nm, 322 nm, and 280 nm, and emission spectrum peaks at 451 nm and 478 nm (excitation wavelength: 408 nm). As can be seen in FIG. 42, 3,10mmEtPCA2Nbf(IV)-02 in the thin film has absorption peaks at 436 nm, 418 nm, 348 nm, 322 nm, and 280 nm, and an emission spectrum peak at 480 nm (excitation wavelength: 400 nm). These results indicate that 3,10mmEtPCA2Nbf(IV)-02 emits blue light and can be used as a host for a light-emitting substance or a substance which emits fluorescence in the visible region.

The measured quantum yield of 3,10mmEtPCA2Nbf(IV)-02 in the toluene solution was as high as 88%, which indicates that 3,10mmEtPCA2Nbf(IV)-02 is suitable for a light-emitting material.

Reference Example 2

Reference Synthesis Example 2

In this reference synthesis example, a synthesis method of N,N-bis[9-(3,5-dihexylphenyl)-9H-carbazol-2-yl]-N,N-diphenyl-naphtho[2,3-b;6,7-b']bisbenzofuran-3,10-diamine (abbreviation: 3,10mmHexPCA2Nbf(IV)-02), which is used in Example 2, will be described. The structural formula of 3,10mmHexPCA2Nbf(IV)-02 is shown below.

[Chemical Formula 65]

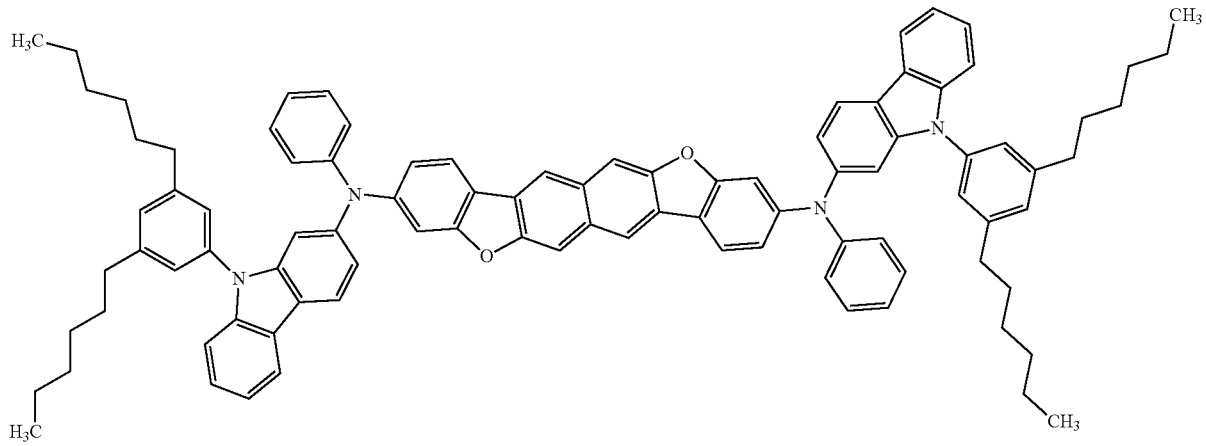

3,10mmHexPCA2Nbf(IV)-02

Step 1: Synthesis of 2-chloro-9-(3,5-dihexylphenyl)-9H-carbazole

Into a 300-mL three-neck flask, 2.9 g (14 mmol) of 2-chloro-9H-carbazole, 8.4 g (26 mmol) of 1-bromo-3,5-dihexylbenzene, and 4.2 g (43 mmol) of sodium tert-butoxide were put. To this mixture, 75 mL of xylene and 0.2 mL of tri(tert-butyl)phosphine (a 10% hexane solution) were added, and this mixture was degassed by being stirred while the pressure was reduced. Then, 82 mg (10.14 mmol) of bis(dibenzylideneacetone)palladium(0) was added to this mixture, and the mixture was heated and stirred under a nitrogen stream at 150° C. for 1.5 hours. After the stirring, toluene was added to the mixture, and the resulting mixture was suction-filtered through Florisil, Celite, and alumina to obtain a filtrate. The filtrate was concentrated to give an oily substance. This oily substance was purified by silica gel column chromatography (silica gel, developing solvent: hexane) to give 1.4 g of a colorless transparent oily substance in 22% yield. The synthesis scheme of Step 1 is shown below.

[Chemical Formula 66]

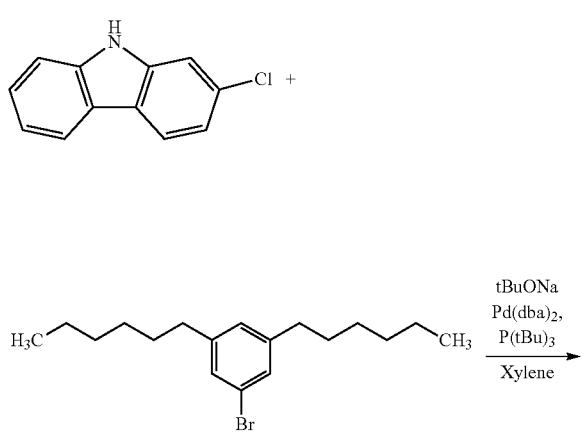

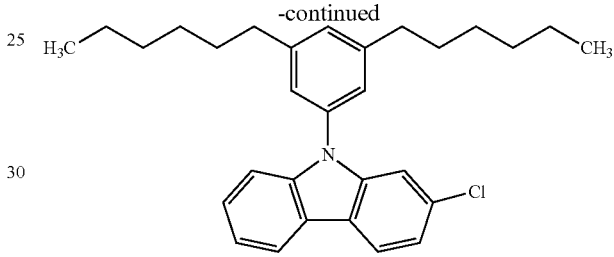

Measurement results by nuclear magnetic resonance ($^1$H-NMR) spectroscopy of the oily substance obtained in Step 1 above are shown below. This indicates that 2-chloro-9-(3,5-dihexylphenyl)-9H-carbazole was obtained in Step 1.

$^1$H NMR (CDCl$_3$, 300 MHz): δ=0.89 (t, J1=6.9 Hz, 6H), 1.29-1.43 (m, 12H), 1.68 (quin, J1=7.8 Hz, 4H), 2.69 (t, J1=7.8 Hz, 4H), 7.11-7.31 (m, 5H), 7.36-7.44 (m, 3H), 8.03 (d, J1=8.4 Hz, 1H), 8.09 (dt, J1=7.8 Hz, J2=0.9 Hz, 1H).

Step 2: Synthesis of N-[9-(3,5-dihexylphenyl)-9H-carbazol-2-yl]-N-phenylamine

Into a 200-mL three-neck flask, 1.4 g (3.1 mmol) of 2-chloro-9-(3,5-dihexylphenyl)-9H-carbazole, 0.55 g (5.9 mmol) of aniline, 0.90 g (9.4 mmol) of sodium tert-butoxide, and 56 mg (0.16 mmol) of di(1-adamantyl)-n-butylphosphine were put. Then, 20 mL of xylene was added to this mixture, and the mixture was degassed by being stirred while the pressure was reduced. To this mixture, 18 mg (31 μmol) of bis(dibenzylideneacetone)palladium(0) was added, and the mixture was heated and stirred under a nitrogen stream at 150° C. for 7 hours. After the stirring, toluene was added to the mixture, the resulting mixture was suction-filtered through Florisil, Celite, and alumina, and the filtrate was concentrated to give a brown oily substance.

Into a 200-mL three-neck flask, 2.7 g (6.1 mmol) of 2-chloro-9-(3,5-dihexylphenyl)-9H-carbazole, 0.85 g (9.1 mmol) of aniline, 1.8 g (18 mmol) of sodium tert-butoxide, and 0.11 g (0.30 mmol) of di(1-adamantyl)-n-butylphosphine were put. Then, 30 mL of xylene was added to this mixture, and the mixture was degassed by being stirred while the pressure was reduced. To this mixture, 35 mg (61

μmol) of bis(dibenzylideneacetone)palladium(0) was added, and the mixture was heated and stirred under a nitrogen stream at 150° C. for 7 hours. After the stirring, toluene was added to the mixture, the resulting mixture was suction-filtered through Florisil, Celite, and alumina, and the filtrate was concentrated to give a brown oily substance. Then, two batches of the oily substance were mixed and purified by silica gel column chromatography (toluene and hexane at 1:4 in the developing solvent) to give 1.7 g of a yellow solid in 31% yield. The synthesis scheme of Step 2 is shown below.

Measurement results by nuclear magnetic resonance ($^1$H-NMR) spectroscopy of the yellow solid obtained in Step 2 above are shown below. This indicates that N-[9-(3,5-dihexylphenyl)-9H-carbazol-2-yl]-N-phenylamine was obtained in Step 2.

$^1$H NMR (DMSO-d$_6$, 300 MHz): =0.84 (t, J1=7.2 Hz, 6H), 1.23-1.35 (m, 12H), 1.62 (quin, J1=7.8 Hz, 4H), 2.66 (t, J1=7.8 Hz, 4H), 6.81 (tt, J1=6.9 Hz, J2=1.2 Hz, 1H), 6.99 (dd, J1=8.7 Hz, J2=1.8 Hz, 1H), 7.07 (d, J1=1.8 Hz, 1H), 7.11-7.15 (m, 3H), 7.18-7.32 (m, 7H), 8.02-8.07 (m, 2H), 8.35 (s, 1H).

Step 3: Synthesis of 3,10mmHexPCA2Nbf(IV)-02

Into a 200-mL three-neck flask, 0.54 g (1.4 mmol) of 3,10-dichloronaphtho[2,3-b;6,7-b']bisbenzofuran, 1.7 g (3.4 mmol) of N-[9-(3,5-dihexylphenyl)-9H-carbazol-2-yl]-N-phenylamine, 51 mg (0.14 mmol) of di(1-adamantyl)-n-butylphosphine, and 0.83 g (8.6 mmol) of sodium tert-butoxide were put. To the mixture, 15 mL of xylene was added. This mixture was degassed by being stirred while the pressure was reduced. To this mixture, 16 mg (29 mol) of bis(dibenzylideneacetone)palladium(0) was added, and stirring was performed under a nitrogen stream at 150° C. for 14.5 hours. After the stirring, toluene was added to this mixture, the mixture was suction-filtered through Florisil, Celite, and alumina, and the filtrate was concentrated to give a solid. The obtained solid was purified by silica gel column chromatography (toluene and hexane at 1:2 in the developing solvent). The obtained solid was reprecipitated with ethyl acetate/ethanol to give 1.7 g of a yellow solid in 93% yield. The synthesis scheme of Step 3 is shown below.

[Chemical Formula 67]

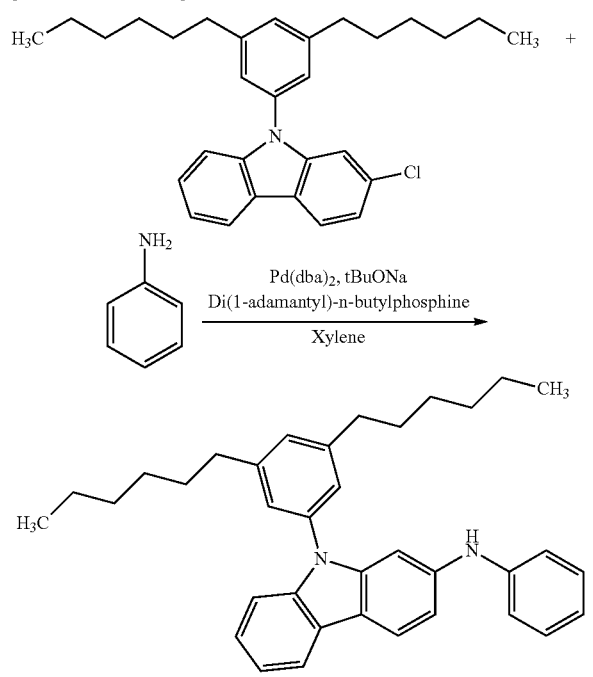

[Chemical Formula 68]

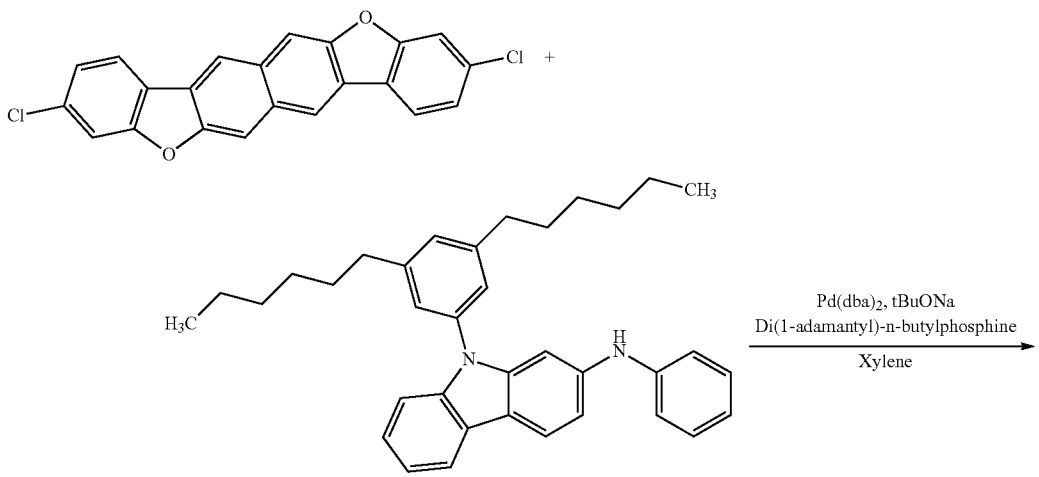

-continued

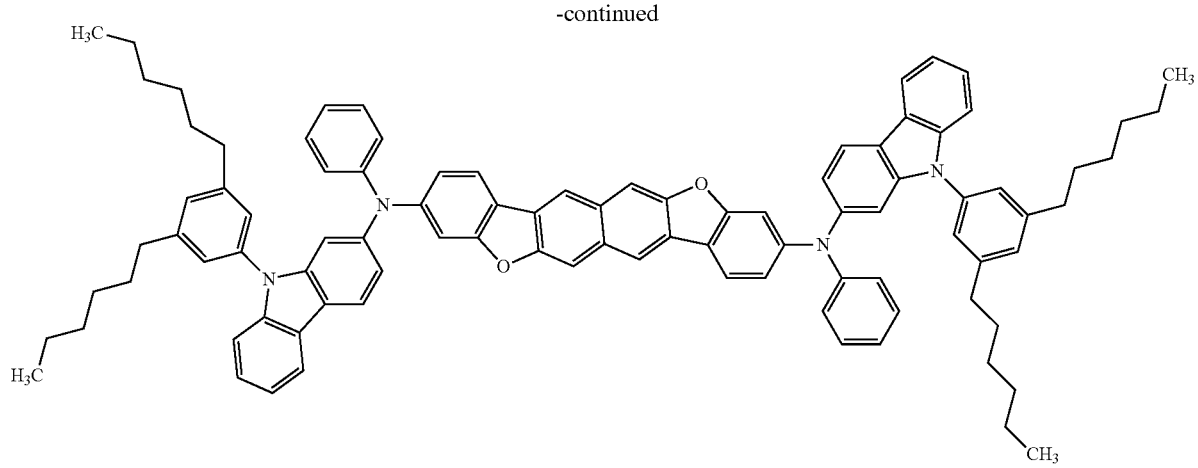

Measurement results by nuclear magnetic resonance (H-NMR) spectroscopy of the yellow solid obtained in Step 3 above are shown below. This indicates that 3,10mmHexPCA2Nbf(IV)-02 was obtained in Step 3.

$^1$H NMR (CD$_2$Cl$_2$, 300 MHz): δ=0.83 (t, J1=6.6 Hz, 12H), 1.17-1.31 (m, 24H), 1.47-1.57 (m, 8H), 2.55 (t, J1=7.8 Hz, 8H), 6.98 (s, 2H), 7.06-7.13 (m, 10H), 7.20-7.43 (m, 18H), 7.88 (d, J1=8.4 Hz, 2H), 7.96 (s, 2H), 8.04-8.09 (m, 4H), 8.35 (s, 2H).

This application is based on Japanese Patent Application Serial No. 2019-224651 filed with Japan Patent Office on Dec. 12, 2019, the entire contents of which are hereby incorporated by reference.

What is claimed is:

1. An organic compound represented by General Formula (G1):

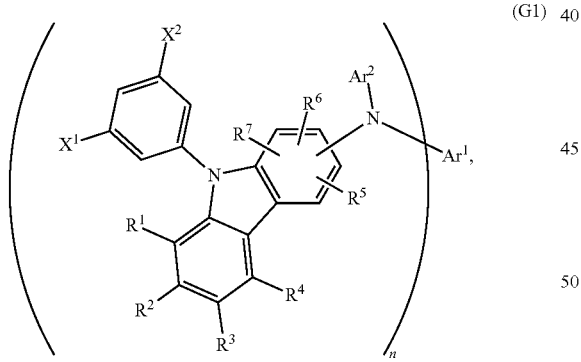

(G1)

wherein X$^1$ and X$^2$ each independently represent a secondary or tertiary alkyl group having 3 to 6 carbon atoms and having a branched carbon atom which is bonded to the phenyl group,
wherein Ar$^1$ represents a substituted or unsubstituted condensed aromatic ring skeleton having 10 to 60 carbon atoms and composed of three or more substituted or unsubstituted rings or a substituted or unsubstituted condensed heteroaromatic ring skeleton having 8 to 60 carbon atoms and composed of three or more substituted or unsubstituted rings,
wherein Ar$^2$ represents a substituted or unsubstituted aryl group having 6 to 25 carbon atoms,
wherein R$^1$ to R$^7$ each independently represent any of hydrogen, an alkyl group having 1 to 6 carbon atoms, a cycloalkyl group having 3 to 12 carbon atoms, and an aryl group having 6 to 13 carbon atoms which is unsubstituted or to which an alkyl group is bonded as a substituent, and
wherein n represents any of 1 to 3, and in the case where n is 2 or more, two or more groups bonded to Ar$^1$ are identical or different.

2. The organic compound according to claim 1, wherein Ar$^1$ is a substituted or unsubstituted condensed heteroaromatic ring skeleton having 8 to 60 carbon atoms and composed of three to seven substituted or unsubstituted rings.

3. The organic compound according to claim 1, wherein X$^1$ or X$^2$ each independently represent a secondary or tertiary alkyl group having 3 or 4 carbon atoms and having a branched carbon atom which is bonded to the phenyl group.

4. The organic compound according to claim 1, wherein n is 2.

5. The organic compound according to claim 1, wherein Ar$^1$ represents any of heteroaromatic ring skeletons represented by General Formulae (B1) to (B4):

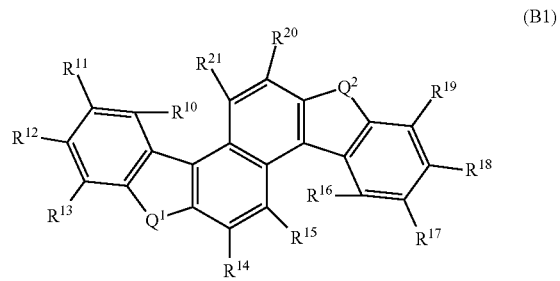

(B1)

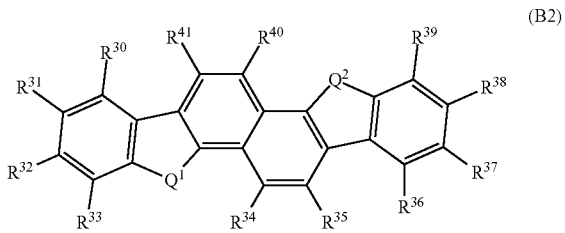

(B2)

-continued (B3)

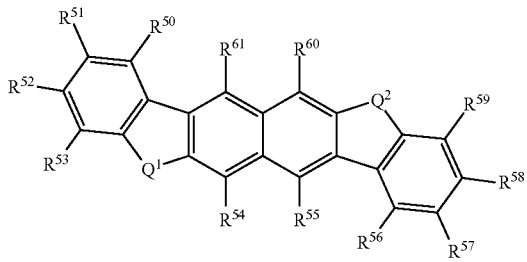

(B4)

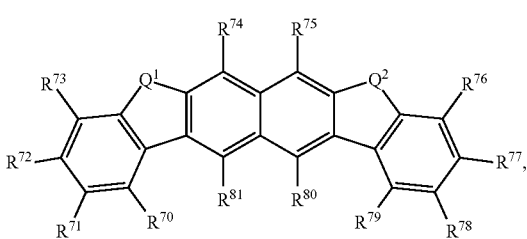

wherein $Q^1$ and $Q^2$ each independently represent an oxygen atom or a sulfur atom, wherein in General Formula (B1), any one, two or three of $R^{10}$ to $R^{20}$ represents a single bond connected to the nitrogen atom, and the others each independently represent any of hydrogen, an alkyl group having 1 to 6 carbon atoms, a cycloalkyl group having 3 to 12 carbon atoms, and an aryl group having 6 to 13 carbon atoms which is unsubstituted or to which an alkyl group is bonded as a substituent, wherein in General Formula (B2), any one, two or three of $R^{30}$ to $R^{41}$ represents a single bond connected to the nitrogen atom, and the others each independently represent any of hydrogen, an alkyl group having 1 to 6 carbon atoms, a cycloalkyl group having 3 to 12 carbon atoms, and an aryl group having 6 to 13 carbon atoms which is unsubstituted or to which an alkyl group is bonded as a substituent, wherein in General Formula (B3), any one, two or three of $R^{50}$ to $R^{61}$ represents a single bond connected to the nitrogen atom, and the others each independently represent any of hydrogen, an alkyl group having 1 to 6 carbon atoms, a cycloalkyl group having 3 to 12 carbon atoms, and an aryl group having 6 to 13 carbon atoms which is unsubstituted or to which an alkyl group is bonded as a substituent, and wherein in General Formula (B4), any one, two or three of $R^{70}$ to $R^{81}$ represents a single bond connected to the nitrogen atom, and the others each independently represent any of hydrogen, an alkyl group having 1 to 6 carbon atoms, a cycloalkyl group having 3 to 12 carbon atoms, and an aryl group having 6 to 13 carbon atoms which is unsubstituted or to which an alkyl group is bonded as a substituent.

6. The organic compound according to claim 1, wherein $Ar^1$ represents a heteroaromatic ring skeleton represented by General Formula (B1-1) or (B3-1):

(B1-1)

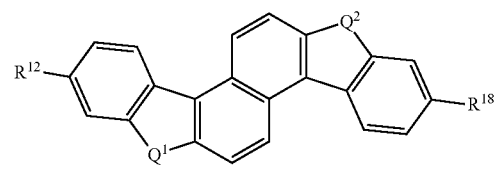

(B3-1)

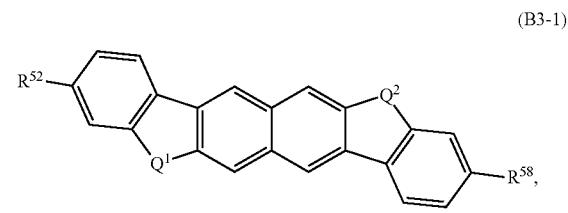

wherein $Q^1$ and $Q^2$ each independently represent an oxygen atom or a sulfur atom, and wherein $R^{12}$, $R^{18}$, $R^{52}$, and $R^{58}$ represent a single bond connected to the nitrogen atom.

7. An organic compound represented by General Formula (G1-1):

(G1-1)

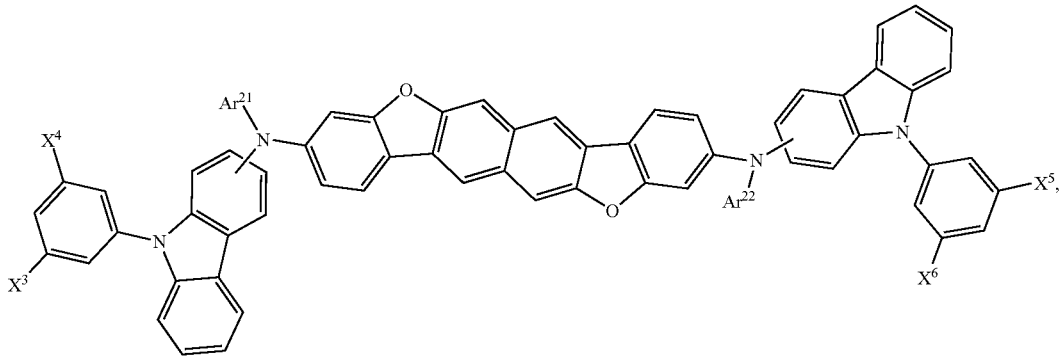

wherein $X^3$ to $X^6$ each independently represent a secondary or tertiary alkyl group having 3 to 6 carbon atoms and having a branched carbon atom which is bonded to a phenyl group, and wherein $Ar^{21}$ and $Ar^{22}$ each independently represent a substituted or unsubstituted aryl group having 6 to 25 carbon atoms.

8. A light-emitting device comprising the organic compound according to claim 1.

9. An optical device comprising the organic compound according to claim 1.

10. An electronic device comprising the light-emitting device according to claim 8 and a sensor, an operation button, a speaker, or a microphone.

11. A light-emitting apparatus comprising the light-emitting device according to claim 8 and a transistor, or a substrate.

12. A lighting device comprising the light-emitting device according to claim 8 and a housing.

* * * * *